(12) United States Patent
Bhattacharya et al.

(10) Patent No.: US 8,609,680 B2
(45) Date of Patent: Dec. 17, 2013

(54) 2,3-DIHYDRO-1H-INDEN-1-YL-2,7-DIAZASPIRO[3.5] NONANE DERIVATIVES

(75) Inventors: Samit K. Bhattacharya, Niantic, CT (US); Kimberly O. Cameron, East Lyme, CT (US); Dilinie P. Fernando, Niantic, CT (US); Kim F. McClure, Mystic, CT (US); Daniel W. Kung, Salem, CT (US); Allyn T. Londregan, Barrington, RI (US); Suvi T. M. Simila, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 295 days.

(21) Appl. No.: 13/049,225

(22) Filed: Mar. 16, 2011

(65) Prior Publication Data
US 2011/0230461 A1 Sep. 22, 2011

Related U.S. Application Data

(60) Provisional application No. 61/315,522, filed on Mar. 19, 2010, provisional application No. 61/444,401, filed on Feb. 18, 2011.

(51) Int. Cl.
*A61K 31/438* (2006.01)
*C07D 401/04* (2006.01)

(52) U.S. Cl.
USPC .......................................... 514/278; 546/16

(58) Field of Classification Search
USPC .......................................... 546/16; 514/278
See application file for complete search history.

(56) References Cited

U.S. PATENT DOCUMENTS

2009/0169567 A1 7/2009 Kokubo et al.

FOREIGN PATENT DOCUMENTS

| WO | WO 94 17038 | 8/1994 | ............ C07D 205/12 |
|---|---|---|---|
| WO | WO 03 026643 | 4/2003 | ............ A61K 31/397 |
| WO | WO 2005 040167 | 5/2005 | ............ C07D 471/10 |
| WO | WO 2007 007069 | 1/2007 | ............ C07D 487/08 |
| WO | WO 2007 075702 | 7/2007 | ............ A61K 31/397 |
| WO | WO 2008 033456 | 3/2008 | ............ C07D 471/08 |

OTHER PUBLICATIONS

Dorwald F. A. Side Reactions in Organic Synthesis, 2005, Wiley: VCH, Weinheim p. IX of Preface. and p. 10.*
Tong et al. ADA Conference, "Ghrelin Suppresses Glucose-Stimulated Insulin Secretion in Healthy Humans", 2009.
Carpino et al., Expert Opinion on Therapeutic Patents, 18(11), p. 1253-1263, 2008.
Carpino et al., Expert Opinion on Therapeutic Patents, 12(11), p. 1599-1618, 2002.
Suvi Simila, et al., ACS National Meeting Poster Abstract, Washington DC, Aug. 2009.
Lu et al., Neuroscience Lett., 321, pp. 157-160, 2002.
Lucidi et al., Nutr. Metab. Cardiovasc. Dis., 15, pp. 410-417, 2005.
Mager et al., Diabet. Med., 23(6), pp. 685-689, 2006.
Mondal et al., Regul. Pept., 126, pp. 55-59, 2005.
Mori et al., FEBS let., 486, pp. 213-216, 2000.
Muccioli et al., Eur. J. Pharmacol, 440, pp. 235-254, 2002.
Nakazato et al., Nature, 409, pp. 194-198, 2001.
Poykko et al., Diabetologia, 46, pp. 455-458, 2003.
Reimer et al., Endocrinology, 144, pp. 916-921, 2003.
Rindi et al., Histochem. Cell Biol., 117, pp. 511-519, 2002.
Robitaille et al., Obesity, 15, pp. 2336-2347, 2007.
Rodriquez et al., Int. J. Obes., 33, pp. 541-552, 2009.
Roth et al., Obes. Surg., 19, pp. 29-35, 2008.
Sakata et al., Peptides, 23, pp. 531-536, 2002.
Shuto et al., J. Clin. Invest., 109, pp. 1429-1436, 2002.
Sun et al., Cell Metab., 3, pp. 379-386, 2006.
Tanaka et al., Biochim. Biophys. Acta., 1522, pp. 62-65, 2001.
Tang et al., Clin. Chim. Acta., 387, pp. 42-47, 2008.
Tena-Sempere et al., Endocrinology, 143, pp. 717-725, 2002.
Ukkola et al., Obes. Res., 10, pp. 782-791, 2002.
Vestergaard et al., Am. J. Physiol. Endocrinol. Metab., 292, pp. E1829-E1836, 2007.
Vestergaard et al., J. Clin. Endocinol. Metabol., 93, pp. 438-444, 2008a.
Vestergaard et al., Diabetes, 57, pp. 3205-3210, 2008b.
Volante et al., J. Clin. Endocrinol. Metab., 87, pp. 1300-1308, 2002a.
Volante et al., J. Histochem. Cytochem., 50, pp. 1013-1021, 2002b.
Wierup et al., Regul. Pept., 107, pp. 63-69, 2002.
Wierup et al., J. Hostochem. Cytochem., 52, pp. 301-310, 2004.
Wierup et al., Cell Tissue Res., 319, pp. 423-428, 2005.
Wortley et al., J. Clin. Invest., 115, pp. 3573-3578, 2005.
Wren et al., J. Clin. Endocrinol. Metab., 86, pp. 5992-5995, 2001.
Zigman et al., J. Clin. Invest., 115, pp. 3564-3572, 2005.
Andralojc et al., Diabetologia, 52, pp. 486-493, 2009.
Ando et al., Am. J. Clin. Nutr., 86, pp. 25-32, 2007.
Ariyasu et al., J. Clin. Endocrinol. Metab., 86, pp. 4753-4758, 2001.
Arosia et al., J. Clin. Endocrinol. Metab, 88, pp. 701-704, 2003.
Asakawa et al., Gut, 52, pp. 947-952, 2003.
Barazzoni et al., J. Clin. Endocrinol. & Met., 92, pp. 3935-3940, 2007.

(Continued)

*Primary Examiner* — Rita Desai
(74) *Attorney, Agent, or Firm* — Mary J. Hosley; John A. Wichtowski

(57) ABSTRACT

The present invention provides a compound of Formula (I)

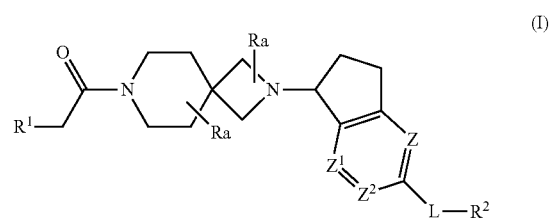

or a pharmaceutically salt thereof wherein $R^1$, $R^2$, Ra, L, Z, $Z^1$ and $Z^2$ are as defined herein, that act as Ghrelin antagonists or inverse agonists; pharmaceutical compositions thereof; and methods of treating diseases, disorders, or conditions mediated by the antagonism of the Ghrelin receptor.

13 Claims, 1 Drawing Sheet

(56) References Cited

OTHER PUBLICATIONS

Broglio et al., J. Clin. Endocrinol. Metab., 86, pp. 5083-5086, 2001.
Broglio et al., J. Clin. Endocrinol. Metab., 87, pp. 3783-3790, 2002.
Broglio et al., J. Clin. Endocrinol. Metab., 88, pp. 1537-1542, 2003a.
Broglio et al., J. Endocrinol. Invest., 26, pp. 192-196, 2003b.
Broglio et al., J. Clin. Endocrinol. Metab., 89, pp. 3062-3065, 2004.
Chen et al., Pharm. Rev., 61, pp. 430-481, 2009.
Chung et al., Hum. Hered., 67, pp. 193-205, 2009.
Colombo et al., Pancreas, 27, pp. 161-166, 2003.
Cummings et al., Diabetes, 50, pp. 1714-1719, 2001.
Cummings et al., N. Engl. J. Med., 346, pp. 1623-1630, 2002.
Damjanovic et al., J. Clin. Endocrinol. Metab., 91, pp. 2574-2581, 2006.
Date et al., Endocrinology, 141, pp. 4255-4261, 2000.
Date et al., Diabetes, 51, pp. 124-129, 2002.
Dezaki et al., Diabetes, 53, pp. 3142-3151, 2004.
Dezaki et al., Diabetes, 55, pp. 3486-3493, 2006.
Dezaki et al., Diabetes, 56, pp. 2319-2327, 2007.
Dezaki et al., Pharmacology & Therapeutics, 118, pp. 239-249, 2008.
Dornonville de la Cour et al., Reg. Pept., 99, pp. 141-150, 2001.
Druce et al., Int. J. Obes., 29, pp. 1130-1136, 2005.
Egido et al., Eur. J. Endocrinol, 146, pp. 241-244, 2002.
Esler et al., Endocrinology, 148, pp. 5175-5185, 2007.
Gnanapavan et al., J. Clin. Endocrinol. Metab., 87, pp. 2988-2991, 2002.
Gualillo et al., Endocrinology, 142, pp. 788-794, 2001.
Gauna et al., J. Clin. Endocrinol. Metab., 89, pp. 5035-5042, 2004.
Hattori et al., J. Clin. Endocrinol. Metab., 86, pp. 4284-4291, 2001.
Hosoda et al., Biochem. Biophys. Res. Commun., 279, pp. 909-913, 2000.
Huda et al., Int. J. Obesity, 33, pp. 317-325, 2009.
Iwakura et al., Am. J. Physiol. Endocrinol. Metab., 297, pp. 802-811, 2009.
Klipelainen et al., Metabolism, 57, pp. 428-436, 2008.
Kojima et al., Nature, 402, pp. 656-660, 1999.
Korbonits et al., J. Clin. Endocrinol. Metab., 87, pp. 4004-4008, 2002.
Li et al., Chin. Med. J., 121, pp. 1666-1669, 2008.
Longo et al., Reg. Peptides, 150, pp. 55-61, 2008.

\* cited by examiner

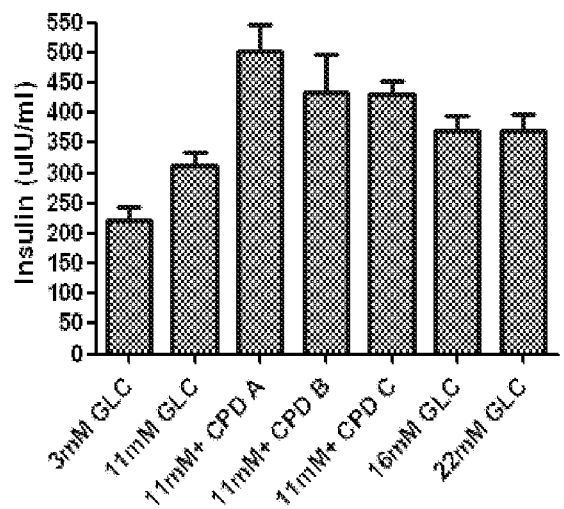

2,3-DIHYDRO-1H-INDEN-1-YL-2,7-DIAZASPIRO[3.5] NONANE DERIVATIVES

This application claims the benefit of U.S. Provisional Application Nos. 61/444,401, filed Feb. 18, 2011 and 61/315,522 filed Mar. 19, 2010.

FIELD OF THE INVENTION

The present invention relates to 2,3-dihydro-1H-inden-1-yl-2,7-diazaspiro[3.5]nonane derivatives, as well as pharmaceutical compositions and uses thereof as ghrelin inverse agonists or antagonists.

BACKGROUND OF THE INVENTION

Diabetes mellitus is a condition in which the body either does not produce enough, or does not properly respond to, insulin, a hormone produced in the pancreas. There are 2 main types of diabetes. Type 1 diabetes is when the body does not produce insulin, of which only 5-10% of people with diabetes have Type 1 diabetes. 23.6 million children and adults in the United States have Type 2 diabetes (T2D; www.diabetes.org). In T2D, either the body does not produce enough insulin or cells in the body do not response to insulin resulting in high levels of sugar in the blood. Pregnant women who have never had diabetes before but who have high blood glucose levels during pregnancy are said to have gestational diabetes. Gestational diabetes affects about 4% of all pregnant women and may precede development of T2D. Studies have shown that an increase in abdominal fat is associated with glucose intolerance. A body mass index of over 40 has been linked to a higher chance of developing diabetes. T2D and obesity are major public health priorities because of their high prevalence and incidence nationwide and their long-term health implications. The complete citation for the references cited are provided hereinbelow.

The underlying pathophysiology associated with both obesity and diabetes has been linked to the naturally occurring hormone ghrelin. Ghrelin is an acylated 28 amino acid peptide which in 1999 was discovered to be the endogenous ligand of the growth hormone secretagogue receptor (GHS-R; Kojima et al., 1999). The n-octanoyl group at serine 3 of ghrelin is essential for GHS-R binding and function, whereas the unacylated des-acyl ghrelin, does not activate the GHS-R (Kojima et al., 1999; 2001; Boglio et al., 2003b). Ghrelin is predominantly expressed in specialized cells located within the gastric oxyntic mucosa which provides the major source of circulating ghrelin (Date et al., 2000; Ariyasu et al., 2001; Dornonville de la Cour et al., 2001; Rindi et al., 2002). In addition, ghrelin-producing epsilon cells have been identified in the developing and adult human pancreas (Wierup et al., 2002; Andralojc et al., 2009) and to a lesser extent in the intestine, kidney, immune system, placenta, testis, pituitary, lung and hypothalamus (Kojima et al., 1999; Hosoda et al., 2000; Date et al., 2000; Mori et al., 2000; Gualillo et al., 2001; Tanaka et al., 2001; Date et al., 2002; Gnanapavan et al., 2002; Hattori et al., 2001; Lu et al., 2002; Mucciolo et al., 2002; Sakata et al., 2002; Tena-Sempere et al., 2002; Volante et al., 2002 a,b; Mondal et al., 2005).

To date, ghrelin is the only identified hunger hormone. The preprandial rise and postprandial fall in plasma ghrelin levels support the hypothesis that ghrelin plays a physiological role in meal initiation in humans (Cummings et al., 2001). The baseline and pulsatile pattern of ghrelin is inhibited in obese subjects following gastric bypass surgery (Cummings et al., 2002; Roth et al., 2008). Endogenous acylated ghrelin has been reported to be elevated in obese T2D (Rodriguez et al., 2009) and these levels have an inverse correlation with insulin sensitivity (Barazzoni et al., 2007). Several human genetic studies have demonstrated an association between ghrelin polymorphisms and body mass index or other obesity-related phenotypes (Chung et al., 2009; Tang et al., 2008; Robitaille et al., 2007; Ando et al., 2007; Korbonits et al., 2002; Ukkola et al., 2002; Kilpelainen et al., 2008). A few studies have also shown a ghrelin variant association with T2D (Mager et al., 2006; Poykko et al., 2003). In addition to ghrelin itself, human genetic data also support the role of the GHS-R in metabolic disease. It has recently been shown that the A/A genotype (rs2922126) in the promoter is linked with metabolic syndrome, increased waist circumference and increased fasting plasma glucose in women. The A/A genotype (rs509030) in the intron was also associated with lower plasma high density lipoprotein in women. These data suggest that polymorphisms within GHS-R might be a genetic risk factor for metabolic syndrome in women (Li et al., 2008).

Deletion of ghrelin in ob/ob mice augments insulin secretion in response to a glucose challenge (Sun et al., 2006). In contrast, an over-expressing ghrelin mouse model has a decreased insulin secretion in response to a glucose challenge (Iwakura et al., 2009). These data supporting the hypothesis that endogenous ghrelin can cause glucose intolerance.

Exogenous ghrelin also increases blood glucose and decreases insulin levels in humans and rodents (Broglio et al., 2001, 2002, 2003a,b; Arosia et al., 2003; Broglio et al., 2004; Sun et al., 2006; Dezaki et al., 2004). The ghrelin-induced hyperglycemia is abolished by the peptide GHS-R antagonist [D-Lys$^3$]-GHRP-6 (Dezaki et al., 2004). In addition, ghrelin infusion in rodents and humans inhibits glucose-stimulated insulin secretion in vivo (Reimer et al., 2003; Dezaki et al., 2007; Tong et al., 2009).

The effects of ghrelin on insulin secretion are directly within the pancreatic islet as many authors have confirmed that the GHS-R is present in islets (Date et al., 2002; Gnanapavan et al., 2002; Volante et al., 2002a; Wierup et al., 2004; Wierup & Sunder, 2005; Kageyama et al. 2005). Exogenous ghrelin also decreases glucose-induced insulin release in rat and mouse islets and in the rat perfused pancreas (Egido et al., 2002; Colombo et al., 2003; Reimer et al., 2003; Dezaki et al., 2004; Dezaki et al., 2006). Dezaki et al. (2004; 2006; 2007; 2008) provided the first evidence to support the hypothesis that endogenous ghrelin in rodent islets acts directly on β-cells to inhibit glucose-induced insulin, as the peptide GHS-R antagonist and a ghrelin anti-serum increased intracellular calcium in response to glucose. In addition, the glucose-induced insulin release from isolated islets of ghrelin knock-out mice is greater than wild type. The inhibitory effects of ghrelin on glucose-induced changes in intracellular calcium is abolished by pertussis toxin, an inhibitor of G$_{i/o}$ subtypes of GTP binding proteins.

GHS-R peptide antagonists have been reported to reduce fasting blood glucose in mice (Asakawa et al., 2003; Dezaki et al., 2004). More recently, a small molecule non-peptide antagonist has been shown to improve glucose tolerance in rats by stimulating insulin release without hypoglycemia (Elser et al., 2007).

In addition to modulating insulin secretion and glucose tolerance, exogenous ghrelin has been shown to modulate insulin sensitivity. Intravenous infusion of ghrelin in man increases plasma glucose, increases free fatty acids, and reduces glucose disposal rates compatible with an impairment of insulin sensitivity (Gauna et al., 2004; Lucidi et al., 2005; Damjanovic et al., 2006; Vestergaard et al., 2007; 2008a, b).

The effects of ghrelin are mediated via the GHS-R as Longo et al., (2008) have reported loss of the ghrelin receptor in mice improves insulin sensitivity. GHS-R knock-out mice fed a high-fat diet had several measures of greater insulin sensitivity, including: lower fasted blood glucose and plasma insulin, lower % HbA1c, lower insulin levels during glucose tolerance tests, and improved performance in hyperinsulinemic-euglycemic and hyperglycemic clamp studies. The knockout mice fed a high-fat diet also did not develop hepatic steatosis and had lower total cholesterol, relative to controls. Furthermore, the knock-out demonstrated a lower intestinal triglyceride secretion rate of dietary lipid.

It is well established that ghrelin increases food intake in rodents (see Chen et al., 2009). In addition to preclinical data, acute administration of exogenous ghrelin has been shown to stimulate food intake humans (Wren et al., 2001; Druce et al., 2005; Huda et al., 2009). Several lines of evidence support a role for endogenous ghrelin in the control of food intake. Anti-ghrelin antibodies and knockdown of the GHS-R suppress food intake in rats (Nakazato et al., 2001, Shuto et al, 2002). Both ghrelin knockout and GHS-R null mice have been reported by separate groups (Zigman et al., 2005; Wortley et al., 2005). GHS-R null mice were leaner than wild type when fed normal chow and were resistant to high fat diet-induced obesity. Ghrelin knock-out mice also have a reduced Respiratory Quotient, suggesting that ghrelin may act as a nutrient sensor and its absence may promote increased fat utilization.

The following references were cited above:

Andralojc, K. M., Mercalli A., Nowak, K. W., Albarello, L., Calcagno, R., Luzi, L., et al. (2009); Ghrelin-producing epsilon cells in the developing and adult human pancreas; Diabetologia 52, 486-493.

Ando, T., Ichimaru, Y., Konjiki, F., Shoji, M & Komaki, G. (2007); Variations in the preproghrelin gene correlate with higher body mass index, fat mass, and body dissatisfaction in young Japanese women; Am. J. Clin. Nutr. 86, 25-32.

Ariyasu, H., Takaya, K., Tagami, T., Ogawa, Y., Hosoda, K., Akamizu, T., et al. (2001); Stomach is a major source of circulating ghrelin, and feeding state determines plasma ghrelin-like immunoreactivity levels in humans; J. Clin. Endocrinol. Metab. 86, 4753-4758.

Arosia, M., Ronchi, C. L., Gebbia, C., Cappiello, V., Beck-Peccoz, P. B., & Peracchi, M. (2003); Stimulatory Effects of Ghrelin on Circulating Somatostatin and Pancreatic Polypeptide Levels; J. Clin. Endocrinol. Metab. 88, 701-704.

Asakawa, A., Inui, A., Kaga, T., Katsuura, G., Fujimiya, M., Fujino, M. A., et al. (2003); Antagonism of ghrelin receptor reduces food intake and body weight gain in mice; Gut 52, 947-952.

Barazzoni, R., Zanetti, M., Ferreira, C., Vinci, P., Pirulli, A., Mucci, M. et al. (2007); Relationships between Desacylated and acylated ghrelin and insulin sensitivity in metabolic syndrome; J. Clin. Endocrinol. & Met. 92, 3935-3940.

Broglio, F., Arvat, E., Benso, A., Gottero, C., Muccioli, G., Papotti, M., et al. (2001); Ghrelin, a natural GH secretagogue produced by the stomach, induces hyperglycemia and reduces insulin secretion in humans; J. Clin. Endocrinol. Metab. 86, 5083-5086.

Broglio, F., Arvat, E., Benso, A., Gottero, C., Prodam, F., Grottoli, S., et al. (2002); Endocrine activities of cortistatin-14 and its interaction with GHRH and ghrelin in humans; J. Clin. Endocrinol. Metab. 87, 3783-3790.

Broglio, F., Benso, A., Castiglioni, C., Gottero, C., Prodam, F., Destefanis, S., et al. (2003a); The endocrine response to ghrelin as a function of gender in humans in young and elderly subjects; J. Clin. Endocrinol. Metab. 88, 1537-1542.

Broglio, F., Benso, A., Gottero, C., Prodam, F., Gauna, C., Filtri, L., et al. (2003b); Nonacylated ghrelin does not possess the pituitaric and pancreatic endocrine activity of acylated ghrelin in humans; J. Endocrinol. Invest. 26, 192-196.

Broglio, F., Gottero, C., Prodam, F., Gauna, C., Muccioli, M., Papotti, M., et al. (2004); Non-acylated ghrelin counteracts the metabolic but not the neuroendocrine response to acylated ghrelin in humans; J. Clin. Endocrinol. Metab. 89, 3062-3065.

Chen, C. Y., Asakawa, A., Fujimiya, M, Lee, S. D. & Inui A. (2009); Ghrelin gene products and the regulation of food intake and gut motility; Pharm. Rev. 61: 430-481.

Chung, W. K., Patki, A., Matsuoka, N., Boyer, B. B., Liu, N., Musani, S. K., et al. (2009); Analysis of 30 genes (355 SNPs) related to energy homeostasis for association with adiposity in European-American and Yup'ik Eskimo populations; Hum. Hered. 67, 193-205.

Colombo, M., Gregersen, S., Xiao, J., & Hermansen, K. (2003); Effects of ghrelin and other neuropeptides (CART, MCH, orexin A and B, and GLP-1) on the release of insulin from isolated rat islets; Pancreas 27, 161-166.

Cummings, Purnell, Frayo, Schmidova, Wisse & Weigle. (2001); A preprandial rise in plasma ghrelin levels suggests a role in meal initiation in humans. Diabetes 50, 1714-1719.

Cummings, D. E., Weigle, D. S., Frayo, R. S., Breen, P. A., Ma, M. K., Dellinger, E. P., et al. (2002); Plasma ghrelin levels after diet-induced weight loss or gastric bypass surgery. N. Engl. J. Med. 346, 1623-1630.

Damjanovic, S. S., Lalic, N. M., Pesko, P. M., Petakov, M. S., Jotic, A., Miljic, D., et al. (2006). Acute effects of ghrelin on insulin secretion and glucose disposal rate in gastrectomized patients. J. Clin. Endocrinol. Metab. 91, 2574-2581.

Date, Y., Kojima, M., Hosoda, H., Sawaguchi, A., Mondal, M. S., Suganuma, T., et al. (2000); Ghrelin, a novel growth hormone-releasing acylated peptide, is synthesized in a distinct endocrine cell type in the gastrointestinal tracts of rats and humans; Endocrinology 141, 4255-4261.

Date, Y., Nakazato, M., Hashiguchi, S., Dezaki, K., Mondal, M. S., Hosoda, H., et al. (2002). Ghrelin is present in pancreatic $\alpha$-cells of humans and rats and stimulates insulin secretion; Diabetes 51, 124-129.

Dezaki, K., Hosoda, H., Kakei, M., Hashiguchi, S., Watanabe, M., Kangawa, K., et al. (2004); Endogenous ghrelin in pancreatic islets restricts insulin release by attenuating Ca2+ signaling in $\beta$-cells: implication in the glycemic control in rodents; Diabetes; 53, 3142-3151.

Dezaki, K., Sone, H., Koizumi, M., Nakata, M., Kakei, M., Nagai, H., et al. (2006); Blockade of pancreatic islet-derived ghrelin enhances insulin secretion to prevent high-fat diet-induced glucose intolerance. Diabetes 55, 3486-3493.

Dezaki, K., Kakei, M., & Yada, T. (2007); Ghrelin uses G$\alpha$i2 and activates Kv channels to attenuate glucose-induced Ca2+ signaling and insulin release in islet $\beta$-cells: novel signal transduction of ghrelin; Diabetes 56, 2319-2327.

Dezaki, Sone & Yada (2008); Ghrelin is a physiological regulator of insulin release in pancreatic islets and glucose homeostasis; Pharmacology & Therapeutics 118, 239-249.

Dornonville de la Cour, C., Björkqvist, M., Sandvik, A. K., Bakke, I., Zhao, C. M., Chen, D. & Håkanson, R. (2001); A-like cells in the rat stomach contain ghrelin and do not operate under gastrin control. Reg. Pept. 99, 141-150.

Druce, M. R., Wren, A. M., Park, A. J., Milton, J. E., Patterson, M., Frost, G. et al. (2005); Ghrelin increases food intake in obese as well as lean subjects; Int. J. Obes. 29, 1130-1136.

Egido, E. M., Rodriguez-Gallardo, J., Silvestre, R. A., & Marco, J. (2002). Inhibitory effect of ghrelin on insulin and pancreatic somatostatin secretion; Eur. J. Endocrinol. 146, 241-244.

Esler, W. P., Rudolph, J., Claus, T. H., Tang, W., Barucci, N., Brown, S. E., et al. (2007). Small molecule ghrelin receptor antagonists improve glucose tolerance, suppress appetite, and promote weight loss. Endocrinology 148, 5175-5185.

Gnanapavan, S., Kola, B., Bustin, S. A., Morris, D. G., McGee, P., Fairclough, P., et al. (2002); The tissue distribution of the mRNA of ghrelin and subtypes of its receptor, GHS-R, in humans; J. Clin. Endocrinol. Metab. 87, 2988-2991.

Gualillo, O., Caminos, J., Blanco, M., Garcia-Caballero, T., Kojima, M., Kangawa, K., et al. (2001); Ghrelin, a novel placental-derived hormone; Endocrinology 142, 788-794.

Gauna, C., Meyler, F. M., Janssen, J. A., Delhanty, P. J., Abribat, T., van koetsveld, P., et al. (2004); Adminstration of acylated ghrelin reduces insulin sensitivity, whereas the combination of acylated plus unacylated ghrelin strongly improves insulin sensitivity; J. Clin. Endocrinol. Metab. 89, 5035-5042.

Hattori, N., Saito, T., Yagyu, T., Jiang, B. H., Kitagawa, K., & Inagaki, C. (2001); GH, GH receptor, GH secretagogue receptor, and ghrelin expression in human T cells, B cells, and neutrophils. J. Clin. Endocrinol. Metab. 86, 4284-4291.

Hosoda, H., Kojima, M., Matsuo, H., & Kangawa, K. (2000); Ghrelin and des-acyl ghrelin: two major forms of rat ghrelin peptide in gastrointestinal tissue; Biochem. Biophys. Res. Commun. 279, 909-913.

Huda, M. S. B., Dovey, T., Wong, S. P., English, P. J., Halford, J., McCulloch, P., et al. (2009). Ghrelin restores 'lean-type' hunger and energy expenditure profiles in morbidly obese subjects but has no effect on postgastrectomy subjects; Int. J. Obesity 33, 317-325.

Iwakura, H., Ariyasu, H., Li, Y., Kanamoto, N., Bando, M., Yamada, G., Hosoda, H., et al. (2009); A mouse model of ghrelinoma exhibited activated growth hormone-insulin-like growth factor I axis and glucose intolerance; Am. J. Physiol. Endocrinol. Metab. 297, 802-811.

Kilpelainen, T. O., Lakka, T. A., Laaksonen, D. E., Mager, U., Salopuro, T., Kubaszek, A., et al. (2008); Interaction of single nucleotide polymorphisms in ADRB2, ADRB3, TNF, IL6, IGF1R, LIPC, LEPR, and GHRL with physical activity on the risk of type 2 diabetes mellitus and changes in characteristics of the metabolic syndrome: the Finnish Diabetes Prevention Study; Metabolism 57, 428-436.

Kojima, M., Hosoda, H., Date, Y., Nakazato, M., Matsuo, H., & Kangawa, K. (1999); Ghrelin is a growth-hormone-releasing peptide from stomach; Nature 402, 656-660.

Korbonits, M., Gueorguiev, M., O'Grady, E., Lecoeur, C., Swan, D. C., Mein, C. A., et al. (2002); A variation in the ghrelin gene increases weight and decreases insulin secretion in tall, obese children; J. Clin. Endocrinol. Metab. 87, 4005-4008.

Li, W. J., Zhen, Y. S., Sun, K., Xue, H., song, X. D., Wang, Y. B., Fan, X. H., Han, Y. F. & Hui, R. T. (2008); Ghrelin receptor gene polymorphisms are assocated with female metabolic syndrome in Chinese population; Chin. Med. J. 121, 1666-1669.

Longo, K. A., Charoenthongtrakul, S., Giuliana, D. J., Govek, E. K., McDonagh, T., Qi, T., et al. (2008); Improved insulin sensitivity and metabolic flexibility in ghrelin receptor knockout mice. Reg Peptides 150, 55-61.

Lu, S., Guan, J L., Wang, Q. P., Uehara, K., Yamada, S., Goto, N., et al. (2002). Immunocytochemical observation of ghrelin-containing neurons in the rat arcuate nucleus. Neuroscience Lett. 321, 157-160.

Lucidi, P., Murdolo, G., Di Loreto, C., Parlanti, N., De Cicco, A., Fatone, C. (2005); Metabolic and endocrine effects of physiological increments in plasma ghrelin concentrations. Nutr. Metab. Cardiovasc. Dis. 15, 410-417.

Mager, U., Kolehmainen, M., Lindström, J., Eriksson, J. G., Valle, T. T. & Hämäläinen H., et al. (2006); Association of the Leu72Met polymorphism of the ghrelin gene with the risk of Type 2 diabetes in subjects with impaired glucose tolerance in the Finnish Diabetes Prevention Study; Diabet Med. 23(6): 685-689.

Mondal, M. E, Date, Y., Yamaguchi, H., Toshinai, K., Tsuruta, T., Kangawa, K. & Nakazato, M. (2005); Identification of ghrelin and its receptor in neurons of the rat arcuate nucleus. Regul Pept 126, 55-59.

Mori, K., Yoshimoto, A., Takaya, K., Hosoda, K., Ariyasu, H., Yahata, K., et al. (2000); Kidney produces a novel acylated peptide, ghrelin; FEBS Lett. 486, 213-216.

Muccioli, G., Tschop, M., Papotti, M., Deghenghi, R., Heiman, M., & Ghigo, E. (2002); Neuroendocrine and peripheral activities of ghrelin: implications in metabolism and obesity. Eur. J. Pharmacol. 440, 235-254.

Nakazato, M., Murakami, N., Date, Y., Kojima, M., Matsuo, H., Kangawa, K., et al. (2001); A role for ghrelin in the central regulation of feeding; Nature 409, 194-198.

Poykko, S., Ukkola, O., Kauma, H., Savolainen, M. J. & Kesäniemi, Y. A. et al. (2003); Ghrelin Arg51Gln mutation is a risk factor for Type 2 diabetes and hypertension in a random sample of middle-aged subjects; Diabetologia; 46, 455-458.

Reimer, M. K., Pacini, G., & Ahrén, B. (2003); Dose-dependent inhibition by ghrelin of insulin secretion in the mouse; Endocrinology; 144, 916-921.

Rindi, G., Necchi, V., Savio, A., Torsello, A., Zoli, M., Locatelli, V., Raimondo, F., Cocchi, D. & Solcia E. (2002); Characterisation of gastric ghrelin cells in man and other mammals: study in adult and fetal tissues. Histochem Cell Biol 117, 511-519.

Robitaille, J., Pérusse, L., Bouchard, C. & Vohl, M. C. (2007); Genes, fat intake, and cardiovascular disease risk factors in the Quebec Family Study; Obesity 15, 2336-2347.

Rodriguez, A., Gómez-Ambrosi, J., Catalán, Gil, M. J., Becerril, S., Sáinz, N., Silva, C. et al., (2009); Acylated and desacyl ghrelin stimulate lipid accumulation in human visceral adipocytes. Int. J. Obes. 33, 541-552.

Roth, C. L., Reinehr, T., Schernthaner, g. H., Kopp, H. P., Kriwanek, S & Schernthaner, G. (2008); Ghrelin and obestatin levels in severely obese women before and after weight loss after Roux-en-Y gastric bypass surgery; Obes. Surg.; 19, 29-35.

Sakata, I., Nakamura, K., Yamazaki, M., Matsubara, M., Hayashi, Y., Kangawa, K., & Sakai, T. (2002); Ghrelin-producing cells exist as two types of cells, closed- and opened-type cells, in the rat gastrointestinal tract. Peptides; 23, 531-536.

Shuto, Y., Shibasaki, T., Otagiri, A., Kuriyama, H., Ohata, H., Tamura, H., et al. (2002). Hypothalamic growth hormone secretagogue receptor regulates growth hormone secretion, feeding, and adiposity; J. Clin. Invest.; 109, 1429-1436.

Sun, Y., Asnicar, M., Saha, P. K., Chan, L., & Smith, R. G. (2006); Ablation of ghrelin improves the diabetic but not obese phenotype of ob/ob mice; Cell Metab.; 3, 379-386.

Tanaka, M., Hayashida, Y., Nakao, N., Nakai, N., & Nakashima, K. (2001). Testis specific and developmentally induced expression of a ghrelin gene-derived transcript that encodes a novel polypeptide in the mouse; Biochim Biophys Acta; 1522, 62-65.

Tang, N. P., Wang, L. S., Yang, L., Gu, H. J., Zhu, H. J., Zhou, B., et al. (2008); Preproghrelin Leu72Met polymorphism in Chinese subjects with coronary artery disease and controls; Clin. Chim Acta; 387, 42-47.

Tena-Sempere, M., Barreiro, M. L., Gonzalez, L. C., Gaytan, F., Zhang, F. P., Caminos, J. E., et al. (2002); Novel expression and functional role of ghrelin in rat testis; Endocrinology; 143, 717-725.

Tong, J., Prigeon, R. L., Salehi, M., Davis, H. W., Kahn, S. E., Cummings, D. E., et al. (2009); Ghrelin suppresses glucose-stimulated insulin secretion in healthy volunteers. (ADA conference).

Ukkola, O., Ravussin, E., Jacobson, P., Pérusse, L., Rankinen, T., Tschöp, M., et al. (2002); Role of ghrelin polymorphisms in obesity based on three different studies; Obes. Res.; 10, 782-791.

Vestergaard, E. T., Hansen, T. K., Gormsen, L. C., Jakobsen, P., Møller, N., Christiansen, J. S., et al., (2007); Clinical pharmacokinetics and metabolic effects; Am. J. Physiol. Endocrinol. Metab. 292, E1829-E1836.

Vestergaard, E. T., Djurhuus, C. B., Gjedsted, J., Nielsen, S., Møller, N., Holst, J. J., et al. (2008a); Acute effects of ghrelin administration on glucose and lipid metabolism; J. Clin. Endocinol. Metabol. 93, 438-444.

Vestergaard, E. T., Gormsen L C, Jessen N, Lund S, Hansen T K, Moller N., et al. (2008b); Ghrelin infusion in humans induces acute insulin resistance and lipolysis independent of growth hormone signaling; Diabetes 57, 3205-3210.

Volante, M., Allia, E., Gugliotta, P., Funaro, A., Broglio, F., Deghenghi, R., et al. (2002a). Expression of ghrelin and of the GH secretagogue receptor by pancreatic islet cells and related endocrine tumors; J. Clin. Endocrinol. Metab. 87, 1300-1308.

Volante, M., Fulcheri, E., Allia, E., Cerrato, M., Pucci, A., & Papotti, M. (2002b); Ghrelin expression in fetal, infant, and adult human lung; J. Histochem. Cytochem. 50, 1013-1021.

Wierup, N., Svensson H., Mulder, H. & Sundler, F (2002); The ghrelin cell: a novel developmentally regulated islet cell in the human pancreas; Regul. Pept. 107, 63-69.

Wierup, N., Yang, S., McEvilly, R. J., Mulder, H., & Sundler, F. (2004). Ghrelin is expressed in a novel endocrine cell type in developing rat islets and inhibits insulin secretion from INS-1 (832/13) cells; J. Histochem. Cytochem. 52, 301-310.

Wierup, N., & Sundler, F. (2005); Ultrastructure of islet ghrelin cells in the human fetus; Cell Tissue Res. 319, 423-428.

Wortley, K., del Rincon, J. P., Murray, J. D., Garcia, K., Lida, K., Thorner, M. O., et al. (2005); Absence of ghrelin protects against early-onset obesity; J. Clin. Invest. 115, 3573-3578.

Wren, A. M., Seal, L. J., Cohen, M. A., Brynes, A. E., Frost, G. S., Murphy, K. G., et al. (2001); Ghrelin enhances appetite and increases food intake in humans; J. Clin. Endocrinol. Metab. 86, 5992-5995.

Zigman, J. M., Nakano, Y., Coppari R, Balthasar, N., Marcus, J. N., Lee, C. E., et al. (2005); J. Clin Invest 115, 3564-3572.

SUMMARY OF THE INVENTION

The present invention provides compounds of Formula (I) that act as ghrelin inverse agonists or antagonists; and therefore, may be used in the treatment of diseases mediated by such antagonism or inverse agonism (e.g., diseases related to type 2 diabetes, and diabetes-related and obesity-related co-morbidities).

An embodiment of the present invention is the compound of Formula (I)

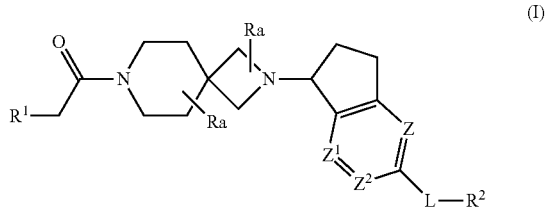

wherein:

$R^1$ is -$L^1$-$R^{1'}$, phenyl or a 5- to 6-membered heteroaryl containing 1 to 4 heteroatoms each independently selected from N, O, or S, where said phenyl or said 5- to 6-membered heteroaryl is optionally fused to a ($C_4$-$C_7$)cycloalkyl, ($C_5$-$C_6$) cycloalkenyl, phenyl, saturated or partially unsaturated 5- to 6-membered heterocyclyl containing 1 to 4 heteroatoms each independently selected from N, O or S, or a 5- to 6-membered heteroaryl containing 1 to 4 heteroatoms each independently selected from N, O, or S, wherein said optionally fused phenyl and said optionally fused 5- to 6-membered heteroaryl is optionally substituted with 1 to 3 substituents selected from halo, hydroxy, oxo, cyano, ($C_1$-$C_3$)alkyl, halo-substituted ($C_1$-$C_3$)alkyl, ($C_1$-$C_3$)alkoxy, halo-substituted ($C_1$-$C_3$)alkoxy, ($C_1$-$C_3$)alkyl-S(O)$_n$—, ($C_3$-$C_6$)cycloalkyl, ($C_3$-$C_6$)cycloalkoxy, —($C_0$-$C_3$)alkylNR$^x$R$^y$, —($C_0$-$C_3$)alkylNR$^x$C(O)R$^y$, and —($C_0$-$C_3$)alkylC(O)NR$^x$R$^y$;

$R^{1'}$ is phenyl or a 5- to 6-membered heteroaryl containing 1 to 4 heteroatoms each independently selected from N, O, or S, where said phenyl or said 5- to 6-membered heteroaryl is optionally fused to a ($C_4$-$C_7$)cycloalkyl, ($C_5$-$C_6$)cycloalkenyl, phenyl, saturated or partially unsaturated 5- to 6-membered heterocyclyl containing 1 to 4 heteroatoms each independently selected from N, O or S, or a 5- to 6-membered heteroaryl containing 1 to 4 heteroatoms each independently selected from N, O, or S, wherein said optionally fused phenyl and said optionally fused 5- to 6-membered heteroaryl is optionally substituted with 1 to 3 substituents selected from halo, hydroxy, oxo, cyano, ($C_1$-$C_3$)alkyl, halo-substituted ($C_1$-$C_3$)alkyl, ($C_1$-$C_3$)alkoxy, halo-substituted ($C_1$-$C_3$) alkoxy, ($C_1$-$C_3$)alkyl-S(O)$_n$—, ($C_3$-$C_6$)cycloalkyl, ($C_3$-$C_6$) cycloalkoxy, —($C_0$-$C_3$)alkylNR$^x$R$^y$, —($C_0$-$C_3$)alkylNR$^x$C(O)R$^y$, and —($C_0$-$C_3$)alkylC(O)NR$^x$R$^y$;

$L^1$ is O, S, NH, N($C_1$-$C_3$)alkyl or ($C_1$-$C_3$)alkylene;

$R^a$ at each occurrence is independently selected from hydrogen, ($C_1$-$C_3$)alkyl and halogen;

Z, $Z^1$ and $Z^2$ are each independently N or CH optionally substituted with halo, ($C_1$-$C_3$)alkoxy or ($C_1$-$C_3$)alkyl;

L is a direct bond, O, S, NH, N($C_1$-$C_3$)alkyl or ($C_1$-$C_3$) alkylene;

$R^2$ is hydrogen, halo, cyano, ($C_1$-$C_6$)alkyl, ($C_3$-$C_6$)cycloalkyl, phenyl, saturated or partially unsaturated 5- to 6-membered heterocyclyl containing 1 to 4 heteroatoms each independently selected from N, O or S, or 5- to 6-membered heteroaryl containing 1 to 4 heteroatoms each independently selected from N, O, or S, where said $(C_1$-$C_6)$alkyl, $(C_3$-$C_6)$ cycloalkyl, phenyl, saturated or partially unsaturated 5- to 6-membered heterocyclyl, or 5- to 6-membered heteroaryl is optionally substituted with 1 to 3 substituents independently selected from the group consisting of halo, hydroxy, cyano, $(C_1$-$C_3)$alkyl, halo-substituted $(C_1$-$C_3)$alkyl, $(C_1$-$C_3)$alkoxy, halo-substituted $(C_1$-$C_3)$alkoxy, $(C_1$-$C_3)$alkyl-S(O)$_n$—, $(C_3$-$C_6)$cycloalkyl, $(C_3$-$C_6)$cycloalkoxy, —$(C_0$-$C_3)$alkylNR$^x$R$^y$, —$(C_0$-$C_3)$alkylNR$^x$C(O)R$^y$, and —$(C_0$-$C_3)$alkylC(O)NR$^x$R$^y$; with the proviso that when L is O, S, NH or N($C_1$-$C_3$)alkyl then R$^2$ is not halo;

n at each occurrence is independently 0, 1 or 2; and

R$^x$ and R$^y$ at each occurrence are independently selected from hydrogen and $(C_1$-$C_6)$alkyl where said $(C_1$-$C_6)$alkyl is optionally interrupted with one or two groups independently selected from NH, N($C_1$-$C_3$)alkyl, O and S, and is optionally substituted with 1 to 4 halo; or R$^x$ and R$^y$ taken together are a $(C_2$-$C_6)$alkylene which is optionally interrupted with one or two groups independently selected from NH, N($C_1$-$C_3$)alkyl, O and S; or a pharmaceutically acceptable salt thereof.

Another embodiment of the present invention is the compound of Formula (I) wherein R$^1$ is phenyl or a 5- to 6-membered heteroaryl containing 1 to 4 heteroatoms each independently selected from N, O, or S, where said phenyl or said 5- to 6-membered heteroaryl is optionally fused to a $(C_4$-$C_7)$ cycloalkyl, $(C_5$-$C_6)$cycloalkenyl, phenyl, saturated or partially unsaturated 5- to 6-membered heterocyclyl containing 1 to 4 heteroatoms each independently selected from N, O or S, or a 5- to 6-membered heteroaryl containing 1 to 4 heteroatoms each independently selected from N, O, or S, wherein said optionally fused phenyl and said optionally fused 5- to 6-membered heteroaryl is optionally substituted with 1 to 3 substituents selected from halo, hydroxy, oxo, cyano, $(C_1$-$C_3)$ alkyl, halo-substituted $(C_1$-$C_3)$alkyl, $(C_1$-$C_3)$alkoxy, halo-substituted $(C_1$-$C_3)$alkoxy, $(C_1$-$C_3)$alkyl-S(O)$_n$—, $(C_3$-$C_6)$ cycloalkyl, $(C_3$-$C_6)$cycloalkoxy, —$(C_0$-$C_3)$alkylNR$^x$R$^y$, —$(C_0$-$C_3)$alkylNR$^x$C(O)R$^y$, and —$(C_0$-$C_3)$alkylC(O)NR$^x$R$^y$; R$^a$ at each occurrence is independently selected from hydrogen, $(C_1$-$C_3)$alkyl and halogen; Z, Z$^1$ and Z$^2$ are each independently N or CH optionally substituted with halo, $(C_1$-$C_3)$alkoxy or $(C_1$-$C_3)$alkyl; L is a direct bond, O, S, NH, N($C_1$-$C_3$)alkyl or $(C_1$-$C_3)$alkylene; R$^2$ is hydrogen, halo, cyano, $(C_1$-$C_6)$alkyl, $(C_3$-$C_6)$cycloalkyl, phenyl, saturated or partially unsaturated 5- to 6-membered heterocyclyl containing 1 to 4 heteroatoms each independently selected from N, O or S, or 5- to 6-membered heteroaryl containing 1 to 4 heteroatoms each independently selected from N, O, or S, where said $(C_1$-$C_6)$alkyl, $(C_3$-$C_6)$cycloalkyl, phenyl, saturated or partially unsaturated 5- to 6-membered heterocyclyl, or 5- to 6-membered heteroaryl is optionally substituted with 1 to 3 substituents independently selected from the group consisting of halo, hydroxy, cyano, $(C_1$-$C_3)$alkyl, halo-substituted $(C_1$-$C_3)$alkyl, $(C_1$-$C_3)$alkoxy, halo-substituted $(C_1$-$C_3)$ alkoxy, $(C_1$-$C_3)$alkyl-S(O)$_n$—, $(C_3$-$C_6)$cycloalkyl, $(C_3$-$C_6)$ cycloalkoxy, —$(C_0$-$C_3)$alkylNR$^x$R$^y$, —$(C_0$-$C_3)$alkylNR$^x$C(O)R$^y$, and —$(C_0$-$C_3)$alkylC(O)NR$^x$R$^y$; with the proviso that when L is O, S, NH or N($C_1$-$C_3$)alkyl then R$^2$ is not halo; n at each occurrence is independently 0, 1 or 2; and R$^x$ and R$^y$ at each occurrence are independently selected from hydrogen and $(C_1$-$C_6)$alkyl where said $(C_1$-$C_6)$alkyl is optionally interrupted with one or two groups independently selected from NH, N($C_1$-$C_3$)alkyl, O and S, and is optionally substituted with 1 to 4 halo; or R$^x$ and R$^y$ taken together are a $(C_2$-$C_6)$ alkylene which is optionally interrupted with one or two groups independently selected from NH, N($C_1$-$C_3$)alkyl, O and S; or a pharmaceutically acceptable salt thereof.

Another embodiment of the present invention is the compound of Formula (I) wherein R$^1$ is phenyl, naphthyl, imidazolyl, pyrazolyl, pyrazinyl, pyrimidinyl, thiazolyl, oxazolyl, thiazolyl, benzthiazolyl, benzoxazolyl, quinolinyl, 2,3-dihydrobenzofuranyl, chromanyl, 3,4-dihydro-2H-pyrano[3,2-b] pyridinyl, 2,3-dihydrofurano[3,2-b]pyridinyl, indolyl, 5,6-dihydro-4H-pyrrolo[1,2-b]pyrazolyl, [1,2,4]triazolo[4,3-a] pyridine, imidazo[2,1-b][1,3]thiazolyl, pyridinyl, pyrazolo [1,5-a]pyridinyl, 4,5,6,7-tetrahydropyrazolo[1,5-a]pyridinyl, imidazo[2,1-b][1,3,4]thiadiazolyl, 1H-indazolyl, pyridazinyl, imidazo[1,2-b][1,2,4]triazinyl, 1H-pyrazolo[3,4-b]pyridinyl, imidazo[1,2-b]pyridazinyl, 2,3-dihydro-[1,4]dioxino [2,3-b]pyridinyl, oxadiazolyl or imidazo[1,2-a]pyridinyl; each optionally substituted with 1 to 3 substituents independently selected from fluoro, chloro, $(C_1$-$C_3)$alkyl, $(C_1$-$C_3)$ alkoxy, trifluoromethyl, trifluoromethoxy, cyano, cyclopropyl, —C(O)NR$^x$R$^y$ and —$(C_0$-$C_1)$alkylNHC(O)CH$_3$; or a pharmaceutically acceptable salt thereof.

Another embodiment of the present invention is the compound of Formula (I) wherein R$^1$ is phenyl, imidazo[2,1-b] [1,3]thiazolyl, pyridinyl, pyrazolo[1,5-a]pyridinyl, 4,5,6,7-tetrahydropyrazolo[1,5-a]pyridinyl, imidazo[2,1-b][1,3,4] thiadiazolyl, 1H-indazolyl, pyridazinyl, imidazo[1,2-b][1,2, 4]triazinyl, 1H-pyrazolo[3,4-b]pyridinyl, imidazo[1,2-b] pyridazinyl, 2,3-dihydro-[1,4]dioxino[2,3-b]pyridinyl, oxadiazolyl or imidazo[1,2-a]pyridinyl; each optionally substituted with 1 to 3 substituents independently selected from methyl, methoxy, cyano, cyclopropyl, —C(O)NH$_2$ and —NHC(O)CH$_3$; R$^a$ at each occurrence is hydrogen; and Z, Z$^1$ and Z$^2$ are each CH; or a pharmaceutically acceptable salt thereof.

A further embodiment of the present invention is the compound of Formula (I) wherein L is a direct bond; and R$^2$ is hydrogen, phenyl, phenoxy, pyrimidinyl, imidazolyl, triazolyl, tetrazolyl, thiazolyl, thiadiazolyl, pyridinyl, oxazolyl, oxadiazolyl, pyrazolyl, pyridazinyl, triazinyl or pyrazinyl; each optionally substituted with 1 to 3 substituents independently selected from methyl, trifluoromethyl, ethyl, methoxy, cyano or —C(O)NH$_2$; or a pharmaceutically acceptable salt thereof.

Yet another embodiment of the present invention is the compound of Formula (IA)

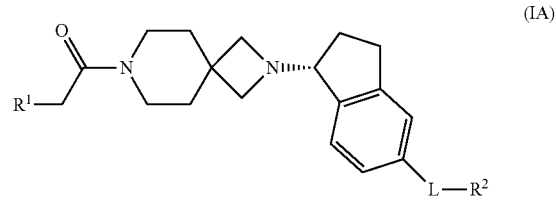

(IA)

or a pharmaceutically acceptable salt thereof; wherein R$^1$, R$^2$ and L are as described herein.

A further embodiment of the present invention is the compound of Formula (IA) wherein R$^1$ is phenyl, naphthyl, imidazolyl, pyrazolyl, pyrazinyl, pyrimidinyl, thiazolyl, oxazolyl, thiazolyl, benzthiazolyl, benzoxazolyl, quinolinyl, 2,3-dihydrobenzofuranyl, chromanyl, 3,4-dihydro-2H-pyrano[3,2-b]pyridinyl, 2,3-dihydrofurano[3,2-b]pyridinyl, indolyl, 5,6-dihydro-4H-pyrrolo[1,2-b]pyrazolyl, [1,2,4]triazolo[4,3-a]pyridine, imidazo[2,1-b][1,3]thiazolyl, pyridinyl, pyrazolo[1,5-a]pyridinyl, 4,5,6,7-tetrahydropyrazolo[1,5-a] pyridinyl, imidazo[2,1-b][1,3,4]thiadiazolyl, 1H-indazolyl, imidazo[1,2-b][1,2,4]triazinyl, 1H-pyrazolo[3,4-b]pyridinyl, imidazo[1,2-b]pyridazinyl, 2,3-dihydro-[1,4]dioxino[2, 3-b]pyridinyl or imidazo[1,2-a]pyridinyl; each optionally substituted with 1 to 3 substituents independently selected from fluoro, chloro, ($C_1$-$C_3$)alkyl, ($C_1$-$C_3$)alkoxy, trifluoromethyl, trifluoromethoxy, cyano, cyclopropyl, —C(O)NH$_2$ and —NHC(O)CH$_3$; or a pharmaceutically acceptable salt thereof.

Yet another embodiment of the present invention is the compound of Formula (IA) wherein R$^2$ is phenyl, pyrimidinyl, imidazolyl, triazolyl, tetrazolyl, thiazolyl, thiadiazolyl, pyridinyl, oxazolyl, oxadiazolyl, pyrimidinyl, pyrazolyl, pyridazinyl, triazinyl or pyrazinyl each optionally substituted with 1 to 3 substituents independently selected from methyl, ethyl, methoxy, cyano or —C(O)NH$_2$; and L is a direct bond or O; or a pharmaceutically acceptable salt thereof.

Still another embodiment of the present invention is the compound of Formula (IA) wherein R$^2$ is phenyl, pyrimidinyl, triazolyl, thiazolyl, pyridinyl, oxazolyl, pyrimidinyl, pyrazolyl, or pyrazinyl; each optionally substituted with 1 to 3 substituents independently selected from methyl, ethyl, methoxy, cyano or —C(O)NH$_2$; and L is a direct bond; or a pharmaceutically acceptable salt thereof.

Another embodiment of the present invention is a compound selected from the group consisting of:

5-[1-{7-[(5-methoxypyridin-2-yl)acetyl]-2,7-diazaspiro[3.5]non-2-yl}-2,3-dihydro-1H-inden-5-yl]pyrazine-2-carboxamide;
5-[1-{7-[(7-methylimidazo[1,2-a]pyridin-2-yl)acetyl]-2,7-diazaspiro[3.5]non-2-yl}-2,3-dihydro-1H-inden-5-yl]pyrazine-2-carboxamide;
5-{1-[7-(imidazo[1,2-a]pyridin-2-ylacetyl)-2,7-diazaspiro[3.5]non-2-yl]-2,3-dihydro-1H-inden-5-yl}pyrazine-2-carboxamide;
6-[1-{7-[(5-methoxypyridin-2-yl)acetyl]-2,7-diazaspiro[3.5]non-2-yl}-2,3-dihydro-1H-inden-5-yl]pyrimidine-4-carboxamide;
5-[1-{7-[(5-cyclopropylpyridin-2-yl)acetyl]-2,7-diazaspiro[3.5]non-2-yl}-2,3-dihydro-1H-inden-5-yl]pyridine-2-carboxamide;
5-[1-{7-[(2-methylimidazo[2,1-b][1,3,4]thiadiazol-6-yl)acetyl]-2,7-diazaspiro[3.5]non-2-yl}-2,3-dihydro-1H-inden-5-yl]pyridine-2-carboxamide;
6-[1-{7-[(7-methylimidazo[1,2-a]pyridin-2-yl)acetyl]-2,7-diazaspiro[3.5]non-2-yl}-2,3-dihydro-1H-inden-5-yl]pyrimidine-4-carboxamide;
5-[1-{7-[(5-ethylpyridin-2-yl)acetyl]-2,7-diazaspiro[3.5]non-2-yl}-2,3-dihydro-1H-inden-5-yl]pyrazine-2-carboxamide;
6-[1-{7-[(5-methoxypyridin-2-yl)acetyl]-2,7-diazaspiro[3.5]non-2-yl}-2,3-dihydro-1H-inden-5-yl]nicotinamide;
7-[(4-methoxyphenyl)acetyl]-2-(5-pyrimidin-2-yl-2,3-dihydro-1H-inden-1-yl)-2,7-diazaspiro[3.5]nonane;
7-[(2-methylimidazo[2,1-b][1,3]thiazol-6-yl)acetyl]-2-[5-pyrimidin-2-yl-2,3-dihydro-1H-inden-1-yl]-2,7-diazaspiro[3.5]nonane;
3-(2-oxo-2-{2-[5-pyrimidin-2-yl-2,3-dihydro-1H-inden-1-yl]-2,7-diazaspiro[3.5]non-7-yl}ethyl)-1H-indazole;
7-[(4-methoxyphenyl)acetyl]-2-[5-(2-methylpyrimidin-4-yl)-2,3-dihydro-1H-inden-1-yl]-2,7-diazaspiro[3.5]nonane;
7-[(4-methoxyphenyl)acetyl]-2-[5-(5-methylpyrimidin-2-yl)-2,3-dihydro-1H-inden-1-yl]-2,7-diazaspiro[3.5]nonane;
7-[(5-methoxypyridin-2-yl)acetyl]-2-[5-(1,3-thiazol-2-yl)-2,3-dihydro-1H-inden-1-yl]-2,7-diazaspiro[3.5]nonane;
7-[(5-methoxypyridin-2-yl)acetyl]-2-[5-(5-methyl-1,3-thiazol-2-yl)-2,3-dihydro-1H-inden-1-yl]-2,7-diazaspiro[3.5]nonane;
7-[(2-methylimidazo[2,1-b][1,3,4]thiadiazol-6-yl)acetyl]-2-[5-(2H-1,2,3-triazol-2-yl)-2,3-dihydro-1H-inden-1-yl]-2,7-diazaspiro[3.5]nonane;
7-[(5-methoxypyridin-2-yl)acetyl]-2-(5-phenoxy-2,3-dihydro-1H-inden-1-yl)-2,7-diazaspiro[3.5]nonane;
7-[(4-methoxyphenyl)acetyl]-2-[5-(4-methylpyrimidin-2-yl)-2,3-dihydro-1H-inden-1-yl]-2,7-diazaspiro[3.5]nonane;
7-[(2-methylimidazo[2,1-b][1,3]thiazol-6-yl)acetyl]-2-[5-(4-methyl pyrimidin-2-yl)-2,3-dihydro-1H-inden-1-yl]-2,7-diazaspiro[3.5]nonane;
7-[(5-methoxypyridin-2-yl)acetyl]-2-[5-(5-methoxypyridin-2-yl)-2,3-dihydro-1H-inden-1-yl]-2,7-diazaspiro[3.5]nonane;
7-[(5-methoxypyridin-2-yl)acetyl]-2-[5-(2-methylpyridin-4-yl)-2,3-dihydro-1H-inden-1-yl]-2,7-diazaspiro[3.5]nonane;
2-(1-{7-[(5-methoxypyridin-2-yl)acetyl]-2,7-diazaspiro[3.5]non-2-yl}-2,3-dihydro-1H-inden-5-yl)isonicotinonitrile;
7-[(5-methoxypyridin-2-yl)acetyl]-2-[5-(5-methylpyridin-2-yl)-2,3-dihydro-1H-inden-1-yl]-2,7-diazaspiro[3.5]nonane;
7-[(5-methoxypyridin-2-yl)acetyl]-2-[5-(5-methoxypyrimidin-2-yl)-2,3-dihydro-1H-inden-1-yl]-2,7-diazaspiro[3.5]nonane;
7-[(5-methoxypyridin-2-yl)acetyl]-2-[5-(6-methoxypyrimidin-4-yl)-2,3-dihydro-1H-inden-1-yl]-2,7-diazaspiro[3.5]nonane;
7-[(5-methoxypyridin-2-yl)acetyl]-2-[5-(4-methylpyridin-2-yl)-2,3-dihydro-1H-inden-1-yl]-2,7-diazaspiro[3.5]nonane;
7-[(5-methoxypyridin-2-yl)acetyl]-2-(5-pyrazin-2-yl-2,3-dihydro-1H-inden-1-yl)-2,7-diazaspiro[3.5]nonane;
2-[5-(4,6-dimethylpyrimidin-2-yl)-2,3-dihydro-1H-inden-1-yl]-7-[(5-methoxypyridin-2-yl)acetyl]-2,7-diazaspiro[3.5]nonane;
7-[(5-methoxypyridin-2-yl)acetyl]-2-[5-(6-methylpyridin-2-yl)-2,3-dihydro-1H-inden-1-yl]-2,7-diazaspiro[3.5]nonane;
2-[5-(5-ethylpyrimidin-2-yl)-2,3-dihydro-1H-inden-1-yl]-7-[(5-methoxypyridin-2-yl)acetyl]-2,7-diazaspiro[3.5]nonane;
2-[5-(6-ethylpyrimidin-4-yl)-2,3-dihydro-1H-inden-1-yl]-7-[(5-methoxypyridin-2-yl)acetyl]-2,7-diazaspiro[3.5]nonane;
2-(2-{2-[5-(6-ethylpyrimidin-4-yl)-2,3-dihydro-1H-inden-1-yl]-2,7-diazaspiro[3.5]non-7-yl}-2-oxoethyl)-5-methoxybenzonitrile;
6-[1-{7-[(5-methoxypyridin-2-yl)acetyl]-2,7-diazaspiro[3.5]non-2-yl}-2,3-dihydro-1H-inden-5-yl]pyrimidine-4-carbonitrile;
7-[(4-methoxyphenyl)acetyl]-2-[5-(1,3-oxazol-2-yl)-2,3-dihydro-1H-inden-1-yl]-2,7-diazaspiro[3.5]nonane;
7-[(5-methoxypyridin-2-yl)acetyl]-2-[5-pyrimidin-4-yl-2,3-dihydro-1H-inden-1-yl]-2,7-diazaspiro[3.5]nonane;
7-[(5-cyclopropylpyridin-2-yl)acetyl]-2-[5-pyrimidin-2-yl-2,3-dihydro-1H-inden-1-yl]-2,7-diazaspiro[3.5]nonane;
7-[(5-methoxypyridin-2-yl)acetyl]-2-[5-(1,3-oxazol-2-yl)-2,3-dihydro-1H-inden-1-yl]-2,7-diazaspiro[3.5]nonane;
2-(5-pyrimidin-2-yl-2,3-dihydro-1H-inden-1-yl)-7-{[4-(trifluoromethyl)phenyl]acetyl}-2,7-diazaspiro[3.5]nonane;
5-methoxy-2-(2-{2-[5-(6-methylpyrimidin-4-yl)-2,3-dihydro-1H-inden-1-yl]-2,7-diazaspiro[3.5]non-7-yl}-2-oxoethoxy)benzonitrile;
2-[2,3-dihydro-1H-inden-1-yl]-7-[(4-methoxyphenyl)acetyl]-2,7-diazaspiro[3.5]nonane;

7-[(5-cyclopropylpyridin-2-yl)acetyl]-2-[5-(6-methylpyrimidin-4-yl)-2,3-dihydro-1H-inden-1-yl]-2,7-diazaspiro[3.5]nonane;

2-[5-(4,6-dimethylpyrimidin-2-yl)-2,3-dihydro-1H-inden-1-yl]-7-[(2-methylimidazo[2,1-b][1,3,4]thiadiazol-6-yl)acetyl]-2,7-diazaspiro[3.5]nonane;

5-methoxy-2-(2-{2-[5-(6-methylpyrimidin-4-yl)-2,3-dihydro-1H-inden-1-yl]-2,7-diazaspiro[3.5]non-7-yl}-2-oxoethyl)benzonitrile;

7-[(2-methylimidazo[2,1-b][1,3,4]thiadiazol-6-yl)acetyl]-2-[5-(5-methylpyrimidin-2-yl)-2,3-dihydro-1H-inden-1-yl]-2,7-diazaspiro[3.5]nonane;

2-[5-(2,6-dimethylpyrimidin-4-yl)-2,3-dihydro-1H-inden-1-yl]-7-[(2-methylimidazo[2,1-b][1,3,4]thiadiazol-6-yl)acetyl]-2,7-diazaspiro[3.5]nonane;

6-[1-{7-[(7-methylimidazo[1,2-a]pyridin-2-yl)acetyl]-2,7-diazaspiro[3.5]non-2-yl}-2,3-dihydro-1H-inden-5-yl]pyrimidine-4-carbonitrile;

N-[5-methoxy-2-(2-{2-[5-(6-methylpyrimidin-4-yl)-2,3-dihydro-1H-inden-1-yl]-2,7-diazaspiro[3.5]non-7-yl}-2-oxoethyl)phenyl]acetamide;

7-[(2,3-dimethylimidazo[2,1-b][1,3]thiazol-6-yl)acetyl]-2-[5-(6-methylpyrimidin-4-yl)-2,3-dihydro-1H-inden-1-yl]-2,7-diazaspiro[3.5]nonane;

7-[(1-ethyl-1H-pyrazol-3-yl)acetyl]-2-[5-pyrimidin-2-yl-2,3-dihydro-1H-inden-1-yl]-2,7-diazaspiro[3.5]nonane;

1-methyl-3-(2-{2-[5-(6-methylpyrimidin-4-yl)-2,3-dihydro-1H-inden-1-yl]-2,7-diazaspiro[3.5]non-7-yl}-2-oxoethyl)-1H-pyrazolo[3,4-b]pyridine;

1-ethyl-3-(2-{2-[5-(6-methylpyrimidin-4-yl)-2,3-dihydro-1H-inden-1-yl]-2,7-diazaspiro[3.5]non-7-yl}-2-oxoethyl)-1H-pyrazolo[3,4-b]pyridine;

7-[(1-phenyl-1H-imidazol-4-yl)acetyl]-2-[5-pyrimidin-2-yl-2,3-dihydro-1H-inden-1-yl]-2,7-diazaspiro[3.5]nonane;

7-{[5-(difluoromethyl)pyridin-2-yl]acetyl}-2-[5-pyrimidin-2-yl-2,3-dihydro-1H-inden-1-yl]-2,7-diazaspiro[3.5]nonane;

7-[(3-methyl-1H-pyrazol-5-yl)acetyl]-2-[5-pyrimidin-2-yl-2,3-dihydro-1H-inden-1-yl]-2,7-diazaspiro[3.5]nonane;

6-(2-{2-[5-(6-methylpyrimidin-4-yl)-2,3-dihydro-1H-inden-1-yl]-2,7-diazaspiro[3.5]non-7-yl}-2-oxoethyl)imidazo[1,2-b][1,2,4]triazine;

6-[1-{7-[(5-cyclopropylpyridin-2-yl)acetyl]-2,7-diazaspiro[3.5]non-2-yl}-2,3-dihydro-1H-inden-5-yl]pyrimidine-4-carbonitrile;

7-[(5-methoxypyridin-2-yl)acetyl]-2-[5-(6-methylpyrimidin-4-yl)-2,3-dihydro-1H-inden-1-yl]-2,7-diazaspiro[3.5]nonane;

6-(2-{2-[5-(6-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;

6-(2-{2-[5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;

7-[(2-methylimidazo[2,1-b][1,3]thiazol-6-yl)acetyl]-2-[5-(6-methylpyrimidin-4-yl)-2,3-dihydro-1H-inden-1-yl]-2,7-diazaspiro[3.5]nonane;

7-[(5-methoxypyridin-2-yl)acetyl]-2-[5-pyrimidin-2-yl-2,3-dihydro-1H-inden-1-yl]-2,7-diazaspiro[3.5]nonane;

7-[(5-methoxypyridin-2-yl)acetyl]-2-[5-(5-methylpyrimidin-2-yl)-2,3-dihydro-1H-inden-1-yl]-2,7-diazaspiro[3.5]nonane;

7-[(5-methoxypyridin-2-yl)acetyl]-2-[5-pyrimidin-2-yl-2,3-dihydro-1H-inden-1-yl]-2,7-diazaspiro[3.5]nonane;

2-[5-(1-methyl-1H-pyrazol-3-yl)-2,3-dihydro-1H-inden-1-yl]-7-[(5-methylpyridin-2-yl)acetyl]-2,7-diazaspiro[3.5]nonane;

7-[(5-methoxypyridin-2-yl)acetyl]-2-[5-(2-methylpyrimidin-4-yl)-2,3-dihydro-1H-inden-1-yl]-2,7-diazaspiro[3.5]nonane;

2-(2-{2-[5-(6-methylpyrimidin-4-yl)-2,3-dihydro-1H-inden-1-yl]-2,7-diazaspiro[3.5]non-7-yl}-2-oxoethyl)imidazo[1,2-a]pyridine;

7-[(5-methylpyridin-2-yl)acetyl]-2-[5-(1,3-thiazol-2-yl)-2,3-dihydro-1H-inden-1-yl]-2,7-diazaspiro[3.5]nonane;

7-[(5-methylpyridin-2-yl)acetyl]-2-[5-(6-methylpyrimidin-4-yl)-2,3-dihydro-1H-inden-1-yl]-2,7-diazaspiro[3.5]nonane;

7-[(5-methoxypyridin-2-yl)acetyl]-2-[5-(1-methyl-1H-pyrazol-3-yl)-2,3-dihydro-1H-inden-1-yl]-2,7-diazaspiro[3.5]nonane;

7-[(2-methylimidazo[2,1-b][1,3,4]thiadiazol-6-yl)acetyl]-2-[5-pyrimidin-2-yl-2,3-dihydro-1H-inden-1-yl]-2,7-diazaspiro[3.5]nonane;

N-[5-methoxy-2-(2-oxo-2-{2-[5-pyrimidin-2-yl-2,3-dihydro-1H-inden-1-yl]-2,7-diazaspiro[3.5]non-7-yl}ethyl)phenyl]acetamide;

2-(2-oxo-2-{2-[5-pyrimidin-2-yl-2,3-dihydro-1H-inden-1-yl]-2,7-diazaspiro[3.5]non-7-yl}ethyl)imidazo[1,2-a]pyridine;

6-(2-oxo-2-{2-[5-pyrimidin-2-yl-2,3-dihydro-1H-inden-1-yl]-2,7-diazaspiro[3.5]non-7-yl}ethyl)-2,3-dihydro[1,4]dioxino[2,3-b]pyridine;

7-[(5-methoxypyridin-2-yl)acetyl]-2-[5-(4-methylpyrimidin-2-yl)-2,3-dihydro-1H-inden-1-yl]-2,7-diazaspiro[3.5]nonane;

7-[(5-methylpyridin-2-yl)acetyl]-2-[5-(4-methylpyrimidin-2-yl)-2,3-dihydro-1H-inden-1-yl]-2,7-diazaspiro[3.5]nonane;

6-(2-{2-[5-(4-methylpyrimidin-2-yl)-2,3-dihydro-1H-inden-1-yl]-2,7-diazaspiro[3.5]non-7-yl}-2-oxoethyl)-2,3-dihydro[1,4]dioxino[2,3-b]pyridine;

7-[(5-methoxypyridin-2-yl)acetyl]-2-[5-(6-methoxypyrimidin-4-yl)-2,3-dihydro-1H-inden-1-yl]-2,7-diazaspiro[3.5]nonane;

2-[5-(5-ethylpyrimidin-2-yl)-2,3-dihydro-1H-inden-1-yl]-7-[(4-methoxyphenyl)acetyl]-2,7-diazaspiro[3.5]nonane;

7-methyl-2-(2-oxo-2-{2-[5-pyrimidin-2-yl-2,3-dihydro-1H-inden-1-yl]-2,7-diazaspiro[3.5]non-7-yl}ethyl)imidazo[1,2-a]pyridine;

7-[(2-methylimidazo[2,1-b][1,3,4]thiadiazol-6-yl)acetyl]-2-[5-(4-methylpyrimidin-2-yl)-2,3-dihydro-1H-inden-1-yl]-2,7-diazaspiro[3.5]nonane;

7-[(2-methylimidazo[2,1-b][1,3,4]thiadiazol-6-yl)acetyl]-2-[5-(6-methylpyrimidin-4-yl)-2,3-dihydro-1H-inden-1-yl]-2,7-diazaspiro[3.5]nonane;

4-[1-{7-[(7-methylimidazo[1,2-a]pyridin-2-yl)acetyl]-2,7-diazaspiro[3.5]non-2-yl}-2,3-dihydro-1H-inden-5-yl]benzamide;

5-[1-{7-[(5-methoxypyridin-2-yl)acetyl]-2,7-diazaspiro[3.5]non-2-yl}-2,3-dihydro-1H-inden-5-yl]pyridine-2-carbonitrile;

4-[1-{7-[(5-ethylpyridin-2-yl)acetyl]-2,7-diazaspiro[3.5]non-2-yl}-2,3-dihydro-1H-inden-5-yl]benzamide;

4-[1-{7-[(5-methoxypyridin-2-yl)acetyl]-2,7-diazaspiro[3.5]non-2-yl}-2,3-dihydro-1H-inden-5-yl]benzamide;

4-{1-[7-(imidazo[1,2-a]pyridin-2-ylacetyl)-2,7-diazaspiro[3.5]non-2-yl]-2,3-dihydro-1H-inden-5-yl}benzamide;

7-[(4-cyclopropylphenyl)acetyl]-2-(5-pyrimidin-2-yl-2,3-dihydro-1H-inden-1-yl)-2,7-diazaspiro[3.5]nonane;

7-[(4-cyclopropylphenyl)acetyl]-2-[5-pyrimidin-2-yl-2,3-dihydro-1H-inden-1-yl]-2,7-diazaspiro[3.5]nonane;

7-[(5-ethylpyridin-2-yl)acetyl]-2-[5-pyrimidin-2-yl-2,3-dihydro-1H-inden-1-yl]-2,7-diazaspiro[3.5]nonane;

7-[(5-methylpyridin-2-yl)acetyl]-2-[5-(2H-1,2,3-triazol-2-yl)-2,3-dihydro-1H-inden-1-yl]-2,7-diazaspiro[3.5]nonane;

7-[(5-ethylpyridin-2-yl)acetyl]-2-[5-(2H-1,2,3-triazol-2-yl)-2,3-dihydro-1H-inden-1-yl]-2,7-diazaspiro[3.5]nonane;

7-[(4-methylphenyl)acetyl]-2-[5-pyrimidin-2-yl-2,3-dihydro-1H-inden-1-yl]-2,7-diazaspiro[3.5]nonane;

7-[(4-ethylphenyl)acetyl]-2-[5-pyrimidin-2-yl-2,3-dihydro-1H-inden-1-yl]-2,7-diazaspiro[3.5]nonane;

2-[5-(2,6-dimethylpyrimidin-4-yl)-2,3-dihydro-1H-inden-1-yl]-7-[(5-methoxypyridin-2-yl)acetyl]-2,7-diazaspiro[3.5]nonane;

2-{2-oxo-2-[2-(5-pyrimidin-2-yl-2,3-dihydro-1H-inden-1-yl)-2,7-diazaspiro[3.5]non-7-yl]ethyl}pyrazolo[1,5-a]pyridine;

2-{2-oxo-2-[2-(5-pyrimidin-2-yl-2,3-dihydro-1H-inden-1-yl)-2,7-diazaspiro[3.5]non-7-yl]ethyl}-4,5,6,7-tetrahydropyrazolo[1,5-a]pyridine;

7-methyl-2-(2-oxo-2-{2-[5-(2H-1,2,3-triazol-2-yl)-2,3-dihydro-1H-inden-1-yl]-2,7-diazaspiro[3.5]non-7-yl}ethyl)imidazo[1,2-a]pyridine;

7-[(5-methoxypyridin-2-yl)acetyl]-2-[5-(2H-1,2,3-triazol-2-yl)-2,3-dihydro-1H-inden-1-yl]-2,7-diazaspiro[3.5]nonane;

7-[(4-methoxyphenyl)acetyl]-2-[5-(2H-1,2,3-triazol-2-yl)-2,3-dihydro-1H-inden-1-yl]-2,7-diazaspiro[3.5]nonane;

7-[(2-methylimidazo[2,1-b][1,3]thiazol-6-yl)acetyl]-2-[5-(2H-1,2,3-triazol-2-yl)-2,3-dihydro-1H-inden-1-yl]-2,7-diazaspiro[3.5]nonane;

7-[(5-ethoxypyridin-2-yl)acetyl]-2-[5-(2H-1,2,3-triazol-2-yl)-2,3-dihydro-1H-inden-1-yl]-2,7-diazaspiro[3.5]nonane;

N-[5-methoxy-2-(2-oxo-2-{2-[5-(2H-1,2,3-triazol-2-yl)-2,3-dihydro-1H-inden-1-yl]-2,7-diazaspiro[3.5]non-7-yl}ethyl)phenyl]acetamide;

7-[(5-methoxypyridin-2-yl)acetyl]-2-[5-(1H-1,2,4-triazol-1-yl)-2,3-dihydro-1H-inden-1-yl]-2,7-diazaspiro[3.5]nonane;

7-[(5-methoxypyridin-2-yl)acetyl]-2-[5-(5-methyl-1,3,4-thiadiazol-2-yl)-2,3-dihydro-1H-inden-1-yl]-2,7-diazaspiro[3.5]nonane;

5-methyl-2-(2-oxo-2-{2-[5-pyrimidin-2-yl-2,3-dihydro-1H-inden-1-yl]-2,7-diazaspiro[3.5]non-7-yl}ethyl)benzamide;

5-methoxy-2-(2-oxo-2-{2-[5-pyrimidin-2-yl-2,3-dihydro-1H-inden-1-yl]-2,7-diazaspiro[3.5]non-7-yl}ethyl)benzamide;

5-methoxy-2-(2-{2-[5-(6-methylpyrimidin-4-yl)-2,3-dihydro-1H-inden-1-yl]-2,7-diazaspiro[3.5]non-7-yl}-2-oxoethyl)benzamide;

5-methoxy-2-(3-{2-[5-(6-methylpyrimidin-4-yl)-2,3-dihydro-1H-inden-1-yl]-2,7-diazaspiro[3.5]non-7-yl}-3-oxopropyl)benzamide;

7-[(5-methoxypyridin-2-yl)acetyl]-2-[5-(4-methyl-1H-pyrazol-1-yl)-2,3-dihydro-1H-inden-1-yl]-2,7-diazaspiro[3.5]nonane;

7-[(4-methoxyphenyl)acetyl]-2-[5-(4-methyl-1H-pyrazol-1-yl)-2,3-dihydro-1H-inden-1-yl]-2,7-diazaspiro[3.5]nonane;

7-[(5-methoxypyridin-2-yl)acetyl]-2-[5-(1H-pyrazol-1-yl)-2,3-dihydro-1H-inden-1-yl]-2,7-diazaspiro[3.5]nonane;

5-{1-[7-(2,3-dihydro[1,4]dioxino[2,3-b]pyridin-6-ylacetyl)-2,7-diazaspiro[3.5]non-2-yl]-2,3-dihydro-1H-inden-5-yl}pyridine-2-carboxamide;

5-[1-{7-[(5-methoxypyridin-2-yl)acetyl]-2,7-diazaspiro[3.5]non-2-yl}-2,3-dihydro-1H-inden-5-yl]pyridine-2-carboxamide;

5-[1-{7-[(5-methylpyridin-2-yl)acetyl]-2,7-diazaspiro[3.5]non-2-yl}-2,3-dihydro-1H-inden-5-yl]pyridine-2-carboxamide;

5-[1-{7-[(2-methylimidazo[2,1-b][1,3]thiazol-6-yl)acetyl]-2,7-diazaspiro[3.5]non-2-yl}-2,3-dihydro-1H-inden-5-yl]pyridine-2-carboxamide;

5-{1-[7-(imidazo[1,2-a]pyridin-2-ylacetyl)-2,7-diazaspiro[3.5]non-2-yl]-2,3-dihydro-1H-inden-5-yl}pyridine-2-carboxamide; and 5-[1-{7-[(7-methylimidazo[1,2-a]pyridin-2-yl)acetyl]-2,7-diazaspiro[3.5]non-2-yl}-2,3-dihydro-1H-inden-5-yl]pyridine-2-carboxamide;

or a pharmaceutically acceptable salt thereof.

Another embodiment of the present invention is a compound selected from the group consisting of:

7-[(2-methylimidazo[2,1-b][1,3]thiazol-6-yl)acetyl]-2-[(1R)-5-pyrimidin-2-yl-2,3-dihydro-1H-inden-1-yl]-2,7-diazaspiro[3.5]nonane;

7-[(4-methoxyphenyl)acetyl]-2-[(1R)-5-(2H-1,2,3-triazol-2-yl)-2,3-dihydro-1H-inden-1-yl]-2,7-diazaspiro[3.5]nonane;

7-[(5-methoxypyridin-2-yl)acetyl]-2-[(1R)-5-(1,3-thiazol-2-yl)-2,3-dihydro-1H-inden-1-yl]-2,7-diazaspiro[3.5]nonane;

2-[(1R)-5-(5-ethylpyrimidin-2-yl)-2,3-dihydro-1H-inden-1-yl]-7-[(5-methoxypyridin-2-yl)acetyl]-2,7-diazaspiro[3.5]nonane;

7-[(5-methoxypyridin-2-yl)acetyl]-2-[(1R)-5-(2H-1,2,3-triazol-2-yl)-2,3-dihydro-1H-inden-1-yl]-2,7-diazaspiro[3.5]nonane;

7-[(5-methoxypyridin-2-yl)acetyl]-2-[(1R)-5-(5-methylpyrimidin-2-yl)-2,3-dihydro-1H-inden-1-yl]-2,7-diazaspiro[3.5]nonane;

7-[(5-ethylpyridin-2-yl)acetyl]-2-[(1R)-5-pyrimidin-2-yl-2,3-dihydro-1H-inden-1-yl]-2,7-diazaspiro[3.5]nonane;

7-[(5-methoxypyridin-2-yl)acetyl]-2-[(1R)-5-(6-methylpyrimidin-4-yl)-2,3-dihydro-1H-inden-1-yl]-2,7-diazaspiro[3.5]nonane;

7-[(5-methylpyridin-2-yl)acetyl]-2-[(1R)-5-(2H-1,2,3-triazol-2-yl)-2,3-dihydro-1H-inden-1-yl]-2,7-diazaspiro[3.5]nonane;

2-[(1R)-5-(2,6-dimethylpyrimidin-4-yl)-2,3-dihydro-1H-inden-1-yl]-7-[(5-methoxypyridin-2-yl)acetyl]-2,7-diazaspiro[3.5]nonane;

7-[(2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane;

6-(2-{2-[(1R)-5-(6-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;

5-{(1R)-1-[7-(2,3-dihydro[1,4]dioxino[2,3-b]pyridin-6-ylacetyl)-2,7-diazaspiro[3.5]non-2-yl]-2,3-dihydro-1H-inden-5-yl}pyridine-2-carboxamide;

7-[(5-methoxypyridin-2-yl)acetyl]-2-[(1R)-5-(4-methylpyrimidin-2-yl)-2,3-dihydro-1H-inden-1-yl]-2,7-diazaspiro[3.5]nonane;

2-(2-{2-[(1R)-5-(6-methylpyrimidin-4-yl)-2,3-dihydro-1H-inden-1-yl]-2,7-diazaspiro[3.5]non-7-yl}-2-oxoethyl)imidazo[1,2-a]pyridine;

7-[(2-methylimidazo[2,1-b][1,3,4]thiadiazol-6-yl)acetyl]-2-[(1R)-5-(6-methylpyrimidin-4-yl)-2,3-dihydro-1H-inden-1-yl]-2,7-diazaspiro[3.5]nonane;

5-methoxy-2-(2-oxo-2-{2-[(1R)-5-pyrimidin-2-yl-2,3-dihydro-1H-inden-1-yl]-2,7-diazaspiro[3.5]non-7-yl}ethyl)benzamide;

5-methoxy-2-(2-{2-[(1R)-5-(6-methylpyrimidin-4-yl)-2,3-dihydro-1H-inden-1-yl]-2,7-diazaspiro[3.5]non-7-yl}-2-oxoethyl)benzamide;

N-[5-methoxy-2-(2-oxo-2-{2-[(1R)-5-pyrimidin-2-yl-2,3-dihydro-1H-inden-1-yl]-2,7-diazaspiro[3.5]non-7-yl}ethyl)phenyl]acetamide; and 6-(2-{2-[(1R)-5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;

or a pharmaceutically acceptable salt thereof.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by the Ghrelin receptor, in particular, by antagonism of said receptor, in a mammal that includes the step of administering to a mammal, preferably a human, in need of such treatment a therapeutically effective amount of a compound of the present invention, or a pharmaceutical composition thereof.

Diseases, disorders, or conditions mediated by the Ghrelin receptor include but are not limited to type II diabetes, hyperglycemia, metabolic syndrome, impaired glucose tolerance, glucosuria, cataracts, diabetic neuropathy, diabetic nephropathy, diabetic retinopathy, obesity, dyslididemia, hypertension, hyperinsulinemia, and insulin resistance syndrome. Preferred diseases, disorders, or conditions include type II diabetes, hyperglycemia, impaired glucose tolerance, obesity, and insulin resistance syndrome. More preferred are type II diabetes, hyperglycemia, and obesity. Most preferred is type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Definitions

As used herein, the term "alkyl" refers to a hydrocarbon radical of the general formula $C_nH_{2n+1}$. The alkane radical may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). The term "($C_0$-$C_3$)alkyl" indicates that the alkyl moiety is not present when it is "$C_0$" or can have up to three carbons present. Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, 1,1-difluoroethyl and the like). Where "$C_0$" is indicated the carbon is absent and thus represents a direct bond.

The term "cycloalkyl" refers to nonaromatic carbocyclic rings that are fully saturated and may exist as a single ring, bicyclic ring or a spiro ring. Unless specified otherwise, the carbocyclic ring is generally a 3- to 8-membered ring. For example, cycloalkyl include groups such as cyclopropyl, cyclobutyl, cyclopentyl, cyclohexyl, norbornyl (bicyclo[2.2.1]heptyl), bicyclo[2.2.2]octyl, and the like.

The term "cycloalkenyl" refers to nonaromatic carbocyclic rings that are not fully saturated and may exist as a single ring, bicyclic ring or a spiro ring. Unless specified otherwise, the carbocyclic ring is generally a 5- to 8-membered ring. For example, cycloalkenyl include groups such as cyclopentenyl, cyclopentadienyl, cyclohexenyl, cyclohexadienyl, cycloheptenyl, cycloheptadienyl, and the like.

The term "heterocyclyl" refers to nonaromatic rings that are fully saturated or partially unsaturated (but not a fully unsaturated heteroaromatic) and may exist as a single ring, bicyclic ring or a spiro ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholinyl, thiomorpholinyl, tetrahydrothienyl, tetrahydrothienyl 1,1-dioxide, and the like.

The term "5- to 6-membered heteroaryl containing 1 to 4 heteroatoms" refers to a radical of a 5 or 6 membered heteroaromatic ring which may contain 1 to 4 heteroatoms independently selected from nitrogen, sulfur and oxygen. Examples of such groups include, but are not limited to, pyridinyl, pyrimidinyl, pyrazinyl, triazinyl, imidazolyl, thiazolyl, oxazolyl, pyrazolyl, thiadiazolyl, triazolyl, or tetrazolyl. The "5- to 6-membered heteroaryl containing 1 to 4 heteroatoms" is optionally fused to a saturated, partially unsaturated or fully unsaturated cycloalkyl or a saturated, partially unsaturated or fully unsaturated 5 to 6 membered heterocycle. In this context the fused cycloalkyl group thus may contain double bonds and be partially unsaturated. For example, the fused cycloalkyl group may be derived from a saturated ring such as cyclopentane or cyclohexane. The optionally fused cycloalkene can be a partially unsaturated ring such as cyclopentene or cyclohexene. Alternatively, the optionally fused group can be a phenyl group. Likewise, the fused heterocyclyl group may be derived from a saturated heterocycle such as pyrrolidine a partially unsaturated heterocycle such as dihydropyrrole. The optionally fused group can also be a fully unsaturated heteroaryl group such as pyrrole.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "antagonist" includes both full antagonists and partial antagonists, as well as inverse agonists.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by acting as an antagonist or inverse agonist at the Ghrelin receptor.

The term "compounds of the present invention" (unless specifically identified otherwise) refer to compounds of Formulae (I) and (IA) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively. It is to be understood that the compounds of the invention can be named using different nomenclature systems and thus different synonyms can exist for the same compound.

BRIEF DESCRIPTION OF THE DRAWINGS

FIG. 1 provides results from the Human Dispersed Islet Cell Assay. The assay results show the measured insulin concentration when the assay is run in the presence of 3 mM glucose, 11 mM glucose, 11 mM glucose+test compound, 16 mM glucose and 22 mM glucose. The test compounds designated as compounds A, B and C are the compounds of Examples 3A, 3B and 6E, respectively. For the data provided one way ANOVA was used to test the null hypothesis of equal treatment means. P-values from post-hoc pairwise comparisons were unadjusted.

DETAILED DESCRIPTION OF THE INVENTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (N-Pg) include acetyl, trifluoroacetyl, t-butoxycarbonyl (BOC), benzyloxycarbonyl (Cbz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

The Reaction Schemes described below are intended to provide a general description of the methodology employed in the preparation of the compounds of the present invention. The compounds of the present invention contain a single chiral center with stereochemical designation R. In the following Schemes, the general methods for the preparation of the compounds are shown either in racemic or enantioenriched form. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

Reaction Scheme I outlines the general procedures that can be used to provide compounds of the present invention having Formula (I).

Reaction Scheme I

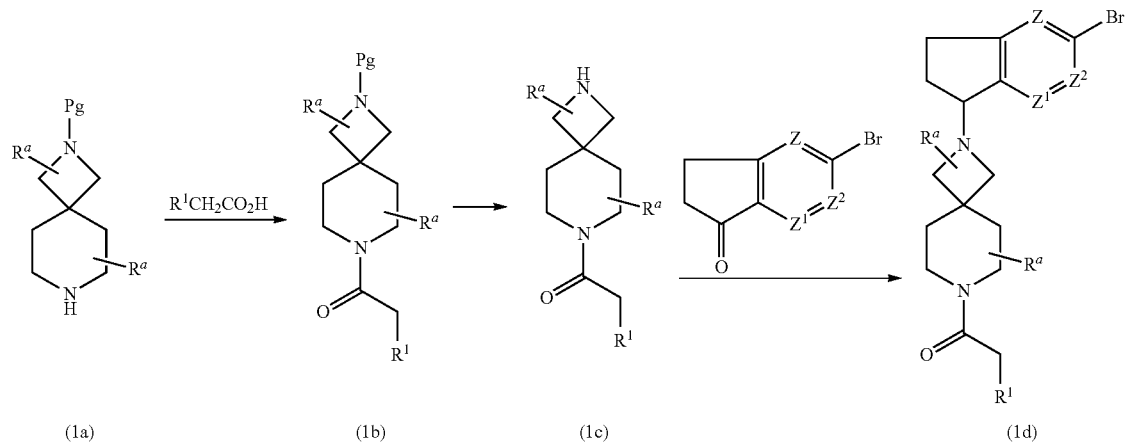

(1a)  (1b)  (1c)  (1d)

Pg = protecting group

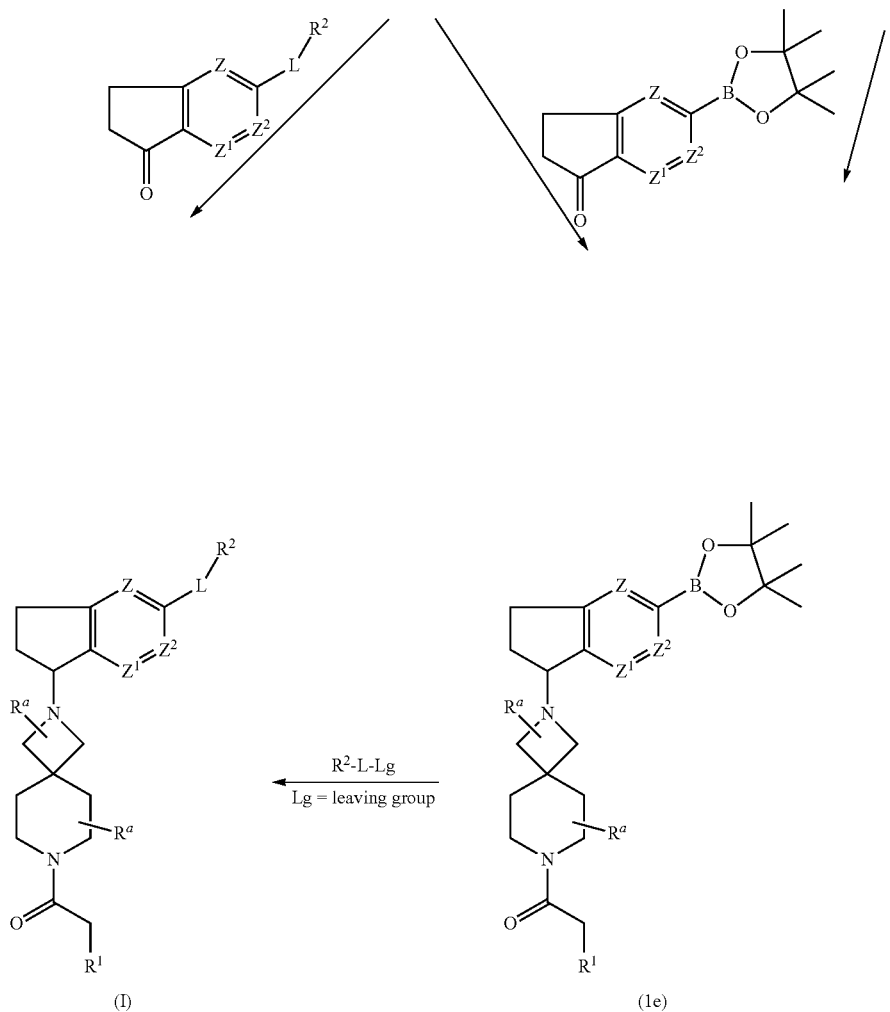

(I)  (1e)

Intermediate (1a) may be prepared by incorporating the desired amino-protecting group onto 2,7-diazaspiro[3.4]nonane. A preferred amino-protecting group is a carbamate group such as t-butyoxycarbonyl (BOC) or benzyloxycarbonyl (Cbz). Intermediate (1b) may be made from Intermediate (1a) by reaction with a carboxylic acid of the formula $R^1CH_2CO_2H$ where $R^1$ is as described above. Suitable conditions include combining the acid and amine with a carbodiimide reagent such as dicyclohexylcarbodiimide (DCC) or N-(3-dimethylaminopropyl)-N'-ethylcarbodiimide (EDCI) in a reaction inert solvent such as dichloromethane or acetonitrile at a temperature between −10° C. to 30° C., preferably 0° C. Other suitable coupling agents include benzotriazo-1-yloxytris(dimethylamino)phosphonium hexafluorophosphate (BOP), O-benzotriazol-1-yl-N,N,N',N'-tetramethyluronium hexafluoro phosphate (HBTU), O-(Benzotriazol-1-yl)-N,N,N',N'-tetramethyluronium tetrafluoroborate (TBTU), 2-(1H-7-azabenzotriazol-1-yl)-1,1,3,3-tetramethyl uronium hexafluorophosphate methanaminium (HATU), propane phosphonic acid anhydride (T3P) or 1,1'-carbonyldiimidazole (CDI) in a reaction inert solvent such as dichloromethane or dimethylformamide (DMF) in the presence of a base, such as triethylamine or diisopropylethylamine, at a temperature between −10° C. to 30° C., preferably ambient. Many other reagents for creating an amide bond are well known to those skilled in the art, for example as described in L. A. Paquette (Ed), *Encyclopedia of Reagents for Organic Synthesis*, John Wiley and Sons, Chichester, England, 1995.

Intermediate (1c) may be prepared from Intermediate (1b) by removal of the protecting group. If the protecting group is t-butoxycarbonyl (BOC), this may be removed by treatment with trifluoroacetic acid in a solvent such as methylene chloride at a temperature between about 0° C. to 30° C., typically ambient, for a period of about 10 minutes to 3 hours. Alternatively, the BOC group may be removed by treatment with hydrogen chloride in a reaction inert solvent such as ethyl acetate, diethyl ether or dioxane at a temperature between about −78° C. to 60° C. for a period of about 10 minutes to 24 hours. When the protecting group is benzyloxycarbonyl (Cbz), then the Cbz group may be removed by transfer hydrogenation in the presence of a suitable hydrogenation catalyst such as palladium on carbon or palladium hydroxide and ammonium formate in a reaction inert solvent such as ethyl acetate, methanol or ethanol at a temperature between 20° C. to 60° C., for a period of about 10 minutes to 24 hours.

The compounds of Formula (I) may be prepared from Intermediate (1c) by reductive amination with the desired indanone and a suitable reducing agent such as sodium borohydride, sodium triacetoxyborohydride, or sodium cyanoborohydride, in a suitable solvent such as THF, methylene chloride, dioxane or toluene. When the amine is in the form of a salt it is beneficial to add an equivalent of a base, such as triethylamine or diisopropylethylamine to generate the free amine in situ. The reaction proceeds via formation of an imine which may be facilitated by a dehydrating agent such as 4 Å molecular sieves in toluene at a temperature between 20° C. and 111° C., preferably between 100° C. and 111° C., followed by removal of the solvent. Alternatively, a titanium compound, preferably titanium tetraisopropoxide may be employed, preferably in a reaction inert solvent such as dichloroethane or dichloromethane at room temperature. The imine is then reduced in a suitable polar solvent, preferably ethanol, with a suitable hydride reducing agent, preferably sodium triacetoxyborohydride, at a temperature between 0° C. and 80° C., preferably between 20° C. and 50° C.

Alternatively, the compounds of Formula (I) may be prepared from Intermediate (1e) by a Suzuki reaction with an aryl or heteroaryl compound $R^2$-L-Lg (where L is typically a direct bond and Lg is an appropriate leaving group such as Cl, Br, I or triflate) in a reaction inert solvent such as dioxane, dimethoxyethane, toluene or acetonitrile in the presence of water, a suitable palladium catalyst such as palladium tetrakis (triphenylphosphine), 1,1'-bis(diphenylphosphino)ferrocene palladium dichloride dichloromethane complex and a suitable base such as triethylamine, sodium carbonate, sodium bicarbonate or potassium acetate at a temperature between 25° C. and 120° C., preferably between 25° C. and 100° C. Intermediate (1e) may be prepared from Intermediate (1c) by reductive amination with 5-(4,4,5,5-tetramethyl-[1,3,2]dioxaborolan-2-yl)-indan-1-one using the conditions described above. Alternatively, Intermediate (1e) may be prepared by first forming Intermediate (1d) via reductive amination of Intermediate (1c) with 5-bromo-indan-1-one using conditions described above. Borylation of Intermediate (1d) with (bispinacolato)diborane (also known as (4,4,5,5,4',4',5',5'-octamethyl-[2,2']bi[[1,3,2]dioxaborolanyl]) is typically achieved in a reaction inert solvent such as dioxane, dimethoxyethane, toluene or acetonitrile, preferably dioxane, in the presence of a suitable palladium catalyst such as 1,1'-bis(diphenylphosphino)ferrocene palladium dichloride dichloromethane complex and a suitable base such as potassium acetate at a temperature between 25° C. and 120° C., preferably between 25° C. and 100° C. Intermediate (1d) can be taken on to compounds of Formula I using conditions described above.

Alternatively, the compounds of Formula (I) may be prepared from intermediate (1d) by a Suzuki reaction with an aryl compound $R^2B(OR)_2$ where R is H or where both OR groups are taken together to form a pinacol group. The coupling is conducted in a reaction inert solvent such as dioxane, dimethoxyethane, toluene or acetonitrile in the presence of water, a suitable palladium catalyst such as palladium tetrakis (triphenylphosphine), 1,1'-bis(diphenylphosphino)ferrocene palladium dichloride dichloromethane complex and a suitable base such as triethylamine, sodium carbonate, sodium bicarbonate or potassium acetate at a temperature between about 25° C. and about 120° C., preferably between 100° C. and 120° C.

Reaction Scheme II depicts the synthesis of compounds within Formula (I) of Formula (I') where L is a direct bond, Z, $Z^1$ and $Z^2$ are each CH and each Ra is hydrogen. Intermediate (2b) may be prepared from Intermediate (2a) by reductive amination with the desired indanone and a suitable reducing agent such as those described above in Scheme I. Alternatively, intermediate (2b) may be prepared from intermediate (2c), described below, by a Suzuki reaction with an aryl compound $R^2$-L-Lg (where Lg is a leaving group) in a reaction inert solvent such as dioxane, dimethoxyethane, toluene or acetonitrile in the presence of water, a suitable palladium catalyst such as palladium tetrakis(triphenylphosphine), (1,1'-bis(diphenylphosphino)ferrocene palladium dichloride dichloromethane complex and a suitable base such as triethylamine, sodium carbonate, sodium bicarbonate or potassium acetate at a temperature between about 25° C. and about 125° C., preferably between 100° C. and 125° C.

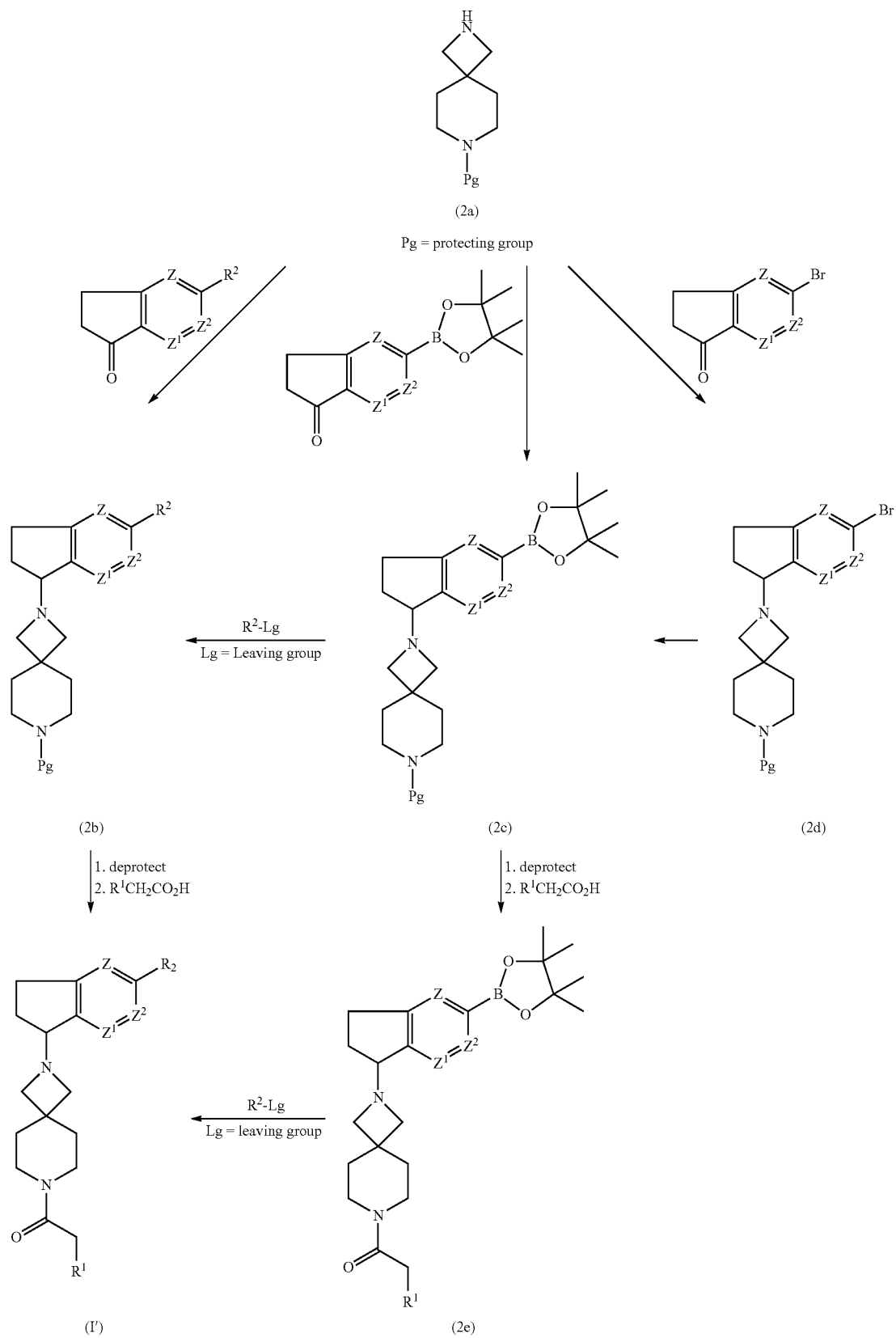

The compounds of Formula (I') may be prepared from Intermediate (2b) by a two step sequence. Firstly, the protecting group (Pg) is removed using the conditions described above. The amine intermediate is then reacted with a carboxylic acid of the formula $R^1CO_2H$ (where $R^1$ is as described above) to give the desired compound of Formula (I) using the conditions described above in Scheme I.

Alternatively, compounds of Formula (I') may be prepared by means of Intermediate (2c). Intermediate (2c) may be prepared from Intermediate (2a) by reductive amination with (5-(4,4,5,5-tetramethyl-[1,3,2]dioxaborolan-2-yl)-indan-1-one) using the conditions described above in Scheme I. Intermediate (2e) may be prepared from Intermediate (2c) by a two step sequence. The protecting group (Pg) is first removed followed by the reaction of the free amine with a carboxylic acid of the formula $R^1CO_2H$ (where $R^1$ is as described above). Intermediate (2e) may be converted to a compound of Formula (I') using the conditions described above in Reaction Scheme I.

Intermediate (2c) may also be prepared from intermediate (2d) by borylation with (bispinacolato)diborane (also known as (4,4,5,5,4',4',5',5'-octamethyl-[2,2']bi[[1,3,2]dioxaborolanyl]) in a reaction inert solvent such as dioxane, dimethoxyethane, toluene or acetonitrile, preferably dioxane, in the presence of a suitable palladium catalyst such as 1,1'-bis(diphenylphosphino)ferrocene palladium dichloride dichloromethane complex and a suitable base such as potassium acetate at a temperature between 25° C. and 120° C. preferably between 100° C. and 120° C. Intermediate (2d) may be prepared from Intermediate (2a) by reductive amination with 5-bromo-indan-1-one and a suitable reducing agent using the conditions described above in Scheme I.

Intermediates (1a) and (2a), in Scheme I and II, respectively, may be interconverted to provide alternative and preferable synthetic routes when desired. This can be achieved when the protecting groups are distinct and orthogonal such as the tert-butyloxycarbonyl (Boc) and benzyloxycarbonyl (Cbz) groups. For example when the starting material bears the Boc group the free amine can be reacted with benzyl chloroformate in a reaction inert solvent such as dichloromethane in the presence of a base, such as triethylamine or diisopropylethylamine, at a temperature between −10° C. to 30° C., preferably at ambient temperature. The Boc group can then be removed using standard conditions as described above. Alternatively when the starting material bears the Cbz group the free amine can be reacted with di(tert-butyl)dicarbonate (Boc anhydride) in a reaction inert solvent such as dichloromethane at a temperature between −10° C. to 30° C., preferably at ambient temperature. The Cbz group can then be removed using standard conditions as described above.

Reaction Scheme III below provides a specific route for the formation of enantiomeric compounds of Formula (I-A) (which are compounds of Formula (IA) in which L is a direct bond.

Compounds of Formula (I-A) may be prepared using either Intermediate (3b) or (3c). Intermediate (3c) may be prepared from the aldehyde (3a) by reaction with (R)-5-bromo-indan-1-ylamine (SM-1: see, Scheme IV below) in a suitable solvent such as methanol or ethanol with a reducing agent such as sodium borohydride or sodium cyanoborohydride in the presence of an acid such as acetic acid at a temperature between about 0° C. and about 100° C., preferably between 30° C. and 80° C. Intermediate (3d) may be prepared from Intermediate (3c) by a two step sequence. The protecting group is first removed and the free amine is reacted with a carboxylic acid of formula $R^1CH_2CO_2H$ (where $R^1$ is as described herein). Suitable conditions are described in Scheme I above. Intermediate (3e) may be prepared from Intermediate (3d) by borylation with (bispinacolato)diborane (also known as (4,4,5,5,4',4',5',5'-octamethyl-[2,2']bi[[1,3,2]dioxaborolanyl]) using the reaction conditions described above in Scheme I. The compounds of Formula (1-A) may be prepared from Intermediate (3e) by a Suzuki reaction with an aryl compound $R^2$-Lg (where Lg is an appropriate leaving group) as described above in Scheme I.

Reaction Scheme III

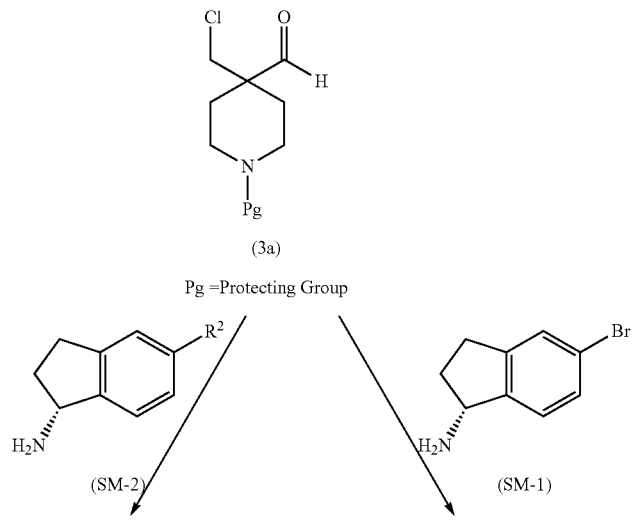

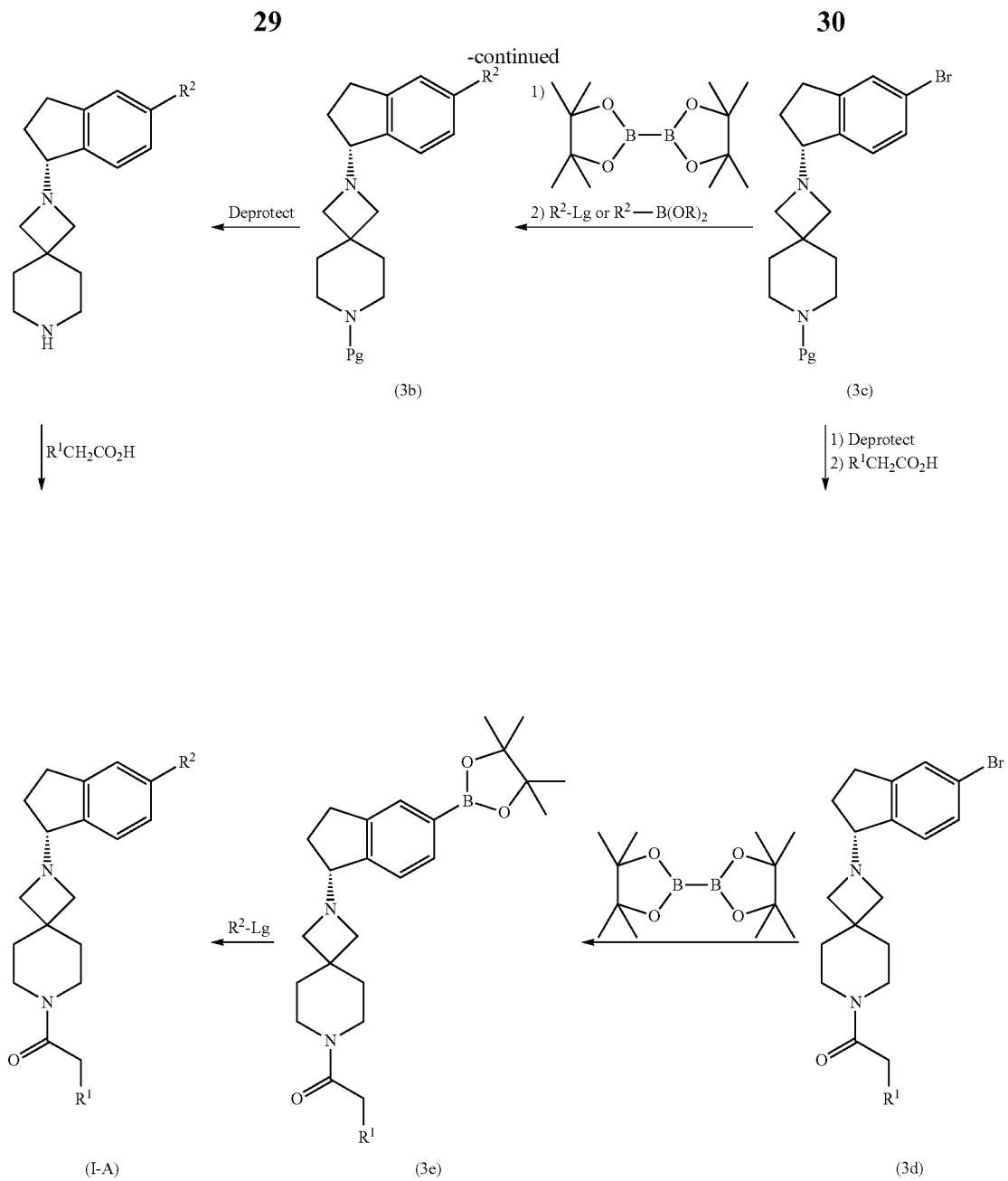

Alternatively, compounds of Formula (1-A) may be prepared using Intermediate (3b). Intermediate (3b) may be prepared from the aldehyde (3a) by reaction with the desired indan-1-ylamine (SM-2) in a suitable solvent such as methanol or ethanol with a reducing agent such as sodium borohydride or sodium cyanoborohydride in the presence of an acid such as acetic acid at a temperature between 0° C. to 100° C., preferably between 30° C. and 80° C. Alternatively, Intermediate (3b) may be prepared from Intermediate (3c) by a Suzuki reaction with an arylboronic acid of formula $R^2B(OR)_2$. The coupling is generally conducted in a reaction inert solvent such as dioxane, dimethoxyethane, toluene or acetonitrile in the presence of water, a suitable palladium catalyst such as palladium tetrakis(triphenylphosphine), (1,1'-bis (diphenylphosphino)ferrocene palladium dichloride dichloromethane complex and a suitable base such as triethylamine, sodium carbonate, sodium bicarbonate or potassium acetate at a temperature between about 25° C. and 120° C., preferably between 100° C. and 120° C. Alternatively, Intermediate (3b) may be prepared from intermediate (3c) via an in situ borylation (with (bispinacolato)diborane using the reaction conditions described above in Reaction Scheme I) followed by a Suzuki reaction with an aryl compound $R^2$-L (where L is a leaving group such as Cl, Br, I or triflate) using the reaction conditions described above in Reaction Scheme I).

Compounds of Formula (I-A) may be prepared from intermediate (3b) by first removing the protecting group followed by reaction with a carboxylic acid of the formula $R^1CH_2CO_2H$ (where $R^1$ is as described herein) using the conditions described in Reaction Scheme I.

Scheme IV below describes the synthesis of the enantioenriched indanyl amines used in Scheme III above from commercially available 5-bromo-indan-1-one.

Reaction Scheme IV

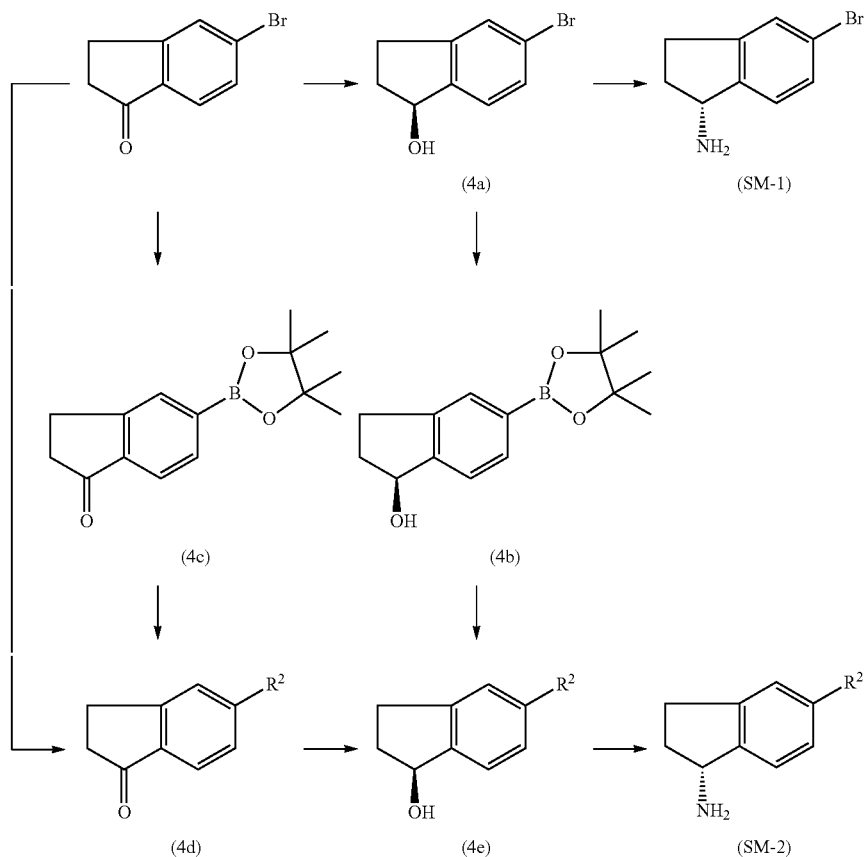

Starting materials SM-1 and SM-2 (from Reaction Scheme III above) may be prepared from the alcohols (4a) and (4e) respectively by a series of transformations involving inversion of the stereochemistry at the chiral center. In one suitable sequence the alcohol is treated with diphenyl phosphorazidate (DPPA) in a reaction inert solvent such as dichloromethane, 2-methyltetrahydrofuran or toluene in the presence of a base, such as DBU, at a temperature between about −10° C. and about 30° C., preferably ambient, to produce the azidoindane intermediate of opposite stereochemistry. Alternatively, the azide may be prepared from the alcohols (4a) and (4e) by conversion of the alcohol to a leaving group such as mesylate, tosylate or triflate followed by treatment with an azide such as sodium azide in a reaction inert solvent such as DMF, DMSO, acetonitrile or acetone using procedures well known to those skilled in the art for example as described in L. A. Paquette (Ed), *Encyclopedia of Reagents for Organic Synthesis*, John Wiley and Sons, Chichester, England, 1995. The azide is then reduced to the corresponding amine by treatment with a phosphine, such as triphenylphosphine or trimethylphosphine followed by aqueous hydrolysis at a temperature between about −10° C. and about 30° C., preferably at ambient temperature. Alternatively, the azide may be reduced by treatment with tin(II) chloride in a reaction inert solvent such as methanol or toluene or a mixture thereof at a temperature between about 20° C. and about 60° C., preferably at about 23° C., for a period of about 10 minutes to 24 hours. Alternatively, the azide may be reduced by hydrogenation in the presence of a suitable hydrogenation catalyst such as palladium on carbon or palladium hydroxide in a reaction inert solvent such as ethyl acetate, methanol or ethanol at a temperature between about 20° C. and about 60° C., preferably at ambient temperature, for a period of about 10 minutes to 24 hours.

Alcohols (4a) and (4e) may be prepared by reduction of 5-bromo-indan-1-one and ketone (4d), respectively, using an enantioselective reduction procedure. The preferred procedure uses borane-methyl sulfide complex in the presence of the catalyst R-(+)-2-Methyl-CBS-oxazaborolidine (also known as (3aR)-tetrahydro-1-methyl-3,3-diphenyl-1H,3H-pyrrolo[1,2-c][1,3,2]oxazaborole) in a reaction inert solvent such as tetrahydrofuran at a temperature between −10° C. and 0° C.

Certain compounds of Formula (I-B) may be prepared using either Intermediate (5b) or (5c). Intermediate (5b) may be prepared from Intermediate (3c) by a Suzuki reaction with carbamoyl-aryl-B(OR)$_2$ or carbamoyl-heteroaryl-B(OR)$_2$ (where carbamoyl-aryl and carbamoyl-heteroaryl are within the definition of R$^2$ as provided herein) using the reaction conditions described above in Reaction Scheme I. Alternatively, Intermediate (5b) may be prepared from Intermediate (5a) by hydration of the cyano group in a suitable solvent such as water, with a reducing agent such as urea-hydrogen peroxide, in the presence of base such as sodium hydroxide at a temperature between 0° C. and 30° C., preferably at about 23° C., for a period of about 10 minutes to 24 hours.

Reaction Scheme V
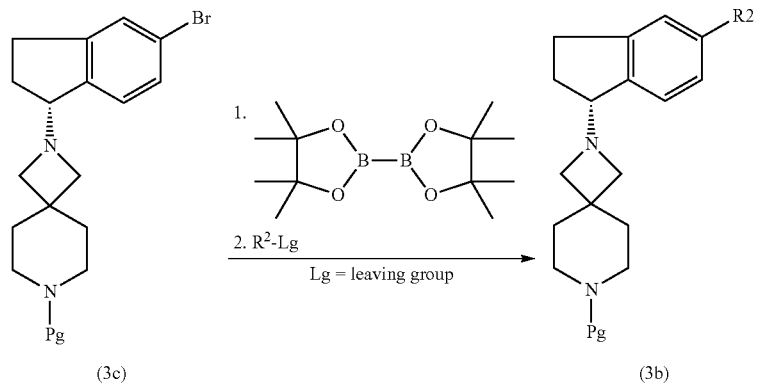
(3c) → (3b)
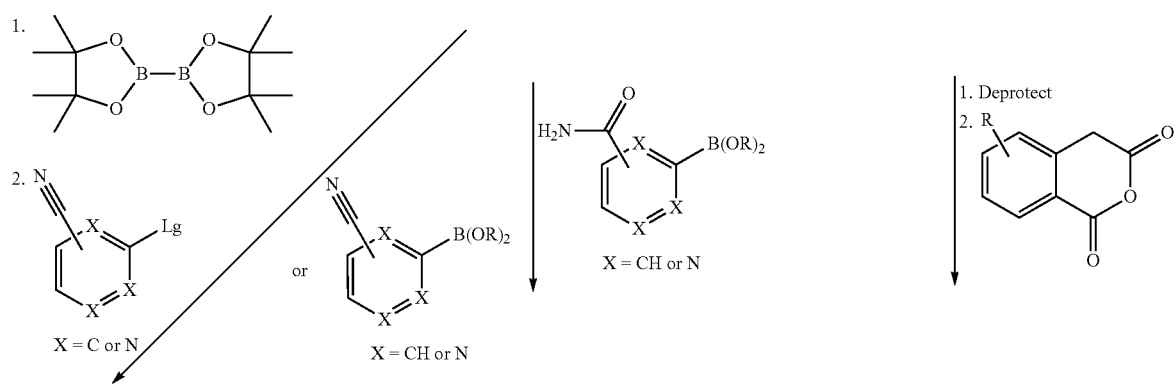
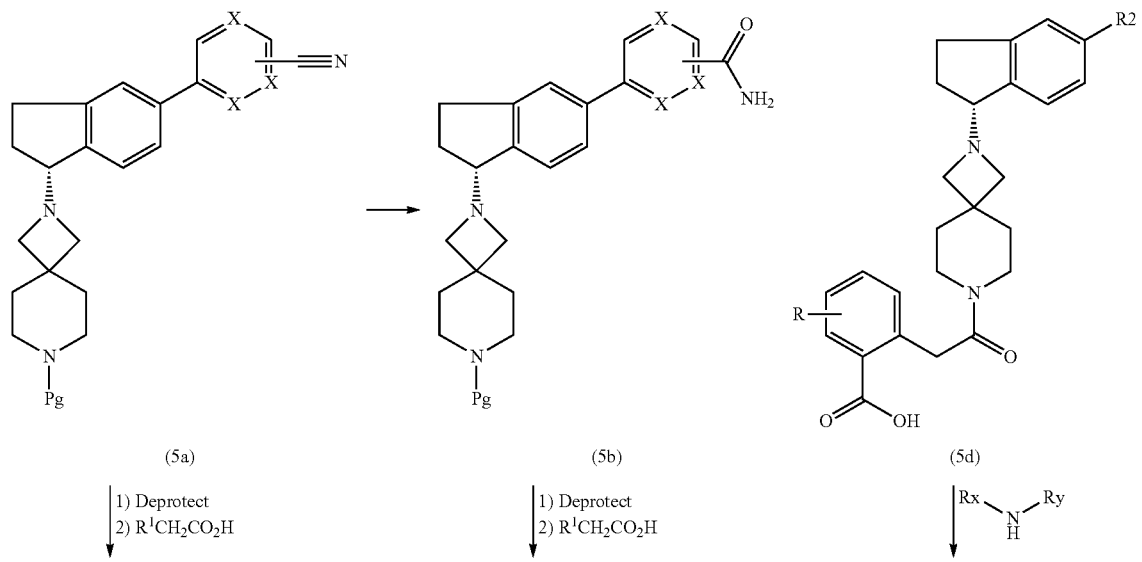
(5a) (5b) (5d)
1) Deprotect
2) $R^1CH_2CO_2H$
1) Deprotect
2) $R^1CH_2CO_2H$
Rx-NH-Ry

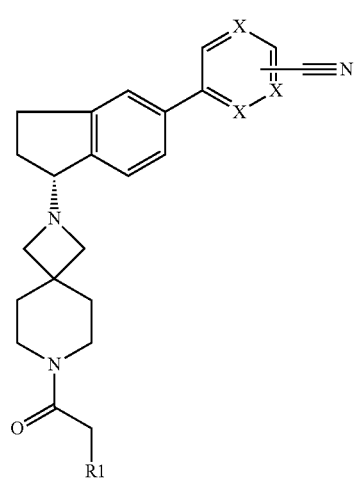 (5c)

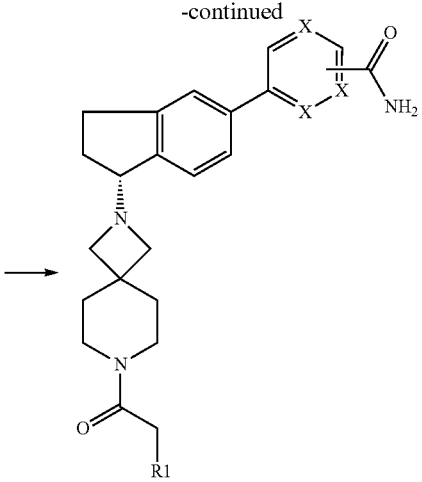 (I-B)

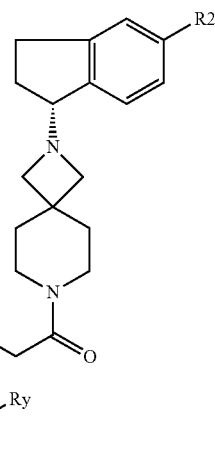 (I-C)

Intermediate (5c) may be prepared from Intermediate (5a) by a two step sequence. The protecting group is first removed and then the free amine is reacted with a carboxylic acid of the formula $R^1CH_2CO_2H$ (where $R^1$ is as described herein). Suitable conditions are described in Scheme I above. Intermediate (5a) may be prepared from Intermediate (3c) (Scheme III above) by a Suzuki reaction with cyano-aryl-$B(OR)_2$ or cyano-heteroaryl-$B(OR)_2$ (where the cyano-aryl and cyano-heteroaryl are within the definition of $R^2$ as provided herein). Alternatively, Intermediate (5a) may be prepared from Intermediate (3c) via an in situ borylation (with (bispinacolato) diborane using the reaction conditions described above in Scheme I) followed by a Suzuki reaction with cyano-aryl-Lg or cyano-heteroaryl-Lg (where Lg is a leaving group such as Cl, Br, I or triflate and cyano-aryl and cyano-heteroaryl are defined as above) using the reaction conditions described above.

Compounds of formula (1-B) may be prepared from Intermediate (5b) by a two step sequence. The protecting group is first removed and the free amine is reacted with a carboxylic acid of the formula $R^1CH_2CO_2H$ (where $R^1$ is as described above). Suitable conditions are described in Scheme I above. Alternatively, compounds of formula (1-B) may be prepared from Intermediate (5c) by hydrolysis of the cyano group using the reaction conditions described above.

Compounds of formula (1-C) may be prepared using Intermediate (5d). Intermediate (5d) may be prepared by treatment of Intermediate (3b) (as prepared above in Scheme III) with an optionally substituted isochroman-1,3-dione (where R is an appropriate substituent as provided within the definition of $R^1$) in a suitable solvent such as acetonitrile, in the presence of base such as triethylamine at a temperature between 0° C. and 80° C., preferably 23° C., for a period of about 10 minutes to 24 hours.

Compounds of formula (1-C) may be prepared by an aminolysis of Intermediate (5d) with an amine of formula $R^xN$-$HR^y$ (where $R^x$ and $R^y$ are an appropriate group as provided for in the definition of $R^1$) using the conditions described above in Scheme 1. Intermediate (5d) may be prepared from Intermediate (3b) by a two-step sequence. The protecting group is first removed and the free amine is reacted with a homophthalide derivative (wherein R is methyl or methoxyl) in a reaction inert solvent such as acetonitrile and in the presence of a base such as triethylamine at a temperature between 0° C. and 50° C., preferably room temperature, for a period of about 10 minutes to 24 hours.

Reaction Scheme VI

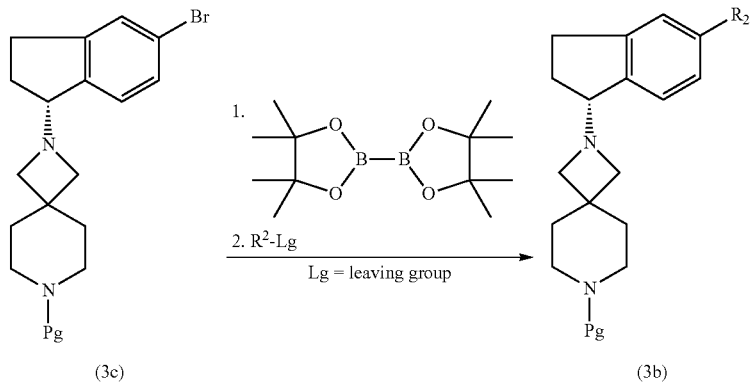

(3c)  (3b)

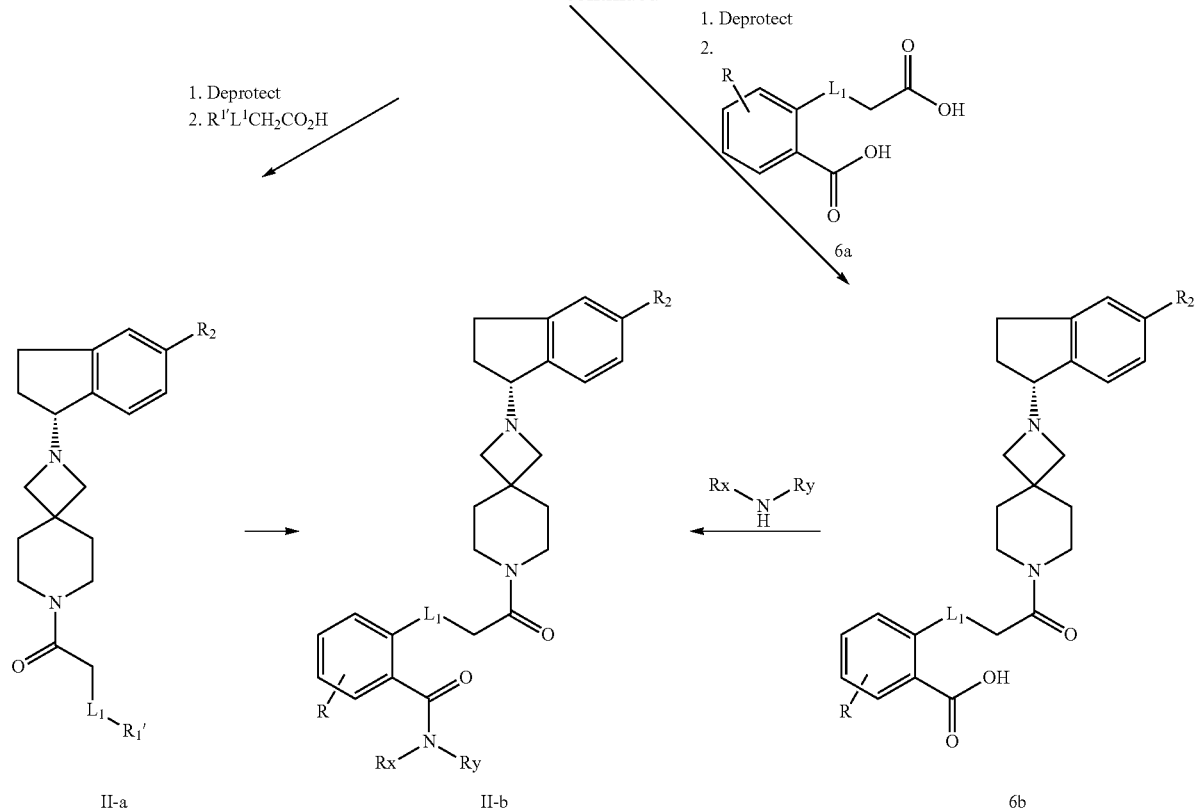

Reaction Scheme VI provides a further reaction scheme which depicts the preparation of compounds within Formula I wherein $R^1$ is -$L^{1}$-$R^{1'}$. Compounds of formula (II-a) may be prepared from Intermediate (3b) by a two step sequence. The protecting group is first removed and the free amine is reacted with a carboxylic acid of the formula $R^{1'}L^1CH_2CO_2H$ (where $R^1$ is as described above). Suitable conditions are described in Scheme I above. Compounds of formula (II-B) may be prepared from compounds IIa by transformation of key functional groups, e.g hydrolysis of nitrile to amide.

Compounds of formula (II-b) may be prepared using Intermediate (6b). Intermediate (6b) may be prepared by treatment of Intermediate (3b) (as prepared above in Scheme III) with an optionally substituted diacid 6a (where R is an appropriate substituent as provided within the definition of $R^1$) in a suitable solvent such as dichloromethane in the presence of base such as triethylamine using an amide coupling reagent such as 1,1'-carbonyldiimidazole.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.* 66, 1-19 (1977).

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Certain compounds of the present invention may exist in different stable conformational forms which may be separable. Torsional asymmetry due to restricted rotation about an asymmetric single bond, for example, because of steric hindrance or ring strain, may permit separation of different conformers.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning colorimetry, powder X-ray diffraction or such other techniques.

Compounds of the present invention are useful for treating diseases, conditions and/or disorders that are mediated by the antagonism or inverse agonism of the ghrelin receptor; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula (I). The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl tert-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders mediated by the antagonism of the ghrelin receptor in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including type 1 (insulin-dependent diabetes mellitus, also referred to as "IDDM") and type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

Yet another aspect of the present invention is the treatment of diabetes- or obesity-related co-morbidities, such as metabolic syndrome. Metabolic syndrome includes diseases, conditions or disorders such as dyslipidemia, hypertension, insulin resistance, diabetes (e.g., type 2 diabetes), weight gain, coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

The present invention also relates to therapeutic methods for treating the above described conditions in a mammal, including a human, wherein a compound of Formula (I) of this invention is administered as part of an appropriate dosage regimen designed to obtain the benefits of the therapy. The appropriate dosage regimen, the amount of each dose administered and the intervals between doses of the compound will depend upon the compound of Formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be combined with the compounds of the present invention include, for example, those described at page 30, line 20 through page 31, line 30 of WO 2011005611. The lipid lowering agents include bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR α agonists, FXR receptor modulators, LXR receptor modulators, lipoprotein synthesis inhibitors, rennin angiotensisn system inhibitors, PPAR δ partial agonists, bile acid reabsorption inhibitors, PPAR γ agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin bound chromium and other agents that affect lipid composition.

Suitable anti-hypertensive agents that can be combined with the compounds of the present invention include, for example, those described at page 31, line 31 through page 32, line 18 of WO 2011005611. The anti-hypertensive agents include diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, α/β adrenergic blockers, alpha 1 blockers, alpha 2 agonists, aldosterone inhibitors, mineraocorticoid receptor inhibitors, renin inhibitors and angiopoietin-2-binding agents.

Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924,TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-

5-oxo-1-phenyl-4,5-dihydro-2,3,6,10b-tetraaza-benzo[e] azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine. Preferably, compounds of the present invention and combination therapies are administered in conjunction with exercise and a sensible diet.

Embodiments of the present invention are illustrated by the following Examples. It is to be understood, however, that the embodiments of the invention are not to be construed in a limiting manner nor limited to the specific details of these Examples, as other variations thereof will be known, or apparent in light of the instant disclosure, to one of ordinary skill in the art.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England). Certain common abbreviations and acronyms have been employed which may include: AcOH (acetic acid), AIBN (azoisobutylnitrile), CDMT (2-chloro-4, 6-dimethyoxy-1,3,5-triazine), DBU (1,8-diazabicyclo[5.4.0] undec-7-ene), DCM (dichloromethane), DMAP (4-dimethylaminopyridine), DMF (dimethylformamide), DMSO (dimethylsulfoxide), Et₂O (diethyl ether), EtOAc (ethyl acetate), EtOH (ethanol), IPA (isopropyl alcohol), HBTU (O-benzotriazole-N,N,N',N'-tetramethyl-uronium-hexafluoro-phosphate), KHMDS (potassium hexamethyldisilazane), MeOH (methanol), MTBE (tert-butyl methyl ether), $NaBH(OAc)_3$ (sodium triacetoxyborohydride), NaHMDS (sodium hexamethyldisilazane), PyBOP (benzotriazol-1-yl-oxytripyrrolidino-phosphonium hexafluorophosphate), TFA (trifluoroacetic acid) and THF (tetrahydrofuran).

General Experimental Procedures

NMR spectra were recorded on a Varian Unity™ 400 (available from Varian Inc., Palo Alto, Calif.) at room temperature at 400 and 500 MHz 1H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet. In some cases only representative $^1H$ NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments.

Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer (Waters Corp., Milford, Mass.) equipped with Gilson 215 liquid handling system (Gilson, Inc., Middleton, Wis.) and HP 1100 DAD (Hewlett Packard) was used to carry out the experiments.

Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and only the lower mass ion is given. Optical rotations were determined on a PerkinElmer™ 241 polarimeter (available from PerkinElmer Inc., Wellesley, Mass.) using the sodium D line (wavelength=589 nm) at the indicated temperature and are reported as follows $[\alpha]_D^{temp}$, concentration (c=g/100 mL), and solvent.

Column chromatography can be performed with either Baker™ silica gel (40 µm, J. T. Baker, Phillipsburg, N.J.) or Silica Gel 50 (EM Sciences™, Gibbstown, N.J.) in glass columns, in Biotage™ columns (Biotage, Inc., Charlottesville, USA) or using an Isco Combiflash Separation System (Teledyne Isco Inc., Lincoln, Nebr.) under low nitrogen pressure. Selected purifications were performed using Shimadzu Preparation Liquid Chromatography. Chiral separations can be made using a Chiralpak AD, (S,S)-Whelk-O 1 or Chiralcel OD column. References to "enantiomer 1" or "enantiomer 2" merely refer to the order in which the compounds elute from the column and do not imply a relative absolute stereochemistry. Celite® is a registered trademark for a form of diatomaceous earth available from J T Baker, Phillipsburg, N.J.

Preparation of Starting Materials and Intermediates

Preparation of (1R)-5-Bromoindan-1-amine (SM-1)

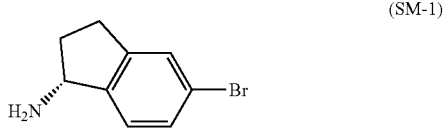 [SMILES: N[C@@H]1CCc2cc(Br)ccc21]

(SM-1)

A 22 L 5-necked round-bottomed flask was charged with 5-bromo-1-indanone (1.0 kg, 4.72 mol), anhydrous THF (8 L) and (R)-methyl-CBS-oxazaborolidine (730 mL, 0.73 mol) and was cooled to −10° C. under N₂. Borane-methylsulfide (10.0 M, 650 mL, 6.5 mol) was added dropwise over 1 hour while maintaining the temperature below −5° C. The mixture was stirred at −10° C. to 0° C. for 3 hours and was quenched with water (4 L) at such a rate to maintain the reaction temperature below 5° C. The mixture was extracted with EtOAc (3×3 L). The combined organic extracts were washed with brine (2 L), dried over MgSO₄, filtered and concentrated to give yellow solid. The crude product was passed through a short silica gel column (3 L silica gel packed with 1% Et₃N in hexanes) and eluted with EtOAc/hexanes(⅓). The filtrate was concentrated and the residue was slurried with 10% EtOAc in hexanes, filtered, and dried to give 585 g of an off-white solid as (S)-5-bromo-indan-1-ol. The mother liquors were re-concentrated, slurried with 10% EtOAc in hexanes and filtered to give another 200 g yellow solid as (S)-5-bromo-indan-1-ol. The combined lots (785 g, 78%) were carried on to the next step without further purification.

A solution of (S)-5-bromo-indan-1-ol (288 g, 1.35 mol) in toluene (2 L) was cooled in an ice bath under N₂ and treated with diphenylphosphoric azide (DPPA, 400 mL, 1.85 mol) in one portion followed by a solution of 1,8-diazabicyclo[5,4,0] undec-7-ene (300 mL, 2.01 mol) in toluene (600 mL). The reaction temperature was kept between 3 and 10° C. during the 3 hour addition and the mixture was warmed to 15° C. over 3 hours (TLC indicated no starting material). The mixture was diluted with EtOAc (1 L) and washed with water (3×2 L). The organic layer was dried over MgSO$_4$, filtered and concentrated to give 516 g of a dark oil. The crude product was purified by silica gel column (packed with 1% Et$_3$N in hexanes, hexane eluant) to give (R)-1-azido-5-bromo-indane (291 g, 90%) as an oil which was used directly in the next step.

A solution of (R)-1-azido-5-bromo-indane (154 g, 0.645 mol) was dissolved in methanol (2.4 L) and SnCl$_2$.2H$_2$O (265 g, 1.18 mol) was added. The mixture was stirred at room temperature overnight (TLC indicated no starting material) and was concentrated to dryness. The resulting residue was treated with 2N aqueous NaOH (2.5 L) and EtOAc (1.5 L). The mixture was stirred for 1 hour and filtered through Celite® with the aid of EtOAc (3×250 ml). The organic solution was separated and the aqueous layer was extracted with EtOAc (3×2 L). The combined organic extracts were washed with 1 N HCl (2×2 L) followed by water (2 L). The pH of the combined aqueous layers was adjusted to 11 with cold saturated NaOH solution and the mixture was extracted with EtOAc (3×2 L). The combined organic extracts were dried over MgSO$_4$, filtered and concentrated to give (87.5 g, 64.0%) (1R)-5-bromoindan-1-amine as a dark yellow oil which solidified upon refrigeration. MS (ES+) 213.9 (M+H)$^+$. $^1$H NMR (CDCl$_3$) δ 1.70-1.75 (m, 1H), 2.40-2.45 (m, 1H), 2.77-2.82 (m, 1H), 2.93-2.97 (m, 1H), 4.28-4.33 (m, 1H), 7.18-7.23 (m, 1H), 7.36-7.41 (m, 2H).

Alternative Preparation of Starting Material (1R)-5-Bromoindan-1-amine (SM-1)

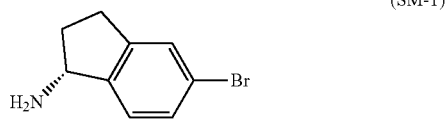

(SM-1)

A round-bottomed flask was charged with 5-bromo-1-indanone (50.0 g, 0.24 mol), anhydrous THF (500 mL) and (R)-methyl-CBS-oxazaborolidine (10.0 g, 0.04 mol) and the solution was heated to 35° C. under N$_2$. Borane-methylsulfide (10.0 M, 650 mL, 6.5 mol) was added dropwise over 1.5 hours. The mixture was stirred at 35° C. for 1 hour. Upon consumption of the starting material (TLC analysis), the reaction was cooled to 0° C. and was quenched with water (200 mL) at such a rate to maintain the reaction temperature below 5° C. The mixture was extracted with EtOAc (4×200 mL). The combined organic extracts were washed with brine, dried over MgSO$_4$, filtered and concentrated to give a yellow solid. The solids were dissolved in hot CHCl$_3$ (150 mL) and hexane (300 mL) and upon cooling to room temperature solids precipitated from the solution. After further cooling at 0° C., the solids were collected by vacuum filtration to afford (S)-5-bromo-indan-1-ol (22 g, 44%) as a light-yellow solid. This material was carried on to the next step without further purification.

A solution of (S)-5-bromo-indan-1-ol (15.0 g, 70.4 mmol) in toluene (150 mL) was cooled in an ice bath under N$_2$ and was treated with diphenylphosphoric azide (DPPA, 22.0 g, 91.5 mmol) in one portion followed by 1,8-diazabicyclo[5,4,0]undec-7-ene (15.0 g, 98.6 mmol). The reaction temperature was kept between 3 and 10° C. during 3 hours of addition and the mixture was warmed to 15° C. over the next hour (TLC indicated no starting material). The mixture was diluted with EtOAc (300 mL) and was washed with water. The organic layer was dried over Na$_2$SO$_4$, filtered and concentrated to give a dark oil. The crude product was purified by silica gel column (packed with 1% Et$_3$N in hexanes, hexane eluant) to give (R)-1-azido-5-bromo-indane (14 g, 83%) as an oil which was used directly in the next step.

A solution of (R)-1-azido-5-bromo-indane (14.0 g, 58.8 mmol) was dissolved in methanol (150 mL) and was treated with SnCl$_2$.2H$_2$O (23.0 g, 106 mmol). The mixture was stirred at room temperature overnight (TLC indicated no starting material) and was concentrated to dryness. The resulting residue was treated with 2N aqueous NaOH (300 mL) and was extracted with EtOAc (2×300 mL). The combined organic extracts were washed with 1N HCl followed by water (2 L). The pH of the combined aqueous layers was adjusted to 11 with cold saturated NaOH solution and the mixture was extracted with EtOAc (2×300 mL). The combined organic extracts were dried over Na$_2$SO$_4$, filtered and concentrated to give 10.0 g (80%) of (1R)-5-bromoindan-1-amine as a dark yellow oil which solidified upon refrigeration. MS (ES+) 213.9 (M+H)$^+$. $^1$H NMR (CDCl$_3$) δ 1.70-1.75 (m, 1H), 2.40-2.45 (m, 1H), 2.77-2.82 (m, 1H), 2.93-2.97 (m, 1H), 4.28-4.33 (m, 1H), 7.18-7.23 (m, 1H), 7.36-7.41 (m, 2H).

Preparation of 5-(4,4,5,5-Tetramethyl-1,3,2-dioxaborolan-2-yl)indan-1-one (SM-1a)

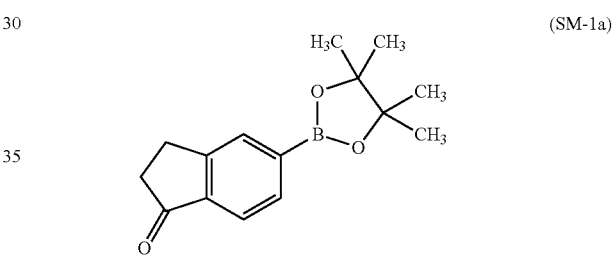

(SM-1a)

An oven-dried round-bottomed flask was charged with 5-bromo-1-indanone (9.75 g, 46.2 mmol), bis(pinacolato)diboron (12.9 g, 50.8 mmol), potassium acetate (13.6 g, 139 mmol) and 150 mL of anhydrous dioxane. The resulting mixture was purged of oxygen with a nitrogen gas stream for 15 minutes. Pd(dppf)Cl$_2$ (1.89 g, 5 mol %) was added and the nitrogen purge was continued for an additional 15 minutes. The reaction was heated under nitrogen atmosphere at reflux for 4 hours (silicone oil bath temperature of 95° C.). LCMS analysis of the reaction mixture showed complete reaction. The reaction mixture was cooled to ambient temperature and diluted with ethyl acetate (150 mL) and water (200 mL). A dark, nearly black, mixture formed. The mixture was filtered through a plug of Celite® with an ethyl acetate rinse. The mixture was transferred to a separation funnel. The organic phase was separated and the aqueous layer was washed with ethyl acetate (2×50 mL). The combined organic solutions were washed with brine, dried over anhydrous MgSO$_4$ and decolorized with charcoal while warm. Filtration and solvent removal afforded 14.5 g of a brown sticky solid. This solid was triturated with a diethyl ether/heptanes mixture. The light brown powder was filtered off and dried in a high vacuum (4.35 g). The filtrate was concentrated to dryness and purified by silica chromatography on a Combiflash ISCO purification system (Teledyne Isco Inc., Lincoln, Nebr.) (heptanes/ethyl acetate) to afford another 6.6 g of product (SM-1a) as a brown/orange solid (11.0 g, 91%). MS (ES+) 259.3 (M+H)$^+$.

$^1$H NMR (CDCl$_3$) δ 1.36 (s, 12H), 2.69 (t, 2H), 3.14 (t, 2H), 7.75-7.78 (m, 2H), 7.93 (s, 1H).

Preparation of Starting Material
5-Pyrimidin-2-ylindan-1-one (SM-1b)

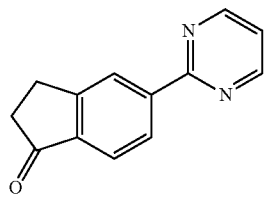

To a 500 mL round-bottomed flask was added 5-(4,4,5,5-tetramethyl-1,3,2-dioxaborolan-2-yl)indan-1-one (SM-1a, 12.9 g, 35.0 mmol), 2-chloropyrimidine (4.00 g, 35.0 mmol) and 400 mL of dimethoxyethane. Dry nitrogen gas was bubbled through the solution for 10 minutes. Aqueous sodium carbonate (2M in water, 140 mmol) was added followed by Pd(dppf)Cl$_2$ catalyst (100 mg, 0.12 mmol). The reaction mixture was degassed for another 15 minutes. The reaction was heated to 95° C. (silicon oil bath temperature) for 2 hours. A second aliquot of 2-chloropyrimidine (1 g, 8.73 mmol) and Pd(dppf)Cl$_2$ (100 mg, 0.12 mmol) were added to the reaction and heating was continued for another 2 hours. The reaction was cooled to room temperature overnight and 200 mL of water was added. The mixture was filtered through a Celite® pad and the organic phase was separated. The aqueous phase was extracted with ethyl acetate. The combined organic phases were washed with brine, dried over anhydrous MgSO$_4$ and evaporated to afford 13.2 g of an orange brown solid. This material was triturated with hexane to give 6.72 g of a light brown solid (SM-1b). The filtrate was concentrated and purified by silica chromatography (ethyl acetate/heptanes) on a Combiflash ISCO purification system (Teledyne Isco Inc., Lincoln, Nebr.) to afford another 600 mg of product (7.32 g, 98%). MS (ES+) 211.2 (M+H)$^+$. $^1$H NMR (CDCl$_3$) δ 2.77 (t, 2H), 3.24 (t, 2H), 7.28 (d, 1H), 7.87 (d, 1H), 8.48 (d, 1H), 8.57 (s, 1H), 8.87 (d, 2H).

Preparation of 5-(2-Methyl-pyrimidin-4-yl)-indan-1-one (SM-1c)

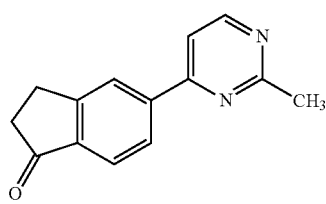

To a 50 mL flask containing 5-(4,4,5,5-tetramethyl-1,3,2-dioxaborolan-2-yl)indan-1-one (SM-1a, 600 mg, 2.32 mmol) was added 2-methyl-6-chloropyrimidine (298 mg, 2.32 mmol) and sodium carbonate (984 mg, 9.28 mmol). The mixture was dissolved in 20 mL 1,4-dioxane and 2.2 mL water. The mixture was purged with nitrogen for 15 minutes. Palladium tetrakis(triphenylphosphine) (53.2 mg, 0.046 mmol) was added and the solution was degassed for an additional 15 minutes. The reaction was heated under reflux for 16 hours and was concentrated to dryness. The residue was partitioned between ethyl acetate and water. The water layer was extracted with ethyl acetate and the combined organic layers were washed twice with water and once with brine. The solution was dried over anhydrous sodium sulfate, filtered and concentrated to afford 550 mg of an orange solid. The material was suspended in a minimal amount of ethyl acetate, and stirred at room temperature for 3 hours to afford a light yellow solid (SM-1c, 253 mg, 49%). MS (ES) 225.2 (M+H)$^+$. $^1$H NMR (CDCl$_3$) δ 2.74-2.78 (m, 2H), 2.81 (s, 3H), 3.23 (t, 2H), 7.55 (d, 1H), 7.86 (d, 1H), 8.01-8.04 (m, 1H), 8.21 (s, 1H), 8.72 (d, 1H).

Preparation of 5-(5-Methyl-pyrimidin-2-yl)-indan-1-one (SM-1d)

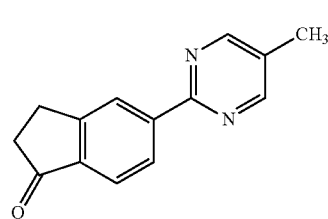

To a 100 mL round-bottomed flask was added 5-(4,4,5,5-tetramethyl-1,3,2-dioxaborolan-2-yl)indan-1-one (SM-1a, 1.50 g, 5.81 mmol), 2-chloro-5-methylpyrimidine (747 mg, 5.81 mmol), sodium carbonate (2.47 g, 23.3 mmol), 27 mL of dioxane, and 3 mL of water. The mixture was degassed with nitrogen for 15 minutes. Palladium tetrakis(triphenylphosphine) (356 mg, 0.31 mmol) was added and the mixture was degassed with nitrogen for an additional 15 minutes. The reaction was heated at reflux overnight. The reaction was cooled to room temperature and was partitioned between ethyl acetate and water. The aqueous layer was extracted with ethyl acetate (2×). The combined organic layers were washed with brine, dried over anhydrous MgSO$_4$, filtered and concentrated. The final product was purified by silica chromatography on a Combiflash ISCO purification system (Teledyne Isco Inc., Lincoln, Nebr.) eluting with 20-35% ethyl acetate in heptanes to provide a white solid (SM-1d, 1.12 g, 86%). MS (ES+) 225.2 (M+H$^+$). $^1$H NMR (CDCl$_3$) δ 2.38 (s, 3H), 2.74-2.78 (m, 2H), 3.23 (t, 2H), 7.85 (d, 1H), 8.44 (d, 1H), 8.53 (s, 1H), 8.68 (s, 2H).

Preparation of 5-(4-Methyl-pyrimidin-2-yl)-indan-1-one (SM-1e)

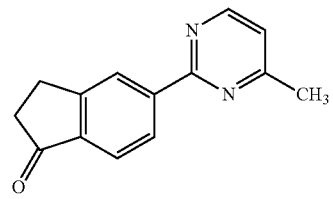

To a 25 mL flask containing 5-(4,4,5,5-tetramethyl-1,3,2-dioxaborolan-2-yl)indan-1-one (SM-1a, 50.0 mg, 0.19 mmol) was added 2-bromo-4-methyl pyrimidine (33.6 mg, 0.16 mmol) and sodium carbonate (23 mg, 0.76 mmol). The mixture was dissolved in 2 mL DME and 0.5 mL water. The mixture was purged with nitrogen for 15 minutes. Pd(dppf)Cl$_2$ (2.9 mg, 5 mol %) was added and the solution was degassed for an additional 15 minutes. The reaction was heated under reflux for 16 hours. The reaction was concentrated to dryness and was partitioned between ethyl acetate and water. The water layer was extracted with ethyl acetate and the combined organic layers were washed twice with water and once with brine. The solution was dried over anhydrous sodium sulfate, filtered and concentrated. The final product was purified by silica chromatography on a Combiflash ISCO purification system (Teledyne Corp., Lincoln, Nebr.) eluting with 0-50% ethyl acetate in heptanes. The product was obtained as a white solid (SM-1e, 8.7 mg, 20%). MS (ES+) 225.2 (M+H$^+$). $^1$H NMR (CDCl$_3$) δ 2.61 (s, 3H), 2.74-2.78 (m, 2H), 3.20 (t, 2H), 7.15 (d, 1H), 7.85 (d, 1H), 8.53 (d, 1H), 8.59 (s, 1H), 8.75 (d, 1H).

Preparation of 5-(1,3-Thiazol-2-yl)indan-1-one (SM-1f)

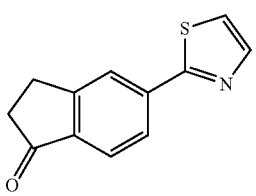

5-(4,4,5,5-Tetramethyl-1,3,2-dioxaborolan-2-yl)indan-1-one (SM-1a, 350 mg, 0.95 mmol) and 2-bromothiazole (156 mg, 0.95 mmol) were combined in DME (10 mL), and the mixture was purged with nitrogen for 10 minutes. Aqueous sodium carbonate solution (2M, 0.95 mL) and Pd(dppf)Cl$_2$ (34 mg, 5 mol %) were added. The solution was purged with nitrogen for 10 minutes and was heated at reflux for 5 hours. The reaction was cooled and held at room temperature overnight. The reaction mixture was partitioned between ethyl acetate and water and separated. The aqueous layer was washed with 15 mL ethyl acetate (2×), and the combined organic portions were washed with brine and dried over MgSO$_4$. Filtration and solvent removal afforded the crude product as a brown paste which was purified by silica chromatography on Combiflash ISCO purification system (Teledyne Corp., Lincoln Nebr.) eluting with a heptanes/ethyl acetate gradient. The final product was obtained as a light yellow flaky solid (SM-1f, 195 mg, 95%). MS (ES+) 216.2, $^1$H NMR (CDCl$_3$) δ 2.72-2.75 (m, 2H), 3.20 (t, 2H), 7.42 (d, 1H), 7.80 (d, 1H), 7.92 (d, 1H), 7.94-7.97 (m, 1H), 8.10 (br s, 1H).

Preparation of 5-(5-Methyl-1,3-thiazol-2-yl)indan-1-one (SM-1g)

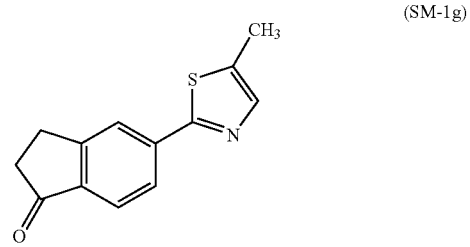 [SMILES: Cc1cnc(-c2ccc3c(c2)CCC3=O)s1]

In a 200 mL flask, a mixture of 2-chloro-5-methylthiazole (1.00 g, 7.48 mmol), 5-(4,4,5,5-tetramethyl-1,3,2-dioxaborolan-2-yl)indan-1-one (SM-1a, 1.93 g, 7.48 mmol) and sodium carbonate (3.18 g, 30 mmol) was dissolved in 68 mL dioxane and 6.8 mL water. The solution was degassed for 15 minutes with nitrogen. Palladium tetrakis(triphenylphosphine) (174 mg, 0.15 mmol) was added and the solution was degassed for an additional 15 minutes. The reaction was heated under reflux for 16 hours. After cooling, the mixture was concentrated to dryness and the residue partitioned between ethyl acetate and water. The water layer was extracted once with ethyl acetate. The combined organic layers were washed twice with water, once with brine, and were dried over anhydrous sodium sulfate. Evaporation afforded the crude product as an orange solid (1.96 g). The material was suspended in a minimal amount of ethyl acetate and was stirred at room temperature for 16 hours. The resulting solid was filtered off and dried to afford the title compound as a brown solid (609 mg, 35%). MS (ES+) 230.2 (M+H$^+$). $^1$H NMR (CDCl$_3$) δ 2.53 (s, 3H), 2.71-2.75 (m, 2H), 3.18 (t, 2H), 7.56-7.57 (m, 1H), 7.76-7.79 (m, 1H), 7.85-7.89 (m, 1H), 8.02 (br S, 1H).

Preparation of 5-(2H-1,2,3-Triazol-2-yl)indan-1-one (SM-1h)

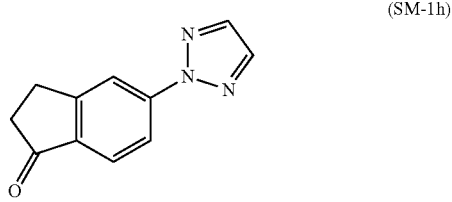 [SMILES: O=C1CCc2cc(-n3nccn3)ccc21]

To a solution of 5-bromo-1-indanone (5.0 g, 24 mmol) and 1H-triazole (4.90 g, 71.1 mmol) in 20 mL of DMF was added Fe(acac)$_3$ (838 mg, 2.37 mmol), copper (II) oxide (188 mg, 2.36 mmol) and potassium carbonate (3.27 g, 23.7 mmol). The reaction mixture was degassed with nitrogen for 10 minutes. The mixture was stirred at 90° C. for 6.5 hours and at 80° C. for 15 hours. The cooled reaction mixture was diluted with ethyl acetate and water. The biphasic mixture was passed through a thin Celite® pad, which was washed thoroughly with ethyl acetate. The combined organic layers were washed with water, brine and dried over anhydrous magnesium sulfate. Filtration and solvent removal afforded the crude product which was purified by silica chromatography using an ISCO (Teledyne Isco Inc., Lincoln Nebr.) column eluting with a 0-40% ethyl acetate/heptanes gradient to give the desired product as a pale yellow solid (2.60 g, 55%). MS (ES+) 200.1 (M+H)+. $^1$H NMR (CDCl$_3$) δ 2.85 (t, 2H), 3.24 (t, 2H), 7.83-7.90 (m, 3H), 8.15 (d, 1H), 8.21 (s, 1H).

Preparation of 5-Phenoxy-indan-1-one (SM-1i)

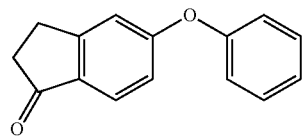
(SM-1i)

In an oven-dried round-bottomed flask was combined 5-hydroxy-1-indanone (112 mg, 0.76 mmol), phenylboronic acid (170 mg, 1.51 mmol) and anhydrous copper (II) acetate (195 mg, 1.13 mmol) in 2.5 mL of dichloromethane. Anhydrous pyridine (0.11 mL, 1.5 mmol) was added and the reaction was stirred overnight at room temperature. The reaction was concentrated to dryness and was purified with ISCO column chromatography (Teledyne Isco Inc., Lincoln Nebr.) (0-40% ethyl acetate/heptanes gradient) to give the desired product (SM-1i, 170 mg, 97%) as a clear oil which solidified on standing. MS (ES+) 225.3 (M+H)+. $^1$H NMR (CDCl$_3$) δ 2.48-2.70 (m, 2H), 2.87-3.08 (m, 2H), 6.78-7.01 (m, 2H), 7.03-7.11 (m, 2H), 7.15-7.30 (m, 1H), 7.32-7.53 (m, 2H), 7.70 (d, 1H).

Preparation of (5-Methoxypyridin-2-yl)acetic acid (SM-1aa)

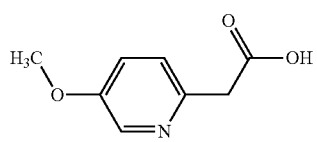
(SM-1aa)

A solution of tert-butyl cyanoacetate (3.75 mL, 26.2 mmol) in 20 mL of anhydrous dioxane was purged with nitrogen. To the solution was added 21.5 mL of potassium tert-butoxide (21.5 mmol, 1M in THF). After stirring for 5 minutes, 2-bromo-5-methoxypyridine (2 g, 10.7 mmol) dissolved in 4 mL of dioxane was added followed by 1,1'-bis(diphenylphosphino)ferrocene palladium dichloride-CH$_2$Cl$_2$ (1:1 complex) (239 mg, 0.29 mmol). The mixture was heated at 70° C. overnight after which a second aliquot of catalyst (120 mg, 0.15 mmol) was added. After heating for an additional 3 hours the mixture was cooled to room temperature and 2N acetic acid (80 mL) was added. The mixture was filtered, washing with water (2×) and the obtained crude product was dried in a current of air (1.22 g). The filtrate was extracted twice with ethyl acetate. The combined extracts were washed with brine, dried over anhydrous sodium sulfate and concentrated to a black oil which was combined with the above solids to yield 3.46 g of crude material. This material was used directly in the next step.

The crude tert-butyl cyano(5-methoxypyridin-2-yl)acetate (3.46 g) was suspended in a mixture of 45 mL of water and 45 mL of concentrated HCl. The mixture was heated at 60° C. for 1 hour and at reflux overnight. The reaction was cooled and the water was removed under vacuum. The oily solid residue was redissolved in a minimal amount of water (~50-70 mL) and 2N NaOH was added to adjust the pH to approximately 14. The solution was washed with diethyl ether and was reacidified to pH 4 with 2N HCl and concentrated to dryness to give a white solid. This solid was triturated in hot THF (3×) and the combined supernatants were cooled in an icebath to initiate crystallization. After 20 minutes, the solid was collected by filtration washing with heptanes to give (5-methoxypyridin-2-yl)acetic acid (1.25 g). A second crop of product precipitated from the filtrate (0.39 g). The filtrate was concentrated, and the material was triturated with hot ethyl acetate and heptanes to provide a third crop of product as a brown solid (0.11 g of lower purity). The total yield of SM-1aa was 1.75 g (98%). MS (ES+) 168.1 (M+H)+. $^1$H NMR (DMSO-d$_6$) δ 3.66 (s, 2H), 3.81 (s, 3H), 7.27 (d, 1H), 7.33-7.36 (m, 1H), 8.18 (d, 1H).

Preparation of (5-Methylpyridin-2-yl)acetic acid (SM-1ab)

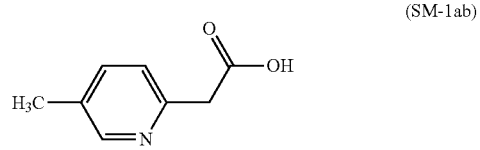
(SM-1ab)

(5-Methylpyridin-2-yl)acetic acid was prepared using analogous procedures to those used for the preparation of (5-methoxypyridin-2-yl)acetic acid (SM-1ab) substituting 2-bromo-5-methylpyridine for 2-bromo-5-methoxypyridine. *Note: The title compound is prone to base-mediated decarboxylation and should be stored in the refrigerator. Care must be used when handling the material. MS (ES+) 152.1 (M+H)+. $^1$H NMR (DMSO-d$_6$) δ 2.21-2.30 (m, 3H), 3.67 (s, 2H), 7.22 (d, 1H), 7.52-7.67 (m, 1H), 8.29 (s, 1H).

Preparation of (5-Ethylpyridin-2-yl)acetic acid (SM-1ac)

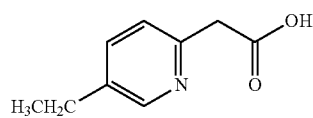
(SM-1ac)

A solution of tert-butyl cyanoacetate (11.6 mL, 81.2 mmol) in 110 mL of anhydrous dioxane was purged with nitrogen. To the solution was added 164 mL of potassium tert-butoxide (164 mmol, 1M in THF). After stirring for 5 minutes, 2,5-dibromopyridine (19.4 g, 82.9 mmol) was added followed by Pd(dppf)$_2$ (1.86 g, 2.27 mmol). The orange mixture was heated at 70° C. and became very thick. After 20 minutes, the heating bath was removed and the mixture was cooled to room temperature. The reaction was placed in a cooling bath and 380 mL of 2N AcOH was added. The mixture was stirred for 10 minutes and the solids were removed by filtration. The orange filter cake residue was washed several times with water followed by heptanes. The orange solid was dissolved in dichloromethane and the solution was washed with water and brine, dried ($Na_2SO_4$) and concentrated to afford a dark orange solid (20.1 g) which was used directly in the following procedure.

The crude (5-bromo-pyridin-2-yl)-cyano-acetic acid tert-butyl ester (20.1 g) was dissolved in anhydrous THF (300 mL) and the dark red solution was cooled in an ice-water bath. After purging in a stream of nitrogen, diethylzinc (88.0 mL, 88.0 mmol, 1M in hexane) was slowly added over 50 minutes. The internal temperature was maintained below 4° C. The catalyst 1,1'-bis(diphenylphosphino)ferrocene palladium dichloride-$CH_2Cl_2$ (1:1 complex) (1.61 g, 1.97 mmol) was added and the mixture was heated at 50° C. for 35 minutes. The reaction was cooled in an ice bath and saturated aqueous ammonium chloride solution was added. The mixture was stirred for 10 minutes and EtOAc was added. The mixture was filtered through Celite® with the aid of EtOAc. The filtrate layers were separated and the organic layer was washed with brine and was dried over anhydrous sodium sulfate. The organic solution was concentrated to dryness and the residue was purified by ISCO (Teledyne Isco Inc., Lincoln) column chromatography (EtOAc/heptanes gradient) to give cyano-(5-ethyl-pyridin-2-yl)-acetic acid tert-butyl ester as a dark yellow solid (7.31 g). This material was used directly in the next step.

Cyano-(5-ethyl-pyridin-2-yl)-acetic acid tert-butyl ester (7.3 g) was mixed with 70 mL of water and 70 mL of 12N HCl and was heated at 104° C. for 3 hours before removing the volatiles in vacuo. Water was added to dissolve the solids and the pH of the solution was adjusted to 9-10 with 2N NaOH. The solution was washed with 2-methylTHF (2×). The aqueous solution was adjusted to pH 4 with 2N HCl and was concentrated under vacuum to an oily solid. The residue was triturated with hot chloroform and heptanes to afford (5-ethylpyridin-2-yl)acetic acid (SM-1ac) as a tan solid (3.88 g, 31%, 3 steps). MS (ES+) 166.1 (M+H)$^+$. $^1$H NMR (DMSO-$d_6$) δ 1.16 (t, 3H), 2.57 (q, 2H), 3.66 (s, 2H), 7.22 (d, 1H), 7.56 (dd, 1H), 8.31 (d, 1H), 12.44 (br s, 1H).

Preparation of (2-Methylimidazo[2,1-b][1,3]thiazol-6-yl)acetic acid hydrochloride (SM-1ad)

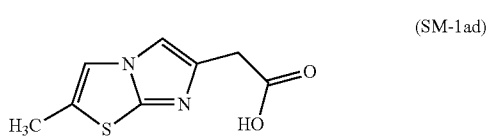

A solution of bromine (436 g, 2.73 mol) in acetic acid (750 mL) was added to a solution of ethyl 3-oxobutanoate (355 g, 2.73 mol) in acetic acid (1000 mL). The mixture was stirred at room temperature for 72 hours and was concentrated under reduced pressure at 45° C. to remove the acetic acid. The residue was partitioned between methylene chloride (400 mL) and water (250 mL). The organic layer was washed with saturated sodium bicarbonate (2×300 mL), water (300 mL), brine (125 mL) and was dried over anhydrous magnesium sulfate. The solution was filtered and concentrated to give ethyl 4-bromo-3-oxobutanoate as a yellow oil (421 g).

To a solution of 2-amino-5-methylthiazole (150 g, 1.31 mol) in acetone (1500 mL) was slowly added ethyl 4-bromo-3-oxobutanoate (345 g, 1.65 mol). The temperature of the reaction mixture was maintained between 22-40° C. The mixture turned into a thick paste and acetone (300 mL) was added to facilitate stirring. After stirring at room temperature overnight, the mixture was filtered and the filter cake was washed with acetone to provide a white solid. The solid was washed with hexanes and was dried in a vacuum oven at 40° C. for 4 hours to give 4-(2-amino-5-methyl-thiazol)-3-oxobutyric acid ethyl ester hydrobromide (272 g).

To 4-(2-amino-5-methyl-thiazol)-3-oxobutyric acid ethyl ester hydrobromide (272 g, 0.84 mol) was added anhydrous ethanol (675 mL) and the thick mixture was heated at 90° C. for 2 hours. During this time, the solids went into solution. The reaction mixture was concentrated to give a brown semi-solid which was triturated with ethanol to provide a white fluffy solid which was collected by filtration. The solids were washed with $Et_2O$ and dried under vacuum at 40° C. for 4 hours to give ethyl(2-methylimidazo[2,1-b][1,3]thiazol-6-yl)acetate hydrobromide (226 g).

Ethyl(2-methylimidazo[2,1-b][1,3]thiazol-6-yl)acetate hydrobromide (226 g, 0.74 mol) was dissolved in water (350 mL) and the solution was adjusted to pH 7 by addition of potassium carbonate (51.0 g, 0.37 mol). The aqueous solution was extracted with methylene chloride (300 mL) and the organic phase was washed with brine (150 mL), dried over anhydrous magnesium sulfate, filtered and concentrated to give ethyl (2-methylimidazo[2,1-b][1,3]thiazol-6-yl)acetate as a brown oil (151.3 g).

Ethyl(2-methylimidazo[2,1-b][1,3]thiazol-6-yl)acetate (151.3 g, 0.67 mol) was dissolved in 10% aqueous HCl (435 mL) and the mixture was heated at reflux for 2 hours. The reaction mixture was cooled to room temperature and was concentrated in vacuo to give a yellow oil. Ethanol (100 mL) and diethylether (200 mL) were added and the resulting white precipitate was collected by filtration and dried in a vacuum oven overnight to give 144.3 g (93%) of final product, (2-methylimidazo[2,1-b][1,3]thiazol-6-yl)acetic acid hydrochloride). MS (ES+) 197.1 (M+H)$^+$. $^1$H NMR ($CD_3OD$) δ 2.48 (s, 3H), 3.88 (s, 2H), 7.81 (s, 1H), 7.85 (s, 1H).

Preparation of 2-(2-Methylimidazo[2,1-b][1,3,4]thiadiazol-6-yl)acetic acid (SM-1ae)

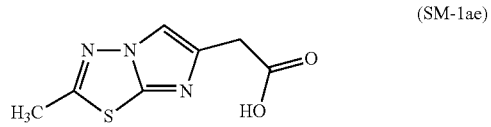

To a solution of 3-oxo-butyric acid ethyl ester (10.0 g, 78 mmol) in 100 mL of chloroform was added bromine (2.02 mL, 78 mmol) dropwise. The solution was stirred at room temperature for 60 hours without capping the flask (extended stirring at room temperature in an open system with oxygen flow facilitated the bromine migration from C-2 to C-4). The reaction mixture was partitioned between chloroform and water and the organic phase was dried over sodium sulfate. The organic solution was concentrated to provide 4-bromo-3-oxo-butyric acid ethyl ester (12.5 g, 45%). The crude product was taken on to the next step without further purification.

A mixture of 5-methyl-[1,3,4]thiadiazol-2-ylamine (300 mg, 2.6 mmol), 4-bromo-3-oxo-butyric acid ethyl ester (908 mg, 2.6 mmol) and 5 mL of MeOH was combined in a sealed tube and was heated to 80° C. for 3 hours. The reaction was cooled and the MeOH was removed in vacuo. The residue was dissolved in dichloromethane and the organic solution was washed with saturated aqueous NaHCO₃ solution (2×). The organic solution was dried over sodium sulfate, filtered and concentrated. The crude product was purified by Combiflash (Teledyne ISCO, Lincoln, Nebr.) chromatography using 0-100% EtOAc/heptanes. Both the desired product and (2-methyl-imidazo[2,1-b][1,3,4]thiadiazol-6-yl)acetic acid methyl ester (formed by trans esterification with solvent MeOH) were obtained with a total mass of 333 mg (54%). The crude mixture was used directly in the next step To (2-methyl-imidazo[2,1-b][1,3,4]thiadiazol-6-yl)acetic acid methyl ester/ethyl ester (600 mg, 2.84 mmol) in 5 mL MeOH was added aqueous NaOH (3M, 2.8 mL) and the mixture was stirred at room temperature overnight. To the mixture was added Amberlyst 15 (wet) ion-exchange resin (Aldrich) until the pH reached 5. The resin was removed by filtration and the filtrate was concentrated to obtain the title compound (300 mg, 56%) SM-1ae which required no futher purification. MS (ES+) 198.1 (M+H)⁺ 1H NMR (DMSO-d₆) δ 2.66 (s, 3H), 3.53 (s, 2H), 7.86 (s, 1H), 12.31 (br s, 1H).

Alternative Preparation of 2-(2-Methylimidazo[2,1-b][1,3,4]thiadiazol-6-yl)acetic acid (SM-1ae)

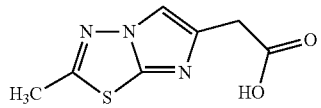

(SM-1ae)

A mixture of 5-methyl-[1,3,4]thiadiazol-2-ylamine (10 g, 86.8 mmol), 4-chloro-3-oxo-butyric acid ethyl ester (42.9 g, 261 mmol) and 50 mL of EtOH was combined in a sealed tube and was heated to 90° C. overnight. The reaction was cooled and the EtOH was removed in vacuo. The residue was dissolved in dichloromethane and the organic solution was washed with saturated aqueous NaHCO₃ solution (2×). The organic solution was dried over sodium sulfate, filtered and concentrated. The crude product was purified by Combiflash (Teledyne ISCO, Lincoln, Nebr.) chromatography using 0-100% EtOAc/heptanes to give 4.1 g of (2-methyl-imidazo [2,1-b][1,3,4]thiadiazol-6-yl)acetic acid ethyl ester.

To (2-methyl-imidazo[2,1-b][1,3,4]thiadiazol-6-yl)acetic acid ethyl ester (4.0 g, 17.76 mmol) in 30 mL EtOH was added aqueous NaOH (1M, 19.5 mL) and the mixture was stirred at room temperature for 1 hour or until LC-MS showed complete consumption of starting material. To the mixture was added Amberlyst 15 (wet) ion-exchange resin (Aldrich) until the pH reached 5. The resin was removed by filtration and the filtrate was concentrated to obtain 1.7 g (50%) of the title compound (SM-1ae). Further purification was performed by trituration with water and ethyl ester to obtain a white solid. MS (ES+) 198.1 (M+H)⁺ ¹H NMR (DMSO-d₆) δ 2.66 (s, 3H), 3.53 (s, 2H), 7.86 (s, 1H), 12.31 (br s, 1H).

Preparation of Pyrazolo[1,5-a]pyridin-2-ylacetic acid (SM-1af)

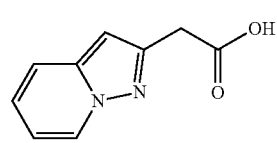

(SM-1af)

The above compound (SM-1af) was prepared according the procedure described in Stefan Löber, S.; Hübner, H.; Gmeiner B.; *Biorg. Med. Chem. Lett.* 12(17), 2377 (2002).

Preparation of (4-Cyclopropylphenyl)acetic acid (SM-1ag)

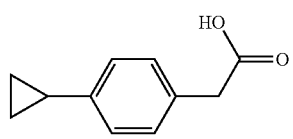

(SM-1ag)

To a solution of methyl(4-iodophenyl)acetate (1.5 g, 5.4 mmol), cyclopropylboronic acid (607 mg, 7.06 mmol), potassium phosphate (4.04 g, 29.7 mmol) and tricyclohexylphosphine (152 mg, 10 mol %) in 25 mL toluene under nitrogen was added water (1.25 mL) and palladium acetate (61 mg, 5 mol %). The mixture was heated to 100° C. for 10 hours. After cooling to room temperature, water and ethyl acetate were added and the mixture was filtered through a Celite® pad to remove insoluble material. The layers were separated and the water layer was washed 2× with ethyl acetate. The combined organic layers were washed with brine and dried over anhydrous magnesium sulfate. Solvent removal gave 1.5 g of a dark yellow paste which was purified by silica chromatography on an ISCO (Teledyne Corp., Thousand Oaks, Calif.) column, eluting with a gradient 0/100 to 30/70 ethyl acetate/heptanes, to give methyl(4-cyclopropylphenyl)acetate as a yellow semi-solid (718 mg, 69%).

Methyl(4-cyclopropylphenyl)acetate (710 mg, 3.73 mmol) was dissolved in 5 mL THF, 5 mL MeOH, and aqueous 1N NaOH (7.46 mmol) and the resulting mixture was heated at 45° C. overnight. After cooling to ambient temperature, the reaction was concentrated in vacuo and the residue was diluted with water (50 mL). The aqueous material was acidified with 1N HCl to pH~3. A light brown precipitate formed which was collected by filtration and dried in a vacuum oven for 3 days to give (4-cyclopropylphenyl)acetic acid (SM-1ag, 395 mg, 60%). MS (ES−) 175.2 (M−H). ¹H NMR (DMSO-d$_6$) δ 0.57-0.61 (m, 2H), 0.86-0.91 (m, 2H), 1.81-1.88 (m, 1H), 3.45 (s, 2H), 6.97 (d, 2H), 7.08 (d, 2H), 12.20 (br s, 1H).

Preparation of 2-(2-cyano-4-methoxyphenyl)acetic acid (SM-1ah)

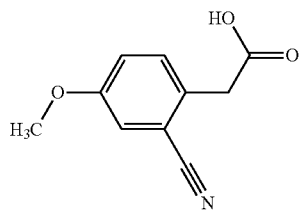
(SM-1ah)

To a solution of (2-bromo-4-methoxy-phenyl)-acetic acid (1.07 g, 4.37 mmol) in 25 mL MeOH was added two drops of concentrated H$_2$SO$_4$ and the reaction was heated to reflux. After 18 hours, the solvent was removed in vacuo to give 920 mg of (2-bromo-4-methoxy-phenyl)-acetic acid methyl ester. This material was used directly in the next step without further purification.

To a microwave vial was added (2-bromo-4-methoxy-phenyl)-acetic acid methyl ester (200 mg, 0.77 mmol), copper (I) cyanide (138 mg, 1.54 mmol), a stir bar and 1 mL of N-methyl-pyrrolidinone. The vial was capped and heated at 170° C. for 15 minutes in a microwave reactor. The resulting dark solution was purified directly on an ISCO (Teledyne Isco Inc., Lincoln Nebr.) 12 g column using a 0-20% MeOH in dichloromethane gradient. The desired product eluted in 100% dichloromethane to give 120 mg (76%) of (2-cyano-4-methoxy-phenyl)-acetic acid methyl ester as an orange oil.

The (2-cyano-4-methoxy-phenyl)-acetic acid methyl ester (120 mg, 0.585 mmol) was dissolved in 10 mL THF and 2 mL water and LiOH monohydrate (101 mg, 2.34 mmol) was added. The mixture was heated at 55° C. overnight. The mixture was cooled to room temperature and the solvent was removed in vacuo. The residue was dissolved in 30 mL water and adjusted to pH ~14 with aqueous 1N NaOH. The aqueous layer was washed with 50 mL of ethyl acetate. The organic extract was discarded and the aqueous phase was treated with 1N HCl (aq.) to pH~2-3. The aqueous solution was washed with 75 mL ethyl acetate and the organic solution was dried (MgSO$_4$), filtered and concentrated to give 86 mg (77%) of the title compound (SM-1ah) as a yellow solid. MS (ES+) 192.2 (M+H)$^+$ $^1$H NMR (CDCl$_3$) δ 3.81 (s, 3H), 3.84 (s, 2H), 7.09 (dd, 1H), 7.13 (d, 1H), 7.30 (d, 1H), 10.22 (br s, 1H).

Preparation of (2-Acetylamino-4-methoxy-phenyl)-acetic acid (SM-1ai)

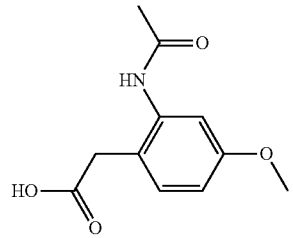
(SM-1ai)

Ethyl cyanoacetate (2.56 mL, 24.0 mmol) was added dropwise to a suspension of 959 mg of NaH (60%, 24.0 mmol) in 10 mL of DMF. The mixture was stirred for 1 h at room temperature. CsF (61 mg, 0.4 mmol) and a solution of 4-chloro-3-nitro-anisole (1.5 g, 8.0 mmol) in 2 mL of DMF were added and the mixture was stirred overnight at 70° C. The reaction mixture was cooled to room temperature and was quenched by the addition of 5 mL of water. Aqueous 1N HCl (5 mL) was added to adjust the pH to 3-4 and the mixture was diluted with dichloromethane. The organic layer was washed with saturated brine, dried over Na$_2$SO$_4$, and dried in vacuo. The crude product was purified on a Biotage (Biotage Inc.) 50 g silica column, eluting with 0-40% EtOAc in heptane over 40 minutes to provide 1.83 g (87%) of cyano-(4-methoxy-2-nitro-phenyl)-acetic acid ethyl ester.

To cyano-(4-methoxy-2-nitro-phenyl)-acetic acid ethyl ester (945 mg, 3.58 mmol) was added 30 mL of a saturated solution of aqueous sodium carbonate. The mixture was stirred overnight at 55° C. After cooling to room temperature, the mixture was diluted with ethyl acetate. The organic layer was washed with saturated brine, dried over Na$_2$SO$_4$ and concentrated in vacuo. The crude product was purified on a Biotage (Biotage Inc.) 10 g silica column, eluting with 0-40% EtOAc in heptanes to provide 258 mg (37%) of (4-methoxy-2-nitro-phenyl)-acetonitrile.

To a suspension of (4-methoxy-2-nitro-phenyl)-acetonitrile (258 mg, 1.34 mmol) in 3 mL of water was added 2 mL of concentrated sulfuric acid. After 20 minutes, the reaction mixture was treated with ice resulting in the precipitation of brown solids. After filtration, 149 mg of (4-methoxy-2-nitro-phenyl)-acetic acid was obtained as a brown solid. The acid was dissolved in methanol (2 mL) and thionyl chloride (0.15 mL, 2.05 mmol) was added. The mixture was stirred overnight and was concentrated in vacuo. The residue was partitioned between 50 mL of ethyl acetate and 10 mL of saturated aqueous NaHCO$_3$. The organic layer was washed with saturated brine, dried over Na$_2$SO$_4$ and concentrated in vacuo to afford 154 mg (97%) of (4-methoxy-2-nitro-phenyl)-acetic acid methyl ester.

To a suspension of (4-methoxy-2-nitro-phenyl)-acetic acid methyl ester (154 mg, 0.68 mmol) in 3 mL of acetic acid was added acetic anhydride (3.0 mL, 30.0 mmol) and zinc (nanopowder, 220 mg, 3.36 mmol) in portions over 5 min at 0° C. The reaction mixture was maintained for 30 minutes at 0° C. and 1.5 h at room temperature. Additional zinc powder (110 mg, 1.68 mmol) was added, and the reaction mixture was stirred overnight at room temperature. After filtration, the mixture was partitioned between 50 mL of ethyl acetate and 10 mL of saturated aqueous NaHCO$_3$. The organic layer was washed with brine, dried over Na$_2$SO$_4$ and concentrated in vacuo. The crude product was purified on a Biotage (Biotage Inc.) 10 g silica column, eluted with 0-40% EtOAc in heptane to provide 49 mg (68%) of (2-acetylamino-4-methoxy-phenyl)-acetic acid methyl ester. $^1$H NMR (CDCl$_3$) δ 2.23 (s, 3H), 3.57 (s, 2H), 3.73 (s, 3H), 3.81 (s, 3H), 6.66 (dd, 1H), 7.09 (d, 1H), 7.57 (d, 1H).

To a solution of (2-acetylamino-4-methoxy-phenyl)-acetic acid methyl ester (49 mg, 0.21 mmol) in 1.5 mL of methanol was added aqueous 1N NaOH (1.5 mL, 1.5 mmol). The mixture was stirred for 3 h at room temperature. and the pH was adjusted to ~4 by the addition of Amberlyst 15 ion-exchange resin. After filtration, the filtrate was concentrated to give 46 mg (100%) of 2-acetylamino-4-methoxy-phenyl)-acetic acid which was used without further purification.

Preparation of 2-(2,3-Dihydro-[1,4]dioxino[2,3-b] pyridin-6-yl)acetic acid (SM-1aj)

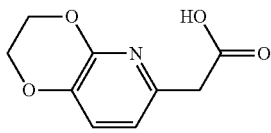

(SM-1aj)

To a mixture of 6-methylpyridin-3-ol (235 g, 2.75 mol) and water (5.28 L) at 0° C. was added Na$_2$CO$_3$ (440 g, 5.5 mol) and the mixture was stirred at room temperature for 30 minutes. A solution of I$_2$ (760 g, 3.85 mol) and KI (760 g, 5.83 mol) in water (5.28 L) was added dropwise to the reaction over a period of 1 hour. The mixture was stirred at room temperature for 3 hours and the resulting precipitate was collected by filtration to afford 2-iodo-6-methylpyridin-3-ol (390 g, 77.0%) as a yellow solid which was used without further purification.

To a stirred mixture of 2-iodo-6-methylpyridin-3-ol (530 g, 2.25 mol), Cs$_2$CO$_3$ (876 g, 2.7 mol) and DMF (2.5 L) was added 2-bromo-ethanol (560 g, 4.51 mol) dropwise at 0° C. The mixture was stirred at 90° C. overnight. The reaction was cooled and the solvent was removed in vacuo. The residue was diluted with water (2 L) and the aqueous solution was extracted with CH$_2$Cl$_2$ (3×350 mL). The combined organic layers were washed with brine (2×150 mL), dried over anhydrous Na$_2$SO$_4$ and concentrated to afford 2-(2-iodo-6-methylpyridin-3-yloxy)ethanol (630 g) as a brown solid which was used directly in the next step without further purification.

To a stirred solution of 2-(2-iodo-6-methylpyridin-3-yloxy)ethanol (350 g, 1.25 mol) in anhydrous DMF (3.5 L) was added NaH (60 g, 1.5 mol), Cu (33.7 g, 0.53 mol) and CuSO$_4$ (100 g, 0.63 mol) at 0° C. After the addition, the mixture was stirred at 100° C. overnight. After cooling, the solvent was removed in vacuo and the residue was diluted with water (1.5 L). The aqueous solution was extracted with CH$_2$Cl$_2$ (3×350 mL). The combined organic layers were washed with brine (2×100 mL), dried over anhydrous Na$_2$SO$_4$ and concentrated. The residue was purified via column chromatography (silica gel, EtOAc/petroleum ether 1:20) to yield 6-methyl-2,3-dihydro-[1,4]dioxino[2,3-b]pyridine (30.0 g, 16%) as a yellow oil.

To a 0° C. solution of 6-methyl-2,3-dihydro-[1,4]dioxino [2,3-b]pyridine (19 g, 0.12 mol) in anhydrous CH$_2$Cl$_2$ (250 mL) was added m-CPBA (32 g, 0.15 mol) portionwise. The mixture was stirred at room temperature overnight. The solvent was removed in vacuo and the residue was purified via column chromatography (silica gel, EtOAc/petroleum ether 1:1) to yield 6-methyl-2,3-dihydro-[1,4]dioxino[2,3-b]pyridine 5-oxide (15.0 g, 72%) as a white solid.

A solution of 6-methyl-2,3-dihydro-[1,4]dioxino[2,3-b] pyridine 5-oxide (60 g, 0.36 mol) in Ac$_2$O (500 mL) was stirred at reflux for 5 hours. The reaction was cooled and the solvent was removed in vacuo to yield (2,3-dihydro-[1,4] dioxino[2,3-b]pyridin-6-yl)methyl acetate (75 g, 99%) as a dark oil, which was used in the next step without further purification.

To a stirred solution of (2,3-dihydro-[1,4]dioxino[2,3-b] pyridin-6-yl)methyl acetate (75.0 g, 0.36 mol) in MeOH (500 mL) was added aqueous NaOH (2M, 350 mL, 0.72 mol) dropwise at 0° C. After the addition, the mixture was stirred at room temperature overnight. The solvent was removed in vacuo and the residue was diluted with water (250 mL). The aqueous solution was washed with CH$_2$Cl$_2$ (2×200 mL). The combined organic layers were washed with brine (2×100 mL), dried over anhydrous Na$_2$SO$_4$ and concentrated to yield (2,3-dihydro-[1,4]dioxino[2,3-b]pyridin-6-yl)methanol (48.0 g, 80%) as a grey solid. The crude material was used directly in the next step.

To a stirred solution of (2,3-dihydro-[1,4]dioxino[2,3-b] pyridin-6-yl)methanol (24 g, 0.14 mol) in anhydrous CH$_2$Cl$_2$ (500 mL) was added activated MnO$_2$ (25.0 g, 0.28 mol) at 0° C. in portions. The mixture was stirred at room temperature for 5 hours and another batch of activated MnO$_2$ (25.0 g, 0.28 mol) was added in identical fashion. The mixture was stirred at room temperature overnight. The mixture was filtered through a Celite® pad and the filtrate was concentrated. The residue was purified via column chromatography (silica gel, EtOAc/petroleum ether 1:15 to 1:10) to yield 2,3-dihydro-[1, 4]dioxino[2,3-b]pyridine-6-carbaldehyde (16.0 g, 67%) as a yellow solid. MS (ES+) 166.2 (M+H)$^+$. $^1$H NMR δ (CDCl$_3$) 4.40 (s, 2H), 4.91 (s, 2H), 7.37 (d, 1H), 7.61 (d, 1H), 9.65 (s, 1H).

To a 0° C. solution of diethyl 1,3-dithian-2-ylphosphonate (12.0 g, 46.8 mmol, prepared as described in Saito, T. et al., J. Am. Chem. Soc. 1998 120 (45) 11633-11644) in THF (300 mL) was added n-BuLi (20.0 mL, 49.9 mmol, 2.5 M in hexanes) dropwise. The mixture was stirred at 0° C. for 10 minutes and was cooled to −78° C. A solution of 2,3-dihydro-[1,4]dioxino[2,3-b]pyridine-6-carbaldehyde (5.15 g, 31.2 mmol) in THF (50 mL) was added dropwise via a cannula to the phosphonate solution. The mixture was slowly warmed to room temperature over 4 hours. Saturated NH$_4$Cl was added and the aqueous solution was washed with EtOAc. The organic solution was dried (Na$_2$SO$_4$) and concentrated in vacuo to provide the crude ketene dithioacetal. To a solution of the crude ketene in MeOH (400 mL) was added silver nitrate (17.2 g, 101 mmol). The reaction was heated to 60° C. overnight. The reaction was cooled to room temperature and was filtered through Celite®. The filter cake was washed with EtOAc and the filtrate was concentrated to afford methyl 2-(2,3-dihydro-[1,4]dioxino[2,3-b]pyridin-6-yl)acetate (5.50 g) which was used without further purification in the next step.

To methyl 2-(2,3-dihydro-[1,4]dioxino[2,3-b]pyridin-6-yl)acetate (5.50 g, 25.1 mmol) in methanol (100 mL) was added aqueous 1N NaOH (50.2 mmol). The reaction was stirred at room temperature for 1 hour. The reaction mixture was concentrated and water (200 mL) was added. The aqueous solution was washed with 2-methyl-THF (2×200 mL). The aqueous layer was adjusted to pH~5 and was concentrated. The resulting solids were suspended in chloroform (200 mL) and the mixture was heated to reflux with stirring. The mixture was heated at reflux for 10 minutes and was filtered while hot. The resulting filtrate was concentrated in vacuo to afford 2-(2,3-dihydro-[1,4]dioxino[2,3-b]pyridin-6-yl)acetic acid (SM-1aj, 2.5 g, 57%). MS (ES+) 196.2 (M+H)$^+$. $^1$H NMR (CDCl$_3$) δ 3.23 (s, 2H), 4.14 (s, 2H), 4.30 (s, 2H), 6.77 (d, 1H), 7.08 (d, 1H).

Preparation of (4,5,6,7-Tetrahydro-pyrazolo[1,5-a]pyridin-2-yl)-acetic acid hydrochloride (SM-1ak)

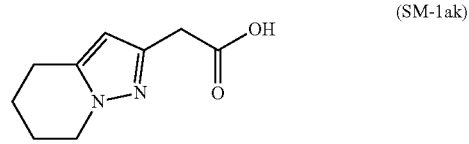 [SMILES: O=C(O)Cc1cc2n(n1)CCCC2]

(SM-1ak)

Methyl 2-(2-methoxy-2-oxoethyl)pyrazolo[1,5-a]pyridine-3-carboxylate (42.0 mg, 0.17 mmol), as prepared according to the procedure described in Stefan Löber, S.; Hübner, H.; Gmeiner B.; *Biorg. Med. Chem. Lett.* 12(17), 2377 (2002), was dissolved in MeOH (5 mL) and was hydrogenated on an H-Cube® hydrogenation apparatus with 10% Pd/C at 40° C. for 1 hour. The methanol solution was removed in vacuo to afford methyl 2-(2-methoxy-2-oxoethyl)-4,5,6,7-tetrahydropyrazolo[1,5-a]pyridine-3-carboxylate (39 mg, 91%), which was used in the next step without further purification.

The crude 2-(2-methoxy-2-oxoethyl)-4,5,6,7-tetrahydropyrazolo[1,5-a]pyridine-3-carboxylate (39 mg, 0.16 mmol) was suspended in concentrated HCl (5 mL) and was heated at reflux for 2 hours. The reaction was cooled and concentrated in vacuo to afford the title compound (30 mg, 88%). The material was used directly without further purification. MS (ES+) 181.2 (M+H)$^+$. Retention time: 1.26 min XBridge C18 4.6×50 mm 5 um, 5-100% acetonitrile:water (0.1% formic acid).

Preparation of Benzyl 2,7-diazaspiro[3.5]nonane-7-carboxylate (SM-2a)

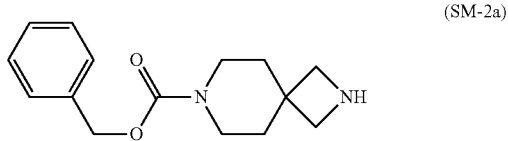 [SMILES: O=C(OCc1ccccc1)N1CCC2(CC1)CNC2]

(SM-2a)

Tert-butyl 2,7-diazaspiro[3.5]nonane-2-carboxylate (21.0 g, 92.8 mmol) and triethylamine (20 mL, 186 mmol) were dissolved in dichloromethane (200 mL). The reaction was cooled to 0° C. and a solution of benzyl 2,5-dioxopyrrolidin-1-yl carbonate (23.1 g, 92.8 mmol) in dichloromethane (25 mL) was added dropwise. The ice-bath was removed and the reaction was stirred at room temperature for 6 hours. The reaction was diluted with dichloromethane (100 mL), washed with 10% aqueous citric acid solution (100 mL), water (100 mL) and brine (100 mL). The organic solution was dried over MgSO$_4$, filtered and concentrated to afford 7-benzyl 2-tert-butyl 2,7-diazaspiro[3.5]nonane-2,7-dicarboxylate (33.5 g, 100%) as colorless oil, which was used in the next step without further purification.

7-Benzyl 2-tert-butyl 2,7-diazaspiro[3.5]nonane-2,7-dicarboxylate (33.4 g, 92.8 mmol) was dissolved in a solution of TFA (50 mL) and dichloromethane (200 mL) and the reaction was stirred at room temperature overnight. The reaction was concentrated in vacuo and the residue was neutralized with saturated aqueous Na$_2$CO$_3$ (100 mL). The aqueous solution was washed with ethyl acetate (2×100 mL). The combined organic layers were washed with brine (100 mL), dried (Na$_2$SO$_4$) and concentrated to give a yellow oil, which upon co-evaporation with dichloromethane provided benzyl 2,7-diazaspiro[3.5]nonane-7-carboxylate (SM-2a) as a white solid. (17.6 g, 73%). MS (ES+) 261.4 (M+H)$^+$. $^1$H NMR (CDCl$_3$) δ 1.67-1.89 (m, 4H), 2.86-3.18 (m, 2H), 3.40-3.64 (m, 7H), 5.12 (s, 2H), 7.30-7.39 (m, 5H).

Preparation of tert-Butyl 4-(chloromethyl)-4-formylpiperidine-1-carboxylate (SM-3a)

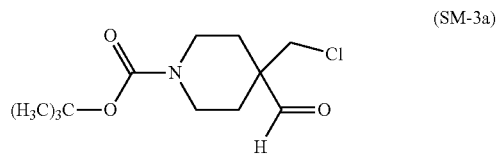 [SMILES: CC(C)(C)OC(=O)N1CCC(C=O)(CCl)CC1]

(SM-3a)

To a solution of diisopropylamine (22.6 mL, 159 mmol) in anhydrous THF (140 mL) in an oven-dried round-bottomed flask was added n-BuLi (65.4 mL, 163 mmol, 2.50 M in hexanes) dropwise at 0° C. The solution was stirred for 45 minutes and 1-tert-butyl 4-methyl piperidine-1,4-dicarboxylate (20 g, 80 mmol) in THF (60 mL) was added dropwise at 0° C. and the mixture was stirred at 0° C. for 1 hour. Chloroiodomethane (17.9 mL, 239 mmol) was added dropwise and the mixture was stirred for 1 h. The mixture was quenched with 250 mL of saturated aqueous NaHCO$_3$ followed by extraction with ethyl acetate (3×250 mL). The combined organic layers were washed (brine, 250 mL), dried (Na$_2$SO$_4$) and concentrated under reduced pressure to give a yellow oil that was purified by silica chromatography using a Combiflash ISCO purification system (Teledyne Isco Inc., Lincoln, Nebr.) system to give 1-tert-butyl 4-methyl 4-(chloromethyl) piperidine-1,4-dicarboxylate (12 g, 52%). $^1$H NMR (CDCl$_3$) δ 1.43 (s, 9H), 2.10-2.17 (m, 4H), 2.97 (br s, 2H), 3.56 (s, 2H), 3.74 (s, 3H), 3.83 (br s, 2H).

A solution of 1-tert-butyl 4-methyl 4-(chloromethyl)piperidine-1,4-dicarboxylate (11.7 g, 40.2 mmol) in anhydrous THF (100 mL) was cooled to 0° C. Lithium aluminum hydride (1N in THF, 44.3 mL, 44.3 mmol), was added slowly (15-20 min) and the solution was stirred at 0° C. for 25 minutes. The mixture was quenched by adding water (1.8 mL) dropwise with great caution. Aqueous 1N NaOH (1.8 mL) was added dropwise, and the mixture was stirred for 5 minutes. The cooling bath was removed, the solids were filtered off, and the cake was washed with Et$_2$O (2×100 mL). The filtrate was washed with water (2×100 mL), brine (100 mL), dried (Na$_2$SO$_4$) and concentrated under reduced pressure to give tert-butyl 4-(chloromethyl)-4-(hydroxymethyl) piperidine-1-carboxylate as a solid (9.96 g, 93.8%). $^1$H NMR (CDCl$_3$) δ 1.43 (s, 9H), 1.48-1.55 (m, 4H), 3.36-3.41 (m, 4H), 3.57 (s, 2H), 3.59 (br s, 2H).

To a −78° C. solution of oxalyl chloride (5.1 mL, 57 mmol) in dichloromethane (100 mL) in an oven-dried round-bottomed flask was added dimethylsulfoxide (8.2 mL, 114 mmol) in dichloromethane (17 mL). The mixture was stirred for 2 minutes and tert-butyl 4-(chloromethyl)-4-(hydroxymethyl)piperidine-1-carboxylate (13.7 g, 52 mmol) in dichloromethane (50 mL) was added over 10 minutes. The solution was stirred for 15 minutes at −78° C. and triethylamine (36 mL, 260 mmol) was added. The mixture was stirred at −78° C. for 15 minutes and was warmed to room temperature. The mixture was stirred for 15 minutes at room temperature and was quenched with saturated aqueous NaHCO₃ (200 mL). The aqueous solution was washed with Et₂O (2×300 mL). The combined organic layers were washed with brine, dried (Na₂SO₄) and concentrated under reduced pressure to give the title compound (SM-3a) as a yellow oil that solidified upon standing under nitrogen atmosphere at room temperature (13.7 g, 99%). ¹H NMR (CDCl₃) δ 1.43 (s, 9H), 1.48-1.60 (m, 2H), 2.00-2.07 (m, 2H), 3.07 (t, 2H), 3.57 (s, 2H), 3.69-3.79 (m, 2H), 9.55 (s, 1H).

Preparation of tert-Butyl 7-[(4-methoxyphenyl)acetyl]-2,7-diazaspiro[3.5]nonane-2-carboxylate (I-1a)

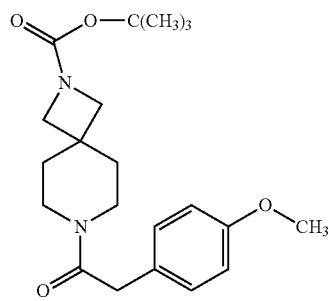

(I-1a)

To a solution of p-methoxyphenylacetic acid (1.26 g, 7.61 mmol) and tert-butyl 2,7-diazaspiro[3.5]nonane-2-carboxylate (2.00 g, 7.61 mmol) in dichloromethane (25 mL) was added triethylamine (2.12 mL, 15.2 mmol) and HATU (3.47 g, 9.12 mmol). The reaction was stirred for 15 hours. The reaction mixture was partitioned between dichloromethane and saturated sodium bicarbonate and the aqueous phase was washed with dichloromethane (2×20 mL). The combined organic layers were washed with water and brine, and dried over anhydrous MgSO₄. Filtration and solvent removal afforded a crude product which was purified by silica chromatography on a Combiflash ISCO purification system (Teledyne Isco Inc., Lincoln, Nebr.), 100/0 to 50/50 heptanes/ethyl acetate gradient. The final product (I-1a) was obtained as clear oil which solidified upon standing at ambient temperature (2.75 g, 96%). MS (ES+) 375.4 (M+H)⁺. ¹H NMR (CDCl₃) δ 1.41 (s, 9H), 1.50 (br t, 2H), 1.65 (br t, 2H), 3.32 (br t, 2H), 3.52 (br t, 2H), 3.57-3.64 (m, 6H), 3.77 (s, 3H), 6.83 (d, 2H), 7.12 (d, 2H).

Preparation of 7-[(4-methoxyphenyl)acetyl]-2,7-diazaspiro[3.5]nonane hydrochloride (I-1b)

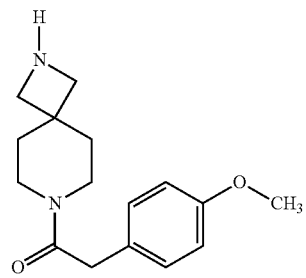

(I-1b)

To a solution of tert-butyl 7-[(4-methoxyphenyl)acetyl]-2,7-diazaspiro[3.5]nonane-2-carboxylate (2.75 g, 11.2 mmol) in 15 mL of anhydrous dioxane was added 4N HCl in dioxane (3.8 mL). The reaction mixture was stirred at room temperature overnight. Methanol (3 mL) was added to dissolve the solids and the mixture was stirred at ambient temperature for another 2 hours. The reaction was concentrated to dryness and dried on high vacuum overnight to provide the product as a light yellow foam (2.31 g). MS (ES+) 275.4 (M+H)⁺. ¹H NMR (D₂O) δ 1.58 (t, 2H), 1.75 (t, 2H), 3.39 (t, 4H), 3.63 (s, 2H), 3.70 (s, 3H), 3.72-3.82 (m, 4H), 6.86 (d, 2H), 7.08 (d, 2H).

Preparation of tert-Butyl 7-[(5-methoxypyridin-2-yl)acetyl]-2,7-diazaspiro[3.5]nonane-2-carboxylate (2-1a)

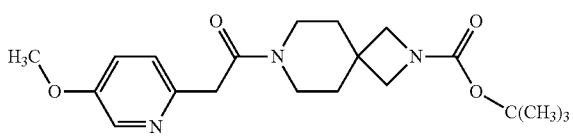

(2-1a)

In an oven dried round-bottomed flask was suspended tert-butyl 2,7-diazaspiro[3.5]nonane-2-carboxylate hydrochloride (1.89 g, 7.18 mmol) in anhydrous dichloromethane (50 mL). Triethylamine (2 mL, 14.4 mmol) followed by 5-methoxypyridin-2-yl)acetic acid (SM-1aa, 1.2 g, 7.18 mmol) were added. HATU (3.28 g, 8.62 mmol) was added and the resulting bright yellow solution was stirred at room temperature for 15 hours. The reaction mixture was washed consecutively with saturated aqueous sodium bicarbonate, water and brine and was dried over anhydrous MgSO₄. Filtration and solvent removal afforded the crude material as a brownish oil (4.8 g). The product was purified by silica chromatography using a Combiflash ISCO (Teledyne Isco Inc., Lincoln, Nebr.) system to give the title compound (2-1a) as a light yellow foam (2.57 g, 96%). MS (ES+) 376.4 (M+H)⁺. ¹H NMR (CDCl₃) δ 1.42 (s, 9H), 1.57-1.61 (m, 2H), 1.65-1.69 (m, 2H), 3.47-3.54

(m, 4H), 3.58-3.64 (m, 4H), 3.83 (s, 3H), 3.85 (s, 2H), 7.15-7.18 (m, 1H), 7.23-7.26 (m, 1H), 8.18 (d, 1H).

Preparation of 7-[(5-Methoxypyridin-2-yl)acetyl]-2,7-diazaspiro-[3.5]nonane dihydrochloride (2-1b)

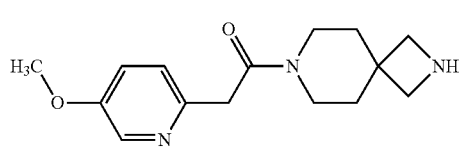

To a solution of tert-butyl 7-[(5-methoxypyridin-2-yl)acetyl]-2,7-diazaspiro[3.5]nonane-2-carboxylate (2-1a, 2.57 g, 6.85 mmol) in dioxane (5 mL) was added 4N HCl in dioxane (1.72 mL). The mixture was stirred at room temperature for 5 hours and heated at 45° C. overnight. The light-yellow mixture was concentrated to give a light-yellow sticky foam. The residue was suspended in ethyl acetate and evaporated to dryness (3×) to afford the title compound (2-1b, 1.86 g, 78%) MS (ES+) 276.4 (M+H)$^+$. $^1$H NMR (CD$_3$OD) δ 2.17-2.42 (m, 2H), 2.48 (d, 2H), 3.94-4.13 (m, 4H), 4.40 (d, 4H), 4.51 (s, 3H), 4.74 (s, 2H), 8.34 (d, 1H), 8.61-8.64 (m, 1H), 8.99-9.01 (m 1H).

Preparation of 7-[(5-Methoxypyridin-2-yl)acetyl]-2-[5-(4,4,5,5-tetramethyl-1,3,2-dioxaborolan-2-yl)-2,3-dihydro-1H-inden-1-yl]-2,7-diazaspiro[3.5]nonane (2-1c)

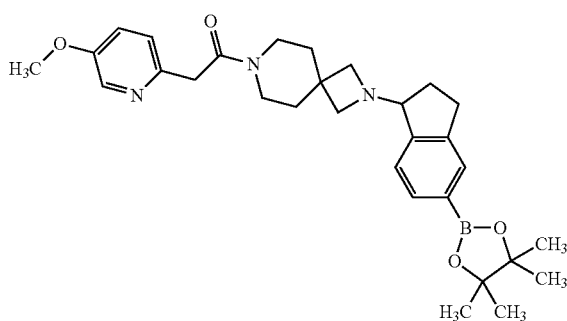

7-[(5-Methoxypyridin-2-yl)acetyl]-2,7-diazaspiro[3.5]nonane dihydrochloride (2-1b, 1.8 g, 5.2 mmol) and 5-(4,4,5,5-tetramethyl-1,3,2-dioxaborolan-2-yl)indan-1-one (SM-1a, 2.0 g, 7.75 mmol) were dissolved in anhydrous dichloroethane (50 mL). Triethylamine (2.88 mL, 20.6 mmol) was added to the solution followed by titanium(IV) isopropoxide (3.06 mL, 2.09 g) and the reaction mixture was stirred at ambient temperature for 1 hour. Sodium triacetoxyborohydride (4.38 g, 20.7 mmol) was added and the reaction was stirred at room temperature for 15 hours. The reaction was quenched by the addition of 20 mL saturated sodium bicarbonate. The aqueous solution was washed with 100 mL of dichloromethane and the organic solution was washed with brine and dried over anhydrous Na$_2$SO$_4$. Removal of the solvent under vacuum afforded the crude product (4.0 g) as a brown foam. The crude product was purified by silica chromatography on an Analogix system (Analogix Inc., Burlington, Wis.), eluting with 1-10% MeOH in CH$_2$Cl$_2$ to give the title compound (2-1c) as a brown paste (1.1 g, 41%). MS (ES+) 518.6 (M+H)$^+$. $^1$H NMR (CDCl$_3$) δ1.27 (s, 12H), 1.50-1.65 (m, 4H), 1.76-1.85 (m, 1H), 1.99-2.10 (m, 1H), 2.64-2.76 (m, 1H), 2.90-2.98 (m, 1H), 3.00-3.13 (m, 4H), 3.42 (d, 4H), 3.77 (s, 3H), 3.80 (s, 2H), 3.85 (s, 1H), 7.08-7.12 (m, 1H), 7.18-7.22 (m, 2H), 7.54-7.58 (m, 1H), 7.63 (s, 1H), 8.14-8.16 (m, 1H).

Preparation of tert-Butyl 2-(-(1R)-5-bromo-2,3-dihydro-1H-inden-1-yl)-2,7-diazaspiro[3.5]nonane-7-carboxylate (3-1a) Method A In a dry 1 L flask was combined tert-butyl 2,7-diazaspiro[3.5]nonane-7-carboxylate (6.53 g, 30.9 mmol) and 5-bromoindanone (7.00 g, 30.9 mmol) in 200 mL dichloroethane. Titanium (IV) isopropoxide (18.3 mL, 61.8 mmol) was added and the reaction was stirred at room temperature for 2 hours. Sodium triacetoxyborohydride (26.2 g, 123.6 mmol) was added and the reaction was stirred at room temperature for an additional 16 hours. The reaction was quenched with 400 mL saturated sodium bicarbonate and was stirred for 15 minutes. The mixture was passed through a thin layer of Celite®, resulting in a clear bi-phasic mixture. The two layers were separated and the aqueous layer was extracted twice with dichloromethane. The combined organic layers were washed with brine, dried over anhydrous sodium sulfate, filtered and concentrated to afford 17 g of a crude product as a brown oil. This material was purified via Analogix (Analogix Inc., Burlington, Wis.) chromatography eluting with 100:0→85:15 dichloromethane/methanol over 30 minutes to afford the desired product (9.82 g, 76%) as a brown foam. The enantiomers were separated via preparative chiral HPLC (Column chiralcel OJ-H, 250 mm×4.6 mm, flow-rate 2.5 ml/min, CO$_2$/MeOH (80/20/) mobile phase with 0.1% isopropylamine) to afford the desired product (3-1a, 4.6 g, 36%). MS (ES+) 422.3 (M+H)+. $^1$H NMR (CDCl$_3$) δ 1.44 (s, 9H), 1.67 (dd, 4H), 1.84-1.93 (m, 1H), 2.07-2.16 (m, 1H), 2.72-2.81 (m, 1H), 2.95-3.15 (m, 5H), 3.31 (dd, 4H), 3.85 (br s, 1H), 7.12 (d, 1H), 7.28 (br s, 1H), 7.35 (br s, 1H).

Preparation of tert-Butyl 2-[(1R)-5-bromo-2,3-dihydro-1H-inden-1-yl]-2,7-diazaspiro[3.5]honane-7-carboxylate (3-1a) Method B

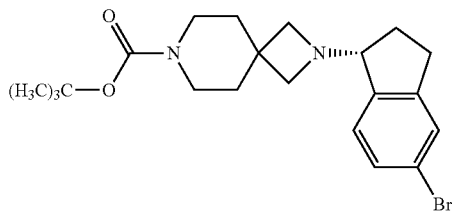

(3-1a)

To a solution of (1R)-5-bromoindan-1-amine (SM-1, 1835 g, 8.66 mol) in anhydrous methanol (24 L) was added tert-butyl 4-(chloromethyl)-4-formylpiperidine-1-carboxylate (SM-3a, 2310 g, 8.83 mol). The mixture was stirred at 50° C. for 16 h, and cooled to rt. Sodium cyanoborohydride (1000 g, 15.9 mol) in THF (15 L) was added via a syringe pump over 2 hours. The mixture was stirred at 60° C. for 24 hours under nitrogen with a vent into a bleach bath. The reaction was cooled to 20° C. and transferred via a cannula into a vessel containing 24 L of 2.5M sodium hydroxide, and 30 L of DCM. The layers were separated and the aqueous layer was extracted with DCM (2×5 L). The aqueous layer was treated to destruct residual sodium cyanoborohydride. The combined organic layers were dried (MgSO$_4$) and concentrated under reduced pressure. The crude material was slurried in MTBE (7 L) by stirring at 40° C. for 1 h and at rt for 1 h. The solid was filtered, and washed with MTBE (2×500 mL) and dried under vacuum oven at 50° C. to give the title product as a white crystals (3657 g, 90%). MS (ES+) 422.3 (M+H)$^+$. $^1$H NMR (CDCl$_3$) δ 1.44 (s, 9H), 1.67 (dd, 4H), 1.84-1.93 (m, 1H), 2.07-2.16 (m, 1H), 2.72-2.81 (m, 1H), 2.95-3.15 (m, 5H), 3.31 (dd, 4H), 3.85 (br s, 1H), 7.12 (d, 1H), 7.28 (br s, 1H), 7.35 (br s, 1H). [α]$_D^{20}$=+39.6 deg (c=1.06 mg/mL, MeOH).

Preparation of tert-Butyl 2-[(1R)-5-(5-ethylpyrimidin-2-yl)-2,3-dihydro-1H-inden-1-yl]-2,7-diazaspiro[3.5]nonane-7-carboxylate (3-1b)

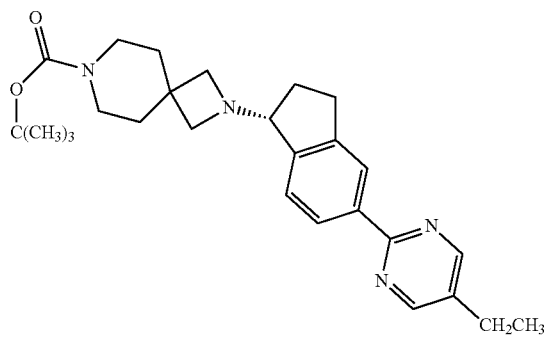

(3-1b)

To an oven-dried round-bottomed flask was added (R)-tert-butyl-2-(5-bromo-2,3-dihydro-1H-inden-1-yl)-2,7-diazaspiro[3.5]nonane-7-carboxylate (3-1a, 600 mg, 1.42 mmol), bispinacolatodiboron (398 mg, 1.71 mmol), 559 mg potassium acetate (559 mg, 5.70 mmol) and anhydrous dioxane (20 mL). The resulting mixture was purged with nitrogen (3×). Pd(dppf)Cl$_2$ (58.0 mg, 0.07 mmol) was added and the reaction mixture was purged with nitrogen (3×). The reaction was heated under nitrogen at 110° C. for 4 hours at which time LCMS showed conversion to the desired boronate intermediate. Pd(dppf)Cl$_2$ catalyst (58.0 mg, 0.07 mmol), 2-chloro-5-ethylpyrimidine (224 mg, 1.57 mmol) and aqueous K$_2$CO$_3$ solution (de-oxygenated with nitrogen for 15 minutes prior to addition, 2M, 5.0 mL) were added to the reaction mixture. The reaction was purged with nitrogen (3×) and heated for 6 hours at 110° C. The reaction was cooled to room temperature and the dioxane solvent was removed under reduced pressure. The residue was partitioned between 100 mL of ethyl acetate and 100 mL of 1N NaOH solution. The organic layer was washed with 100 mL of brine, dried (Na$_2$SO$_4$) and concentrated to afford thecrude product as a dark brown oil. The crude product was purified on an Analogix (Analogix Inc., Burlington, Wis.) 8 g silica column, eluted with 0-10% MeOH in CH$_2$Cl$_2$ over 20 minutes to afford 583 mg (92%) of the desired product (3-1b) as a brown foam. MS (ES+) 449.5 (M+H)$^+$. $^1$H NMR (CDCl$_3$) δ 1.23 (t, 3H), 1.40 (s, 9H), 1.56-1.67 (m, 4H), 1.83-1.91 (m, 1H), 2.07-2.16 (m, 1H), 2.59 (q, 2H), 2.76-2.85 (m, 1H), 2.99-3.13 (m, 5H), 3.24-3.31 (m, 4H), 3.91 (dd, 1H), 7.27-7.34 (m, 1H), 8.17-8.23 (m, 2H), 8.56 (s, 2H).

Preparation of 2-[(1R)-5-(5-Ethylpyrimidin-2-yl]-2,3-dihydro-1H-inden-1-yl]-2,7-diazaspiro[3.5]nonane dihydrochloride (3-1c)

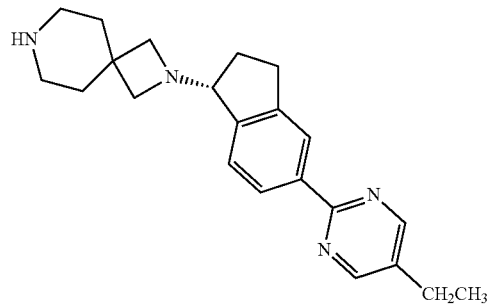

(3-1c)

To a flask charged with tert-butyl 2-[(1R)-5-(5-ethylpyrimidin-2-yl)-2,3-dihydro-1H-inden-1-yl]-2,7-diazaspiro[3.5]nonane-7-carboxylate (3-1b, 583 mg, 1.39 mmol) was added 8.0 mL of 4N HCl in dioxane at room temperature. A yellow precipitate formed immediately after the addition. The mixture was stirred at room temperature for 40 minutes. Anhydrous methanol (4 mL) was added to solublize the reaction. The resulting solution was stirred at room temperature for 4 hours. Solvent and excess HCl were removed and dried in vacuo to afford 630 mg (100%) of a light yellow solid (3-1c). The crude product was taken on to the next step without further purification. MS (ES+) 349.4 (M+H)$^+$. $^1$H NMR (CD$_3$OD) δ 1.40 (t, 3H) 2.21-2.28 (m, 5H) 2.61 (br s, 1H) 2.93 (q, 2H) 3.16-3.34 (m, 4H) 3.38-3.51 (m, 1H), 4.12-4.29 (m, 4H) 4.52-4.56 (m, 1H) 5.08-5.12 (m, 1H) 7.89-7.93 (m, 1H) 8.29-8.33 (m, 2H), 9.15-9.19 (m, 2H).

Preparation of tert-Butyl 2-[(1R)-5-pyrimidin-2-yl-2,3-dihydro-1H-inden-1-yl]-2,7-diazaspiro[3.5]nonane-7-carboxylate (3-1d)

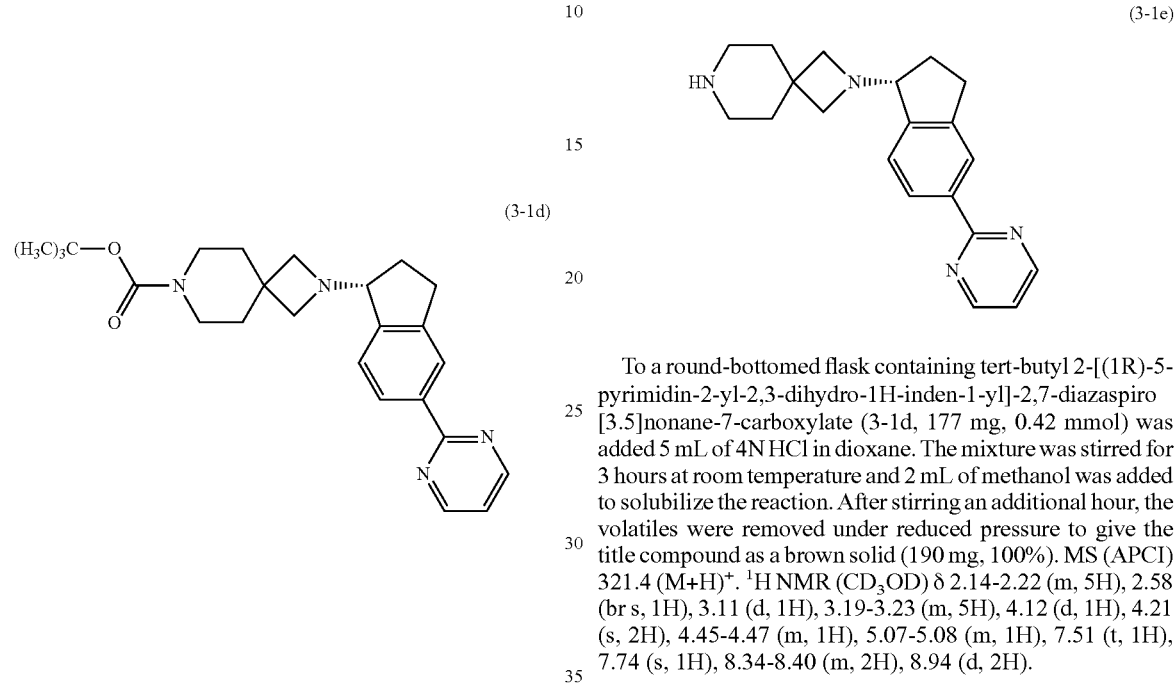

To an oven-dried round-bottomed flask was added tert-butyl 2-[(1R)-5-bromo-2,3-dihydro-1H-inden-1-yl]-2,7-diazaspiro[3.5]nonane-7-carboxylate (3-1a, 267 mg, 0.63 mmol), anhydrous dioxane (9 mL), bis(pinacolato)diboron (177 mg, 0.69 mmol) and potassium acetate (249 mg, 2.53 mmol). The resulting mixture was purged with nitrogen for 15 minutes. Pd(dppf)Cl$_2$ (15 mg, 0.02 mmol) was added and the reaction mixture was purged with nitrogen for an additional 15 minutes. The reaction was heated under nitrogen at 110° C. for 5 hours. After consumption of the starting material (as monitored by TLC), the reaction was cooled to room temperature and 2-chloro-pyrimidine (71.0 mg, 0.63 mmol), Pd(dppf)Cl$_2$ (15 mg, 0.02 mmol) and aqueous K$_2$CO$_3$ solution (2M, 2.25 mL, de-oxygenated with nitrogen for 15 minutes prior to addition) were added. The reaction was purged with nitrogen (3×) and heated under nitrogen for 20 hours at 110° C. The reaction was cooled to room temperature and was filtered through a short plug of silica gel, eluting with methanol. The solvents were removed in vacuo and the residue was partitioned between 50 mL of ethyl acetate and 50 mL of 1N NaOH solution. The layers were separated and the organic layer was washed with 50 mL of brine. The organic layer was dried (Na$_2$SO$_4$) and concentrated to give the crude product as a black semi-solid. The crude product was purified by column chromatography using a Combiflash ISCO purification system (Teledyne Isco Inc., Lincoln, Nebr.) system, eluting with 0-10% MeOH in CH$_2$Cl$_2$ to give the title compound as a black gum (208 mg, 78%). MS (ES+) 421.2 (M+H)$^+$. $^1$H NMR (CDCl$_3$) δ 1.39 (s, 9H), 1.59-1.69 (m, 4H), 1.75-1.94 (m, 1H), 2.12 (dq, 1H), 2.76-2.92 (m, 1H), 2.95-3.18 (m, 5H), 3.19-3.36 (m, 4H), 3.92 (dd, 1H), 7.09 (t, 1H), 7.33 (d, 1H), 8.18-8.26 (m, 2H), 8.71 (d, 2H).

Preparation of 2-[(1S)-5-Pyrimidin-2-yl-2,3-dihydro-1H-inden-1-yl]-2,7-diazaspiro[3.5]nonane dihydrochloride (3-1e)

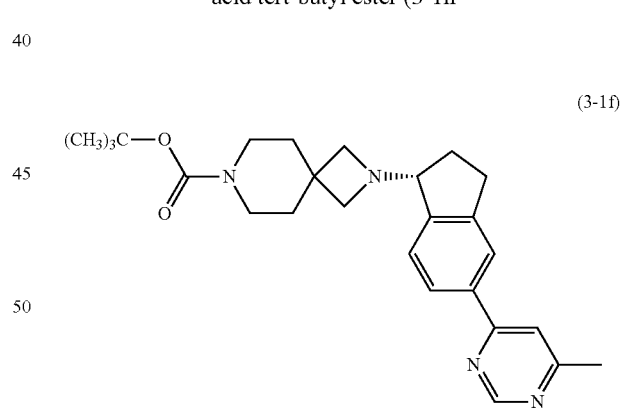

To a round-bottomed flask containing tert-butyl 2-[(1R)-5-pyrimidin-2-yl-2,3-dihydro-1H-inden-1-yl]-2,7-diazaspiro[3.5]nonane-7-carboxylate (3-1d, 177 mg, 0.42 mmol) was added 5 mL of 4N HCl in dioxane. The mixture was stirred for 3 hours at room temperature and 2 mL of methanol was added to solubilize the reaction. After stirring an additional hour, the volatiles were removed under reduced pressure to give the title compound as a brown solid (190 mg, 100%). MS (APCI) 321.4 (M+H)$^+$. $^1$H NMR (CD$_3$OD) δ 2.14-2.22 (m, 5H), 2.58 (br s, 1H), 3.11 (d, 1H), 3.19-3.23 (m, 5H), 4.12 (d, 1H), 4.21 (s, 2H), 4.45-4.47 (m, 1H), 5.07-5.08 (m, 1H), 7.51 (t, 1H), 7.74 (s, 1H), 8.34-8.40 (m, 2H), 8.94 (d, 2H).

Preparation of 2-[(R)-5-(6-Methylpyrimidin-4-yl)-indan-1-yl]-2,7-diazaspiro[3.5]nonane-7-carboxylic acid tert-butyl ester (3-1n (3-1f)

To a 50 mL flask charged with (R)-tert-butyl 2-(5-bromo-2,3-dihydro-1H-inden-1-yl)-2,7-diazaspiro[3.5]nonane-7-carboxylate (3-1a, 4.0 g, 9.49 mmol) was added bis(triphenylphosphine)palladium(II) chloride (0.17 g, 0.24 mmol), potassium acetate (3.73 g, 37.97 mmol), bis(pinacolato)diboron (2.65 g, 10.44 mmol) followed by degassing via vacuum then backfilling with nitrogen 5 times. De-oxygenated (nitrogen stream for 30 minutes prior to addition) toluene (40 mL) was added to the mixture and the reaction was heated at 100° C. for 1.5 hours. The reaction was monitored for completion by HPLC. Upon formation of the boronic ester intermediate, the reaction was cooled to 40° C. and charged with a degassed solution of 4 M sodium hydroxide (11.87 mL, 47.46 mmol) followed by addition of 4-chloro-6-methylpyrimidine (1.53 g, 11.87 mmol). The resulting mixture was then heated to 90° C. for 5 hours under nitrogen. The reaction was cooled to room temperature and charged with water (25 mL). After stirring for 20 minutes, the mixture was filtered to remove black solids. The organic layer was extracted to an aqueous solution containing 1.5 equiv of HCl (40 mL). The organic layer was removed and the resulting solution was treated with (4 g) ISOLUTE® Ultra Pure Si-Thiol silica gel for 1.5 hours and filtered. The aqueous solution was adjusted to pH 7.8 with 4N NaOH and extracted with toluene (40 mL). The toluene layer was concentrated to approximately 15 mL under vacuum at 45° C. and heptane (75 mL) was added slowly and the mixture was stirred at 20° C. for 1 hour. The product was filtered and dried under vacuum at 45° C. for 8 hours to afford the title compound (3-1f) as a white solid (3.56 g, 86%). MS (ES+) 435.5 (M+H)+. $^1$H NMR (CDCl$_3$) δ 1.46 (s, 9H), 1.70-1.74 (m, 4H), 1.90-2.01 (m, 1H), 2.13-2.26 (m, 1H), 2.59 (s, 3H), 2.84-2.93 (m, 1H), 3.04-3.21 (m, 5H), 3.30-3.38 (m, 4H), 3.95-4.02 (m, 1H), 7.40 (d, 1H), 7.56 (s, 1H), 7.87 (d, 1H), 7.95 (s, 1H), 9.12 (s, 1H).

Preparation of 2-[5-(6-Methyl-pyrimidin-4-yl)-indan-1-yl]-2,7-diaza-spiro[3.5]nonane dihydrochloride (3-1g) Method A

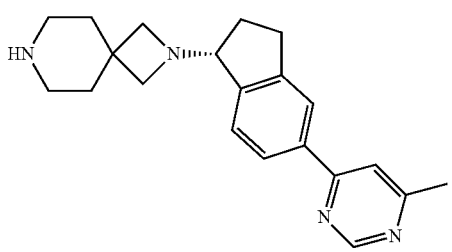

(3-1g)

2-[(R)-5-(6-Methyl-pyrimidin-4-yl)-indan-1-yl]-2,7-diaza-spiro[3.5]nonane-7-carboxylic acid tert-butyl ester (3-1f, 72.6 g, 167 mmol) was suspended in methanol (363 mL) and 4M HCl in 1,4-dioxane (251 mL) was added. After stirring for 2 hours, the slurry was concentrated to dryness. The crude material was re-suspended in MeOH (500 mL) and concentrated (3×). The resulting solids were further dried under vacuum at 45° C. to afford 2-[5-(6-methyl-pyrimidin-4-yl)-indan-1-yl]-2,7-diaza-spiro[3.5]nonane-dihydrochloride (3-1g, 74.1 g, 99.9%). MS (ES+) 335.2 (M+H)+. $^1$H NMR (CD$_3$OD) δ 2.16-2.23 (m, 5H), 2.59 (br s, 1H), 2.78-2.80 (m, 3H), 3.12 (br s, 1H), 3.19-3.24 (m, 4H), 3.37-3.49 (m, 1H), 4.14-4.23 (m, 3H), 4.49 (br s, 1H), 5.11 (br s, 1H), 7.84 (d, 1H), 8.30-8.34 (m, 2H), 8.46 (s, 1H), 9.36 (s, 1H).

Preparation of 2-[5-(6-Methylpyrimidin-4-yl)-indan-1-yl]-2,7-diazaspiro[3.5]nonane dihydrochloride (3-1g) Method B

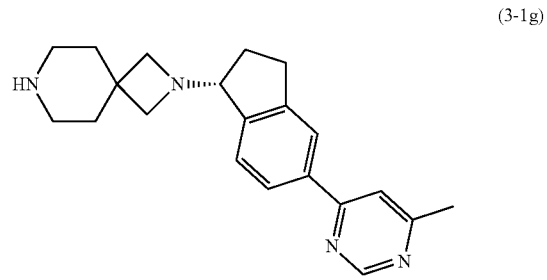 [SMILES: Cc1cc(-c2ccc3c(c2)CC[C@H]3N2CC3(CCNCC3)C2)ncn1]

(3-1g)

A flask containing methanol (100 mL) was cooled to 0° C. The solution was then charged dropwise with acetyl chloride (16.38 mL, 230.11 mmol) over 1 h maintaining a temperature of 10° C. The resulting mixture was charged with 2-[(R)-5-(6-methylpyrimidin-4-yl)-indan-1-yl]-2,7-diazaspiro[3.5]nonane-7-carboxylic acid tert-butyl ester (3-1f, 10.0 g, 23.01 mmol) in methanol (50 mL). The resulting mixture was stirred while warming to 20° C. for 18 h. HPLC after 18 h indicated disappearance of starting material. The resulting slurry was concentrated under reduced pressure removing approximately half the total volume. Isopropylacetate (50 mL) was then added and the resulting slurry was stirred for 1 h at 20° C. The solid was filtered and washed with isopropyl acetate (20 mL) under nitrogen. The solids were dried using a filter press with a nitrogen stream followed by drying under vacuum at 45° C. to afford 2-[5-(6-methyl-pyrimidin-4-yl)-indan-1-yl]-2,7-diaza-spiro[3.5]nonane-dihydrochloride (3-1g, 9.6 g, 98%). MS (ES+) 335.2 (M+H)+. $^1$H NMR (CD$_3$OD) δ 2.16-2.23 (m, 5H), 2.59 (br s, 1H), 2.78-2.80 (m, 3H), 3.12 (br s, 1H), 3.19-3.24 (m, 4H), 3.37-3.49 (m, 1H), 4.14-4.23 (m, 3H), 4.49 (br s, 1H), 5.11 (br s, 1H), 7.84 (d, 1H), 8.30-8.34 (m, 2H), 8.46 (s, 1H), 9.36 (s, 1H).

Preparation of 2-[5-(2-Methylpyrimidin-4-yl)-indan-1-yl]-2,7-diazaspiro[3.5]nonane dihydrochloride (3-1h)

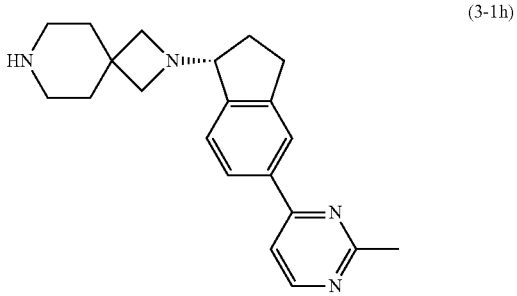 [SMILES: Cc1nccc(-c2ccc3c(c2)CC[C@H]3N2CC3(CCNCC3)C2)n1]

(3-1h)

To a 50 mL flask charged with (R)-tert-butyl 2-(5-bromo-2,3-dihydro-1H-inden-1-yl)-2,7-diazaspiro[3.5]nonane-7-carboxylate (3-1a, 26.22 g, 62.22 mmol) was added bis(triphenylphosphine)palladium(II) chloride (1.09 g, 1.56 mmol), potassium acetate (24.43 g, 248.90 mmol), bis(pinacolato)

diboron (17.38 g, 68.45 mmol) followed by degassing via vacuum then backfilling with nitrogen 5 times. De-oxygenated (nitrogen stream for 30 minutes prior to addition) toluene (262 mL) was added to the mixture and the reaction was heated at 100° C. for 1.5 hours. The reaction was monitored for completion by HPLC. Upon formation of the boronic ester intermediate, the reaction was cooled to 40° C. and charged with a degassed solution of 4 M sodium hydroxide (62.22 mL, 248.90 mmol) followed by addition of 2-methyl-4-chloropyrimidine (10.00 g, 77.78 mmol). The resulting mixture was then heated to 90° C. for 5 hours under nitrogen, and then 18 hours at room temperature. Water (100 mL) was added, and after stirring for 10 minutes the mixture was filtered and the layers separated. The organic layer was charged with water (200 mL) and the layer was acidified to pH 2.5 with 1 N HCl. The resulting mixture was filtered, the layers were separated and the aqueous layer was adjusted to pH 7.8 with 4 N $K_2CO_3$ and extracted with dichloromethane. The solution was treated with ISOLUTEO Ultra Pure Si-Thiol silica gel for 1 h, followed by filtration. The filtrate was concentrated under reduced pressure to give a viscous oil (24.0 g) that was carried forward to the following step without further purification.

A flask containing methanol (20 mL) was cooled to 0° C. The solution was then charged dropwise with acetyl chloride (39.30 mL, 552.25 mmol) over 20 min maintaining a temperature below 10° C. After stirring for 10 min, the resulting mixture was charged with the crude product above (24.0 g, 55.23 mmol) as a solution in methanol (240 mL), keeping the temperature at 10° C. The resulting mixture was stirred while warming to 20° C. for 18 hours. The resulting slurry was concentrated under reduced pressure removing approximately half the total volume. Ethyl acetate (500 mL) was added and the resulting slurry was further concentrated to about a volume of 150 mL, and the mixture was stirred for 2 hour at 20° C. The solid was filtered and washed with ethyl acetate (75 mL) to afford the title compound 3-1h as an off-white solid (19.55 g, 87%). MS (ES+) 355.3 (M+H)+. $^1$H NMR (DMSO-$d_6$) δ 2.00-2.05 (m, 3H), 2.10-2.22 (m, 4H), 2.37-2.47 (m, 1H), 2.73 (s, 3H), 2.91-3.11 (m, 4H), 3.40 (dt, 1H), 3.90 (dd, 1H), 4.00 (d, 1H), 4.31 (dd, 1H), 4.97-5.05 (m, 1H), 7.79 (d, 1H), 8.02 (d, 1H), 8.13 (d, 1H), 8.20 (s, 1H), 8.84 (d, 1H), 9.09 (br s, 1H).

Preparation of 2-[(R)-5-(4-Carbamoyl-phenyl)-indan-1-yl]-2,7-diazaspiro[3.5]nonane-7-carboxylic acid tert-butyl ester (4-1a)

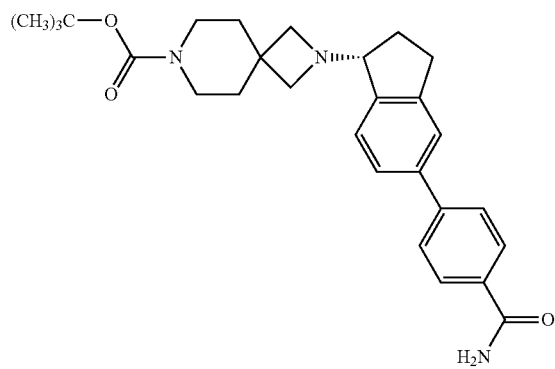

(4-1a)

2-((R)-5-Bromo-indan-1-yl)-2,7-diaza-spiro[3.5]nonane-7-carboxylic acid tert-butyl ester (3-1a, 500 mg, 1.19 mmol), 4-carbamoylphenylboronic acid (587 mg, 3.56 mmol), $Pd(OAc)_2$ (14 mg, 0.06 mmol) and TPPTS ligand (3,3',3''-phosphinidynetris[benzenesulfonic acid]trisodium salt, 135 mg, 0.24 mmol) were suspended in 10 mL water and 5 mL acetonitrile. Diisopropylamine (291 mg, 2.85 mmol) was added, and the mixture was heated to 90° C. for 2 hours. The mixture was cooled to room temperature and was diluted with ethyl acetate (150 mL). The organic solution was washed with water (50 mL), dried ($MgSO_4$), filtered through Celite® and concentrated to give 499 mg (91%) of the title compound as a light pink powder. MS (ES+) 462.1 (M+H)+. $^1$H NMR ($CD_3OD$) δ 1.42 (s, 9H), 1.64-1.74 (m, 4H), 1.83-1.96 (m, 1H), 2.17-2.30 (m, 1H), 2.80-2.93 (m, 1H), 3.10 (dt, 1H), 3.24-3.28 (m, 2H), 3.31-3.38 (m, 6H), 4.06 (dd, 1H), 6.79 (d, 1H), 7.39-7.49 (m, 2H), 7.53 (s, 1H), 7.67 (d, 2H), 7.73 (d, 1H), 7.89-7.94 (m, 2H).

Preparation of 4-[(R)-1-(2,7-Diaza-spiro[3.5]non-2-yl)-indan-5-yl]-benzamide hydrochloride (4-1 b)

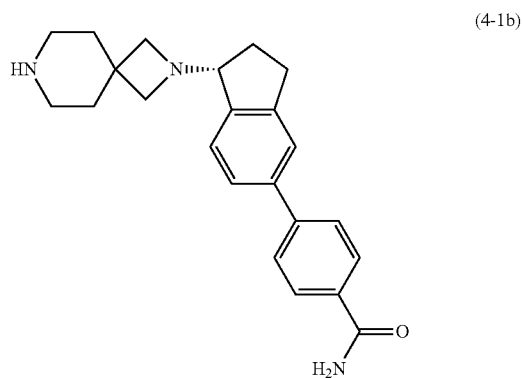

(4-1b)

To a solution of 2-[(R)-5-(4-carbamoyl-phenyl)-indan-1-yl]-2,7-diazaspiro[3.5]nonane-7-carboxylic acid tert-butyl ester (4-1a, 124 mg, 0.27 mmol) in EtOAc (10 mL) was added 3 mL of 4N HCl in dioxane, resulting in the immediate precipitation of solids. The reaction was stirred for 3 hours. The reaction was concentrated and the residue was coevaporated with diethylether (3×) to provide 4-[(R)-1-(2,7-diazaspiro[3.5]non-2-yl)-indan-5-yl]-benzamide hydrochloride as a white solid (102 mg, 95%). This material was used without further purification in the next reaction. MS (ES+) 362.5 (M+H)+. $^1$H NMR ($CD_3OD$) δ 2.12-2.27 (m, 4H), 2.51 (dd, 1H), 2.95-3.03 (m, 1H), 3.13-3.24 (m, 4H), 3.31 (d, 3H), 4.08

(d, 1H), 4.19 (s, 2H), 4.43 (d, 1H), 5.05 (br s, 2H), 7.51-7.62 (m, 2H), 7.64-7.83 (m, 3H), 7.89-7.96 (m, 2H).

Preparation of 2-[(R)-5-(6-Cyano-pyridin-3-yl)-indan-1-yl]-2,7-diaza-spiro[3.5]nonane-7-carboxylic acid tert-butyl ester (4-1c)

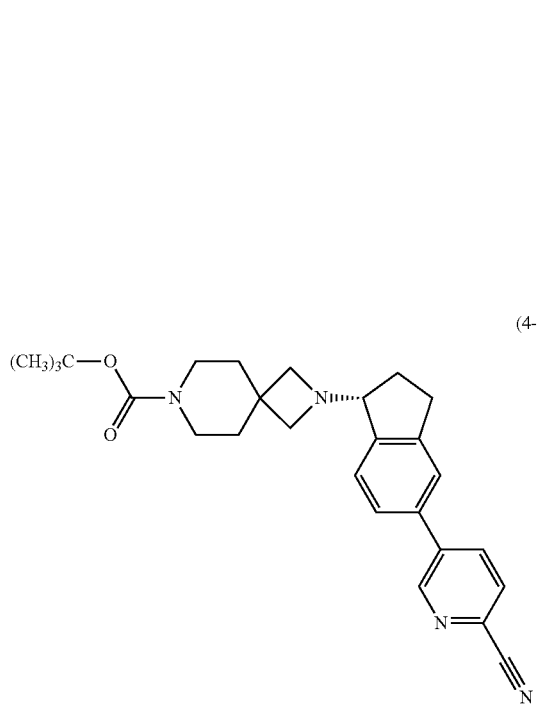

In a round-bottomed flask was combined 2-((R)-5-bromo-indan-1-yl)-2,7-diaza-spiro[3.5]nonane-7-carboxylic acid tert-butyl ester (3-1a, 1.50 g, 3.56 mmol), 5-(4,4,5,5-tetramethyl-[1,3,2]dioxaborolan-2-yl)-pyridine-2-carbonitrile (819 mg, 3.56 mmol), Pd(PPh$_3$)$_4$ (210 mg, 0.18 mmol), and K$_2$CO$_3$ (1.12 g, 7.83 mmol). A mixture of 27 mL 1,4-dioxane and 3 mL water (de-oxygenated with a nitrogen stream for 20 minutes) was added and the reaction was heated to 95° C. overnight. The reaction mixture was cooled to room temperature and was diluted with 200 mL ethyl acetate. The organic solution was washed with 50 mL water, dried (MgSO$_4$), filtered through Celite® and concentrated to give 2.7 g of a yellow oil. The crude material was purified using ISCO (Teledyne Isco Inc., Lincoln Nebr.) column chromatography, eluting with a 0-100% ethyl acetate in heptanes gradient. The title compound was obtained as a white solid (850 mg, 54%). MS (ES+) 445.1 (M+H)$^+$. $^1$H NMR (CDCl$_3$) δ 1.43 (s, 9H), 1.64-1.73 (m, 4H), 1.86-2.00 (m, 1H), 2.09-2.24 (m, 1H), 2.87 (dd, 1H), 3.01-3.10 (m, 1H), 3.10-3.19 (m, 4H), 3.27-3.36 (m, 4H), 3.95 (dd, 1H), 7.33-7.41 (m, 2H), 7.42-7.46 (m, 1H), 7.72 (dd, 1H), 7.94 (dd, 1H), 8.89 (dd, 1H).

Preparation of Intermediate 5-[(R)-1-(2,7-Diazaspiro[3.5]non-2-yl)-indan-5-yl]-pyridine-2-carbonitrile dihydrochloride (4-1d)

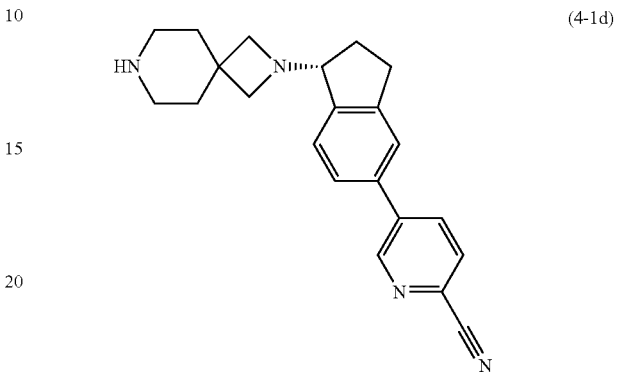

To a solution of 2-[(R)-5-(6-cyano-pyridin-3-yl)-indan-1-yl]-2,7-diaza-spiro[3.5]nonane-7-carboxylic acid tert-butyl ester (4-1c, 75 mg, 0.17 mmol) in EtOAc (10 mL) was added 3 mL of 4N HCl in dioxane, resulting in the immediate precipitation of solids. The reaction was stirred for 3 hours. The reaction was concentrated and the residue was coevaporated with diethylether (3×) to provide 4-[(R)-1-(2,7-diaza-spiro[3.5]non-2-yl)-indan-5-yl]-benzamide hydrochloride as a white solid (70 mg, 82%). This material was used without further purification in the next reaction. MS (ES+) 345.1 (M+H)$^+$. Retention time: 1.09 minutes: Oxbridge C18 4.6×50 mm 5 um, 5-100% acetonitrile:water (0.1% formic acid).

Preparation of tert-Butyl 2-(5-pyrimidin-2-yl-2,3-dihydro-1H-inden-1-yl)-2,7-diazaspiro[3.5]nonane-7-carboxylate (5-1a)

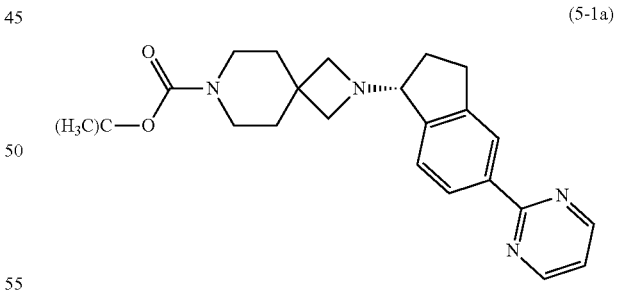

To a solution of tert-butyl 2,7-diazaspiro[3.5]nonane-7-carboxylate hydrochloride (850 mg, 3.23 mmol) and 5-pyrimidin-2-ylindan-1-one (SM-1b, 680 mg, 3.23 mmol) in dichloromethane (10 mL) under nitrogen was added triethylamine (2.5 mL, 17.9 mmol) followed by titanium isopropoxide (2.9 mL, 9.70 mmol). The reaction was stirred at room temperature for 90 minutes and sodium triacetoxyborohydride (2.1 g, 9.9 mmol) was added. After stirring for 4 days, the reaction was quenched with saturated ammonium chloride. The mixture was diluted with 50 mL of dichloromethane and 50 mL of water and filtered through a Celite® pad. The aqueous layer was extracted with dichloromethane (2×30 mL). The combined organics layers were washed with brine and dried over MgSO₄. The solvent was removed to give a dark green/brown paste which was chromatographed on a Combiflash ISCO purification system (Teledyne Corp., Lincoln Nebr.) using a dichloromethane/MeOH gradient to afford the title compound as light brown oil (785 mg, 57.7%). MS (ES+) 421.2 (M+H)⁺. ¹H NMR (CDCl3) δ 1.39 (s, 9H), 1.59-1.69 (m, 4H), 1.75-1.94 (m, 1H), 2.12 (dq, 1H), 2.76-2.92 (m, 1H), 2.95-3.18 (m, 5H), 3.19-3.36 (m, 4H), 3.92 (dd, 1H), 7.09 (t, 1H), 7.33 (d, 1H), 8.18-8.26 (m, 2H), 8.71 (d, 2H).

Preparation of 2-(5-Pyrimidin-2-yl-2,3-dihydro-1H-inden-1-yl)-2,7-diazaspiro[3.5]honane dihydrochloride (5-1b)

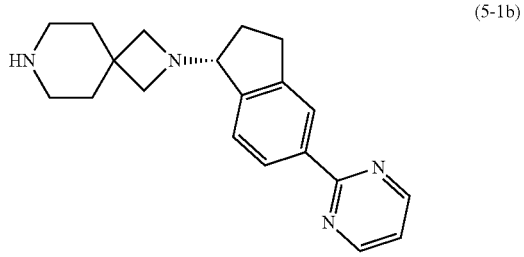 [SMILES: c1cnc(-c2ccc3c(c2)CC[C@H]3N2CC3(CCNCC3)C2)nc1]

(5-1b)

To tert-butyl 2-(5-pyrimidin-2-yl-2,3-dihydro-1H-inden-1-yl)-2,7-diazaspiro[3.5]nonane-7-carboxylate (5-1a, 450 mg, 1.08 mmol) was added 5 mL of 4N HCl in dioxane solution. Methanol (3 mL) was added to solubilize the solids and the reaction was heated at 50° C. for 1 hour. After cooling, the reaction was concentrated. The residue was coevaporated with ethyl acetate (3×) until a free-flowing white solid was obtained (320 mg, 76%). MS (APCI) 321.4 (M+H)⁺. ¹H NMR (CD₃OD) δ 2.14-2.22 (m, 5H), 2.58 (br s, 1H), 3.11 (d, 1H), 3.19-3.23 (m, 5H), 4.12 (d, 1H), 4.21 (s, 2H), 4.46 (d, 1H), 5.07-5.08 (m, 1H), 7.51 (t, 1H), 7.74 (s, 1H), 8.34-8.40 (m, 2H), 8.94 (d, 2H).

Preparation of tert-Butyl 2-((R)-5-(2H-1,2,3-triazol-2-yl)-2,3-dihydro-1H-inden-1-yl)-2,7-diazaspiro[3.5]nonane-7-carboxylate (6-1a)

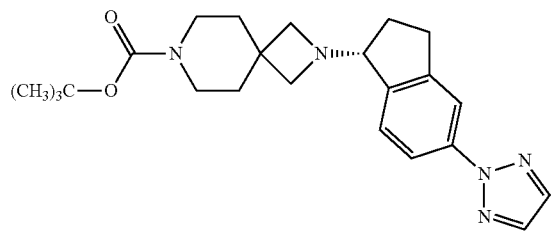

(6-1a)

To a solution of tert-butyl 2,7-diazaspiro[3.5]nonane-7-carboxylate hydrochloride (4.35 g. 16.6 mmol) and 5-(2H-1,2,3-triazol-2-yl)indan-1-one (SM-1h, 3.3 g, 16.6 mmol) in dichloromethane (50 mL) was added triethylamine (6.94 mL, 49.7 mmol) followed by titanium(IV) isopropoxide (9.81 mL, 33.1 mmol). The reaction was stirred at room temperature overnight and sodium triacetoxyborohydride (4.21 g, 19.8 mmol) was added. After stirring for 4 days, the reaction was quenched with saturated ammonium chloride. The mixture was diluted with 50 mL of dichloromethane and 50 mL water and filtered through a Celite® pad. The aqueous layer was extracted with dichloromethane (30 mL×2). The combined organic layers were washed with brine and dried over MgSO₄. The solvent was concentrated and the crude material was chromatographed on a Combiflash ISCO purification system (Teledyne Corp., Lincoln, Nebr.) using an EtOAc/heptanes gradient. The enantiomers were separated via preparative chiral HPLC (Chiralcel OD-H, 250 mm×30 mm, flow-rate—100 g/min, 65/35 CO₂/MeOH, with 0.1% IPA) to afford tert-butyl 2-((R)-5-(2H-1,2,3-triazol-2-yl)-2,3-dihydro-1H-inden-1-yl)-2,7-diazaspiro[3.5]nonane-7-carboxylate (6-1a, 1.58 g, 23%) as a white solid. MS (ES+) 410.5 (M+H)⁺. ¹H NMR (CD₃OD) δ 1.42 (s, 9H), 1.70-1.73 (m, 4H), 1.92-2.02 (m, 1H), 2.23-2.27 (m, 1H), 2.89-2.92 (m, 2H), 3.09-3.14 (m, 2H), 3.23-3.30 (m, 3H), 3.32-3.36 (m, 3H), 4.02-4.05 (m, 1H), 7.45 (d, 1H), 7.87 (s, 2H), 7.89-7.93 (m, 2H).

Preparation of Benzyl 2-((R)-5-(2H-1,2,3-triazol-2-yl)-2,3-dihydro-1H-inden-1-yl)-2,7-diazaspiro[3.5]honane-7-carboxylate (6-1 b)

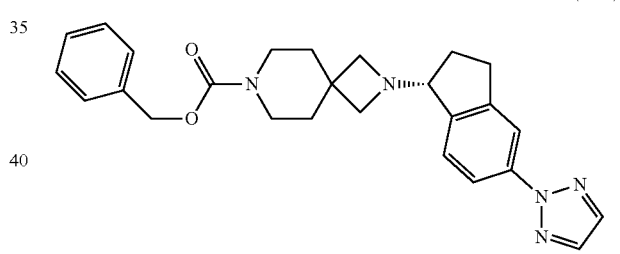

(6-1b)

The title compound, benzyl 2-((R)-5-(2H-1,2,3-triazol-2-yl)-2,3-dihydro-1H-inden-1-yl)-2,7-diazaspiro[3.5]nonane-7-carboxylate (6-1b), was prepared in an analogous fashion to Intermediate tert-butyl 2-((R)-5-(2H-1,2,3-triazol-2-yl)-2,3-dihydro-1H-inden-1-yl)-2,7-diazaspiro[3.5]nonane-7-carboxylate (6-1a) with the substitution of starting material benzyl 2,7-diazaspiro[3.5]nonane-7-carboxylate (SM-2aa) for tert-butyl 2,7-diazaspiro[3.5]nonane-7-carboxylate hydrochloride. The final product, as a racemic mixture, was obtained as a dark brown solid (6-1b, 2.33 g, 65%). The enantiomers were separated via preparative chiral HPLC (Chiralcel OD-H, 250 mm×30 mm, Flow-rate—100 g/min, 65/35 CO₂/MeOH, with 0.1% IPA) to afford benzyl 2-((R)-5-(2H-1,2,3-triazol-2-yl)-2,3-dihydro-1H-inden-1-yl)-2,7-diazaspiro[3.5]nonane-7-carboxylate (1.09 g) as a white solid. MS (ES) 444.5 (M+H)⁺. ¹H NMR (CDCl₃) δ 1.30-1.34 (m, 2H), 1.70-1.75 (m, 4H), 2.05 (br s, 1H), 2.24 (br s, 1H), 2.90-2.95 (m, 1H), 3.21-3.25 (m, 1H), 3.26-3.30 (m, 3H), 3.39-3.43 (m, 3H), 4.05-4.10 (m, 1H), 5.11 (s, 2H), 7.26-7.37 (m, 5H), 7.42-7.44 (m, 1H), 7.79 (s, 2H), 7.85-7.96 (m, 2H).

Preparation of 2-((R)-5-(2H-1,2,3-Triazol-2-yl)-2,3-dihydro-1H-inden-1-yl)-2,7-diazaspiro[3.5]honane (6-1c)

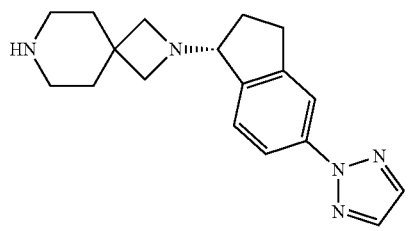

(6-1c)

Preparation A-(dihydrochloride):

To a solution of tert-butyl-2-((R)-5-(2H-1,2,3-triazol-2-yl)-2,3-dihydro-1H-inden-1-yl)-2,7-diazaspiro[3.5]nonane-7-carboxylate (6-1a, 660 mg, 1.61 mmol) in MeOH (5 mL) was added 5 mL of 4N HCl in dioxane solution. The reaction was stirred for 3 hours. The solvents were removed under reduced pressure and the residue coevaporated with dichloromethane (3×) until 2-((R)-5-(2H-1,2,3-triazol-2-yl)-2,3-dihydro-1H-inden-1-yl)-2,7-diazaspiro[3.5]nonane dihydrochloride was obtained as a free flowing solid (616 mg, 100%). This material was used without further purification in the next reaction. MS (ES+) 310.0 (M+H)$^+$. $^1$H NMR (CD$_3$OD) δ 2.12-2.28 (m, 5H), 2.56-2.66 (m, 1H), 3.04-3.08 (m, 1H), 3.19-3.26 (m, 4H), 3.29-3.34 (m, 1H), 4.13 (d, 1H), 4.22 (s, 2H), 4.44 (d, 1H), 5.04 (d, 1H), 7.74 (d, 1H), 7.92 (s, 2H), 8.08 (d, 1H), 8.12 (s, 1H).

Preparation B-(Freebase):

In a Parr® shaker bottle, a solution of benzyl 2-(R)-5-(2H-1,2,3-triazol-2-yl)-2,3-dihydro-1H-inden-1-yl)-2,7-diaza-spiro[3.5]nonane-7-carboxylate (6-1b, 1.20 g, 2.7 mmol) in MeOH (30 mL) was treated with 10% Pd/C (50% wet for safety, 600 mg). The mixture was hydrogenated at 45 psi for 6 hours. The mixture was filtered through a pad of Celite® and concentrated to afford 2-((R)-5-(2H-1,2,3-triazol-2-yl)-2,3-dihydro-1H-inden-1-yl)-2,7-diazaspiro[3.5]nonane as a glass-like solid (690 mg, 82%). MS (ES+) 310.0 (M+H)$^+$. $^1$H NMR (CD$_3$OD) δ 0.95 (s, 1H), 1.27-1.32 (m 2H), 1.88-1.92 (m, 3H), 2.26-2.30 (m, 1H), 2.97-3.01 (m, 5H), 3.13 (s, 3H), 3.33-3.51 (m, 1H), 4.07 (br s, 1H), 7.50 (s, 2H), 7.90 (s, 3H).

Preparation of 5-Methyl-2-{2-oxo-2-[2-((R)-5-pyrimidin-2-yl-indan-1-yl)-2,7-diaza-spiro[3.5]non-7-yl]-ethyl}-benzoic acid (7-1a)

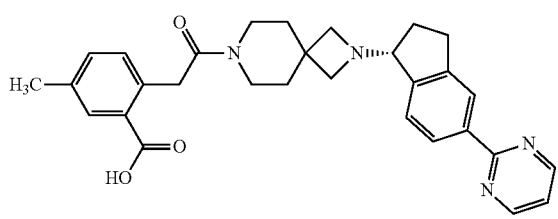

(7-1a)

To 2-(carboxymethyl)-5-methylbenzoic acid (100 mg, 0.52 mmol, prepared according to the procedure described in Tetrahedron, 1975, 31(20), 2607-2619) in a microwave reaction vessel was added acetyl chloride (0.5 mL). The tube was sealed and irradiated (Biotage Inc., microwave) while stirring at 130° C. for 20 minutes. The reaction was cooled to room temperature and the excess acetyl chloride was removed in vacuo. Dichloromethane was added to azeotrope the excess acetyl chloride and the crude anhydride was dried under vacuum. The crude anhydride was dissolved in acetonitrile (2 mL) and 2-[(1S)-5-pyrimidin-2-yl-2,3-dihydro-1H-inden-1-yl]-2,7-diazaspiro[3.5]nonane dihydrochloride (3-1e, 220 mg, 0.52 mmol) was added followed by triethylamine (0.16 mL, 2.06 mmol). The reaction was stirred at room temperature overnight. The reaction was concentrated and the desired product was purified using reverse phase chromatography (Biotage SNAP (15 g), water/CH$_3$CN=95/5% to 50/50%) to afford (176 mg, 69%) 5-methyl-2-{2-oxo-2-[2-(5-pyrimidin-2-yl-indan-1-yl)-2,7-diaza-spiro[3.5]non-7-yl]ethyl}benzoic acid. MS (ES+) 497.6 (M+H)$^+$. $^1$H NMR (CDCl$_3$) δ 1.54-1.58 (m, 2H), 1.60-1.64 (m, 2H), 2.15-2.38 (m, 5H), 2.78-3.02 (m, 2H), 3.04-3.24 (m, 1H), 3.26-3.52 (m, 6H), 3.62-3.66 (m, 2H), 4.41-4.45 (m, 1H), 7.06-7.27 (m, 3H), 7.34-7.57 (m, 1H), 7.68 (s, 1H), 8.31 (s, 2H), 8.73-8.79 (m, 2H).

Preparation of 2-[(R)-5-(4-Methyl-pyrazol-1-yl)-indan-1-yl]-2,7-diaza-spiro[3.5]honane-7-carboxylic acid tert-butyl ester (8-1a)

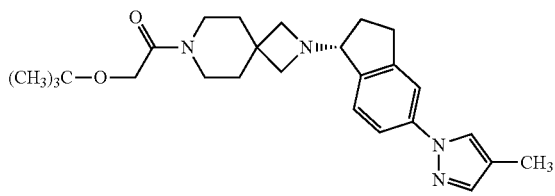

(8-1a)

In a sealable reaction tube was combined 2-(R)-5-bromo-indan-1-yl)-2,7-diaza-spiro[3.5]nonane-7-carboxylic acid tert-butyl ester (3-1a, 300 mg, 0.71 mmol), 4-methyl-1H-pyrazole (88 mg, 1.07 mmol), tris(dibenzylideneacetone)dipalladium (65 mg, 0.071 mmol), 5-(di-tert-butyl-phosphanyl)-1',3',5'-triphenyl-1'H-[1,4']bipyrazolyl (72 mg, 0.14 mmol), cesium carbonate (377 mg, 1.07 mmol) and a stir bar. Anhydrous 1,4-dioxane (3 mL) was added and the mixture was purged with nitrogen for 10 minutes. The reaction was sealed and heated at 100° C. overnight. The reaction was cooled to room temperature, opened, and diluted with 150 mL ethyl acetate. The organic solution was washed with 100 mL water, dried (MgSO$_4$), filtered through a plug of Celite® and concentrated in vacuo to give a yellow oil. Purification on an ISCO (Teledyne Isco Inc., Lincoln Nebr.) silica column eluting with a 0-100% ethyl acetate in heptanes gradient provided 239 mg (79%) of the title compound (8-1a) as a yellow solid. MS (ES+) 423.0 (M+H)$^+$. $^1$H NMR (CDCl$_3$) δ 1.42 (s, 9H), 1.62-1.70 (m, 4H), 1.85-1.96 (m, 1H), 2.09-2.16 (m, 4H), 2.81 (dd, 1H), 3.02 (dd, 1H), 3.06-3.15 (m, 4H), 3.22-3.35 (m, 4H), 3.87-3.91 (m, 1H), 7.27 (d, 1H), 7.39 (dd, 1H), 7.45-7.51 (m, 2H), 7.63 (s, 1H).

Preparation of 2-((R)-5-(4-Methyl-1H-pyrazol-1-yl)-2,3-dihydro-1H-inden-1-yl)-2,7-diazaspiro[3.5]nonane dihydrochloride (8-1b)

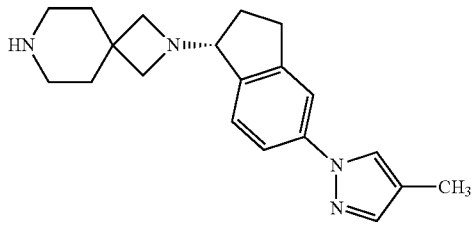

(8-1b)

To a solution of 2-[(R)-5-(4-methyl-pyrazol-1-yl)-indan-1-yl]-2,7-diaza-spiro[3.5]nonane-7-carboxylic acid tert-butyl ester (8-1a, 239 mg, 0.57 mmol) in MeOH (5 mL) was added 9 mL of 4N HCl in dioxane solution. The reaction was stirred for 3 hours. The reaction was concentrated and the residue was coevaporated with diethylether (3×) to afford 2-((R)-5-(4-methyl-1H-pyrazol-1-yl)-2,3-dihydro-1H-inden-1-yl)-2,7-diazaspiro[3.5]nonane dihydrochloride as a white solid (8-1b, 135 mg, 61%). This material was used without further purification in the next reaction. MS (ES+) 322.9 (M+H)+. $^1$H NMR (DMSO-d$_6$) δ 1.89-2.20 (m, 7H), 2.28-2.48 (m, 2H), 2.84-3.14 (m, 4H), 3.28-3.46 (m, 1H), 3.84-4.03 (m, 3H), 4.19-4.33 (m, 2H), 4.83-4.98 (m, 1H), 7.54 (s, 1H), 7.66 (s, 2H), 7.74-7.79 (m, 1H), 8.28 (s, 1H).

Preparation of Intermediate 2-[(R)-5-(6-Carbamoyl-pyridin-3-yl)-indan-1-yl]-2,7-diaza-spiro[3.5]nonane-7-carboxylic acid tert-butyl ester (9-1a)

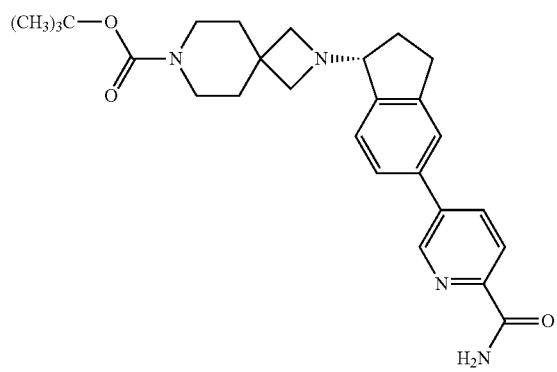

(9-1a)

To a solution of water (150 mL) and urea hydrogen peroxide (916 mg, 9.45 mmol) was added sodium hydroxide (220 mg, 5.51 mmol) and the reaction was stirred at room temperature. Once a clear solution was obtained, the reaction was placed in an ice bath and fitted with an addition funnel. A solution of 2-[(R)-5-(6-cyano-pyridin-3-yl)-indan-1-yl]-2,7-diaza-spiro[3.5]nonane-7-carboxylic acid tert-butyl ester (4-1c, 700 mg, 1.58 mmol) in 50 mL EtOH was added dropwise via the funnel over 30 minutes. The reaction was warmed to room temperature and was stirred overnight. The reaction mixture (a white suspension) was filtered and the solids were washed with 50 mL water and air-dried to give 440 mg (60%) of the title compound as an off-white powder. MS (ES+) 463.1 (M+H)+. $^1$H NMR (DMSO-d$_6$) δ 1.39 (s, 9H), 1.54-1.62 (m, 4H), 1.81-1.91 (m, 1H), 2.06 (dd, 1H), 2.76-2.87 (m, 1H), 2.94-3.02 (m, 3H), 3.10 (d, 2H), 3.24 (br s, 4H), 3.86 (dd, 1H), 7.40 (d, 1H), 7.55 (d, 1H), 7.62-7.68 (m, 2H), 8.09 (d, 1H), 8.12 (br s, 1H), 8.22 (dd, 1H), 8.89 (d, 1H).

Preparation of 5-[(R)-1-(2,7-Diaza-spiro[3.5]non-2-yl)-indan-5-yl]-pyridine-2-carboxylic acid amide dihydrochloride (9-1b)

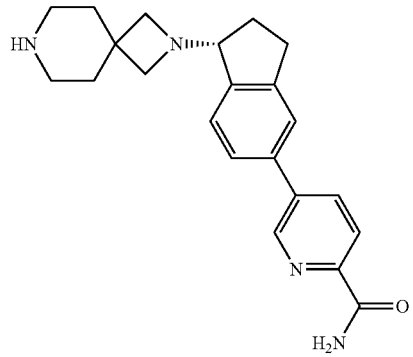

(9-1b)

To a mixture of 2-[(R)-5-(6-carbamoyl-pyridin-3-yl)-indan-1-yl]-2,7-diaza-spiro[3.5]nonane-7-carboxylic acid tert-butyl ester (9-1a, 440 mg, 0.95 mmol) in 1,4-dioxane (10 mL) was added 5 mL of 4N HCl in dioxane. This resulted in the immediate precipitation of solids. The reaction was stirred for 3 hours. The reaction was concentrated and the residue was coevaporated with diethylether (3×) until 5-[(R)-1-(2,7-diaza-spiro[3.5]non-2-yl)-indan-5-yl]-pyridine-2-carboxylic acid amide dihydrochloride (9-1b, 414 mg, 100%) was obtained as a white solid. This material was used without further purification in the next reaction. MS (ES+) 363.1 (M+H)+. $^1$H NMR (CD$_3$OD) δ 2.22-2.26 (m, 5H), 2.56-2.66 (m, 1H), 3.19-3.22 (m, 4H), 3.35 (s, 1H), 3.63-3.66 (m, 1H), 4.15 (d, 1H), 4.24 (s, 2H), 4.47 (s, 1H), 5.09 (br s, 1H), 7.85 (s, 1H), 7.81 (s, 2H), 8.29-8.31 (m, 3H), 8.45 (br s, 1H), 9.07 (br s, 1H).

Preparation of tert-Butyl 2-((R)-5-(5-cyanopyrazin-2-yl)-2,3-dihydro-1H-inden-1-yl)-2,7-diazaspiro[3.5]nonane-7-carboxylate (10-1a)

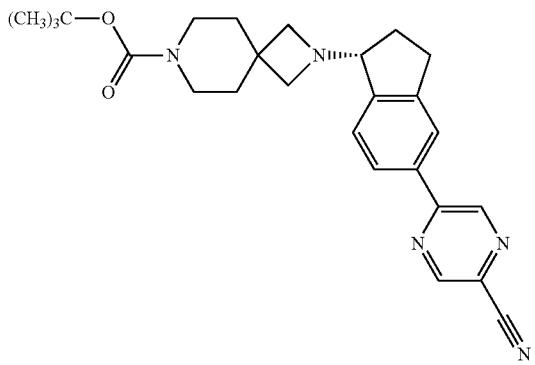

(10-1a)

To a solution of tert-butyl 2-[(1R)-5-bromo-2,3-dihydro-1H-inden-1-yl]-2,7-diazaspiro[3.5]nonane-7-carboxylate (3-1a, 700 mg, 1.66 mmol) in anhydrous dioxane (10 mL) was added bis(pinacolato)diboron (473 mg, 1.86 mmol) and potassium acetate (659 mg, 6.71 mmol). The mixture was purged with nitrogen for 15 minutes. Pd(dppf)Cl$_2$ (62 mg, 0.07 mmol) was added and the reaction mixture was purged with nitrogen for an additional 15 minutes. The reaction was heated to 110° C. under nitrogen for 5 hours. TLC indicated the complete consumption of the starting material (3-1a). The reaction was cooled to room temperature and 5-chloropyrazine-2-carbonitrile (278 mg, 1.99 mmol), Pd(dppf)Cl$_2$ (62 mg, 0.07 mmol) and 5.81 mL of 2M aqueous K$_2$CO$_3$ solution (de-oxygenated with a stream of nitrogen for 15 minutes prior to addition) were added. The reaction was purged with nitrogen (3×) and was heated for 20 hours at 110° C. The reaction was cooled and concentrated in vacuo. The residue was partitioned between 50 mL of ethyl acetate and 50 mL of 1N NaOH solution. The organics layer was washed with 50 mL of brine, dried (Na$_2$SO$_4$) and concentrated to give crude product as black semi-solid. The crude product was purified via silca gel chromatography using a Combiflash ISCO purification system (Teledyne Corp., Lincoln, Nebr.) system, eluting with 0-100% EtOAc:heptanes to give the title compound as a brown solid (440 mg, 59%). MS (ES+) 446.3 (M+H)$^+$. $^1$H NMR (DMSO-d$_6$) δ 1.39 (s, 9H), 1.56-1.64 (m, 4H), 1.81-1.92 (m, 1H), 2.06 (dd, 1H), 2.77-2.87 (m, 1H), 2.92-3.04 (m, 3H), 3.12 (d, 2H), 3.24-3.28 (m, 4H), 3.86 (dd, 1H), 7.41 (d, 1H), 7.55 (d, 1H), 7.62-7.68 (m, 1H), 8.09 (s, 1H), 8.90 (s, 1H).

Preparation of 2-[(R)-5-(5-Carbamoyl-pyrazin-2-yl)-indan-1-yl]-2,7-diaza-spiro[3.5]nonane-7-carboxylic acid tert-butyl ester (10-1b)

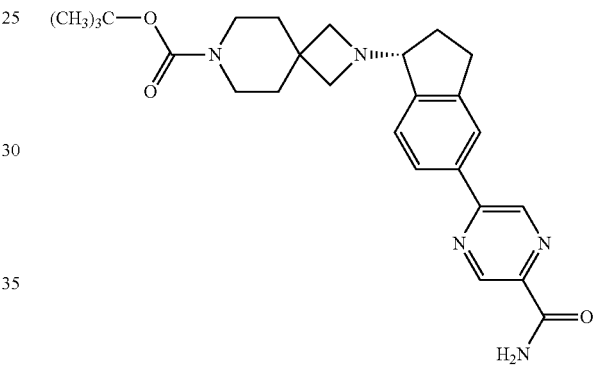

(10-1b)

A round-bottomed flask was charged with water (100 mL) and urea hydrogen peroxide (495 mg, 5.11 mmol). Sodium hydroxide (119 mg, 2.98 mmol) was added and the reaction was stirred at room temperature. Once a clear solution was obtained, the reaction was placed in an ice bath and fitted with an addition funnel. A solution of tert-butyl 2-((R)-5-(5-cyanopyrazin-2-yl)-2,3-dihydro-1H-inden-1-yl)-2,7-diazaspiro[3.5]nonane-7-carboxylate (10-1a, 379 mg, 0.85 mmol) in 25 mL EtOH was added dropwise over a period of 30 minutes via the funnel. The reaction was warmed to room temperature and stirred overnight. The resulting white suspension was collected by vacuum filtration. The solids were washed with 50 mL water and air-dried to give 210 mg (53%) of the title compound as an off-white powder. MS (ES+) 464.4 (M+H)$^+$. $^1$H NMR (DMSO-d$_6$) δ 1.38 (s, 9H), 1.54-1.61 (m, 4H), 1.89 (d, 1H), 2.08 (s, 1H), 2.76-2.80 (m, 2H), 2.99 (d, 3H), 3.11 (d, 2H), 3.19-3.22 (m, 3H), 3.90 (d, 1H), 7.45 (d, 1H), 7.83 (br s, 1H), 8.01 (d, 1H), 8.08 (s, 1H), 8.23 (s, 1H), 9.20 (d, 1H), 9.24 (d, 1H).

Preparation of 5-[(R)-1-(2,7-Diaza-spiro[3.5]non-2-yl)-indan-5-yl]-pyrazine-2-carboxylic acid amide dihydrochloride (10-1c)

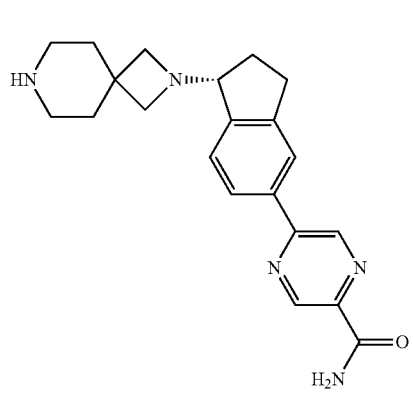

(10-1c)

To 2-[(R)-5-(5-carbamoyl-pyrazin-2-yl)-indan-1-yl]-2,7-diaza-spiro[3.5]nonane-7-carboxylic acid tert-butyl ester (10-1b, 150 mg, 0.32 mmol) was added 5 mL of 4N HCl in dioxane. The mixture was stirred for 3 hours. The volatiles were removed under reduced pressure to give the title compound as a brown solid (65 mg, 45%). MS (APCI) 364.2 (M+H)$^+$. $^1$H NMR (CD$_3$OD) δ 2.20-2.24 (m, 4H), 2.63 (s, 1H), 3.15 (d, 4H), 3.29-3.38 (m, 3H), 4.25 (s, 3H), 4.48 (s, 1H), 5.10 (br s, 1H), 7.79 (d, 1H), 8.18 (d, 1H), 8.24 (s, 1H), 9.22 (s, 1H), 9.30 (s, 1H).

Preparation of 2-[(R)-5-(5-Cyano-pyridin-2-yl)-indan-1-yl]-2,7-diaza-spiro[3.5]nonane-7-carboxylic acid tert-butyl ester (11-1a)

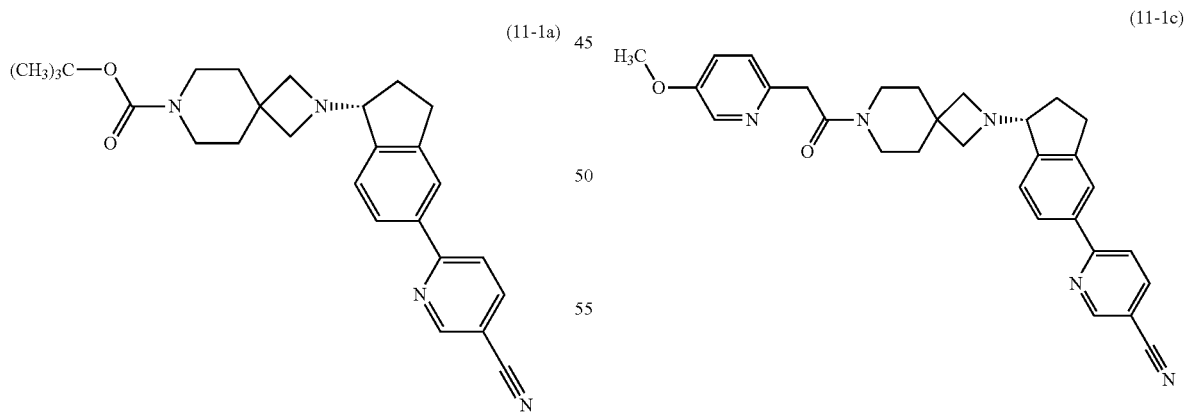

(11-1a)

The title compound was prepared in an analogous fashion to

Intermediate tert-butyl 2-((R)-5-(5-cyanopyrazin-2-yl)-2,3-dihydro-1H-inden-1-yl)-2,7-diazaspiro[3.5]nonane-7-carboxylate (10-1a), substituting 6-bromopyridine-3-carbonitrile for 5-chloropyrazine-2-carbonitrile. MS (ES) 445.1 (M+H)$^+$. $^1$H NMR (CDCl$_3$) δ 1.38-1.46 (m, 9H), 1.63-1.72 (m, 4H), 1.90-1.95 (m, 1H), 2.16-2.23 (m, 1H), 2.79-2.91 (m, 1H), 3.01-3.09 (m, 1H), 3.09-3.18 (m, 4H), 3.26-3.36 (m, 4H), 3.95 (dd, 1H), 7.32-7.41 (m, 1H), 7.72-7.84 (m, 2H), 7.88 (s, 1H), 7.95 (dd, 1H), 8.85-8.92 (m, 1H).

Preparation of 6-[(R)-1-(2,7-Diaza-spiro[3.5]non-2-yl)-indan-5-yl]-nicotinonitrile dihydrochloride (11-1b)

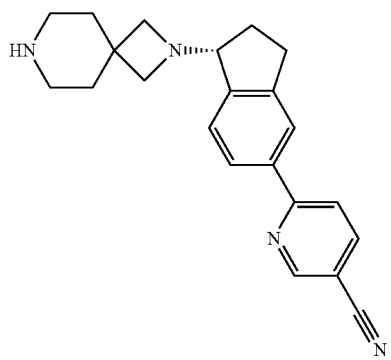

(11-1b)

To a mixture of 2-[(R)-5-(5-cyano-pyridin-2-yl)-indan-1-yl]-2,7-diaza-spiro[3.5]nonane-7-carboxylic acid tert-butyl ester (11-1a, 140 mg, 0.32 mmol) in dioxane (3 mL) was added 5 mL of 4N HCl in dioxane. The mixture was stirred for 3 hours. The volatiles were removed under reduced pressure to give the title compound as a brown solid (65 mg, 48%). MS (APCI) 345.1 (M+H)$^+$. Retention time: 1.26 minutes XBridge C18 4.6×50 mm 5 um, 5-100% acetonitrile:water (0.1% formic acid).

Preparation of 6-(((R)-1-{7-[2-(5-Methoxy-pyridin-2-yl)-acetyl]-2,7-diaza-spiro[3.5]non-2-yl}-indan-5-yl)-nicotinonitrile (11-1c)

(11-1c)

A mixture of (5-methoxypyridin-2-yl)acetic acid (SM-1aa, 0.31 mmol, 52.0 mg) in dichloromethane (5 mL) was charged with 1,1'-carbonyldiimidazole (53.0 mg, 0.31 mmol) and the reaction was stirred for 2 hours at room temperature. In a separate flask, a mixture 6-[(R)-1-(2,7-diaza-spiro[3.5]non-2-yl)-indan-5-yl]-nicotinonitrile dihydrochloride (11-1b, 108 mg, 0.31 mmol) in dichloromethane (10 mL) was charged with triethylamine (0.13 mL, 1.26 mmol). The solution of the activated acid was added to the amine solution and the mixture was stirred at room temperature for 2 hours. The reaction was quenched with 10 mL saturated NaHCO₃ and diluted with 50 mL of dichloromethane. The organic layer was collected, washed with saturated brine, dried over Na₂SO₄ and concentrated. The crude product was used directly in the next step without further purification. MS (ES) 494.0 (M+H)⁺. Retention time: 1.91 minutes XBridge C18 4.6×50 mm 5 um, 5-100% acetonitrile:water (0.1% formic acid).

Example 1

Preparation of 7-[(4-Methoxyphenyl)acetyl]-2-(5-pyrimidin-2-yl-2,3-dihydro-1H-inden-1-yl)-2,7-diazaspiro[3.5]honane (1A)

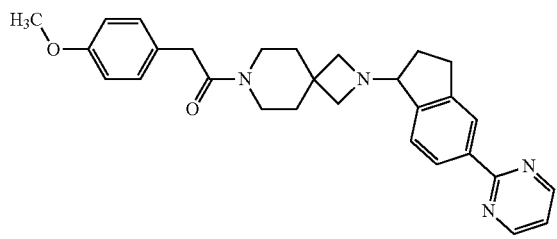

(1A)

An oven dried round-bottomed flask was charged with 7-[(4-methoxyphenyl)acetyl]-2,7-diazaspiro[3.5]nonane hydrochloride (1-1b, 600 mg, 1.93 mmol), 5-pyrimidin-2-ylindan-1-one (SM-1b, 427 mg, 1.93 mmol), anhydrous dichloroethane (30 mL) and triethylamine (1.08 mL, 7.74 mmol). The reaction mixture was treated with titanium (IV) tetraisopropoxide (1.14 mL, 3.85 mmol) and the reaction was stirred at room temperature for 90 minutes. Sodium triacetoxyborohydride (1.02 g, 4.81 mmol) was added in portions and the reaction was stirred for 16 hours. The reaction was diluted with dichloromethane and saturated ammonium chloride. The mixture was filtered through a thin Celite® pad with the aid of dichloromethane. The organic layer was washed with brine, dried over anhydrous magnesium sulfate and concentrated to give the crude product as a dark brown oil (1.12 g). The product was purified by silica chromatography on a Combiflash ISCO purification system (Teledyne Isco Inc., Lincoln, Nebr.) with 0-10% methanol in dichloromethane as eluant to give the product as a brown oil (770 mg, 85%). MS (ES+) 469.5 (M+H)⁺. ¹H NMR (CDCl₃) δ 1.52-1.58 (m, 2H), 1.65-1.72 (m, 2H), 1.87-1.95 (m, 1H), 2.12-2.21 (m, 1H), 2.82-2.90 (m, 1H), 3.02-3.15 (m, 5H), 3.33 (t, 2H), 3.52 (t, 2H), 3.65 (s, 2H), 3.78 (s, 3H), 3.94-3.97 (m, 1H), 6.82-6.87 (m, 2H), 7.12-7.17 (m, 3H), 7.35 (d, 1H), 8.24 (d, 1H), 8.28 (s, 1H), 8.78 (d, 2H).

Preparation of (R)-7-[(4-Methoxyphenyl)acetyl]-2-(5-pyrimidin-2-yl-2,3-dihydro-1H-inden-1-yl)-2,7-diazaspiro[3.5]nonane (1A-1)

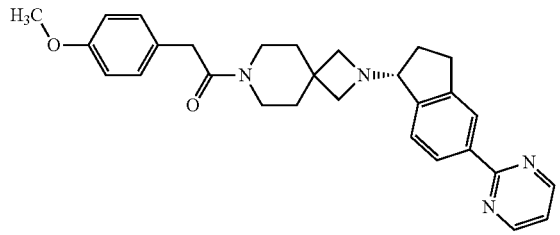

(1A-1)

The racemic mixture obtained above (1A) was separated on a chiral column (Chiralpak AS-H, 1 cm×25 cm, flow-rate 10 g/minutes, CO₂/ethanol (70/30) mobile phase with 0.1% isopropylamine) to afford the title compound (1-1A) as a light brown oil, which solidified on standing (260 mg). MS (ES+) 469.5 (M+H)⁺. ¹H NMR (CDCl₃) δ 1.52-1.58 (m, 2H), 1.65-1.72 (m, 2H), 1.87-1.95 (m, 1H), 2.12-2.21 (m, 1H), 2.82-2.90 (m, 1H), 3.02-3.15 (m, 5H), 3.33 (t, 2H), 3.52 (t, 2H), 3.65 (s, 2H), 3.78 (s, 3H), 3.94-3.97 (m, 1H), 6.82-6.87 (m, 2H), 7.12-7.17 (m, 3H), 7.35 (d, 1H), 8.24 (d, 1H), 8.28 (s, 1H), 8.78 (d, 2H). $[\alpha]_D^{20}$=+43.2 deg (c=8 mg/mL, MeOH)

The compounds in Table 1 (where L is a direct bond and thus $R^2$ is directly attached as shown) were prepared using analogous procedures for the preparation of 7-[(4-methoxyphenyl)acetyl]-2-(5-pyrimidin-2-yl-2,3-dihydro-1H-inden-1-yl)-2,7-diazaspiro[3.5]nonane (1A or 1A-1) using the appropriate starting materials followed by chiral separation when an enantioenriched product is indicated. When designated as enantioenriched, the stereochemistry is (R) as indicated below.

TABLE 1

| Example No. | $R^1$ | $R^2$ |
|---|---|---|
| 1B (enantioenriched) | H₃C— (thiazolo-imidazole group) | pyrimidin-2-yl |

MS (ES+) 499.5 (M + H)⁺.
¹H NMR (CD₃OD) δ 1.83-2.02 (m, 4H), 2.18-2.26 (m, 1H), 2.53 (s, 3H), 2.55-2.65 (m, 1H), 3.04-3.13 (m, 1H), 3.23 (t, 1H), 3.33 (s, 2H), 3.53-3.67 (m, 4H), 4.09-4.22 (m, 3H), 4.33-4.43 (m, 1H), 4.99-5.05 (m, 1H), 7.32 (t, 1H), 7.40 (br s, 2H), 7.46 (d, 1H), 8.22 (d, 1H), 8.26 (s, 1H), 8.85 (d, 2H).

TABLE 1-continued

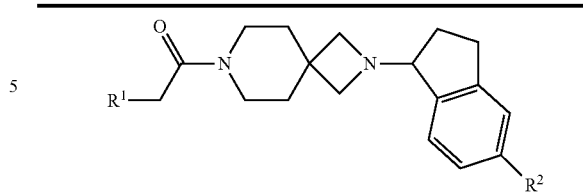

| Example No. | R[1] | R[2] |
|---|---|---|
| 1G (enantioenriched) | 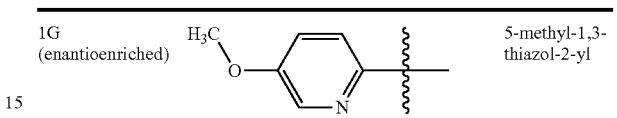 | 5-methyl-1,3-thiazol-2-yl |

MS (ES+) 487.4 (M + H)+
$^1$H NMR (CD3OD) δ 1.86-1.90 (m, 2H), 1.98-2.02 (m, 2H), 2.16-2.24 (m, 1H), 2.52 (s, 3H), 2.53-2.64 (m, 1H), 3.02-3.12 (m, 1H), 3.17-3.24 (m, 1H), 3.51-3.70 (m, 4H), 4.01 (s, 3H), 4.07-4.25 (m, 4H), 4.30-4.40 (m, 2H), 4.94-5.01 (m, 1H), 7.55 (d, 1H), 7.64 (d, 1H), 7.78 (d, 1H), 7.81-7.85 (m, 1H), 7.89 (br s, 1H), 8.08 (dd, 1H), 8.50 (d, 1H).

| 1H (enantioenriched) | 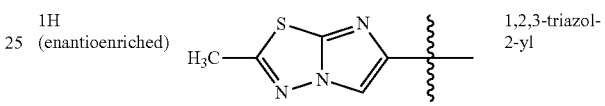 | 1,2,3-triazol-2-yl |

MS MS (ES+) 489.5 (M + H)+
$^1$H NMR (CD3OD) δ 1.71-1.76 (m, 4H), 1.88-1.97 (m, 1H), 2.20-2.30 (m, 1H), 2.68 (s, 3H), 2.84-2.93 (m, 1H), 3.08-3.17 (m, 1H), 3.23-3.32 (m, 4H), 3.51-3.58 (m, 4H), 3.78 (s, 2H), 4.02-4.06 (m, 1H), 7.46 (d, 1H), 7.71 (s, 1H), 7.85-7.89 (m, 3H), 7.92 (br s, 1H).

| 1I (racemic) | 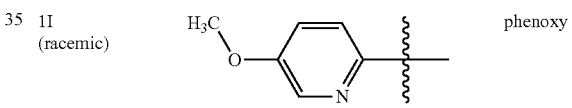 | phenoxy |

MS (ES+) 484.5 (M + H)+
Retention time: 1.78 min XBridge C18 4.6 × 50 mm 5um, 5-100% acetonitrile:water (0.1% formic acid).

| 1J (enantioenriched) | 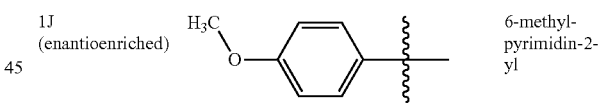 | 6-methyl-pyrimidin-2-yl |

MS (ES+) 483.5 (M + H)+
$^1$H NMR (CDCl3) δ 1.52-1.59 (m, 2 H), 1.60-1.67 (m, 2 H), 1.97-2.08 (m, 2 H), 2.18-2.30 (m, 2 H), 2.57 (s, 3 H), 2.83-2.94 (m, 2 H), 3.02-3.13 (m, 1 H), 3.27-3.37 (m, 4 H), 3.48 (t, 2 H), 3.62 (s, 2 H), 3.77 (s, 3 H), 6.79-6.85 (m, 2 H), 7.03 (d, 1 H), 7.11 (d, 2 H), 7.38 (d, 1 H), 8.27 (d, 1 H), 8.31 (s, 1 H), 8.61 (d, 1 H).

| 1K (enantioenriched) | 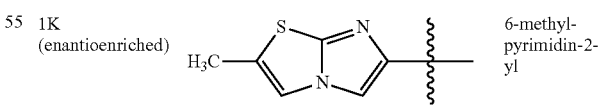 | 6-methyl-pyrimidin-2-yl |

MS (ES+) 513.4 (M + H)+
$^1$H NMR (DMSO-D6) δ 1.50-1.60 (m, 4 H), 1.75-1.88 (m, 1 H), 2.01-2.08 (m, 1 H), 2.35 (s, 3 H), 2.74-2.80 (m, 1 H), 2.95-2.99 (m, 3 H), 3.08-3.10 (m, 2 H), 3.30 (s, 3 H), 3.35-3.45 (m, 4 H), 3.61 (s, 2 H), 3.84-3.87 (m, 1 H), 7.26 (d, 1 H), 7.36 (d, 1 H), 7.44 (s, 1 H), 7.57 (s, 1 H), 8.16 (d, 1 H), 8.22 (s, 1 H). 8.69 (s, 1 H).

TABLE 1-continued

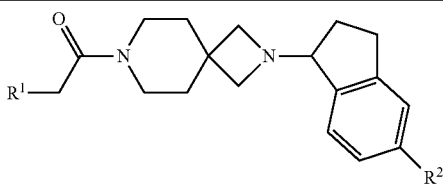

| Example No. | R[1] | R[2] |
|---|---|---|
| 1C (enantioenriched) | 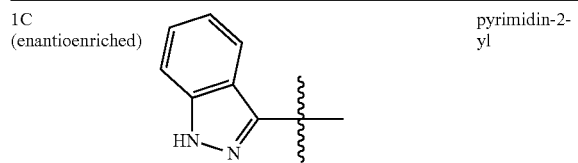 | pyrimidin-2-yl |

MS (ES+) 479.3 (M + H)+
$^1$H NMR (DMSO-d6) δ 1.64-1.68 (m, 4 H), 2.02-2.06 (m, 1 H), 2.29 (s, 1 H), 2.51 (s, 1 H), 2.96-2.99 (m, 1 H), 3.10-3.13 (m, 2 H), 3.43-3.47 (m, 3 H), 3.88-4.05 (m, 4 H), 4.29-4.32 (m, 1 H), 4.96-4.99 (m, 1 H), 7.04 (t, 1 H), 7.30 (s, 1 H), 7.36-7.54 (m, 2 H), 7.67 (d, 2 H), 8.25-8.41 (m, 2 H), 8.89 (d, 2 H), 10.17 (br s, 1 H).

| 1D (enantioenriched) | 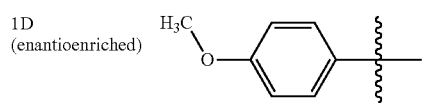 | 2-methyl-pyrimidin-4-yl |

MS (ES+) 483.5 (M + H)+
$^1$H NMR (CDCl3) δ 1.52-1.58 (m, 2H), 1.65-1.72 (m, 2H), 1.87-1.95 (m, 1H), 2.12-2.21 (m, 1H), 2.78 (s, 3H), 2.82-2.90 (m, 1H), 3.02-3.15 (m, 5H), 3.33 (t, 2H), 3.52 (t, 2H), 3.65 (s, 2H), 3.78 (s, 3H), 3.94-3.97 (m, 1 H), 6.79-6.83 (m, 2H), 7.07-7.12 (m, 2H), 7.48 (t, 1H), 7.87 (d, 1H), 8.00 (br s, 1 H), 8.30 (s, 1 H), 8.66 (d, 1H).

| 1E (racemic) | 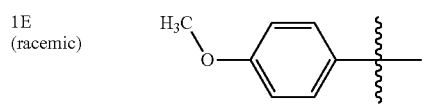 | 5-methyl-pyrimidin-2-yl |

MS (ES+) 483.5 (M + H)+
Retention time: 1.48 min XBridge C18 4.6 × 50 mm 5um, 5-100% acetonitrile:water (0.1% formic acid).

| 1F (racemic) | 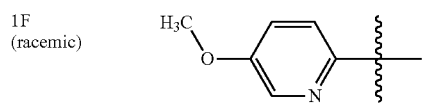 | 1,3-thiazol-2-yl |

MS (APCI) 474.7 (M + H)+
$^1$H NMR (CDCl3) δ 1.56-1.62 (m, 2H), 1.64-1.68 (m, 2H), 1.86-1.94 (m, 1H), 2.09-2.18 (m, 1H), 2.77-2.86 (m, 1H), 3.00-3.14 (m, 5H), 3.45 (t, 2H), 3.50 (t, 2H), 3.82 (s, 3H), 3.83 (s, 2H), 3.90-3.94 (m, 1H), 7.12-7.15 (m, 1H), 7.22-7.25 (m, 1H), 7.27-7.31 (m, 2H), 7.74 (d, 1H), 7.80-7.82 (m, 2H), 8.18 (d, 1H).

| 1F-1 (enantioenriched) | 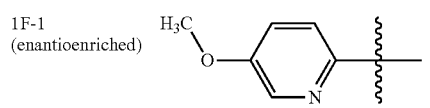 | 1,3-thiazol-2-yl |

MS (ES+) 475.3 (M + H)+
$^1$H NMR (CDCl3) δ 1.56-1.62 (m, 2H), 1.64-1.68 (m, 2H), 1.86-1.94 (m, 1H), 2.09-2.18 (m, 1H), 2.77-2.86 (m, 1H), 3.00-3.14 (m, 5H), 3.45 (t, 2H), 3.50 (t, 2H), 3.82 (s, 3H), 3.83 (s, 2H), 3.90-3.94 (m, 1H), 7.12-7.15 (m, 1H), 7.22-7.25 (m, 1H), 7.27-7.31 (m, 2H), 7.74 (d, 1H), 7.80-7.82 (m, 2H), 8.18 (d, 1H).

Example 2

Preparation of 7-[(5-Methoxypyridin-2-yl)acetyl]-2-[5-(5-methoxypyridin-2-yl)-2,3-dihydro-1H-inden-1-yl]-2,7-diazaspiro[3.5]nonane (2A)

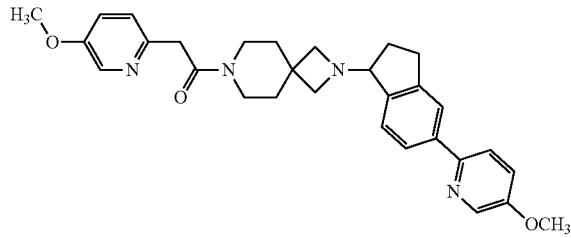

(2A)

A 50 mL solution of 7-[(5-methoxypyridin-2-yl)acetyl]-2-[5-(4,4,5,5-tetramethyl-1,3,2-dioxaborolan-2-yl)-2,3-dihydro-1H-inden-1-yl]-2,7-diazaspiro[3.5]nonane (2-1c, 1.30 g, 2.50 mmol) in de-oxygenated dioxane (nitrogen stream for 15 minutes) was prepared. A 2M solution of aqueous $Na_2CO_3$ solution (30 mL) was made and deoxygenated with a stream of nitrogen for 15 minutes. The above pinacolborate solution (2 mL, 0.1 mmol) was added to a plate of 24 vials containing the appropriate heterohalide; in this case 2-chloro-5-methoxypyridine (14.3 mg, 0.1 mmol). Pd(dppf)$Cl_2$ catalyst (8 mg, 0.009 mmol) was added to each vial. The $Na_2CO_3$ solution (1 mL, 2M) was added to each vial using a multipipette. The reaction mixtures were sealed and heated to 110° C. while shaking for 5 hours. The dioxane was removed under vacuum. Ethyl acetate (2 mL) was added to each vial and, after shaking, the aqueous layer was discarded. The ethyl acetate solution was concentrated and the crude material purified directly by preparative HPLC eluting with water/acetonitrile. MS (ES) 499.13 (M+H)$^+$. Retention time: 2.12 minutes XBridge C18 4.6×50 mm 5 um, 5-100% acetonitrile: water (0.1% formic acid).

The compounds listed in Table 2 below were prepared using the procedure described above for the preparation of 7-[(5-methoxypyridin-2-yl)acetyl]-2-[5-(5-methoxypyridin-2-yl)-2,3-dihydro-1H-inden-1-yl]-2,7-diazaspiro[3.5]nonane (2A) with the appropriate starting materials. All compounds in Table 2 are racemic unless otherwise noted.

TABLE 2

| Example No. | R$^1$ | R$^2$ |
|---|---|---|
| 2B | 5-methoxypyridin-2-yl | 2-methyl-pyridin-4-yl |
| MS (ES) 483.3 (M + H)$^+$ Retention time: 2.04 min | | |
| 2C | 5-methoxypyridin-2-yl | 4-cyano-pyridin-2-yl |
| MS (ES) 494.15 (M + H)$^+$ Retention time: 2.05 min | | |
| 2D | 5-methoxypyridin-2-yl | 5-methyl-pyridin-2-yl |
| MS (ES) 483.17 (M + H)$^+$ Retention time: 2.28 min | | |

TABLE 2-continued

| Example No. | R$^1$ | R$^2$ |
|---|---|---|
| 2E | 5-methoxypyridin-2-yl | 5-methoxy-pyrimidin-2-yl |
| MS (ES) 500.15 (M + H)$^+$ Retention time: 2.13 min | | |
| 2F | 5-methoxypyridin-2-yl | 6-methoxy-pyrimidin-4-yl |
| MS (ES) 500.25 (M + H)$^+$ Retention time: 2.15 min | | |
| 2G | 5-methoxypyridin-2-yl | 4-methyl-pyridin-2-yl |
| MS (ES) 483.16 (M + H)$^+$ Retention time: 2.24 min, | | |
| 2H | 5-methoxypyridin-2-yl | pyrazin-2-yl |
| MS (ES) 470.15 (M + H)$^+$ Retention time: 1.86 min | | |
| 2I | 5-methoxypyridin-2-yl | 4,6-dimethyl-pyrimidin-2-yl |
| MS (ES) 498.15 (M + H)$^+$ Retention time: 2.28 min | | |
| 2J | 5-methoxypyridin-2-yl | 6-methyl-pyridin-2-yl |
| MS (ES) 483.15 (M + H)$^+$ Retention time: 2.35 min | | |

Example 3

Preparation of 2-[(1R)-5-(5-Ethylpyrimidin-2-yl)-2,3-dihydro-1H-inden-1-yl]-7-[(5-methoxypyridin-2-yl)acetyl]-2,7-diazaspiro[3.5]nonane (3A)

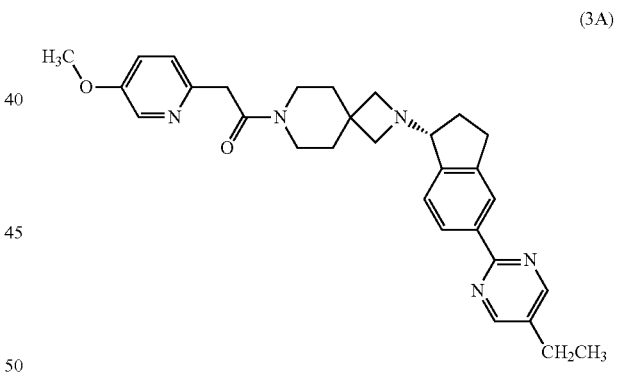

(3A)

To a solution of 2-[(1R)-5-(5-ethylpyrimidin-2-yl)-2,3-dihydro-1H-inden-1-yl]-2,7-diazaspiro[3.5]nonane dihydrochloride (3-1c, 630 mg, 1.38 mmol) in dimethylformamide (5 mL) was added (5-methoxypyridin-2-yl)acetic acid (SM-1aa, 230 mg, 1.38 mmol), HBTU (523 mg, 1.38 mmol) and triethylamine (1.20 mL, 8.5 mmol). The solution was stirred at room temperature for 15 hours. The reaction mixture was concentrated under reduced pressure and the residual DMF was azeotroped with toluene. The residue was partitioned between 50 mL of ethyl acetate and 50 mL 1N NaOH solution. The organic layer was collected, washed with saturated brine, dried over $Na_2SO_4$ and concentrated. The crude product was purified on an Analogix (Analogix Inc., Burlington, Wis.) 8 g silica column (1-10% MeOH in $CH_2Cl_2$ in 20 minutes) to afford the desired product (554 mg, 79.4%) as an off-white foam. The solid was stirred in 50 mL of refluxing diisopropyl ether for 6 hours and filtered to afford a light-grey powder (490 mg, 71%). MS (ES+) 498.5 (M+H)+. $^1$H NMR (CDCl$_3$) δ 1.28 (t, 3H), 1.53-1.77 (m, 4H), 1.77-2.01 (m, 1H), 2.03-2.22 (m, 1H), 2.65 (q, 2H), 2.76-2.94 (m, 1H), 2.95-3.18 (m, 5H), 3.30-3.54 (m, 4H), 3.69-3.86 (m, 5H), 3.88-4.04 (m, 1H), 7.14 (dd, 1H), 7.19-7.26 (m, 1H), 7.33 (d, 1H), 8.13-8.29 (m, 3H), 8.60 (s, 2H). $[α]_D^{20}$=+40.0 deg (c=10 mg/mL, MeOH).

Preparation of 7-[(4-Methoxyphenyl)acetyl]-2-[(1R)-5-pyrimidin-2-yl-2,3-dihydro-1H-inden-1-yl]-2,7-diazaspiro[3.5]nonane (3B)

(3B)

A mixture of 2-[(1R)-5-pyrimidin-2-yl-2,3-dihydro-1H-inden-1-yl]-2,7-diazaspiro[3.5]nonane dihydrochloride (3-1e, 600 mg, 1.40 mmol), p-methoxyphenylacetic acid (232 mg, 1.40 mmol), HBTU (529 mg, 1.40 mmol) and triethylamine (1.2 mL, 8.6 mmol) in 5 mL of DMF was stirred at room temperature for 20 hours. The solvent was removed in vacuo, the residue was azeotroped with toluene and partitioned between 1N NaOH (50 mL) and ethyl acetate (50 mL). The organic layer was washed with brine, dried (Na$_2$SO$_4$) and concentrated. The crude product was purified on an Analogix (Analogix Inc., Burlington, Wis.) 24 g silica column (1-15% MeOH in DCM in 30 minutes) to give the product as a light foam. This solid was stirred with diethyl ether (80 mL) for 18 h and filtered to give the title compound as a light grey solid (540 mg, 82%). MS (ES+) 469.5 (M+H)+ $^1$H NMR (CDCl$_3$) δ 1.52-1.58 (m, 2H), 1.65-1.72 (m, 2H), 1.87-1.95 (m, 1H), 2.12-2.21 (m, 1H), 2.82-2.90 (m, 1H), 3.02-3.15 (m, 5H), 3.33 (t, 2H), 3.52 (t, 2H), 3.65 (s, 2H), 3.78 (s, 3H), 3.94-3.97 (m, 1H), 6.82-6.87 (m, 2H), 7.12-7.17 (m, 3H), 7.35 (d, 1H), 8.24 (d, 1H), 8.28 (s, 1H), 8.78 (d, 2H). $[α]_D^{20}$=+43.2 deg (c=8 mg/mL, MeOH).

Preparation of 7-[(5-methoxypyridin-2-yl)acetyl]-2-[(1R)-5-(6-methylpyrimidin-4-yl)-2,3-dihydro-1H-inden-1-yl]-2,7-diazaspiro[3.5]nonane (3C)

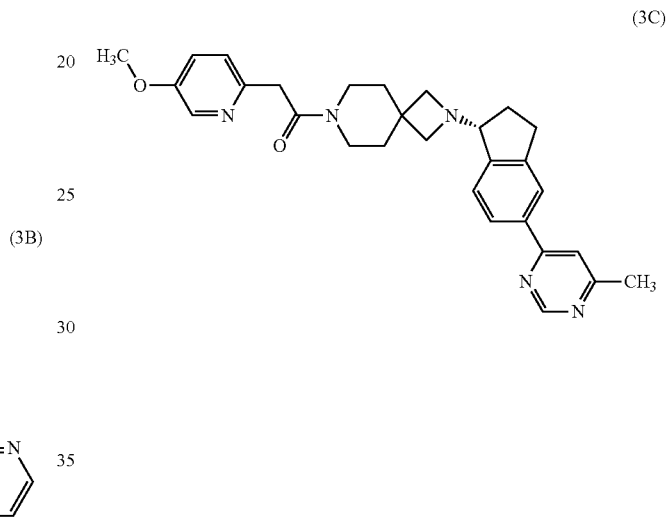

(3C)

To a mixture of (5-methoxypyridin-2-yl)acetic acid (SM-1aa, 8.90 g, 53.2 mmol) in dichloromethane (225 mL) was added 1,1'-carbonyldiimidazole (8.63 g, 53.2 mmol) and the reaction was stirred for 2 hours at room temperature. In a separate flask, triethylamine (28.3 mL, 203 mmol) was added to a mixture of 2-[5-(6-methyl-pyrimidin-4-yl)-indan-1-yl]-2,7-diaza-spiro[3.5]nonane-dihydrochloride (3-1g, 22.5 g, 50.7 mmol) in dichloromethane (113 mL). The activated acid was added to the amine solution and the reaction was stirred at room temperature for 2 hours. Aqueous sodium hydroxide (1N, 80 mL) and 100 mL of water were added and mixture was stirred for 10 minutes. The aqueous layer was washed with 150 mL of dichloromethane. The combined organic layers were washed with aqueous NH$_4$Cl (3×) to remove the residual amine starting material. The organic solution was concentrated to a light green-amber oil and was stirred at 50° C. in EtOAc (150 mL) until a solution was obtained. The solution was cooled to room temperature with stirring. A solid formed and the thick slurry was diluted with 50 mL of EtOAc and 50 mL of heptanes. The slurry was stirred for 1 hour and filtered under nitrogen to afford 2-(5-methoxy-pyridin-2-yl)-1-{2-[(R)-5-(6-methyl-pyrimidin-4-yl)-indan-1-yl]-2,7-diaza-spiro[3.5]non-7-yl}-ethanone (22 g, 89.7%) as an off-white solid. MS (ES+) 484.4 (M+H)+. $^1$H NMR (CDCl$_3$) δ 1.74 (dt, 4H), 1.95-1.99 (m, 1H), 2.25-2.36 (m, 1H), 2.59 (s, 3H), 2.89-2.99 (m, 1H), 3.11-3.21 (m, 1H), 3.34-3.46 (m, 4H), 3.51-3.61 (m, 4H), 3.83-3.92 (m, 5H), 4.17 (dd, 1H), 7.29 (d, 1H), 7.38 (dd, 1H), 7.53 (d, 1H), 7.88 (s, 1H), 8.00 (d, 1H), 8.06 (s, 1H), 8.16 (d, 1H), 9.02 (s, 1H). $[\alpha]_D^{20}$=+55.0 deg (c=1 mg/mL, MeOH).

Preparation of 6-(2-{2-[1R]-5-(6-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine (3D)

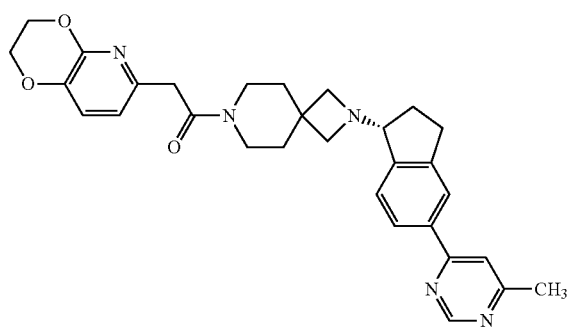

(3D)

To a suspension of 2-[(R)-5-(6-methyl-pyrimidin-4-yl)-indan-1-yl]-2,7-diaza-spiro[3.5]nonane dihydrochloride (3-1g, 450 mg, 1.10 mmol) in 10 mL of dichloromethane was added triethylamine (0.93 mL, 6.63 mmol). Once the mixture became a homogenous solution, it was added to a solution of (2,3-dihydro-[1,4]dioxino[2,3-b]pyridin-6-yl)acetic acid (SM-1aj, 2.87 mg, 1.24 mmol) in 3 mL of dichloromethane. The mixture was stirred for 5 minutes and HBTU (432 mg, 1.10 mmol) in 2 mL of DMF was added. The mixture was stirred at room temperature for 1.5 hours. The reaction mixture was quenched by the addition of 10 mL of NaHCO₃ and diluted with 50 mL of dichloromethane. The organic layer was washed with saturated brine, dried over Na₂SO₄ and concentrated. The crude product was purified on a reverse phase column (Biotage (Biotage Inc.) eluting with 95-50% water in CH₃CN to afford 310 mg (55%) of the desired product as an off-white powder. MS (ES+) 512.0 (M+H)⁺. ¹H NMR (CD₃OD) δ 1.66-1.77 (m, 4H), 1.92 (qd, 1H), 2.18-2.33 (m, 1H), 2.56 (s, 3H), 2.90 (s, 1H), 3.04-3.19 (m, 1H), 3.25-3.30 (m, 2H), 3.31-3.37 (m, 2H), 3.48-3.57 (m, 4H), 3.73 (s, 2H), 4.05-4.09 (m, 1H), 4.18-4.26 (m, 2H), 4.35-4.46 (m, 2H), 6.83 (d, 1H), 7.20 (d, 1H), 7.49 (d, 1H), 7.85 (s, 1H), 7.96 (d, 1H), 8.02 (s, 1H), 8.99 (d, 1H). $[\alpha]_D^{20}$=+49.0 deg (c=2.0 mg/mL, MeOH).

Preparation of 6-(2-{2-[(1R)-5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine (3E)

(3E)

To a mixture of 2-(2,3-dihydro-[1,4]dioxino[2,3-b]pyridin-6-yl)acetic acid (SM-1aj, 27.27 g, 139.73 mmol), dichloromethane (495 mL), and triethylamine (67.74 mL, 468.03 mmol) was added 1,1'-carbonyldiimidazole (22.66 g, 139.73 mmol) at 20° C. and the resulting mixture was heated to 40° C. and stirred for 2 hours. The reaction was charged with 2-[(R)-5-(2-methylpyrimidin-4-yl)-indan-1-yl]-2,7-diazaspiro[3.5]nonane dihydrochloride (3-1 h, 49.50 g, 121.51 mmol). The resulting mixture was stirred at 40° C. for 2 hours, monitoring by HPLC for consumption of amine starting material. The reaction temperature was adjusted below 25° C. and charged with water (1500 mL) and stirred for 5 min. The layers were separated and the organic layer was concentrated to dryness and backfilled with EtOAc (1000 mL) and further concentrated to approximately 300 mL. The resulting thick solution was cooled to 20° C. and stirred until crystals formed. The very thick mixture was diluted with EtOAc (1000 mL) and stirred for 5 min, filtered and dried under vacuum at 45° C. to afford the title compound (21.8 g, 35%). MS (ES+) 512.5 (M+H)⁺. ¹H NMR (CDCl₃) δ 1.64-1.75 (m, 4H), 1.90-2.00 (m, 1H), 2.14-2.23 (m, 1H), 2.81 (s, 3H), 2.85-2.94 (m, 1H), 3.08-3.20 (m, 5H), 3.45-3.57 (m, 4H), 3.77 (s, 2H), 3.98 (dd, 1H), 4.22-4.28 (m, 2H), 4.41-4.46 (m, 2H), 6.91 (d, 1H), 7.15 (d, 1H), 7.38 (d, 1H), 7.48 (d, 1H), 7.86 (d, 1H), 7.96 (s, 1H), 8.65 (d, 1H).

Preparation of 7-[2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane (3F) Method A 4.05-4.09 (m, 1H), 7.33 (s, 2H), 7.55 (d, 1H), 7.78-7.79 (m, 1H), 7.94-8.03 (m, 2H), 8.93 (s, 1H). [α]$_D^{20}$=+45.3 deg (c=2.5 mg/mL, MeOH).

Preparation of 7-[2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane (3F) Method B

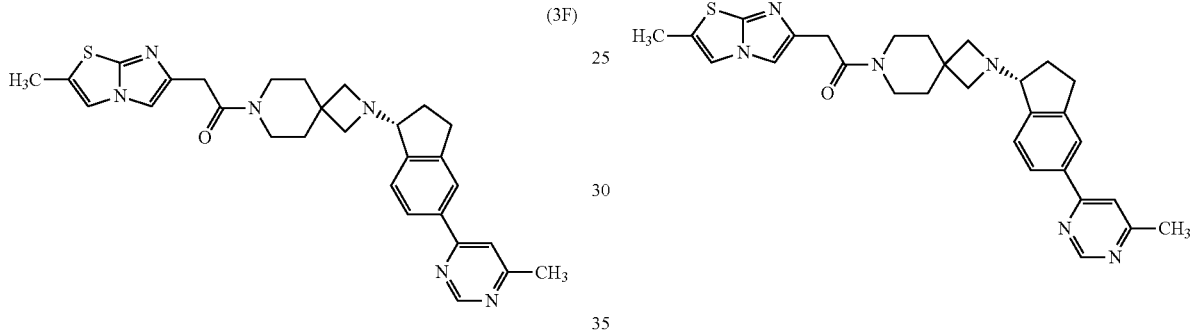

To a suspension of 2-[(R)-5-(6-methyl-pyrimidin-4-yl)-indan-1-yl]-2,7-diaza-spiro[3.5]nonane dihydrochloride (3-1g, 540 mg, 1.22 mmol) in 10 mL of dichloromethane was added triethylamine (492 mg, 4.90 mmol). Once the mixture became a homogenous solution, it was added to a solution of (2-methyl-7,7a-dihydro-imidazo[2,1-b]thiazol-6-yl)-acetic acid (SM-1 ad, 251 mg, 1.28 mmol) in 3 mL of dichloromethane. The mixture was stirred for 5 minutes and HBTU (462 mg, 1.22 mmol) in 2 mL of DMF was added. The reaction was stirred at room temperature for 1.5 hours. The reaction was quenched by the addition of 10 mL of NaHCO$_3$ and was diluted with 50 mL of dichloromethane. The organic layer was washed with saturated brine, dried over Na$_2$SO$_4$, filtered and the filtrate was concentrated. The residue was dissolved in 5 mL of CH$_3$CN and the solution was heated to 100° C. for 1 hour with stirring. The mixture was cooled to room temperature and the resulting solids were vacuum filtered to afford the desired product as an off white powder (428 mg, 69%). MS (ES+) 513.5 (M+H)$^+$. $^1$H NMR (CD$_3$OD) δ 1.70-1.74 (m, 4H), 1.88-1.96 (m, 1H), 2.27-2.34 (m, 2H), 2.40 (s, 3H), 2.58 (s, 3H), 2.86-2.97 (m, 1H), 3.11-3.15 (m, 1H), 3.31-3.34 (m, 3H), 3.52-3.55 (m, 4H), 3.78 (s, 2H), To a mixture of (2-methyl-7,7a-dihydroimidazo[2,1-b]thiazol-6-yl)-acetic acid (SM-1 ad, 2.52 g, 12.85 mmol), dichloromethane (50 mL), and triethylamine (1.63 mL, 11.68 mmol) was added 1,1'-carbonyldiimidazole (2.08 g, 12.85 mmol) at 20° C. and the resulting mixture was heated to 40° C. and was stirred for 2 h. HPLC analysis after 2 h indicated >98% conversion to desired intermediate. The reaction was then charged with triethylamine (6.51 mL, 46.72 mmol) followed by 2-[(R)-5-(6-methyl-pyrimidin-4-yl)-indan-1-yl]-2,7-diaza-spiro[3.5]nonane dihydrochloride (3-1g, 5.0 g, 11.68 mmol). The resulting mixture was stirred at 40° C. for 2 h, monitoring by HPLC for consumption of amine starting material. The reaction temperature was adjusted below 25° C. and charged with water (15 mL) and stirred for 5 min. The layers were separated and the organic layer was washed with water (15 mL). The organic layer was concentrated to remove dichloromethane while replacing with isopropanol to a volume of approximately 70 mL at atmospheric pressure until 81° C. was achieved. The temperature was lowered to 50° C. and held for crystallization. After solids were formed, the temperature was adjusted down to 10° C. at 0.2° C./min (2.5 hours) and held for 1 h. The solid was then filtered and the filter cake was washed with isopropanol and the product was dried under vacuum at 45° C. for 8 h to obtain the desired product 3F as an off white powder (4.73 g, 79%).

Preparation of 7-[(2-methylimidazo[2,1-b][1,3,4]thiadiazol-6-yl)acetyl]-2-[(1R)-5-(6-methylpyrimidin-4-yl)-2,3-dihydro-1H-inden-1-yl]-2,7-diazaspiro[3.5]nonane (3Z)

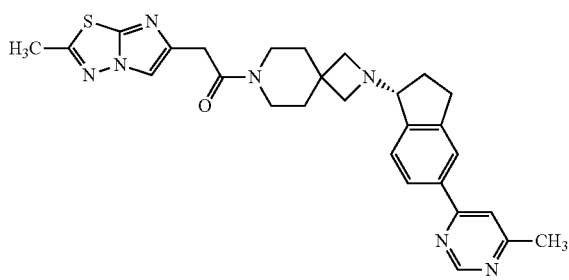

To a mixture of 2-[(R)-5-(6-methyl-pyrimidin-4-yl)-indan-1-yl]-2,7-diaza-spiro[3.5]nonane dihydrochloride (3-1g, 800 g, 1.87 mol), (2-(2-methylimidazo[2,1-b][1,3,4]thiadiazol-6-yl)acetic acid (SM-1ae, 406.4 g, 2.06 mol), and triethylamine (1.31 L, 9.37 mol) in dichloromethane (8 L) was added T3P (2150 g, 3.37 mol) dropwise over 45 min and stirred for 1 h maintaining a temperature between 20 and 30° C. Water was added dropwise (4 L) and the reaction was stirred at 30° C. for 15 min. The layers were separated and the aqueous layer was concentrated to remove residual solvent under partial vacuum at 20° C. The aqueous layer was treated with activated charcoal (20 wt %), stirred for 30 min and filtered through Celite® washing with water. The filtrate was adjusted to pH 7.5-8.0 with 1N NaOH. The resulting slurry was extracted with dichloromethane (12 L) and stirred for 10 min at room temperature. The layers were separated and the organic layer was concentrated under reduced pressure to approximately 4 L. Isopropyl acetate (12 L) was added and the solution was concentrated under reduced pressure at 78° C. to 8 L. The solution was cooled slowly over 4 hours to 20° C. The resulting slurry was stirred for 1 h, filtered and washed with isopropyl acetate (2.4 L). The resulting solid was further dried under vacuum at 45° C. for 8 hours to give the title compound 3Z as a white crystalline solid (883 g, 92%). MS (ES+) 514.0 (M+H)⁺. ¹H NMR (CDCl₃) δ 1.69-1.72 (m, 4H), 1.88-1.96 (m, 1H), 2.11-2.22 (m, 1H), 2.57 (s, 3H), 2.66 (s, 3H), 2.82-2.88 (m, 1H), 3.03-3.20 (m, 5H), 3.49-3.55 (m, 4H), 3.77 (s, 2H), 3.93-3.97 (m, 1H), 7.36 (d, 1H), 7.53 (s, 1H), 7.61 (s, 1H), 7.84 (d, 1H), 7.93 (s, 1H), 9.10 (s, 1H).

Salt Formation: A 5 L reactor equipped with a mechanical stirrer, nitrogen line and condenser was charged with the aforementioned material (200 g, 389.4 mmol) followed by ethanol (2 L). The resulting mixture was then heated to 70° C. and stirred for at least 10 min. In a separate flask, fumaric acid (51.97 g, 447.8 mmol) was charged followed by ethanol (2 L). The resulting mixture was stirred until dissolved and the two ethanolic solutions were mixed, maintaining pot temperature >65° C. The resulting solution was then stirred for 1 h at 70° C. under nitrogen while stirring. This was then cooled at 0.2° C. per min to 55° C., held at 55° C. for at least 1 h, then cooled to 5° C. at 0.2° C./min and held for at least 12 h at 5° C. The solution was then filtered, washed forward with ethanol (400 mL) and dried at 50° C. with a nitrogen bleed overnight. The desired fumarate salt of the title compound (208.4 g, 85% yield) was isolated as an off-white tan solid.

The compounds listed in Table 3 below were prepared using similar procedures to those described above for the preparation of 3A-3F, 3Z with the appropriate starting materials. Unless otherwise noted, the stereochemical designation of the following examples in Table 3 is R.

TABLE 3

| Example No. | R¹ | R² |
|---|---|---|
| 3G | 5-methoxypyridin-2-yl | pyrimidin-2-yl |
| | MS (ES+) 470.5 (M + H)⁺ | |
| | ¹H NMR (CDCl₃) δ 1.52-1.58 (m, 2H), 1.65-1.72 (m, 2H), 1.87-1.95 (m, 1H), 2.12-2.21 (m, 1H), 2.82-2.90 (m, 1H), 3.02-3.15 (m, 5H), 3.33 (t, 2H), 3.52 (t, 2H), 3.65 (s, 2H), 3.78 (s, 3H), 3.94-3.97 (m, 1H), 7.25 (d, 1H), 7.30-7.36 (m, 2H), 7.45 (d, 1H), 8.13 (d, 1H), 8.22 (d, 1H), 8.26 (br s, 1H), 8.80 (d, 2H). | |
| 3H | 5-methoxypyridin-2-yl | 5-methyl-pyrimidin-2-yl |
| | MS (ES+) 484.5 (M + H)⁺ | |
| | ¹H NMR (CDCl₃) δ 1.60-1.70 (m, 4H), 1.92-2.00 (m, 1H), 2.19-2.27 (m, 1H), 2.32 (s, 3H), 2.83-2.91 (m, 1H), 3.01-3.10 (m, 1H), 3.27-3.37 (m, 4H), 3.41-3.50 (m, 4H), 3.77 (s, 2H), 3.81 (s, 3H), 4.13-4.16 (m, 1H), 7.12-7.20 (m, 1H), 7.38 (d, 1H), 8.14 (d, 1H), 8.20-8.25 (m, 3H), 8.60 (s, 2H). | |
| 3I | 5-methylpyridin-2-yl | pyrimidin-2-yl |
| | MS (ES+) 454.2 (M + H)⁺ | |
| | ¹H NMR (CD₃OD) δ 1.66-1.74 (m, 4H), 1.87-1.95 (m, 1H), 2.20-2.28 (m, 1H), 2.31 (s, 3H), 2.84-2.92 (m, 1H), 3.07-3.15 (m, 1H), 3.25-3.33 (m, 4H, overlapping with CD₃OD), 3.48-3.55 (m, 4H), 3.88 (s, 2H), 4.03-4.07 (m, 1H), 7.22 (d, 1H), 7.31 (t, 1H), 7.45 (d, 1H), 7.57-7.60 (m, 1H), 8.21 (d, 1H), 8.24-8.29 (m, 2H), 8.79 (d, 2H). | |
| 3J | 5-methylpyridin-2-yl | 1-Methyl-1H-pyrazol-3-yl |
| | MS (ES+) 456.3 (M + H)⁺ | |
| | ¹H NMR (CD₃OD) δ 1.79-1.83 (m, 4 H), 2.13-2.17 (m, 1 H), 2.31 (s, 3 H), 2.41-2.60 (m, 1 H), 3.01-3.04 (m, 1 H), 3.18-3.22 (m, 1 H), 3.16 (s, 3 H), 3.48-3.54 (m, 4 H), 3.92 (s, 3 H), 4.00-4.04 (m, 2 H), 4.10-4.14 (m, 2 H), 6.63 (s, 1 H), 7.23 (d, 1 H) 7.42-7.63 (m, 2 H) 7.65-7.89 (m, 2 H) 8.17-8.36 (m, 2 H). | |
| 3K | 5-methoxypyridin-2-yl | 2-methyl-pyrimidin-4-yl |
| | MS (ES+) 484.4 (M + H)⁺ | |
| | ¹H NMR (CD₃OD) δ 1.76-1.81 (m, 4 H), 2.04-2.09 (m, 1 H), 2.40-2.46 (m, 1 H), 2.73 (s, 3 H), 2.97-3.03 (m, 1 H), 3.13-3.22 (m, 1 H), 3.55-3.58 (m, 4 H) 3.72-3.75 (m, 2 H), 3.82-3.87 (m, 7 H), 4.57-4.60 (m, 1 H), 7.27-7.29 (m, 1 H), 7.36-7.39 (m, 1 H), 7.62 (d, 1 H), 7.77 (d, 1 H), 8.04 (d, 1 H), 8.12 (d, 1 H), 8.67 (s, 1 H). | |
| 3L | ![imidazo[1,2-a]pyridin-2-yl] | 6-methyl-pyrimidin-4-yl |
| | MS (ES+) 493.1 (M + H)⁺ | |
| | ¹H NMR (CDCl₃) δ 1.67-1.72 (m, 4H),1.94-1.98 (m, 1 H), 2.16-2.20 (m, 1 H), 2.60 (s, 3 H), 2.86-2.91 (m, 1 H) 3.05-3.16 (m, 5 H), 3.54-3.58 (m, 4 H), 3.93 (s, 3 H), 6.75-6.78 (m, 1 H), 7.14-7.17 (m, 1 H), 7.39 (s, 1 H), 7.54-7.58 (m, 3 H), 7.86 (t, 1 H), 7.95 (s, 1 H), 8.07 (d, 1 H), 9.13 (s, 1 H). | |
| 3M | 5-methylpyridin-2-yl | 6-methyl-pyrimidin-4-yl |
| | MS (ES+) 468.4 (M + H)⁺ | |
| | ¹H NMR (CD₃OD) δ 1.80-1.84 (m, 4H), 2.11-2.20 (m, 1H), | |

TABLE 3-continued

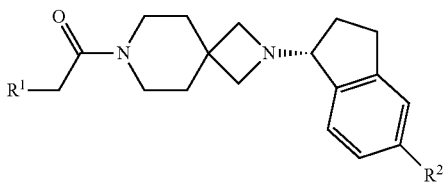

| Example No. | R¹ | R² |
|---|---|---|

2.56 (s, 3H), 2.54-2.58 (m, 1H), 2.61 (s, 3H) 3.13-3.17 (m, 1H), 3.20-3.25 (m, 1H), 3.44-3.53 (m, 3H), 3.96-4.15 (m, 4H), 4.00-4.05 (m, 2H), 4.19-4.24 (m, 2 H), 7.13-7.16 (m, 1H), 7.23-7.26 (m, 1H), 7.35 (d, 1H), 7.53 (br s, 1H), 7.83 (d, 1H), 7.92 (s, 1H), 8.18 (d, 1H), 9.09 (s, 1H).

3N    5-methoxypyridin-2-yl    1-Methyl-1H-pyrazol-3-yl

MS (ES+) 472.4 (M + H)⁺
¹H NMR (CDCl₃) δ 1.13-1.24 (m, 2 H), 1.27 (t, 1 H), 1.30-1.36 (m, 3 H), 1.51-1.60 (m, 1 H), 1.88 (d, 1 H), 2.33-2.43 (m, 1 H), 2.50-2.61 (m, 1 H), 2.80-2.97 (m, 4 H), 2.99-3.10 (m, 1 H), 3.35 (s, 3 H), 3.36-3.44 (m, 2 H), 3.47-3.56 (m, 4 H), 4.26 (t, 1 H), 6.05 (d, 1 H), 6.92 (d, 1 H), 6.98 (d, 1 H), 7.05-7.14 (m, 2 H), 7.17 (s, 1 H), 7.35-7.41 (m, 1 H), 7.70 (d, 1 H).
[α]_D^{20} = +21.2 deg (c = 10 mg/mL, methanol).

3O    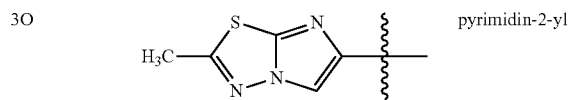    pyrimidin-2-yl

MS (ES+) 500.2 (M + H)⁺
¹H NMR (CD₃OD) δ 1.72-1.75 (m, 4 H), 1.91-1.92 (m, 2 H), 2.25-2.27 (m, 1 H), 2.68 (s, 3 H), 2.89-2.91 (m, 1 H), 3.09-3.12 (m, 1 H), 3.32-3.34 (m, 3 H), 3.53-3.57 (m, 4 H), 3.78 (s, 2 H), 4.07-4.10 (m, 1 H), 7.32 (t, 1 H), 7.46 (d, 1 H), 7.72 (s, 1 H), 8.21 (d, 1 H), 8.26 (s, 1 H), 8.80 (d, 2 H).
[α]_D^{20} = +19.7 deg (c = 4.6 mg/mL, methanol).

3P    5-methoxy-2-acetamido phenyl    pyrimidin-2-yl

MS (ES+) 526.0 (M + H)⁺
¹H NMR (CDCl₃) δ 1.62-1.75 (m, 4 H), 1.84-1.99 (m, 1 H), 2.11-2.21 (m, 1H), 2.20 (s, 3 H), 2.76-2.91 (m, 1 H), 2.97-3.21 (m, 5 H), 3.43-3.49 (m, 2H), 3.54-3.59 (m, 2H), 3.62 (s, 2 H), 3.78 (s, 3 H), 3.88-4.01 (m, 1 H), 6.57 (dd, 1 H), 6.89-7.01 (m, 1 H), 7.16 (t, 1 H), 7.35 (d, 1 H), 7.79 (d, 1 H), 8.23 (dd, 1 H), 8.28 (d, 1 H), 8.77 (d, 2 H), 10.17 (br s, 1 H).

3Q    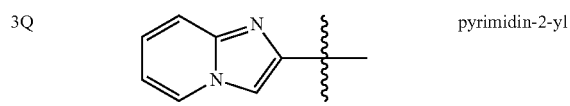    pyrimidin-2-yl

MS (ES+) 479.6 (M + H)⁺
¹H NMR (CD₃OD) δ 1.72-1.76 (m, 4 H), 1.91-1.94 (m, 1 H), 2.25-2.29 (m, 1 H), 2.86-2.94 (m, 1 H), 3.11-3.14 (m, 1 H), 3.28-3.35 (m, 4 H), 3.52-3.63 (m, 4 H), 3.91 (s, 2 H), 4.08 (dd, 1 H), 6.89 (td, 1 H), 7.25-7.31 (m, 1 H), 7.34 (t, 1 H), 7.47 (dd, 2 H), 7.70 (s, 1 H), 8.23 (d, 1 H), 8.28 (s, 1 H), 8.37 (d, 1 H), 8.82 (d, 2 H).

3R    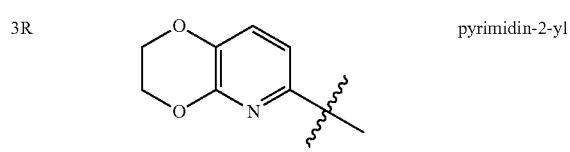    pyrimidin-2-yl

MS (ES+) 498.5 (M + H)⁺
¹H NMR (CDCl₃) δ 1.68 (dt, 3 H), 1.81-1.92 (m, 4 H), 2.13-2.25 (m, 1H), 2.82-2.93 (m, 1 H), 3.02-3.26 (m, 4 H), 3.41-3.51 (m, 4 H), 3.61-3.64 (m, 1H), 3.92-4.04 (m, 1 H), 4.12-4.56 (m, 4 H), 6.89 (d, 1 H), 7.10-7.20 (m, 2 H), 7.34-7.42 (m, 1 H), 8.22-8.28 (m, 1 H), 8.30 (d, 1 H), 8.79 (d, 2 H).

TABLE 3-continued

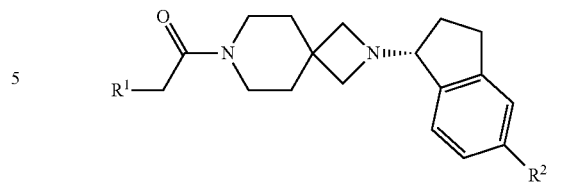

| Example No. | R¹ | R² |
|---|---|---|

3S    5-methoxypyridin-2-yl    4-methyl-pyrimidin-2-yl

MS (ES+) 484.6 (M + H)⁺
¹H NMR (CD₃OD) δ 2.32-2.35 (m, 4 H), 2.60-2.71 (m, 1 H), 2.82-2.94 (m, 1 H), 3.56-3.68 (m, 1 H), 3.80 (d, 3 H), 3.87-3.94 (m, 2 H), 4.12 (s, 3 H), 4.16-4.26 (m, 4 H), 4.58 (s, 2 H), 4.61 (s, 3 H), 4.65-4.72 (m, 1 H), 8.01 (d, 1 H), 8.10 (d, 1 H), 8.14 (dd, 1 H), 8.19 (d, 1 H), 8.96-9.02 (m, 2 H), 9.05 (s, 1 H), 9.52 (d, 1 H).

3T    5-methylpyridin-2-yl    4-methyl-pyrimidin-2-yl

MS (ES+) 468.4 (M + H)⁺
¹H NMR (CD₃OD) δ 1.69-1.72 (m, 4 H), 1.86-1.97 (m, 1 H), 2.19-2.30 (m, 1 H), 2.33 (s, 3 H), 2.57 (s, 3 H), 2.86-2.94 (m, 1 H), 3.08-3.18 (m, 1 H), 3.26-3.33 (m, 4 H), 3.52-3.56 (m, 4 H), 3.90 (s, 2 H), 4.03-4.11 (m, 1 H), 7.20-7.26 (m, 2 H), 7.46 (d, 1 H), 7.61 (dd, 1 H), 8.21 (d, 1 H), 8.24-8.33 (m, 2 H), 8.63 (d, 1 H).

3U        4-methyl-pyrimidin-2-yl

MS (ES+) 512.4 (M + H)⁺
¹H NMR (CD₃OD) δ 1.70-1.77 (m, 4 H), 1.89-1.97 (m, 1 H), 2.21-2.31 (m, 1 H), 2.57 (s, 3 H), 2.84-2.94 (m, 1 H), 3.08-3.18 (m, 1 H), 3.26-3.33 (m, 4 H), 3.50-3.57 (m, 4 H), 3.74 (s, 2 H), 4.05-4.12 (m, 1 H), 4.22-4.27 (m, 2 H), 4.39-4.43 (m, 2 H), 6.84 (d, 1 H), 7.20-7.25 (m, 2 H), 7.46 (d, 1 H), 8.21 (d, 1 H), 8.26 (d, 1 H), 8.63 (d, 1 H).

3V    5-methoxypyridin-2-yl    6-methoxy-pyrimidin-4-yl

MS (ES+) 500.3 (M + H)⁺
¹H NMR (CD₃OD) δ 1.71 (dt, 4 H), 1.91-1.95 (m, 1 H), 2.21-2.30 (m, 1 H), 2.86-2.94 (m, 1 H), 3.12 (ddd, 1 H), 3.26-3.36 (m, 4 H), 3.50-3.58 (m, 4 H), 3.85 (s, 3 H), 3.87 (s, 3 H), 4.02 (s, 2 H), 4.08 (dd, 1 H), 7.24-7.29 (m, 2 H), 7.36 (dd, 1 H), 7.47 (d, 1 H), 7.88 (d, 1 H), 7.94 (s, 1 H), 8.15 (d, 1 H), 8.75 (s, 1 H).

3W    4-methoxyphenyl    5-ethyl-pyrimidin-2-yl

MS (ES+) 497.2 (M + H)⁺
¹H NMR (DMSO-d₆) δ 1.25 (t, 3 H), 1.48-1.58 (m, 4 H), 1.82-1.86 (m, 1 H), 2.03-2.11 (m, 1 H), 2.66 (q, 2 H), 2.78-2.85 (m, 1 H), 2.98 (p, 3 H), 3.06-3.09 (m, 2 H), 3.34-3.41 (m, 4 H), 3.61 (s, 2 H), 3.72 (s, 3 H), 3.85-3.88 (m, 1 H), 6.86 (d, 2 H), 7.13 (d, 2 H), 7.38 (d, 1 H) 8.22 (s, 1 H), 8.76 (s, 2 H).

3X        pyrimidin-2-yl

MS (ES+) 493.0 (M + H)⁺
¹H NMR (CD₃OD) δ 1.74-1.94 (m, 4 H), 2.03 (m, 1 H), 2.28-2.45 (m, 1 H), 2.54 (s, 3 H), 2.93-3.11 (m, 1 H), 3.23 (dt, 1 H), 3.33-3.40 (m, 2 H), 3.42-3.54 (m, 2 H), 3.55-3.71 (m, 4 H), 3.98 (s, 2 H), 4.18 (dd, 1 H), 6.85 (dd, 1 H), 7.35 (s, 1 H), 7.44 (t, 1 H), 7.57 (d, 1 H), 7.70 (s, 1 H), 8.31-8.48 (m, 3 H), 8.92 (d, 2 H).

TABLE 3-continued

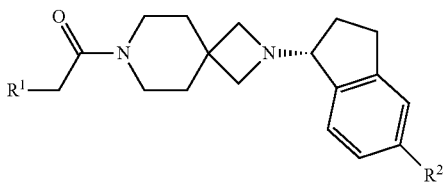 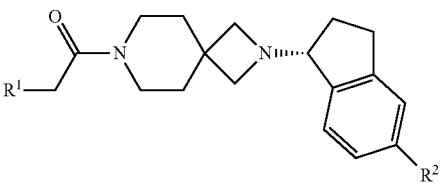

| Example No. | R¹ | R² |
|---|---|---|

3Y  [2-methyl-thiazolo-imidazole structure with H₃C]  4-methyl-pyrimidin-2-yl

MS (ES+) 514.0 (M + H)⁺
¹H NMR (CD₃OD) δ 1.79-1.84 (m, 4 H), 1.98-2.24 (m, 1 H), 2.34-2.59 (m, 4 H), 2.66-2.85 (m, 3 H), 3.03-3.06 (m, 1 H), 3.19-3.21 (m, 1 H), 3.56-3.61 (m, 4 H), 3.79 (s, 2 H), 3.93 (d, 2 H), 4.04 (d, 2 H), 4.73-4.76 (m, 1 H), 7.25 (d, 1 H), 7.61 (d, 1 H), 7.73 (s, 1 H), 8.24-8.49 (m, 2 H), 8.65 (d, 1 H).

3AA  5-methoxypyridin-2-yl  6-ethyl-pyrimidin-4-yl

MS (ES+) 498.1 (M + H)⁺
¹H NMR (CD₃OD) δ 1.33 (t, 3 H), 1.64-1.75 (m, 4 H), 1.89-1.93 (m, 1 H), 2.17-2.31 (m, 1 H), 2.79-2.88 (m, 2 H), 2.92 (d, 1 H), 3.05-3.17 (m, 1 H), 3.21-3.27 (m, 2 H), 3.30-3.34 (m, 2 H), 3.48-3.56 (m, 4 H), 3.84 (s, 3 H), 3.85 (s, 2 H), 4.00-4.11 (m, 1 H), 7.20-7.28 (m, 1 H), 7.34 (dd, 1 H), 7.48 (d, 1 H), 7.83 (s, 1 H), 7.96 (d, 1 H), 8.02 (s, 1 H), 8.13 (d, 1 H), 9.01 (s, 1 H).

3AB  2-cyano-4-methoxyphenyl  6-ethyl-pyrimidin-4-yl

MS (ES+) 522.1 (M + H)⁺
¹H NMR (CD₃OD) δ 1.32-1.39 (t, 3 H), 1.78-1.93 (m, 1 H), 1.80-1.95 (m, 4 H), 2.02-2.08 (m, 1 H), 2.37-2.43 (m, 1 H), 2.88 (q, 2 H), 3.02 (d, 1 H), 3.16-3.26 (m, 1 H), 3.58-3.81 (m, 8 H), 3.83 (s, 3 H), 3.90-3.93 (m, 2 H), 4.40-4.44 (m, 1 H), 7.16-7.20 (m, 1 H), 7.25-7.33 (m, 2 H), 7.60 (d, 1 H), 7.88 (d, 1 H), 8.04 (dd, 1 H), 8.10 (s, 1 H), 9.05 (d, 1 H).

3AC  5-methoxypyridin-2-yl  6-cyano-pyrimidin-4-yl

MS (ES+) 495.1 (M + H)⁺
¹H NMR (CD₃OD) δ 1.73 (dt, 4 H), 1.85-2.03 (m, 1 H), 2.18-2.37 (m, 1 H), 2.82-3.02 (m, 1 H), 3.10-3.21 (m, 1 H), 3.24-3.31 (m, 2 H), 3.34-3.38 (m, 2 H), 3.50-3.63 (m, 4 H), 3.87 (s, 3 H), 3.89 (s, 2 H), 4.10 (dd, 1 H), 7.29 (d, 1 H), 7.38 (dd, 1 H), 7.54 (d, 1 H), 8.10 (d, 1 H), 8.13-8.19 (m, 2 H), 8.46 (d, 1 H), 9.30 (d, 1 H).

3AD  4-methoxyphenyl  oxazol-2-yl
MS (ES+) 458.1 (M + H)⁺
¹H NMR (CD₃OD) δ 1.58 (d, 2 H), 1.67-1.75 (m, 2 H), 1.86-1.97 (m, 1 H), 2.18-2.32 (m, 2 H), 2.83-2.96 (m, 1 H), 3.06-3.17 (m, 1 H), 3.21-3.24 (m, 1 H), 3.42-3.50 (m, 2 H), 3.51-3.59 (m, 2 H), 3.70 (s, 2 H), 3.77 (s, 3 H), 4.03-4.05 (m, 1 H), 6.85-6.90 (m, 2 H), 7.13-7.19 (m, 2 H), 7.28 (d, 1 H), 7.47 (d, 1 H), 7.85 (dd, 1 H), 7.90 (s, 1 H), 7.96 (d, 1 H).

3AE  5-methoxypyridin-2-yl  pyrimidin-4-yl
MS (ES+) 470.2 (M + H)⁺
¹H NMR (CDCl₃) δ 1.64-1.78 (m, 4 H), 1.88-2.00 (m, 1 H), 2.21-2.34 (m, 1 H), 2.87-2.97 (m, 1 H), 3.09-3.20 (m, 1 H), 3.26-3.32 (m, 2 H), 3.33-3.39 (m, 2 H), 3.54 (q, 4 H), 3.85 (s, 3 H), 3.87 (s, 2 H), 4.11 (dd, 1 H), 7.23-7.30 (m, 1 H), 7.33-7.39 (m, 1 H), 7.51 (d, 1 H), 7.94-8.04 (m, 2 H), 8.07 (s, 1 H), 8.15 (d, 1 H), 8.76 (d, 1 H), 9.16 (s, 1 H).

3AF  5-cyclopropylpyridin-2-yl  pyrimidin-2-yl
MS (ES+) 479.7 (M + H)⁺
¹H NMR (CD₃OD) δ 0.71-0.74 (m, 2 H), 1.02-1.05 (m, 2 H), 1.68-1.74 (m, 4 H), 1.88-1.97 (m, 2 H), 2.21-2.29 (m, 1 H), 2.86-2.94 (m, 1 H), 3.09-3.16 (m, 1 H), 3.26-3.30 (m, 4 H), 3.48-3.56 (m, 4 H), 3.88 (s, 2 H), 4.06-4.08 (m, 1 H), 7.22 (d, 1 H), 7.33 (t, 1 H), 7.40 (dd, 1 H), 7.47 (d, 1 H), 8.23 (d, 1 H), 8.27 (s, 2 H), 8.82 (d, 2 H).

3AG  5-methoxypyridin-2-yl  oxazol-2-yl
MS (ES+) 459.1 (M + H)⁺

¹H NMR (CD₃OD) δ 1.43 (t, 1 H), 1.70 (br s, 4 H), 2.19 (s, 2 H), 2.90 (br s, 1 H), 3.06-3.29 (m, 5 H), 3.46-3.56 (m, 4 H), 3.83-3.89 (m, 5 H), 7.17 (dd, 1 H), 7.22-7.28 (m, 2 H), 7.42 (br s, 1 H), 7.69-7.73 (m, 1 H), 7.87-7.92 (m, 1 H), 7.93-7.98 (m, 1 H), 8.21 (d, 1 H).

3AH  4-(trifluoromethyl)phenyl  pyrimidin-2-yl
MS (ES+) 507.9 (M + H)⁺
¹H NMR (CDCl₃) δ 1.63-1.72 (m, 4 H), 1.92-1.98 (m, 1 H), 2.16-2.25 (m, 1 H), 2.84-2.92 (m, 1 H), 3.08-3.11 (m, 1 H), 3.14-3.22 (m, 4 H), 3.33-3.36 (m, 2 H), 3.50-3.53 (m, 2 H), 3.71 (s, 2 H), 4.03 (t, 1 H). 7.17 (t, 1 H), 7.36-7.39 (m, 3 H), 7.57 (d, 2 H), 8.26 (d, 1 H), 8.30 (s, 1 H), 8.78 (d, 1 H).

3AI  [2-cyano-4-methoxyphenoxy methyl structure]  6-methyl-pyrimidin-4-yl

MS (ES+) 524.6 (M + H)⁺
¹H NMR (CDCl₃) δ 1.70-1.76 (m, 2 H), 1.78-1.84 (m, 2 H), 1.93-1.97 (m, 1 H), 2.16-2.20 (m, 1 H), 2.59 (s, 3 H), 2.86-2.30 (m, 1 H), 3.10 (dt, 1 H), 3.15-3.19 (m, 4 H), 3.49-3.59 (m, 4 H), 3.79 (s, 3 H), 3.97 (dd, 1 H), 4.77 (s, 2 H), 7.01-7.04 (m, 1 H), 7.05-7.09 (m, 2 H), 7.38 (d, 1 H), 7.56 (s, 1 H), 7.86 (dd, 1 H), 7.95 (s, 1 H), 9.12 (d, 1 H).

3AJ  4-methoxyphenyl  H
MS (ES+) 391.3 (M + H)⁺
¹H NMR (CD₃OD) δ 1.53-1.59 (m, 2 H), 1.65-1.73 (m, 2 H), 1.84-1.88 (m, 1 H), 2.14-2.25 (m, 1 H), 2.80-2.82 (m, 1 H), 3.04 (dt, 1 H), 3.22-3.27 (m, 2 H), 3.29-3.33 (m, 1 H), 3.42-3.47 (m, 2 H), 3.50-3.56 (m, 2 H), 3.69 (s, 2 H), 3.76 (s, 3 H), 4.04 (dd, 1 H), 6.87 (d, 2 H), 7.12-7.18 (m, 3 H), 7.19-7.27 (m, 2 H), 7.33 (d, 1 H).

3AK  5-cyclopropylpyridin-2-yl  6-methyl-pyrimidin-4-yl
MS (ES+) 494.3 (M + H)⁺
Retention Time: 1.72 min 3AL  [2-methyl-thiazolo-imidazole structure with H₃C]  4,6-dimethyl-pyrimidin-2-yl MS (ES+) 528.3 (M + H)⁺
Retention Time: 1.99 min 3AM  2-cyano-4-methoxyphenyl  6-methyl-pyrimidin-4-yl
MS (ES+) 508.6 (M + H)⁺
¹H NMR (CD₃OD) δ 1.70-1.77 (m, 2 H), 1.78-1.85 (m, 2 H), 1.90-1.94 (m, 1 H), 2.23-2.27 (m, 1 H), 2.55 (s, 3 H), 2.87-2.91 (m, 1 H), 3.12 (dt, 1 H), 3.23-3.27 (m, 2 H), 3.33 (dd, 2 H), 3.50-3.58 (m, 4 H), 3.80 (s, 3 H), 3.88 (s, 2 H), 4.06 (dd, 1 H), 7.13-7.17 (m, 1 H), 7.22 (d, 1 H), 7.28 (d, 1 H), 7.48 (d, 1 H), 7.84 (d, 1 H), 7.96 (dd, 1 H), 8.01 (s, 1 H), 8.98 (d, 1 H).

3AN  [2-methyl-thiazolo-imidazole structure with H₃C]  5-methyl-pyrimidin-2-yl

MS (ES+) 514.3 (M + H)⁺
Retention Time: 1.90 min

TABLE 3-continued

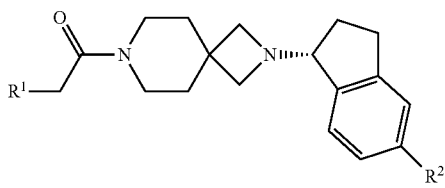

| Example No. | R[1] | R[2] |
|---|---|---|
| 3AO | 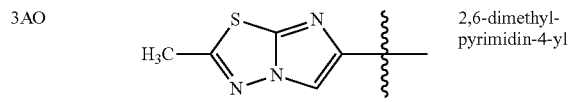 | 2,6-dimethyl-pyrimidin-4-yl |

MS (ES+) 528.3 (M + H)[+]
Retention Time: 1.73 min

| 3AP | 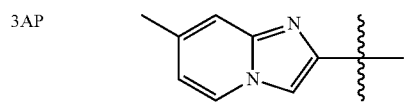 | 6-cyano-pyrimidin-4-yl |

MS (ES+) 518.3 (M + H)[+]
Retention Time: 1.59 min

| 3AQ | 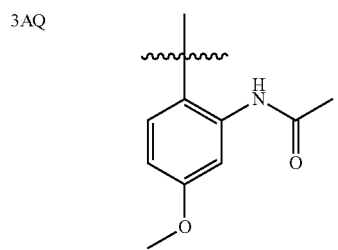 | 6-methyl-pyrimidin-4-yl |

MS (ES+) 540.3 (M + H)[+]
Retention Time: 1.95 min

| 3AR | 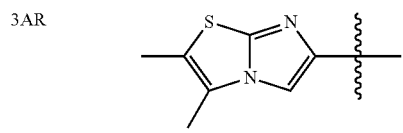 | 6-methyl-pyrimidin-4-yl |

MS (ES+) 527.7 (M + H)[+]
$^1$H NMR (CD$_3$OD) δ 1.73-1.77 (m, 4 H), 1.92-1.96 (m, 1 H), 2.24-2.28 (m, 1 H), 2.31 (s, 3 H), 2.34 (s, 3 H), 2.58 (s, 3 H), 2.90-2.94 (m, 1 H), 3.14 (dt, 1 H), 3.29 (dd, 2 H), 3.35 (dd, 2 H), 3.57 (d, 4 H), 3.79 (s, 2 H), 4.09 (dd, 1 H), 7.39 (s, 1 H), 7.50 (d, 1 H), 7.87 (s, 1 H), 7.98 (d, 1 H), 8.04 (s, 1 H), 9.01 (d, 1 H).

| 3AS | 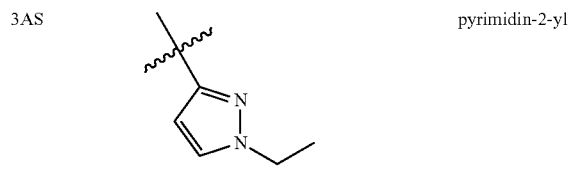 | pyrimidin-2-yl |

MS (ES+) 457.3 (M + H)[+]
$^1$H NMR (CDCl$_3$) δ 1.41 (t, 3 H), 1.56-1.67 (m, 4 H), 1.84-1.91 (m, 1 H), 2.10-2.17 (m, 1 H), 2.79-2.88 (m, 1 H), 3.01-3.04 (m, 1 H), 3.05-3.17 (m, 4 H), 3.33-3.48 (m, 4 H), 3.71 (s, 2 H), 3.92 (dd, 1 H), 4.08 (q, 2 H), 6.13 (s, 1 H), 7.14 (dd, 1 H), 7.28 (s, 1 H), 7.34 (d, 1 H), 8.20 (d, 1 H), 8.25 (s, 1 H), 8.75 (d, 2 H).

TABLE 3-continued

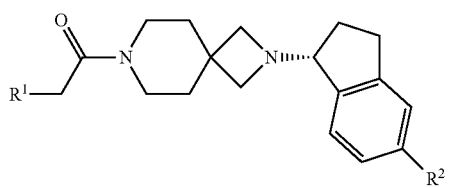

| Example No. | R[1] | R[2] |
|---|---|---|
| 3AT |  | 6-methyl-pyrimidin-4-yl |

MS (ES+) 508.5 (M + H)[+]
$^1$H NMR (CD$_3$OD) δ 1.70-1.76 (m, 4 H), 1.93-1.97 (m, 1 H), 2.26-2.30 (m, 1 H), 2.59 (s, 3 H), 2.91-2.94 (m, 1 H), 3.15 (dt, 1 H), 3.28-3.31 (m, 2 H), 3.36 (d, 2 H), 3.55-3.59 (m, 2 H), 3.60-3.65 (m, 2 H), 4.08 (s, 3 H), 4.11 (dd, 1 H), 4.13 (s, 2 H), 7.21 (dd, 1 H), 7.51 (d, 1 H), 7.88 (s, 1 H), 7.99 (d, 1 H), 8.05 (s, 1 H), 8.22 (dd, 1 H), 8.54 (dd, 1 H), 9.02 (d, 1 H).

| 3AU | 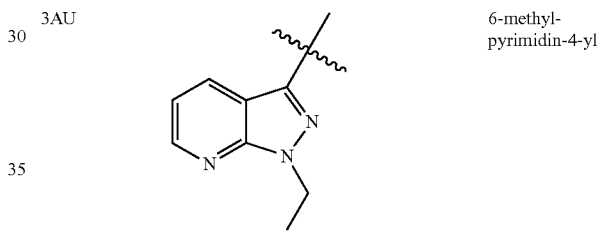 | 6-methyl-pyrimidin-4-yl |

MS (ES+) 522.6 (M + H)[+]
$^1$H NMR (CD$_3$OD) δ 1.44 (td, 3 H), 1.62-1.68 (m, 4 H), 1.88-1.92 (m, 1 H), 2.21-2.24 (m, 1 H), 2.55 (s, 3 H), 2.86-2.30 (m, 1 H), 3.10 (dt, 1 H), 3.19-3.25 (m, 2 H), 3.26-3.31 (m, 2 H), 3.50-3.55 (m, 2 H), 3.56-3.62 (m, 2 H), 4.04 (dd, 1 H), 4.10 (s, 2 H), 4.49 (q, 2 H), 7.16 (ddd, 1 H), 7.46 (d, 1 H), 7.83 (s, 1 H), 7.94 (d, 1 H), 8.00 (s, 1 H), 8.18 (dq, 1 H), 8 49 (d, 1 H), 8.98 (s, 1 H).

| 3AV | 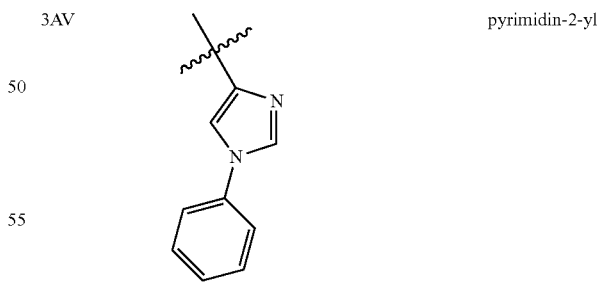 | pyrimidin-2-yl |

MS (ES+) 505.4 (M + H)[+]
$^1$H NMR (CD$_3$OD) δ 1.76-1.82 (m, 4 H), 1.95-1.99 (m, 1 H), 2.29-2.33 (m, 1 H), 2.92-2.96 (m, 1 H), 3.12-3.21 (m, 1 H), 3.38 (dd, 2 H), 3.45 (d, 2 H), 3.57-3.63 (m, 4 H), 3.78 (s, 2 H), 4.18 (dd, 1 H), 7.36 (t, 1 H), 7.41 (tt, 1 H), 7.44 (d, 1 H), 7.48-7.58 (m, 5 H), 8.08 (d, 1 H), 8.26 (d, 1 H), 8.30 (s, 1 H), 8.84 (d, 2 H).

TABLE 3-continued

[Structure with R¹ and R² substituents on a diazaspiro-indane benzamide scaffold]

| Example No. | R¹ | R² |
|---|---|---|
| 3AW | [pyridine with CHF₂ group] | pyrimidin-2-yl |

MS (ES+) 490.3 (M + H)⁺
¹H NMR (CD₃CN) δ 1.80 (t, 1 H), 1.86 (t, 1 H), 1.90 (t, 1 H), 1.97 (t, 1 H), 2.19-2.23 (m, 1 H), 2.47-2.59 (m, 1 H), 3.05-3.09 (m, 1 H), 3.25 (dt, 1 H), 3.42-3.63 (m, 4 H), 3.94-4.06 (m, 2 H), 4.10-4.22 (m, 2 H), 4.26 (s, 2 H), 4.93 (t, 1 H), 6.87-7.16 (m, 2 H), 7.38 (dd, 1 H), 7.64 (d, 1 H), 7.86 (d, 1 H), 8.36 (d, 1 H), 8.40 (s, 1 H), 8.48 (d, 1 H), 8.86 (br s, 1 H), 8.86 (s, 1 H), 8.88 (s, 1 H).

| 3AX | [methylpyrazole NH] | pyrimidin-2-yl |

MS (ES+) 443.1 (M + H)⁺
¹H NMR (CD₃OD) δ 1.65-1.79 (m, 4 H), 1.95-2.06 (m, 1 H), 2.25 (s, 3 H), 2.28-2.42 (m, 1 H), 2.93-2.97 (m, 1 H), 3.11-3.17 (m, 1 H), 3.43-3.59 (m, 8 H), 3.71 (s, 2 H), 4.25-4.33 (m, 1 H), 5.94 (s, 1 H), 7.35 (t, 1 H), 7.52 (d, 1 H), 8.27 (d, 1 H) 8.31 (s, 1 H), 8.83 (d, 2 H).

| 3AY | [imidazo-triazine] | 6-methyl-pyrimidin-4-yl |

MS (ES+) 495.4 (M + H)⁺
Retention Time: 1.84 min

| 3AZ | 5-cyclopropylpyridin-2-yl | 6-cyano-pyrimidin-4-yl |

MS (ES+) 505.3 (M + H)⁺
Retention Time: 1.94 min

Example 4

Preparation of 4-[(1R)-1-{7-[(7-methylimidazo[1,2-a]pyridin-2-yl)acetyl]-2,7-diazaspiro[3.5]non-2-yl}-2,3-dihydro-1H-inden-5-yl]benzamide (4A)

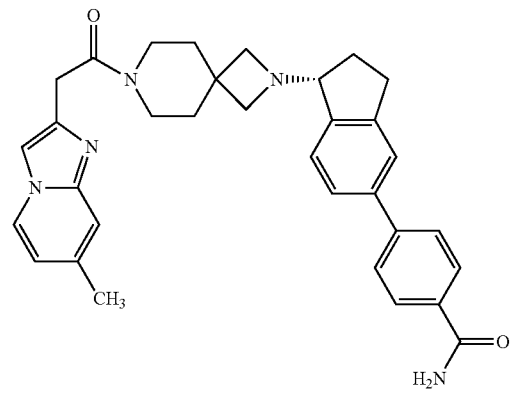

(4A)

To a mixture of 4-[(R)-1-(2,7-diaza-spiro[3.5]non-2-yl)-indan-5-yl]-benzamide hydrochloride (4-1b, 53 mg, 0.14 mmol) in 5 mL of dichloromethane was added 7-methyl-imidazo[1,2-a]pyridine-2-carboxylic acid (25 mg, 0.13 mmol), triethylamine (53 mg, 0.52 mmol), and EDCI (25 mg, 0.13 mmol). The mixture was stirred overnight at room temperature and quenched by the addition of 10 mL of saturated NaHCO₃. Dichloromethane (50 mL) was added and the organic solution was washed with saturated brine, dried over Na₂SO₄ and concentrated. The crude product was purified by preparative HPLC (on Phenomenex Luna (2) C18 21.2×150 mm, 5% H₂O/95% MeOH (0.1% formic acid), 10.0 min, 28 mL/min) to provide the desired product (6.6 mg, 9%) as a gum. MS (ES+) 534.1 (M+H)⁺. ¹H NMR (CD₃OD) δ 1.31-1.35 (m, 1H), 1.76-1.87 (m, 4H), 2.09-2.21 (m, 1H), 2.39 (s, 3H), 2.50 (d, 1H), 2.96-3.09 (m, 1H), 3.16-3.20 (m, 1H), 3.55-3.62 (m, 4H), 3.84-3.91 (m, 2H), 3.96 (d, 2H), 4.04-4.14 (m, 2H), 6.79 (dd, 1H), 7.26 (s, 1H), 7.57-7.64 (m, 3H), 7.67 (s, 1H), 7.67-7.73 (m, 2H), 7.90-7.97 (m, 2H), 8.24 (d, 1H), 8.34 (s, 2H).

Preparation of 5-[(1R)-1-{7-[(5-methoxypyridin-2-yl)acetyl]-2,7-diazaspiro[3.5]non-2-yl}-2,3-dihydro-1H-inden-5-yl]pyridine-2-carbonitrile (4B)

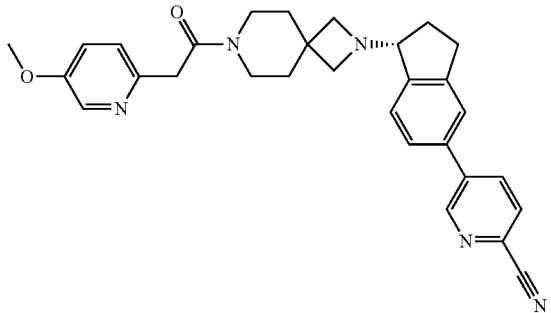

(4B)

To a mixture of (5-methoxypyridin-2-yl)acetic acid (SM-1aa, 28 mg, 0.17 mmol) in dichloromethane (5 mL) was added 1,1'-carbonyldiimidazole (28 mg, 0.17 mmol) and the reaction was stirred for 2 hours at room temperature. In a separate flask, triethylamine (68 mg, 0.67 mmol) was added to a mixture 5-[(R)-1-(2,7-diaza-spiro[3.5]non-2-yl)-indan-5-yl]-pyridine-2-carbonitrile dihydrochloride (4-1d, 58 mg, 0.17 mmol) in dichloromethane (5 mL). The activated acid was added to the amine solution and the reaction was stirred at room temperature overnight. The reaction mixture was quenched by the addition of 10 mL of saturated NaHCO$_3$ and diluted with 50 mL of dichloromethane. The organic solution was collected, washed with saturated brine, dried over MgSO$_4$, filtered and concentrated. Purification by preparative HPLC (on Phenomenex Luna (2) C18 21.2×150 mm, 5% H$_2$0/95% MeOH (0.1% formic acid), 10.0 min, 28 mL/min) provided the title compound (7.5 mg, 9%) as a gum. MS (ES+) 494.1 (M+H)$^+$ $^1$H NMR (CD$_3$OD) δ 1.76-1.87 (m, 4H), 2.14-2.26 (m, 1H), 2.55 (dd, 1H), 3.00-3.12 (m, 1H), 3.18-3.27 (m, 1H), 3.54-3.60 (m, 4H), 3.81-3.85 (m, 4H), 3.86 (s, 1H), 4.04 (d, 2H), 4.18 (d, 2H), 4.94 (dd, 1H), 7.22-7.29 (m, 1H), 7.31-7.38 (m, 1H), 7.63-7.72 (m, 2H), 7.75 (s, 1H), 7.93 (dd, 1H), 8.13 (d, 1H), 8.23 (dd, 1H), 8.97 (d, 1H).

The compounds listed in Table 4 below were prepared using procedures analogous to those described above for the preparation of 4A using the appropriate starting materials. Unless otherwise noted, the stereochemical designation of the following examples in Table 4 is R.

TABLE 4

| Example No. | R$^1$ | R$^2$ |
|---|---|---|
| 4C | 5-ethylpyridin-2-yl | 4-carbamoyl-phenyl |

MS (ES+) 509.1 (M + H)$^+$
$^1$H NMR (CD$_3$OD) δ 1.32 (t, 3 H), 1.94 (d, 4 H), 2.14-2.27 (m, 1 H), 2.50-2.66 (m, 1 H), 2.83-2.87 (m, 2 H), 3.00-3.14 (m, 1 H), 3.24 (t, 1 H), 3.59-3.63 (m, 4 H), 4.14-4.18 (m, 5 H), 4.31-4.43 (m, 1 H), 5.00 (s, 1 H), 7.59-7.68 (m, 3 H), 7.68-7.74 (m, 3 H), 7.90-7.98 (m, 2 H), 8.32 (br s, 1 H), 8.64 (br s, 1 H).

| 4D | 5-methoxypyridin-2-yl | 4-carbamoyl-phenyl |
|---|---|---|

MS (ES+) 511.0 (M + H)$^+$
$^1$H NMR (CD$_3$OD) δ 1.71 (m, 4 H), 1.93 (d, 1 H), 2.25 (d, 1 H), 2.90 (s, 1 H), 3.11 (s, 1 H), 3.21-3.27 (m, 2 H), 3.31-3.37 (m, 2 H), 3.48-3.58 (m, 4 H), 3.84 (s, 3 H), 3.85 (s, 2 H), 4.04-4.10 (m, 1 H), 7.25 (d, 1 H), 7.35 (dd, 1 H), 7.40-7.50 (m, 2 H), 7.55 (s, 1 H), 7.64-7.71 (m, 2 H), 7.88-7.94 (m, 2 H), 8.13 (d, 1 H).

| 4E | 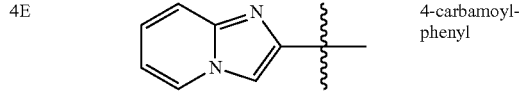 | 4-carbamoyl-phenyl |
|---|---|---|

MS (ES+) 520.1 (M + H)$^+$
$^1$H NMR (CD$_3$OD) δ 1.79-1.89 (m, 4 H), 2.15 (d, 1 H), 2.47-2.59 (m, 1 H), 2.63 (s, 2 H), 3.06 (d, 1 H), 3.15-3.26 (m, 1 H), 3.56-3.63 (m, 4 H), 3.92 (s, 2 H), 4.02 (d,

TABLE 4-continued

| Example No. | R$^1$ | R$^2$ |
|---|---|---|

2 H), 4.12-4.16 (m, 2 H), 4.87-4.94 (m, 1 H), 6.87-6.95 (m, 1 H), 7.27-7.35 (m, 1 H), 7.48 (d, 1 H), 7.56-7.65 (m, 2 H), 7.66-7.75 (m, 4 H), 7.94 (d, 2 H), 8.27 (br s, 2 H), 8.37 (d, 1 H).

Example 5

Preparation of 7-[(4-Cyclopropylphenyl)acetyl]-2-(5-pyrimidin-2-yl-2,3-dihydro-1H-inden-1-yl)-2,7-diazaspiro[3.5]nonane (5A)

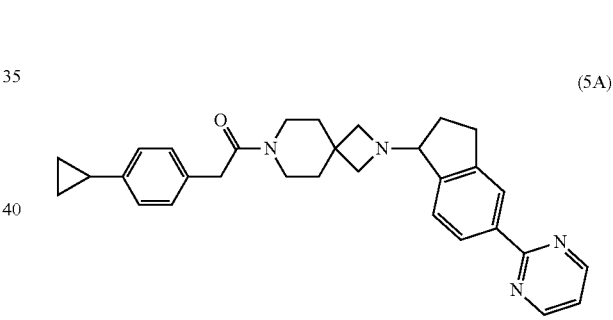

(5A)

Triethylamine (0.1 mL) was added to a solution of 2-(5-pyrimidin-2-yl-2,3-dihydro-1H-inden-1-yl)-2,7-diazaspiro[3.5]nonane dihydrochloride (5-1b, 80 mg, 0.2 mmol), 4-cyclopropylphenylacetic acid (SM-1ag, 31 mg, 0.2 mmol), and HATU (93 mg, 0.24 mmol) in dichloromethane (5 mL) in a vial. The reaction was stirred at room temperature overnight and was quenched with aqueous sodium bicarbonate. The organic layer was dried over MgSO$_4$, filtered and concentrated. The residue was chromatographed on a Combiflash ISCO purification system (Teledyne Corp., Lincoln, Nebr.) using a 12 g silica column with dichloromethane-methanol as eluant. The final product was obtained as off-white solid (89 mg, 92%). MS (APCI) 478.6 (M+H)$^+$. $^1$H NMR (CDCl$_3$) δ 0.65-0.69 (m, 3H), 0.92-0.97 (m, 2H), 1.67-1.71 (m, 2H), 1.83-1.90 (m, 2H), 2.19-2.22 (m, 1H), 2.89 (s, 1H), 3.18-3.26 (m, 5H), 3.31-3.35 (m, 2H), 3.51-3.55 (m, 2H), 3.66-3.70 (m, 3H), 4.01-4.06 (m, 1H), 7.00-7.04 (m, 2H), 7.10-7.13 (m, 2H), 7.17-7.21 (m, 1H), 7.41 (s, 1H), 8.31 (s, 2H), 8.79-8.82 (m, 2H).

Preparation of (R)-7-[(4-cyclopropylphenyl)acetyl]-2-(5-pyrimidin-2-yl-2,3-dihydro-1H-inden-1-yl)-2,7-diazaspiro[3.5]nonane (5A-1)

(5A-1)

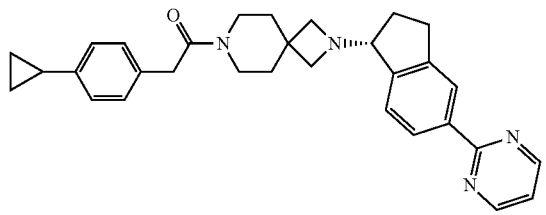

The racemic mixture (5A) was separated on a chiral column (Chiralcel OD-H, 250 mm×30 mm, Flow-rate—100 g/min, 65/35 CO$_2$/MeOH, with 0.1% IPA) to afford the title compound (19 mg) as a white powder. MS (APCI) 478.6 (M+H)$^+$. $^1$H NMR (CDCl$_3$) δ 0.65-0.69 (m, 3H), 0.92-0.97 (m, 2H), 1.67-1.72 (m, 2H), 1.83-1.90 (m, 2H), 2.19-2.22 (m, 1H), 2.89 (s, 1H), 3.18-3.26 (m, 5H), 3.31-3.35 (m, 2H), 3.51-3.55 (m, 2H), 3.66-3.70 (m, 3H), 4.01-4.06 (m, 1H), 7.00-7.04 (m, 2H), 7.10-7.13 (m, 2H), 7.17-7.21 (m, 1H), 7.41 (s, 1H), 8.31 (s, 2H), 8.79-8.82 (m, 2H). [α]$_D^{20}$=+34.8 deg (c=10.4 mg/mL, methanol).

The compounds listed in Table 5 below were prepared using procedures analogous to those described above for the preparation of (R)-7-[(4-cyclopropylphenyl)acetyl]-2-(5-pyrimidin-2-yl-2,3-dihydro-1H-inden-1-yl)-2,7-diazaspiro[3.5]nonane (5A-1) using the appropriate starting materials. Unless otherwise noted, the stereochemical designation of the following examples in Table 5 is R.

TABLE 5

| Example No. | R$^1$ | R$^2$ |
|---|---|---|
| 5B | 5-ethylpyridin-2-yl | pyrimidin-2-yl |

MS (ES+) 468.4 (M + H)$^+$
$^1$H NMR (CD$_3$OD) δ 1.22 (t, 3H), 1.66-1.74 (m, 4H), 1.87-1.95 (m, 1H), 2.19-2.30 (m, 1H), 2.65 (q, 2H), 2.85-2.93 (m, 1H), 3.07-3.15 (m, 1H), 3.25-3.34 (m, 4H), 3.49-3.56 (m, 4H), 3.89 (s, 2H), 4.04-4.08 (m, 1H), 7.25 (d, 1H), 7.32 (t, 1H), 7.45 (d, 1H), 7.62 (dd, 1H), 8.19-8.23 (m, 1H), 8.26 (br s, 1H), 8.29-8.31 (m, 1H), 8.80 (d, 2H).

| 5C | 5-methylpyridin-2-yl | 2H-1,2,3-triazol-2-yl |
|---|---|---|

MS (ES+) 443.4 (M + H)$^+$
$^1$H NMR (CDCl$_3$) δ 1.56-1.60 (m, 2H), 1.63-1.68 (m, 2H), 1.86-1.94 (m, 1H), 2.09-2.19 (m, 1H), 2.25 (s, 3H), 2.78-2.86 (m, 1H), 3.01-3.08 (m, 1H), 3.17-3.23 (m, 4H), 3.41-3.51 (m, 4H), 3.82 (s, 2H), 3.88-3.92 (m, 1H), 7.10-7.14 (m, 1H), 7.22 (d, 1H), 7.30 (d, 1H), 7.75 (s, 2H), 7.82-7.85 (m, 1H), 7.89 (br s, 1H), 8.16 (d, 1H).

| 5D | 5-ethylpyridin-2-yl | 2H-1,2,3-triazol-2-yl |
|---|---|---|

MS (ES+) 457.5 (M + H)$^+$
$^1$H NMR (CD$_3$OD) δ 1.20 (t, 3H), 1.63-1.70 (m, 4H), 1.84-1.92 (m, 1H),

TABLE 5-continued

| Example No. | R$^1$ | R$^2$ |
|---|---|---|

2.14-2.25 (m, 1H), 2.62 (q, 2H), 2.80-2.89 (m, 1H), 3.04-3.13 (m, 1H), 3.16-3.26 (m, 4H), 3.46-3.53 (m, 4H), 3.87 (s, 2H), 3.94-3.98 (m, 1H), 7.24 (d, 1H), 7.41 (d, 1H), 7.60 (dd, 1H), 7.84-7.88 (m, 3H), 7.91 (s, 1H), 8.29 (s, 1H).

| 5E | 4-methylphenyl | pyrimidin-2-yl |
|---|---|---|

MS (ES+) 453.7 (M + H)$^+$
$^1$H NMR (CDCl$_3$) δ 0.84-0.88 (m, 2 H), 1.22-1.27 (m, 3 H), 1.56-1.58 (m, 1 H), 1.67-1.64 (m, 1 H), 2.28 (s, 3 H), 2.29-2.30 (m, 1 H), 2.92-2.96 (m, 1 H), 3.26-3.27 (m, 1 H), 3.31-3.33 (m, 2 H), 3.40-3.49 (m, 4 H), 3.60 (s, 2 H), 4.31-4.35 (m, 1 H), 7.02-7.08 (m, 4 H), 7.19 (t, 1 H), 7.44 (d, 1 H), 8.30 (d, 1 H), 8.32 (s, 1 H), 8.77 (d, 2 H).
[α]$_D^{20}$ = +32.9 deg (c = 10 mg/mL, methanol).

| 5F | 4-ethylphenyl | pyrimidin-2-yl |
|---|---|---|

MS (ES+) 467.5 (M + H)$^+$
$^1$H NMR (CDCl$_3$) δ 1.18 (t, 3 H), 1.56-1.58 (m, 1 H), 1.65-1.68 (m, 1 H), 1.94-1.96 (m, 1 H), 2.26-2.28 (m, 1 H), 2.80 (q, 2 H), 2.92-2.94 (m, 1 H), 3.04-3.13 (m, 3 H), 3.26-3.49 (m, 8 H), 3.61 (s, 2 H), 4.22-4.26 (m, 1 H), 7.05-7.10 (m, 4 H), 7.19 (t, 1 H), 7.41 (d, 1 H), 8.28 (d, 1 H), 8.31 (s, 1 H), 8.77 (d, 2 H).
[α]$_D^{20}$ = +38.1 deg (c = 10 mg/mL, methanol).

| 5G | 5-methoxypyridin-2-yl | 2,6-dimethyl-pyrimidin-4-yl |
|---|---|---|

MS (APCI) 498.4 (M + H)$^+$
$^1$H NMR (DMSO-D6) δ 1.55 (d, 3 H), 1.86-1.88 (m, 1 H), 2.12 (s, 1 H), 2.46 (s, 3 H), 2.61 (s, 3 H), 2.83 (dd, 1 H), 2.99 (d, 2 H), 2.96-2.98 (m, 1 H), 3.11 (s, 1 H), 3.32 (s, 2 H), 3.40 (dd, 3 H), 3.39 (s, 1 H), 3.78-3.89 (m, 5 H), 5.76 (s, 1 H), 7.20 (d, 1 H), 7.33 (dd, 1 H), 7.40 (d, 1 H), 7.73 (s, 1 H), 7.95 (d, 1 H), 8.03 (s, 1 H), 8.17 (d, 1 H).
[α]$_D^{20}$ = +38.5 deg (c = 10 mg/mL, methanol).

| 5H (racemic) | ![structure] | pyrimidin-2-yl |
|---|---|---|

MS (ES+) 479.4 (M + H)$^+$.
$^1$H NMR (CD$_3$OD) δ 1.61-1.76 (m, 4 H), 1.85-1.96 (m, 1 H), 2.16-2.32 (m, 1 H), 2.81-2.95 (m, 1 H), 3.03-3.17 (m, 1 H), 3.25-3.34 (m, 4 H), 3.50-3.59 (m, 4 H), 3.93 (s, 2 H), 4.05 (dd, 1 H), 6.43 (s, 1 H), 6.80 (td, 1 H), 7.13-7.19 (m, 1 H), 7.31 (t, 1 H), 7.44 (d, 1 H), 7.51-7.57 (m, 1 H), 8.20 (dd, 1 H), 8.25 (s, 1 H), 8.42 (dd, 1 H), 8.79 (d, 2 H).

| 5I (racemic) | ![structure] | pyrimidin-2-yl |
|---|---|---|

MS (ES+) 483.4 (M + H)$^+$.
$^1$H NMR (CD$_3$OD) δ 1.63-1.76 (m, 4 H), 1.79-1.88 (m, 3 H), 1.89-1.97 (m, 1 H), 1.97-2.07 (m, 3 H), 2.72-2.80 (m, 3 H), 2.84-2.95 (m, 1 H), 3.07-3.19 (m, 2 H), 3.43-3.57 (m, 4 H), 3.66 (s, 2 H), 3.99-4.09 (m, 4 H), 5.88 (s, 1 H), 7.33 (t, 1 H), 7.46 (d, 1 H), 8.22 (d, 1 H), 8.27 (s, 1 H), 8.81 (d, 2 H).

Example 6

Preparation of 7-[(5-methylpyridin-2-yl)acetyl]-2-[5-(2H-1,2,3-triazol-2-yl)-2,3-dihydro-1H-inden-1-yl]-2,7-diazaspiro[3.5]nonane (6A)

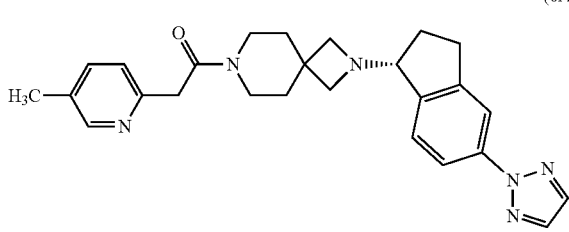

(6A)

To a solution of 2-((R)-5-[1,2,3]triazol-2-yl-indan-1-yl)-2,7-diaza-spiro[3.5]nonane (6-1c, 200 mg, 0.65 mmol) in 3 mL of dimethylformamide was added (5-methyl-pyridin-2-yl)-acetic acid (SM-1ab, 98 mg, 0.65 mmol), triethylamine (131 mg, 1.29 mmol), EDCI (130 mg, 0.68 mmol) and a catalytic amount of DMAP. The mixture was stirred at room temperature overnight. The reaction mixture was quenched by the addition of 10 mL of saturated $NaHCO_3$ and diluted with 50 mL of dichloromethane. The organic layer was washed with saturated brine, dried over $Na_2SO_4$ and concentrated. The crude product was purified on Analogix (Analogix Inc., Burlington, Wis.) 4 g silica column (0-20% MeOH in ethyl acetate (1% triethyl amine)) to provide the title compound (207 mg, 72.4%) as a brown gum. MS (ES+) 443.4 (M+H)$^+$. $^1$H NMR (CD$_3$OD) δ 1.58-1.79 (m, 4H), 1.94-2.16 (m, 2H), 2.20-2.31 (m, 2H), 2.31 (s, 3H), 2.78-2.98 (m, 1H), 3.09-3.16 (m, 1H), 3.17-3.32 (m, 2H), 3.38-3.57 (m, 4H), 3.88 (s, 2H), 3.99-4.20 (m, 1H), 7.21 (d, 1H), 7.39-7.51 (m, 2H), 7.80 (d, 2H), 7.89-7.94 (m, 1H), 7.97 (s, 1H), 8.24-8.38 (m, 1H). $[α]_D^{20}$=+47.2 deg (c=9.4 mg/mL, methanol).

The compounds listed in Table 6 were prepared using procedures analogous to those described above for the preparation of 2-(5-methyl-pyridin-2-yl)-1-[2-(R)-5-[1,2,3]triazol-2-yl-indan-1-yl)-2,7-diaza-spiro[3.5]non-7-yl]-ethanone (6A) with the appropriate starting materials. Unless otherwise noted, the stereochemical designation of the following examples in Table 6 is R.

TABLE 6

| Example No. | R$^1$ | R$^2$ |
|---|---|---|
| 6B (racemic) | 5-ethylpyridin-2-yl | 1,2,3-triazol-2-yl |

MS (ES+) 457.5 (M + H)$^+$
$^1$H NMR (CD$_3$OD) δ 1.20 (t, 3H), 1.63-1.70 (m, 4H), 1.84-1.92 (m, 1H), 2.14-2.25 (m, 1H), 2.62 (q, 2H), 2.80-2.89 (m, 1H), 3.04-3.13 (m, 1H), 3.16-3.26 (m, 4H), 3.46-3.53 (m, 4H), 3.87 (s, 2H), 3.94-3.98 (m, 1H), 7.24 (d, 1H), 7.41 (d, 1H), 7.60 (dd, 1H), 7.84-7.88 (m, 3H), 7.91 (s, 1 H), 8.29 (s, 1H).

TABLE 6-continued

| Example No. | R$^1$ | R$^2$ |
|---|---|---|
| 6C | 7-methylimidazo[1,2-a]pyridin-2-yl | 1,2,3-triazol-2-yl |

MS (ES+) 482.7 (M + H)$^+$
$^1$H NMR (CD$_3$OD) δ 1.93-2.03 (m, 4 H), 2.03-2.08 (m, 1 H), 2.48 (s, 3 H), 2.63 (s, 1 H), 2.94 (d, 1 H), 3.15-3.32 (m, 2 H), 3.55-3.60 (m, 4 H), 3.93-4.16 (m, 3 H), 4.20-4.24 (m, 2 H), 4.97 (d, 1 H), 7.10 (d, 1 H), 7.46 (br s, 1 H), 7.70 (d, 1 H), 7.81-7.93 (m, 2 H), 7.97-8.06 (m, 2 H), 8.15 (br s, 1 H), 8.43 (br s, 1 H).

| 6D | 5-methoxypyridin-2-yl | 1,2,3-triazol-2-yl |

MS (ES+) 459.5 (M + H)$^+$
$^1$H NMR (CD$_3$OD) δ 1.58-1.73 (m, 4 H) 1.90 (ddd, 1 H) 2.16-2.26 (m, 1 H) 2.81-2.90 (m, 1 H) 3.09 (dt,, 1 H) 3.19-3.27 (m, 3 H) 3.45-3.61 (m, 4 H) 3.63-3.86 (m, 5 H) 3.91-4.10 (m, 1 H) 4.84 (s, 1 H) 7.24 (d, 1 H) 7.32 (dd, 1 H) 7.42 (d, 1 H) 7.81-7.88 (m, 3 H) 7.91 (s, 1 H) 8.13 (d, 1 H).

| 6E | 4-methoxyphenyl | 1,2,3-triazol-2-yl |

MS (ES+) 458.1(M + H)$^+$
$^1$H NMR (CD$_3$OD) δ 1.64-1.68 (m, 2 H), 1.78-1.82 (m, 2 H), 2.12-2.22 (m, 1 H), 2.57 (m, 1 H), 3.03-3.13 (m, 1 H), 3.17-3.25 (m, 1 H), 3.42-3.61 (m, 4 H), 3.69 (s, 2 H), 3.74 (s, 2 H), 3.98-4.11 (m, 4 H), 4.29 (br s, 1 H), 4.94 (br s, 1 H), 6.85 (d, 2 H), 7.14 (d, 2 H), 7.67 (d, 1 H), 7.92 (s, 2 H), 8.04 (d, 1 H), 8.09 (s, 1 H).
$[α]_D^{20}$ = +41.0 deg (c = 4.6 mg/mL, methanol).

| 6F | 6-methylimidazo[2,1-b]thiazol-2-yl | 1,2,3-triazol-2-yl |

MS (ES+) 488.0 (M + H)$^+$
$^1$H NMR (CD$_3$OD) δ 1.80-1.86 (m, 4 H), 2.10-2.21 (m, 1 H), 2.40 (s, 3 H), 2.46-2.58 (m, 1 H), 2.98-3.09 (m, 1 H), 3.20-3.25 (m, 1 H), 3.55-3.62 (m, 4 H), 3.76 (s, 2 H), 3.94 (d, 2 H), 4.02-4.09 (m, 2 H), 4.77-4.82 (m, 1 H), 7.39-7.43 (m, 2 H), 7.64 (d, 1 H), 7.91 (s, 2 H), 7.99 (dd, 1 H), 8.03 (s, 1 H).

| 6G | 5-ethoxypyridin-2-yl | 1,2,3-triazol-2-yl |

MS (ES+) 473.5 (M + H)$^+$
$^1$H NMR (CD$_3$OD) δ 1.40 (t, 3 H), 1.64-1.76 (m, 4 H), 1.87-2.00 (m, 1 H), 2.21-2.34 (m, 1 H), 2.84-2.97 (m, 1 H), 3.07-3.19 (m, 1 H), 3.22-3.29 (m, 2 H), 3.31-3.36 (m, 2 H), 3.49-3.59 (m, 4 H), 3.87 (s, 2 H), 4.03-4.13 (m, 3 H), 7.24-7.28 (m, 1 H), 7.31-7.37 (m, 1 H), 7.47 (d, 1 H), 7.87-7.92 (m, 3 H), 7.93-7.96 (m, 1 H), 8.14 (d, 1 H).

| 6H | 2-acetamido-4-methoxyphenyl | 1,2,3-triazol-2-yl |

MS (ES+) 515.3 (M + H)$^+$
$^1$H NMR (CD$_3$OD) δ 1.59-1.64 (m, 2 H), 1.67-1.73 (m, 2 H), 1.90-1.94 (m, 1 H), 2.13 (s, 3 H), 2.23-2.27 (m, 1 H),

TABLE 6-continued

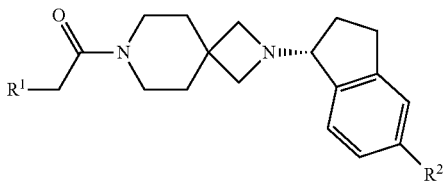

| Example No. | R[1] | R[2] |
|---|---|---|

2.87-2.92 (m, 1 H), 3.07-3.17 (m, 1 H), 3.22-3.27 (m, 2 H), 3.31-3.34 (m, 2 H), 3.44-3.49 (m, 2 H), 3.51-3.56 (m, 2 H), 3.67 (s, 2 H), 3.75 (s, 3 H), 4.05 (dd, 1 H), 6.73 (dd, 1 H), 7.14 (d, 1 H), 7.18 (d, 1 H), 7.45 (d, 1 H), 7.87 (dd, 1 H), 7.87 (s, 2 H), 7.93 (s, 1 H).

| 6I | 5-methoxypyridin-2-yl | 1,2,4-triazol-1-yl |
|---|---|---|

MS (ES+) 458.6 (M + H)+
$^1$H NMR (CD$_3$OD) δ 1.64-1.75 (m, 4 H), 1.91-1.95 (m, 1 H), 2.23-2.27 (m, 1 H), 2.87-2.91 (m, 1 H), 3.12 (dt, 1 H), 3.24 (dd, 2 H), 3.31 (dd, 2 H), 3.52 (m, 4 H), 3.83 (s, 3 H), 3.84-3.86 (m, 2 H), 4.05 (dd, 1 H), 7.25 (d, 1 H), 7.34 (dd, 1 H), 7.48 (d, 1 H), 7.61 (dd, 1 H), 7.69 (d, 1 H), 8.10-8.15 (m, 2 H), 9.03 (s, 1 H).

| 6J | 5-methoxypyridin-2-yl | 5-methyl-1,3,4-thiadiazol-2-yl |
|---|---|---|

MS (ES+) 489.6 (M + H)+
$^1$H NMR (CD$_3$OD) δ 1.73-1.81 (m, 4 H), 2.03-2.12 (m, 1 H), 2.38-2.49 (m, 1 H), 2.79 (s, 3 H), 2.95-3.04 (m, 1 H), 3.10-3.13 (m, 1 H), 3.25-3.28 (m, 2 H), 3.30-3.31 (m, 2 H), 3.52-3.58 (m, 4 H), 3.70-3.78 (m, 1 H), 3.84 (s, 3 H), 3.86 (s, 2 H), 7.26 (d, 1 H), 7.35 (dd, 1 H), 7.60 (d, 1 H), 7.83 (d, 1 H), 7.90 (s, 1 H), 8.13 (d, 1 H).

Example 7

Preparation of 5-Methyl-2-(2-oxo-2-{2-[1R)-5-pyrimidin-2-yl-2,3-dihydro-1H-inden-1-yl]-2,7-diaza-spiro[3.5]non-7-yl}ethyl)benzamide (7A)

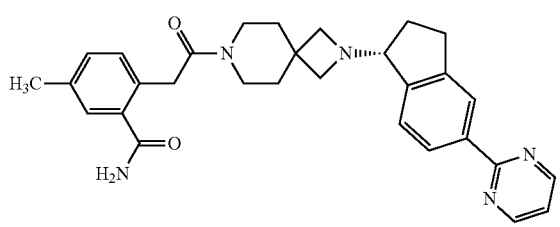

(7A)

To a solution of 5-methyl-2-{2-oxo-2-[2-(R)-5-pyrimidin-2-yl-indan-1-yl)-2,7-diaza-spiro[3.5]non-7-yl]-ethyly}-benzoic acid (7-1a, 50 mg, 0.1 mmol) in 2 mL of dimethylformamide was added BOP (50 mg, 0.11 mmol). The mixture was stirred at room temperature for 10 minutes and ammonia (1.0 mL, 0.5M in dioxane, 0.5 mmol) was added. The reaction was stirred at room temperature for 3 hours, at 40° C. for 5 hours, and was concentrated. The crude product was purified on a Biotage (Biotage Inc.) 10 g reverse phase column, eluting with 95-50% water in acetonitrile over 40 minutes to provide 35 mg (70%) of the desired product as a brown solid. MS (ES+) 496.5 (M+H)+. $^1$H NMR (CD$_3$OD) δ 1.88-1.92 (m, 4H), 2.18-2.30 (m, 1H), 2.37 (s, 3H), 2.60 (dd, 1H), 3.01-3.14 (m, 1H), 3.22-3.30 (m, 1H), 3.38 (s, 2H), 3.57-3.61 (m, 4H), 3.97 (s, 2H), 4.12 (d, 2H), 4.25 (br s, 2H), 5.04 (d, 1H), 7.15 (d, 1H), 7.26 (d, 1H), 7.35-7.46 (m, 2H), 7.72 (d, 1H), 8.39 (d, 1H), 8.42 (s, 1H), 8.88 (d, 2H).

The compounds listed in Table 7 below were prepared using procedures analogous to those described above for the preparation of 5-methyl-2-{2-oxo-2-[2-((R)-5-pyrimidin-2-yl-indan-1-yl)-2,7-diaza-spiro[3.5]non-7-yl]-ethyly}-benzamide (7A) using the appropriate starting materials. Unless otherwise noted, the stereochemical designation of the following examples in Table 7 is R.

TABLE 7

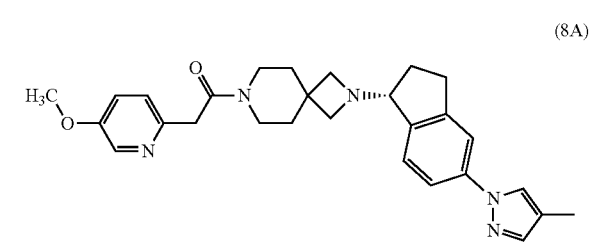

| Example No. | R[1] | R[2] |
|---|---|---|
| 7B | 5-methoxy-2-benzamide | pyrimidin-2-yl |

MS (ES+) 512.5 (M + H)+
$^1$H NMR (DMSO-d$_6$) δ 1.18-1.22 (m, 3 H), 1.56-1.60 (m, 5 H), 1.85-1.89 (m, 2 H), 2.27-2.31 (m, 2 H), 2.81-2.84 (m, 2 H), 2.99-3.02 (m, 2 H), 3.69-3.80 (m, 5 H), 6.89 (dd, 1 H), 6.97 (d, 1 H), 7.05 (d, 1 H), 7.27 (br s, 1 H), 7.33-7.53 (m, 2 H), 7.77 (s, 1 H), 8.24 (s, 2H, 8.85 (d, 2 H).

| 7C | 5-methoxy-benzamide | 6-methyl-pyrimidin-4-yl |
|---|---|---|

MS (ES+) 526.6 (M + H)+
$^1$H NMR (CD$_3$OD) δ 1.70-1.74 (m, 4 H), 1.89-1.93 (m, 1 H), 2.22-2.31 (m, 1 H), 2.57 (s, 3 H), 2.90-2.94 (m, 1 H), 3.10-3.15 (m, 1 H), 3.21-3.25 (m, 2 H), 3.30-3.35 (m, 2 H), 3.51-3.54 (m, 4 H), 3.80 (s, 3 H), 3.90 (s, 2 H), 4.06-4.10 (m, 1 H), 6.95 (dd, 1 H), 7.08 (d, 1 H), 7.14 (d, 1 H), 7.49 (d, 1 H), 7.85 (s, 1 H), 7.97 (d, 1 H), 8.02 (s, 1 H), 8.89 (s, 1 H).

| 7D | | 6-methyl-pyrimidin-4-yl |
|---|---|---|

MS (ES+) 540.1 (M + H)+
Retention Time: 1.78 min

Example 8

Preparation of 7-[(5-methoxypyridin-2-yl)acetyl]-2-[(1R)-5-(4-methyl-1H-pyrazol-1-yl)-2,3-dihydro-1H-inden-1-yl]-2,7-diazaspiro[3.5]nonane (8A)

(8A)

To a mixture of (5-methoxypyridin-2-yl)acetic acid (SM-1aa, 25.9 mg, 0.16 mmol) in dichloromethane (5 mL) was added 1,1'-carbonyldiimidazole (25.9 mg, 0.16 mmol) and the reaction was stirred overnight at room temperature. In a separate flask, to a mixture of 2-((R)-5-(4-methyl-1H-pyrazol-1-yl)-2,3-dihydro-1H-inden-1-yl)-2,7-diazaspiro[3.5]nonane dihydrochloride (8-1b, 60.0 mg, 0.15 mmol) in dichloromethane (10 mL) was added triethylamine (0.31 mL, 0.23 mmol). The activated acid was then added to the amine solution and the resulting mixture was stirred at room temperature for 2 hours. The reaction was concentrated and purified on an ISCO (Teledyne Isco Inc., Lincoln Nebr.) 12 g silica column eluting with 50-100% MeOH in ethyl acetate gradient to give 26 mg (36%) of the title compound (8A) as a gum. MS (ES+) 472.9 (M+H)+. 1H NMR (CD3OD) δ 1.62-1.75 (m, 4H), 1.85-1.97 (m, 1H), 2.13 (s, 3H), 2.17-2.31 (m, 1H), 2.80-2.92 (m, 1H), 3.03-3.15 (m, 1H), 3.20-3.27 (m, 2H), 3.32 (d, 2H), 3.48-3.56 (m, 4H), 3.84 (s, 3H), 3.85 (s, 2H), 4.03 (dd, 1H), 7.22-7.28 (m, 1H), 7.35 (dd, 1H), 7.38-7.44 (m, 1H), 7.44-7.51 (m, 2H), 7.55 (s, 1H), 7.94 (s, 1H), 8.13 (d, 1H).

The compounds listed in Table 8 below were prepared using procedures analogous to those described above for the preparation of 2-(5-methoxy-pyridin-2-yl)-1-{2-[(R)-5-(5-methyl-pyrazol-1-yl)-indan-1-yl]-2,7-diaza-spiro[3.5]non-7-yl}-ethanone (8A) with the appropriate starting materials. Unless otherwise noted, the stereochemical designation of the following examples in Table 8 is R.

TABLE 8

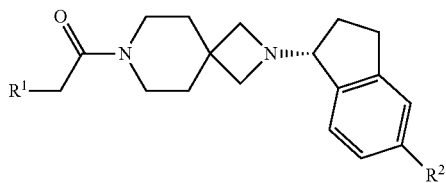

| Example No. | R¹ | R² |
|---|---|---|
| 8B | 4-methoxyphenyl | 4-methyl-pyrazol-1-yl |

MS (ES+) 471.0 (M + H)+

1H NMR (CD3OD) δ 1.51-1.57 (m, 2 H), 1.64-1.71 (m, 2 H), 1.84-1.94 (m, 1 H), 2.13 (s, 3 H), 2.16-2.27 (m, 1 H), 2.79-2.90 (m, 1 H), 3.03-3.14 (m, 1 H), 3.17-3.22 (m, 2 H), 3.25 (d, 2 H), 3.39-3.46 (m, 2 H), 3.48-3.54 (m, 2 H), 3.67 (s, 2 H), 3.74 (s, 3 H), 4.00 (dd, 1 H), 6.83-6.88 (m, 2 H), 7.11-7.17 (m, 2 H), 7.35-7.41 (m, 1 H), 7.44-7.50 (m, 2 H), 7.54 (s, 1 H), 7.93 (s, 1 H).

| 8C | 5-methoxypyridin-2-yl | 1H-pyrazol-1-yl |

MS (ES+) 458.5 (M + H)+

1H NMR (CD3OD) δ 1.65-1.80 (m, 4 H), 1.93-2.04 (m, 1 H), 2.23-2.39 (m, 1 H), 2.84-2.98 (m, 1 H), 3.10-3.18 (m, 1 H), 3.36-3.49 (m, 4 H), 3.55 (q, 4 H), 3.81-3.90 (m, 5 H), 4.20 (dd, 1 H), 6.49-6.54 (m, 1 H), 7.28 (s, 1 H), 7.33-7.40 (m, 1 H), 7.48 (d, 1 H), 7.54-7.59 (m, 1 H), 7.62-7.69 (m, 1 H), 7.70 (d, 1 H), 8.15 (d, 1 H), 8.19 (d, 1 H).

Example 9

Preparation of 5-{(1R)-1-[7-(2,3-dihydro[1,4]dioxino[2,3-b]pyridin-6-yl)acetyl)-2,7-diazaspiro[3.5]non-2-yl]-2,3-dihydro-1H-inden-5-yl}pyridine-2-carboxamide (9A)

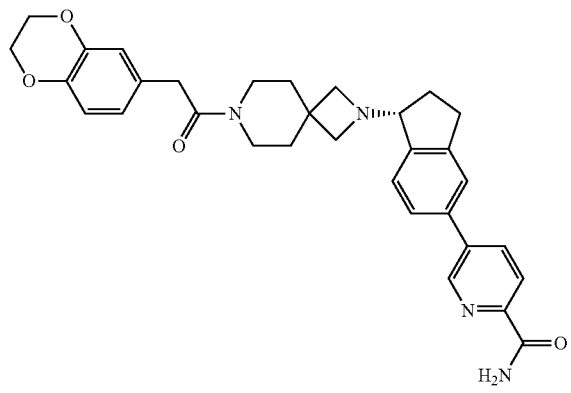

(9A)

To a solution of 5-[(R)-1-(2,7-diaza-spiro[3.5]non-2-yl)-indan-5-yl]-pyridine-2-carboxylic acid amide dihydrochloride (9-1b, 45.3 mg, 0.13 mmol) and 2-(2,3-dihydro-[1,4]dioxino[2,3-b]pyridin-6-yl)acetic acid (SM-1 aj, 29 mg, 0.13 mmol) in 3 mL of DMF was added DIEA (0.12 mL, 0.63 mmol) followed by BOP (63 mg, 0.14 mmol). The mixture was stirred at room temperature overnight. The reaction was quenched by the addition of 25 mL of saturated NaHCO3 and diluted with 100 mL of dichloromethane. The organic solution was washed with saturated brine, dried over MgSO4 and concentrated. The crude product was purified on a Biotage (Biotage Inc.) 10 g reverse phase column, eluting with 0-50% acetonitrile in water to give the desired product (12 mg, 18%) as a white solid. MS (ES+) 540.0 (M+H)+. 1H NMR (CD3OD) δ 1.83-1.87 (m, 2H), 1.97-2.01 (m, 1H), 2.16-2.20 (m, 1H), 2.52-2.66 (m, 2H), 3.08-3.12 (m, 1H), 3.17-3.26 (m, 1H), 3.55-3.59 (m, 3H), 3.74 (s, 2H), 4.10 (br s, 2H), 4.18-4.32 (m, 4H), 4.36-4.49 (m, 3H), 4.98 (br s, 1H), 6.84 (d, 1H), 7.18-7.38 (m, 1H), 7.62-7.78 (m, 3H), 8.13-8.22 (m, 2H), 8.88 (d, 1H).

The compounds listed in Table 9 below were prepared using procedures analogous to those described above for the preparation 5-{(R)-1-[7-(2-2,3-dihydro-[1,4]dioxino[2,3-b]pyridin-6-yl-acetyl)-2,7-diaza-spiro[3.5]non-2-yl]-indan-5-yl}-pyridine-2-carboxylic acid amide (9A). Unless otherwise noted, the stereochemical designation of the following examples in Table 9 is R.

TABLE 9

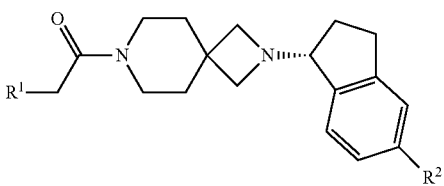

| Example No. | R¹ | R² |
|---|---|---|
| 9B | 5-methoxypyridin-2-yl | 6-carbamoyl-pyridin-3-yl |

MS (ES+) 512.0 (M + H)⁺
¹H NMR (CD$_3$OD) δ 1.24-1.33 (m, 1 H), 1.77-1.86 (m, 4 H), 2.12-2.22 (m, 1 H), 2.47-2.60 (m, 1 H), 3.00-3.11 (m, 1 H), 3.13-3.25 (m, 1 H), 3.54-3.60 (m, 4 H), 3.84 (s, 3 H), 3.87 (s, 2 H), 3.99 (s, 2 H), 4.10 (s, 2 H), 7.20-7.39 (m, 2 H), 7.60-7.70 (m, 2 H), 7.73 (s, 1 H), 8.09-8.22 (m, 3 H), 8.34 (br s, 2 H), 8.88 (s, 1 H).

| 9C | 5-methyl-pyridin-2-yl | 6-carbamoyl-pyridin-3-yl |

MS (ES+) 496.1 (M + H)⁺
¹H NMR (CD$_3$OD) δ 1.62-1.76 (m, 4 H), 1.91 (dd, 1 H), 2.23 (d, 1 H), 2.31 (s, 3 H), 2.91 (d, 1 H), 3.11 (d, 1 H), 3.20-3.27 (m, 2 H), 3.29-3.34 (m, 2 H), 3.52 (t, 4 H), 3.88 (s, 2 H), 4.05 (dd, 1 H), 7.22 (d, 1 H), 7.42-7.54 (m, 2 H), 7.55-7.62 (m, 2 H), 8.14 (d, 2 H), 8.28 (d, 1 H), 8.84 (s, 1 H).

| 9D | (2-methylthiazolo-imidazol-6-yl) | 6-carbamoyl-pyridin-3-yl |

MS (ES+) 541.7 (M + H)⁺
¹H NMR (CD$_3$OD) δ 1.68-1.77 (m, 4 H), 1.86-1.98 (m, 1 H), 2.17-2.32 (m, 1 H), 2.40 (s, 3 H), 2.83-2.96 (m, 1 H), 3.06-3.19 (m, 1 H), 3.30-3.37 (m, 4 H), 3.50-3.58 (m, 4 H), 3.75 (s, 2 H), 4.03-4.12 (m, 1 H), 7.40 (s, 2 H), 7.44-7.55 (m, 2 H), 7.60 (s, 1 H), 8.14 (s, 2 H), 8.85 (t, 1 H).

| 9E | (imidazo[1,2-a]pyridin-2-yl) | 6-carbamoyl-pyridin-3-yl |

MS (ES+) 521.9 (M + H)⁺
¹H NMR (CD$_3$OD) δ 1.65-1.79 (m, 4 H), 1.92 (dt, 1 H), 2.16-2.31 (m, 1 H), 2.82-2.96 (m, 1 H), 3.05-3.18 (m, 1 H), 3.23-3.27 (m, 2 H), 3.30-3.35 (m, 2 H), 3.51-3.60 (m, 4 H), 3.89 (s, 2 H), 4.06 (dd, 1 H), 6.87 (td, 1 H), 7.26 (ddd, 1 H), 7.43-7.54 (m, 3 H), 7.59 (s, 1 H), 7.68 (s, 1 H), 8.11-8.16 (m, 2 H), 8.35 (dt, 1 H), 8.85 (t, 1 H).

| 9F | (7-methylimidazo[1,2-a]pyridin-2-yl) | 6-carbamoyl-pyridin-3-yl |

MS (ES+) 535.3 (M + H)⁺
Retention Time: 1.69 min

Example 10

Preparation of 5-[(1R)-1-{7-[(5-methoxypyridin-2-yl)acetyl]-2,7-diazaspiro[3.5]non-2-yl}-2,3-dihydro-1H-inden-5-yl]pyrazine-2-carboxamide (10A)

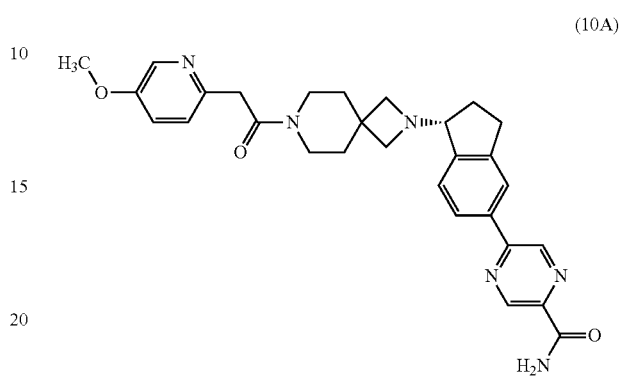

(10A)

To a solution of 5-[(R)-1-(2,7-diaza-spiro[3.5]non-2-yl)-indan-5-yl]-pyrazine-2-carboxylic acid amide (10-1c, 28 mg, 0.08 mmol) in 3 mL of DMF was added (5-methoxy-pyridin-2-yl)-acetic acid (SM-1aa, 13.0 mg, 0.08 mmol), HBTU (33.0 mg, 0.09 mmol) and triethylamine (0.06 mL, 0.46 mmol). The solution was stirred at room temperature overnight. The reaction was concentrated under reduced pressure and coevaporated with toluene. The residue was partitioned between 10 mL of dichloromethane and 10 mL of 1N NaOH solution. The organic layer was washed with saturated brine, dried over Na$_2$SO$_4$ and concentrated. The crude product was purified by Biotage reverse phase column chromatography (Biotage, Inc.) using 100-60% water in acetonitrile to give the desired product 12.0 mg (27%). MS (ES+) 513.4 (M+H)⁺. ¹H NMR (CD$_3$OD) δ 1.56-1.81 (m, 4H), 1.81-2.09 (m, 1H), 2.11-2.35 (m, 1H), 2.93 (d, 1H), 3.12 (d, 1H), 3.20-3.27 (m, 2H), 3.31-3.41 (m, 1H), 3.43-3.66 (m, 4H), 3.69-3.89 (m, 5H), 4.06 (dd, 1H), 4.54-4.81 (m, 2H), 7.25 (d, 1H), 7.34 (dd, 1H), 7.50 (d, 1H), 7.97 (dd, 1H), 8.04 (s, 1H), 8.13 (d, 1H), 9.12 (d, 1H), 9.22 (d, 1H).

The compounds listed in Table 10 below were prepared using procedures analogous to those described above for the preparation of 5-((R)-1-{7-[2-(5-methoxy-pyridin-2-yl)-acetyl]-2,7-diaza-spiro[3.5]non-2-yl}-indan-5-yl)-pyrazine-2-carboxylic acid amide (10A) using the appropriate starting materials. Unless otherwise noted, the stereochemical designation of the following examples in Table 10 is R.

TABLE 10

| Example No. | R¹ | R² |
|---|---|---|
| 10B | (7-methylimidazo[1,2-a]pyridin-2-yl) | 5-carbamoyl-pyrazin-2-yl |

TABLE 10-continued

[Structure shown with R¹-C(O)-N-spiro-N-indane-R² core]

| Example No. | R¹ | R² |
|---|---|---|

MS (ES+) 536.0 (M + H)⁺
¹H NMR (CD₃OD) δ 1.63-1.78 (m, 4 H), 1.84-1.98 (m, 1 H), 2.17-2.32 (m, 1 H), 2.37 (s, 3 H), 2.92 (d, 1 H), 3.06-3.19 (m, 1 H), 3.22-3.28 (m, 2 H), 3.30-3.36 (m, 2 H), 3.49-3.60 (m, 4 H), 3.85 (s, 2 H), 4.07 (dd, 1 H), 6.73 (dd, 1 H), 7.22 (s, 1 H), 7.50 (d, 1 H), 7.58 (s, 1 H), 7.97 (dd, 1 H), 8.04 (s, 1 H), 8.21 (d, 1 H), 9.12 (d, 1 H), 9.22 (d, 1 H).

| 10C | [imidazo[1,2-a]pyridin-2-yl structure] | 5-carbamoyl-pyrazin-2-yl |

MS (ES+) 522.1 (M + H)⁺
¹H NMR (CD₃OD) δ 1.64-1.80 (m, 4 H), 1.85-1.98 (m, 1 H), 2.18-2.32 (m, 1 H), 2.92 (d, 1 H), 3.11 (d, 1 H), 3.23-3.28 (m, 2 H), 3.30-3.35 (m, 2 H), 3.55 (q, 4 H), 3.89 (s, 2 H), 4.07 (dd, 1 H), 6.87 (td, 1 H), 7.26 (ddd, 1 H), 7.40-7.53 (m, 2 H), 7.68 (s, 1 H), 7.97 (dd, 1 H), 8.04 (s, 1 H), 8.35 (dt, 1 H), 9.12 (d, 1 H), 9.22 (d, 1 H).

| 10D | 5-methoxypyridin-2-yl | 6-carbamoyl-pyrimidin-4-yl |

MS (ES+) 513.1 (M + H)⁺
¹H NMR (CD₃OD) δ 1.74 (dt, 4 H), 1.97 (qd, 1 H), 2.19-2.37 (m, 1 H), 2.87-3.06 (m, 1 H), 3.17 (dt, 1 H), 3.34-3.45 (m, 4 H), 3.52-3.72 (m, 4 H), 3.80-3.92 (m, 5 H), 4.17 (dd, 1 H), 7.29 (d, 1 H), 7.38 (dd, 1 H), 7.55 (d, 1 H), 8.08 (d, 1 H), 8.13-8.28 (m, 2 H), 8.51 (d, 1 H), 9.27 (d, 1 H).

| 10E | 5-cyclopropylpyridin-2-yl | 6-carbamoyl-pyridin-3-yl |

MS (ES+) 522.3 (M + H)⁺
Retention Time: 1.72 min

| 10F | [thiadiazolo-imidazo with CH₃] | 6-carbamoyl-pyridin-3-yl |

MS (ES+) 542.3 (M + H)⁺
Retention Time: 1.77 min

| 10G | [methyl-imidazo[1,2-a]pyridin-2-yl] | 6-carbamoyl-pyrimidin-4-yl |

MS (ES+) 536.3 (M + H)⁺
Retention Time: 1.62 min

| 10H | 5-ethyl-pyridin-2-yl | 5-carbamoyl-pyrazin-2-yl |

MS (ES+) 511.1 (M + H)⁺
¹H NMR (CD₃OD) δ 1.23 (t, 3 H), 1.71 (dt, 4 H), 1.91-1.95 (m, 1 H), 2.20-2.32 (m, 1 H), 2.65 (q, 2 H), 2.89-2.92 (m, 1 H), 3.08-3.19 (m, 1 H), 3.22-3.27 (m, 2 H), 3.31-3.35 (m, 2 H), 3.51-3.54 (m, 4 H), 3.89 (s, 2 H), 4.08 (dd, 1 H), 7.25 (d, 1 H), 7.51 (d, 1 H), 7.63 (dd, 1 H), 7.98 (d, 1 H), 8.05 (s, 1 H), 8.30 (d, 1 H), 9.13 (d, 1 H), 9.23 (d, 1 H)

Example 11

Preparation of 6-((R)-1-{7-[2-(5-Methoxy-pyridin-2-yl)-acetyl]-2,7-diaza-spiro[3.5]non-2-yl}indan-5-yl)-nicotinamide (11A)

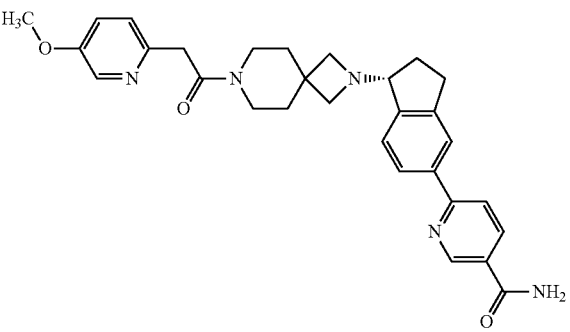

(11A)

To a solution of water (30 mL) and urea hydrogen peroxide (165 mg, 1.70 mmol) was added sodium hydroxide (39.8 mg, 0.99 mmol) and the reaction was stirred at room temperature. Once a clear solution was obtained, the reaction was placed in an ice bath and fitted with an addition funnel. A solution of 6-((R)-1-{7-[2-(5-methoxy-pyridin-2-yl)-acetyl]-2,7-diaza-spiro[3.5]non-2-yl}-indan-5-yl)-nicotinonitrile (11-1c, 379 mg, 0.85 mmol) in 1 mL of EtOH was added dropwise via the funnel over a period of 30 minutes. The solution became cloudy and was stirred overnight while warming to room temperature. After 18 hours, the reaction was concentrated. The crude product was purified on a Biotage (Biotage Inc.) 10 g reverse phase column, eluting with 0-50% acetonitrile in water to give the title compound 12 mg (8%). MS (ES+) 512.0 (M+H)⁺. ¹H NMR (CD₃OD) δ 1.61-1.75 (m, 4H), 1.90 (td, 1H), 2.24 (ddd, 1H), 2.83-2.94 (m, 1H), 3.05-3.17 (m, 1H), 3.20-3.27 (m, 2H), 3.48-3.56 (m, 5H), 3.83 (s, 4H), 3.85 (s, 2H), 4.04 (dd, 1H), 7.21-7.29 (m, 1H), 7.30-7.38 (m, 1H), 7.46 (d, 1H), 7.81-7.88 (m, 1H), 7.89-7.95 (m, 2H), 8.13 (d, 1H), 8.27 (dd, 1H), 9.05 (dd, 1H).

Pharmacological Testing

The practice of the instant invention for the treatment of diseases mediated by the antagonism of the human ghrelin receptor (GHSR1a) can be evidenced by activity in at least one of the protocols described herein below. The following acronyms are used in the assay descriptions below and have the corresponding definitions:

GHSR: growth hormone secretagogue receptor
SPA: scintillation proximity assay
DMSO: Dimethyl sulfoxide
$IC_{50}$: inhibitory concentration to decrease activity by 50%
$K_i$: $K_i=IC_{50}/(1+[ligand]/Kd)$
HEK293: Human Embryonic Kidney 293 cells
GTP: guanosine triphosphate
GDP: guanosine diphosphate
GPCR: G-Protein Coupled Receptor
$EC_{80}$: stimulating concentration to achieve 80% of maximal activity
PEI: polyethyleneimine

Radioligand Binding Assays

To measure the ability of test compounds in the present invention to bind to the ghrelin receptor, and therefore have the potential to modulate ghrelin activity, radioligand displacement assays are performed. The SPA format was utilized for high throughput screening of test compounds and filter binding served for more comprehensive binding characterization. In both formats test compound affinity is expressed as $K_i$ value, defined as the concentration of compound required to decrease [$^{125}$I] ghrelin binding by 50% for a specific membrane batch at a given concentration of radioligand.

Human Ghrelin SPA Binding Assay

Ghrelin SPA binding assays are performed in a final volume of 90 μl containing 250 ng human GHSR1a (HEK293 Tetracycline-Inducible cell line expressing the human growth secretagogue receptor 1a; prepared as membranes) coupled to 0.5 mg SPA beads (wheat germ agglutinin coated, GE Healthcare, RPNQ0060) and 50 μM [$^{125}$I] ghrelin (Perkin Elmer Life Sciences, NEX-388), plus varying concentrations of test compound or vehicle.

Briefly, assays are prepared at room temperature in 384-well plates (Matrix, 4322) containing 2 μl of test compound in DMSO (or DMSO as vehicle). Assays are initiated by addition of 28 μl assay buffer (50 mM HEPES, 10 mM MgCl$_2$, 0.2% BSA, EDTA-free protease inhibitors—1 tablet/50 ml buffer, pH 7.4), 30 μl 8.3 μg/ml hGHSR1a membrane and 30 μl of 150 pM [$^{125}$I] ghrelin, both in assay buffer.

The mixture is incubated for 8 hours to allow binding to reach equilibrium and the amount of receptor-ligand complex is determined by liquid scintillation counting using a 1450 Microbeta Trilux (Wallac).

Human Ghrelin Filter Binding Assay

Ghrelin binding assays are performed in a final volume of 100 μl containing 100 ng human GHSR1a (HEK293 Tetracycline-Inducible cell line expressing the human growth secretagogue receptor 1a; prepared as membranes) and 50 pM [$^{125}$I] ghrelin (Perkin Elmer Life Sciences, NEX-388), plus varying concentrations of test compound or vehicle.

Briefly, assays are prepared at room temperature in 96-well plates (Costar, 3357) containing 2 μl of test compound in DMSO (or DMSO as vehicle). Assays are initiated by addition of 23 μl assay buffer (50 mM HEPES, 10 mM MgCl$_2$, 0.2% BSA, EDTA-free protease inhibitor tablets—1 tablet/50 ml buffer, pH 7.4), 25 μg/ml hGHSR1a membrane and 50 μl of 100 μM [$^{125}$I] ghrelin, both in assay buffer.

The mixture is incubated for 90 minutes at room temperature followed by transfer to a 0.3% PEI-treated, 96-well glass fiber filtration plate (Perkin Elmer, 6005174). The mixture is suctioned dry with vacuum and immediately washed 3 times with 200 μl ice cold 50 mM Tris pH 7.5. Plates are allowed to dry overnight at room temperature and 30 μl Supermix scintillant (Perkin Elmer, 1200-439) is added to each well. The amount of receptor-ligand complex is determined by liquid scintillation counting using a 1450 Microbeta Trilux (Wallac).

Radioligand binding filtration format assays for dog (NM_001099945.1), monkey (XM_001084886.1), mouse (NM_177330), and rat (NM_032075) GHSR1a (all expressed in unique HEK293 Tetracycline-Inducible cell lines) are performed in an identical manner as described for human GHSR1a except that the final amount of membrane to be used is as follows: 2 μg dog GHSR, 250 ng monkey GHSR, 200 ng mouse GHSR, or 125 ng rat GHSR.

Human Ghrelin Functional Assay

To measure the ability of test compounds in the present invention to modulate the activity of human GHSR1a (agonize, antagonize, partially agonize, inversely agonize), a DELFIA GTP-binding assay (Perkin Elmer, AD0260 and AD0261) is performed. The assay monitors the ligand-dependent exchange of GDP for GTP. GPCR activation results in an increase in fluorescence as receptor-bound GDP is replaced by Europium-labeled GTP. Antagonist binding prevents GDP-GTP exchange whereas binding of an inverse agonist pushes the receptor to the GDP bound (inactive) state, both resulting in decreased fluorescence.

Ghrelin functional assays are performed in a final volume of 39.5 μl containing 720 ng human GHSR1a (HEK293 Tetracycline-Inducible cell line expressing the human growth secretagogue receptor 1a, prepared as membranes), 9 nM GTP-Europium and varying concentrations of test compound or vehicle. To test for receptor antagonism, membranes are incubated in the presence of agonist ghrelin (Anaspec, 24158) at the $EC_{80}$ concentration, plus test compound or vehicle.

Briefly, test compounds are prepared at room temperature in 384-well plates (Matrix, 4340). The test compounds are first diluted in DMSO then added as 15 μl to 10 μl of basal buffer (50 mM HEPES pH 7.4, 3.7 mM MgCl$_2$, 250 μM EGTA, 125 nM GDP) with and without 9 nM ghrelin peptide. Samples are then transferred as 6 μl to 384-well filter plates (Pall, 5071) containing 30 μl of 24 μg/ml hGHSR1a membrane and 0.35 mg/ml saponin (Perkin Elmer, AD0261) in basal buffer.

The mixture is incubated 24 minutes at room temperature with gentle shaking, followed by the addition of 3.5 μl of 100 nM GTP-Europium in 50 mM HEPES, pH 7.4. Samples are shielded from light and incubated for 90 minutes further at room temperature with gentle shaking. The reactions are suctioned dry with vacuum, washed three times with 75 μl ice cold 1× GTP Wash Solution (Perkin Elmer, AD0261), and immediately read on the Envision 2101 Multilabel Reader (Perkin Elmer) using excitation filter 320 nm and emission filter 615 nm.

Human Dispersed Islet Cell Assay

Day 1: Human islet cells in an intravenous (iv) bag are obtained. The islet cells are decanted by attaching a coupler to the iv bag and the liquid is decanted into 50 mL conical tubes. The bag is rinsed with 20 mL of media and pooled. The cells are spun 1 minute at 1000 revolutions per minute (rpm). The cells are then incubated overnight at 37° C., 5% $CO_2$ (10 cm$^2$ suspension dishes, 10 mL media/plate).

Day 2: The islet cells are transferred to a 50 mL conical tube, Hank's Working Buffer without calcium is added and mixed, then the mixture is spun for 1 minute at 1000 rpm. The islets are then washed with Hank's Working Buffer without calcium, mixed and then spun at 1000 rpm for 1 minute. All but 15 mL of buffer is then removed by pipette. 30 μL of 500 mM EDTA [1 mM] is then added and then incubated 8 minutes at room temperature. To this is then added 75 μL of 0.25% Trypsin-EDTA and 15 μl of 2 mg/ml DNAse I [2 μg/ml]. The mixture is incubated for 10 minutes at 30° C. with shaking at 60 rpm. The clot is dispersed by triturating with a 1 mL pipette (50 times). 50 mL of Culture Media is added and passed each over 63 μM nylon membrane. The mixture is spun at 1000 rpm for 1 minute then the media is removed by pipette. Resuspend the pellet and washed cells again with approximately 25 mL Culture Media and spun at 1000 rpm for 1 minute. The supernatant is removed then the pellet is resuspended with approximately 5 mL Culture Media and the cells are counted. "V" bottom plates are seeded with 5000 cells/well (200 μl/well). The plates are spun at 1000 rpm for 5 minutes and placed in cell culture incubation. 600,000 cells are removed for calcium imaging.

Day 3: Dispersed Islet Assay

The culture media is replaced with 100 μl of incubation buffer containing 3 mM glucose. The plates are spun for 5 minutes at 1000 rpm to re-pellet the islets. Incubate the plates in a 37° C. waterbath continuously gassed with 95% $O_2$/5%

$CO_2$ for 45 minutes. Replace the pre-incubation buffer with 50 µl of incubation buffer containing the various test compounds in the appropriate concentration of glucose (n=4 for each sample). The plates are spun for 5 minutes at 1000 rpm to re-pellet the cells. The plates are returned to a waterbath continuously gassed with 95% $O_2$/5% $CO_2$ for 60 minutes. Transfered 40 µl to another plate and assay for insulin using an ELISA Human Insulin Assay (ALPCO Human Insulin ELISA; Cat. No. 80-INSHU-E10 available from ALPCO, Salem, N.H., USA).

The following pharmacological data provided in Pharmacological Data Table 1 was obtained for the compounds of the present invention. The IC50 and Ki data was obtained from the Human Ghrelin SPA Binding Assay and is reported in nanomolar concentration of the test compound. The column denoted "n" is the number of times the compound was assayed. The functionality of the test compound, when indicated, was determined using the Human Ghrelin Functional Assay.

PHARMACOLOGICAL DATA TABLE 1

| Example | IC50 (nM) | Ki (nM) | n | functional comment |
|---|---|---|---|---|
| 1A | 12.62 | | 4 | inverse agonist |
| 1A-1/3B | 5.22 | 6.34 | 6 | inverse agonist |
| 1B | 3.79 | 4.59 | 4 | inverse agonist |
| 1C | 16.45 | 14.23 | 5 | inverse agonist |
| 1D | 19.4 | | 4 | inverse agonist |
| 1E | 34.1 | | 4 | inverse agonist |
| 1F | 30.03 | 22.78 | 3 | |
| 1F-1 | 5.46 | 3.98 | 9 | inverse agonist |
| 1G | 7.56 | 8.67 | 3 | |
| 1H | 11.06 | 10.42 | 3 | |
| 1I | 36.56 | 29.52 | 3 | |
| 1J | 5.25 | 5.12 | 3 | |
| 1K | 25.9 | | 4 | inverse agonist |
| 2A | 22.72 | 91.28 | 3 | inverse agonist |
| 2B | 6.75 | | 2 | |
| 2C | 13.73 | 38.04 | 3 | inverse agonist |
| 2D | 21.39 | | 2 | |
| 2E | 35.16 | 63.57 | 3 | |
| 2F | 35.93 | 50.22 | 3 | inverse agonist |
| 2G | 6.22 | | 2 | |
| 2H | 92.17 | 218 | 3 | inverse agonist |
| 2I | 15.27 | 51.16 | 3 | inverse agonist |
| 2J | 22.02 | | 2 | inverse agonist |
| 3A | 9.46 | 9.03 | 7 | inverse agonist |
| 3C | 12.28 | 11.17 | 11 | inverse agonist |
| 3D | 10.21 | 8.91 | 6 | inverse agonist |
| 3E | 20.67 | 18.49 | 3 | inverse agonist |
| 3F | 5.02 | 4.37 | 10 | inverse agonist |
| 3G | 21.24 | 29.77 | 10 | inverse agonist |
| 3H | 9.51 | 9.17 | 5 | inverse agonist |
| 3I | 31.01 | 27.8 | 3 | inverse agonist |
| 3J | 52.89 | 46.51 | 2 | |
| 3K | 99.48 | 87.14 | 3 | |
| 3L | 23 | 20.15 | 2 | inverse agonist |
| 3M | 49.03 | 42.07 | 4 | |
| 3N | 82.58 | 71.26 | 5 | inverse agonist |
| 3O | 30.23 | 28.08 | 4 | |
| 3P | 36.29 | 31.67 | 3 | |
| 3Q | 26.6 | 23.04 | 4 | |
| 3R | 25.49 | 22.16 | 2 | |
| 3S | 17.85 | 15.32 | 4 | inverse agonist |
| 3T | 82.41 | 73.01 | 1 | |
| 3U | 8.08 | 6.90 | 6 | inverse agonist |
| 3V | 20.65 | 17.42 | 3 | |
| 3W | 17.2 | 14.82 | 3 | inverse agonist |
| 3X | 36.57 | 31.64 | 4 | inverse agonist |
| 3Y | 30.74 | 25.94 | 3 | |
| 3Z | 6.78 | 6.07 | 6 | inverse agonist |
| 3AA | 9.80 | 8.59 | 2 | inverse agonist |
| 3AB | 32.95 | 28.81 | 2 | |
| 3AC | 40.47 | 33.82 | 2 | |
| 3AD | 19.49 | 15.52 | 3 | inverse agonist |
| 3AE | 73.15 | 68.93 | 3 | |
| 3AF | 7.41 | 6.13 | 3 | inverse agonist |
| 3AG | 40.05 | 33.11 | 3 | |
| 3AH | 90.19 | 72.84 | 3 | |
| 3AI | 4 | 3.56 | 3 | inverse agonist |
| 3AJ | 292.9 | 261.2 | | |
| 3AK | 6.38 | 5.66 | 3 | inverse agonist |
| 3AL | 7.73 | 6.91 | 3 | inverse agonist |
| 3AM | 13 | 11.61 | 3 | inverse agonist |
| 3AN | 16.57 | 14.93 | 2 | inverse agonist |
| 3AO | 16.8 | 15.14 | 2 | inverse agonist |
| 3AP | 27.2 | 24.45 | 2 | inverse agonist |
| 3AQ | 28.74 | 25.71 | 3 | inverse agonist |
| 3AR | 33.92 | 30.27 | 3 | inverse agonist |
| 3AS | 143 | 121.6 | 2 | |
| 3AT | 166.1 | 149 | 3 | |
| 3AU | 206.6 | 183.5 | 1 | |
| 3AV | 228.7 | 197.9 | 3 | |
| 3AW | 949.1 | 784.7 | 3 | |
| 3AX | 801.4 | 690.7 | 3 | |
| 3AY | 495.2 | 439.9 | 1 | |
| 3AZ | 17.4 | 15.44 | 3 | |
| 4A | 9.29 | 8.02 | 2 | |
| 4B | 70.46 | 60.66 | 3 | |
| 4C | 49.32 | 43.29 | 2 | |
| 4D | 20.05 | 17.48 | 3 | |
| 4E | 42.62 | 36.79 | 2 | |
| 5A | 7.02 | 6.15 | 3 | |
| 5A-1 | 4.50 | 3.77 | 3 | |
| 5B | 11.46 | 10.37 | 3 | inverse agonist |
| 5C | 10.86 | 10.48 | 5 | inverse agonist |
| 5D | 18.65 | 16.07 | 8 | |
| 5E | 18.63 | 15.62 | 3 | |
| 5F | 12.84 | 10.37 | 3 | |
| 5G | 39.87 | 33.03 | 3 | inverse agonist |
| 5H | 5.90 | | 4 | |
| 5I | 8.57 | 9.26 | 3 | |
| 6A | 58.16 | 54.83 | 3 | |
| 6B | 28.05 | 26.45 | 3 | |
| 6C | 37.22 | 32.43 | 3 | inverse agonist |
| 6D | 3.44 | 3.32 | 5 | inverse agonist |
| 6E | 3.77 | 3.09 | 2 | inverse agonist |
| 6F | 6.08 | 5.18 | 3 | inverse agonist |
| 6G | 43.2 | 34.4 | 3 | |
| 6H | 21.72 | 19.43 | 3 | inverse agonist |
| 6I | 483.5 | 416.7 | 3 | |
| 6J | 327.2 | 264.3 | 3 | |
| 7A | 42.18 | 37.51 | 1 | |
| 7B | 25.46 | 22.22 | 3 | |
| 7C | 9.16 | 8.00 | 4 | inverse agonist |
| 7D | 139.7 | 124.9 | | inverse agonist |
| 8A | 29.04 | 24.74 | 3 | |
| 8B | 10.53 | 8.97 | 3 | |
| 8C | 82.26 | 66.44 | 3 | |
| 9A | 15.95 | 13.89 | 5 | inverse agonist |
| 9B | 55.16 | 47.49 | 3 | |
| 9C | 116.7 | 102.3 | 2 | |
| 9D | 12.23 | 10.58 | 3 | |
| 9E | 33.68 | 29.17 | 1 | |
| 9F | 22.77 | 20.21 | 3 | inverse agonist |
| 10A | 62.62 | 55.48 | 1 | |
| 10B | 23.41 | 20.28 | 1 | |
| 10C | 93.09 | 80.78 | 2 | |
| 10D | 94.65 | 82.91 | 3 | |
| 10E | 9.98 | 8.86 | 3 | inverse agonist |
| 10F | 15.77 | 14.18 | 2 | inverse agonist |
| 10G | 60.13 | 53.79 | 3 | inverse agonist |
| 10H | 141.5 | 122.7 | 2 | |
| 11A | 33.31 | 28.58 | 4 | |

All recited patents, patent applications and publications are incorporated herein by reference in their entirety.

We claim:
1. A compound of Formula (I)

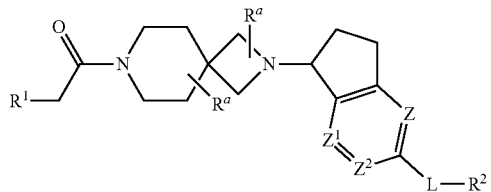

wherein:
R¹ is phenyl, imidazo[2,1-b][1,3]thiazolyl, pyridinyl, pyrazolo[1,5-a]pyridinyl, 4,5,6,7-tetrahydropyrazolo[1,5-a]pyridinyl, imidazo[2,1-b][1,3,4]thiadiazolyl, 1H-indazolyl, pyridazinyl, imidazo[1,2-b][1,2,4]triazinyl, 1H-pyrazolo[3,4-b]pyridinyl, imidazo[1,2-b]pyridazinyl, 2,3-dihydro-[1,4]dioxino[2,3-b]pyridinyl, oxadiazolyl or imidazo[1,2-a]pyridinyl; each optionally substituted with 1 to 3 substituents independently selected from methyl, methoxy, cyano, cyclopropyl, —C(O)NH₂ and —NHC(O)CH₃;
Rᵃ at each occurrence is hydrogen;
Z, Z¹ and Z² are each CH;
L is a direct bond; and
R² is hydrogen, phenyl, phenoxy, pyrimidinyl, imidazolyl, triazolyl, tetrazolyl, thiazolyl, thiadiazolyl, pyridinyl, oxazolyl, oxadiazolyl, pyrazolyl, pyridazinyl, triazinyl or pyrazinyl; each optionally substituted with 1 to 3 substituents independently selected from methyl, trifluoromethyl, ethyl, methoxy, cyano or —C(O)NH₂;
or a pharmaceutically acceptable salt thereof.

2. The compound of claim 1 of Formula (IA)

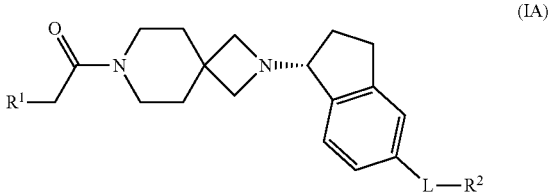

or a pharmaceutically acceptable salt thereof.

3. The compound of claim 2 wherein:
R² is phenyl, pyrimidinyl, imidazolyl, triazolyl, tetrazolyl, thiazolyl, thiadiazolyl, pyridinyl, oxazolyl, oxadiazolyl, pyrazolyl, pyridazinyl, triazinyl or pyrazinyl each optionally substituted with 1 to 3 substituents independently selected from methyl, ethyl, methoxy, cyano or —C(O)NH₂; and L is a direct bond; or a pharmaceutically acceptable salt thereof.

4. The compound of claim 3 wherein
R² is phenyl, pyrimidinyl, triazolyl, thiazolyl, pyridinyl, oxazolyl, pyrimidinyl, pyrazolyl, or pyrazinyl; each optionally substituted with 1 to 3 substituents independently selected from methyl, ethyl, methoxy, cyano or —C(O)NH₂; and L is a direct bond; or a pharmaceutically acceptable salt thereof.

5. The compound of claim 2 selected from the group consisting of
7-[(2-methylimidazo[2,1-b][1,3]thiazol-6-yl)acetyl]-2-[(1R)-5-pyrimidin-2-yl-2,3-dihydro-1H-inden-1-yl]-2,7-diazaspiro[3.5]nonane;
7-[(4-methoxyphenyl)acetyl]-2-[(1R)-5-(2H-1,2,3-triazol-2-yl)-2,3-dihydro-1H-inden-1-yl]-2,7-diazaspiro[3.5]nonane;
7-[(5-methoxypyridin-2-yl)acetyl]-2-[(1R)-5-(1,3-thiazol-2-yl)-2,3-dihydro-1H-inden-1-yl]-2,7-diazaspiro[3.5]nonane;
2-[(1R)-5-(5-ethylpyrimidin-2-yl)-2,3-dihydro-1H-inden-1-yl]-7-[(5-methoxypyridin-2-yl)acetyl]-2,7-diazaspiro[3.5]nonane;
7-[(5-methoxypyridin-2-yl)acetyl]-2-[(1R)-5-(2H-1,2,3-triazol-2-yl)-2,3-dihydro-1H-inden-1-yl]-2,7-diazaspiro[3.5]nonane;
7-[(5-methoxypyridin-2-yl)acetyl]-2-[(1R)-5-(5-methylpyrimidin-2-yl)-2,3-dihydro-1H-inden-1-yl]-2,7-diazaspiro[3.5]nonane;
7-[(5-ethylpyridin-2-yl)acetyl]-2-[(1R)-5-pyrimidin-2-yl-2,3-dihydro-1H-inden-1-yl]-2,7-diazaspiro[3.5]nonane;
7-[(5-methoxypyridin-2-yl)acetyl]-2-[(1R)-5-(6-methylpyrimidin-4-yl)-2,3-dihydro-1H-inden-1-yl]-2,7-diazaspiro[3.5]nonane;
7-[(5-methylpyridin-2-yl)acetyl]-2-[(1R)-5-(2H-1,2,3-triazol-2-yl)-2,3-dihydro-1H-inden-1-yl]-2,7-diazaspiro[3.5]nonane;
2-[(1R)-5-(2,6-dimethylpyrimidin-4-yl)-2,3-dihydro-1H-inden-1-yl]-7-[(5-methoxypyridin-2-yl)acetyl]-2,7-diazaspiro[3.5]nonane;
7-[(2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane;
6-(2-{2-[(1R)-5-(6-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;
5-{(1R)-1-[7-(2,3-dihydro[1,4]dioxin[2,3-b]pyridin-6-ylacetyl)-2,7-diazaspiro[3.5]non-2-yl]-2,3-dihydro-1H-inden-5-yl}pyridine-2-carboxamide;
7-[(5-methoxypyridin-2-yl)acetyl]-2-[(1R)-5-(4-methylpyrimidin-2-yl)-2,3-dihydro-1H-inden-1-yl]-2,7-diazaspiro[3.5]nonane;
2-(2-{2-[(1R)-5-(6-methylpyrimidin-4-yl)-2,3-dihydro-1H-inden-1-yl]-2,7-diazaspiro[3.5]non-7-yl}-2-oxoethyl)imidazo[1,2-a]pyridine;
7-[(2-methylimidazo[2,1-b][1,3,4]thiadiazol-6-yl)acetyl]-2-[(1R)-5-(6-methylpyrimidin-4-yl)-2,3-dihydro-1H-inden-1-yl]-2,7-diazaspiro[3.5]nonane;
5-methoxy-2-(2-oxo-2-{2-[(1R)-5-pyrimidin-2-yl-2,3-dihydro-1H-inden-1-yl]-2,7-diazaspiro[3.5]non-7-yl}ethyl)benzamide;
5-methoxy-2-(2-{2-[(1R)-5-(6-methylpyrimidin-4-yl)-2,3-dihydro-1H-inden-1-yl]-2,7-diazaspiro[3.5]non-7-yl}-2-oxoethyl)benzamide;
N-[5-methoxy-2-(2-oxo-2-{2-[(1R)-5-pyrimidin-2-yl-2,3-dihydro-1H-inden-1-yl]-2,7-diazaspiro[3.5]non-7-yl}ethyl)phenyl]acetamide; and
6-(2-{2-[(1R)-5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;
or a pharmaceutically acceptable salt thereof.

6. A pharmaceutical composition comprising a compound of claim 1 or a pharmaceutically acceptable salt thereof and a pharmaceutically acceptable excipient, diluent, or carrier.

7. The composition of claim 6 further comprising at least one additional pharmaceutical agent selected from the group consisting of an anti-obesity agent, an anti-diabetic agent, a lipid lowering agent or an anti-hypertensive agent.

8. A compound selected from the group consisting of 6-(2-{2-[(1R)-5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine;

7-[(2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane; and 7-[(2-methylimidazo[2,1-b][1,3,4]thiadiazol-6-yl)acetyl]-2-[(1R)-5-(6-methylpyrimidin-4-yl)-2,3-dihydro-1H-inden-1-yl]-2,7-diazaspiro[3.5]nonane; or a pharmaceutically acceptable salt thereof.

9. The compound of claim 8 which is 6-(2-{2-[(1R)-5-(2-methylpyrimidin-4-yl)-2,3-dihydro-1H-inden-1-yl]-2,7-diazaspiro[3.5]non-7-yl}-2-oxoethyl)-2,3-dihydro[1,4]dioxino[2,3-b]pyridine; or a pharmaceutically acceptable salt thereof.

10. The compound of claim 8 which is 7-[(2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane; or a pharmaceutically acceptable salt thereof.

11. The compound of claim 8 which is 7-[(2-methylimidazo[2,1-b][1,3,4]thiadiazol-6-yl)acetyl]-2-[(1R)-5-(6-methylpyrimidin-4-yl)-2,3-dihydro-1H-inden-1-yl]-2,7-diazaspiro[3.5]nonane; or a pharmaceutically acceptable salt thereof.

12. A compound which is 7-[(2-methylimidazo[2,1-b][1,3]thiazol-6-yl)acetyl]-2-[(1R)-5-(6-methylpyrimidin-4-yl)-2,3-dihydro-1H-inden-1-yl]-2,7-diazaspiro[3.5]nonane; or a pharmaceutically acceptable salt thereof.

13. A method for modulating GHSR1a activity with a compound of claim 1, or a pharmaceutically acceptable salt thereof.

* * * * *